US012668800B2

(12) United States Patent
Borrajo et al.

(10) Patent No.: US 12,668,800 B2
(45) Date of Patent: Jun. 30, 2026

(54) METHODS AND COMPOSITIONS FOR TARGETED TRANS-SPLICING

(71) Applicant: Amber Bio Inc., San Francisco, CA (US)

(72) Inventors: Jacob Borrajo, San Francisco, CA (US); Basem Al-Shayeb, San Francisco, CA (US)

(73) Assignee: Amber Bio Inc., San Francisco, CA (US)

( * ) Notice: Subject to any disclaimer, the term of this patent is extended or adjusted under 35 U.S.C. 154(b) by 0 days.

(21) Appl. No.: 18/938,195

(22) Filed: Nov. 5, 2024

(65) Prior Publication Data

US 2025/0059543 A1     Feb. 20, 2025

Related U.S. Application Data

(63) Continuation of application No. PCT/US2023/081868, filed on Nov. 30, 2023.

(60) Provisional application No. 63/429,031, filed on Nov. 30, 2022.

(51) Int. Cl.
*C12N 15/113*     (2010.01)
*C12N 15/85*     (2006.01)

(52) U.S. Cl.
CPC ............ *C12N 15/113* (2013.01); *C12N 15/85* (2013.01); *C12N 2310/14* (2013.01); *C12N 2310/531* (2013.01)

(58) Field of Classification Search
CPC ............................ C12N 15/113; C12N 15/111
See application file for complete search history.

(56) References Cited

U.S. PATENT DOCUMENTS

| | | | |
|---|---|---|---|
| 5,173,414 A | 12/1992 | Lebkowski et al. | |
| 5,658,776 A | 8/1997 | Flotte et al. | |
| 5,786,211 A | 7/1998 | Johnson | |
| 5,871,982 A | 2/1999 | Wilson et al. | |
| 5,942,395 A | 8/1999 | Fournier et al. | |
| 6,258,595 B1 | 7/2001 | Gao et al. | |
| 7,399,753 B2 | 7/2008 | Mitchell et al. | |
| 8,053,232 B2 | 11/2011 | Puttaraju et al. | |
| 8,603,457 B2 * | 12/2013 | Yu ........................ | C12N 15/113 514/44 R |
| 8,735,366 B2 | 5/2014 | Bauer et al. | |
| 8,883,753 B2 | 11/2014 | Puttaraju et al. | |
| 9,040,491 B2 | 5/2015 | Dreyfuss et al. | |
| 9,074,207 B2 | 7/2015 | Pagani et al. | |
| 9,669,109 B1 | 6/2017 | Pagani et al. | |
| 10,987,433 B2 | 4/2021 | Bennett et al. | |
| 11,377,646 B2 | 7/2022 | Doudna et al. | |
| 11,530,398 B2 | 12/2022 | Doudna et al. | |
| 11,578,313 B2 | 2/2023 | Doudna et al. | |
| 11,685,909 B2 | 6/2023 | Doudna et al. | |
| 11,739,309 B2 | 8/2023 | Doudna et al. | |

| | | | |
|---|---|---|---|
| 11,767,528 B2 | 9/2023 | Borrajo | |
| 11,946,050 B2 | 4/2024 | Bruno Quinta De Souza Leal | |
| 11,993,776 B2 | 5/2024 | Johnson et al. | |
| 2004/0058344 A1 | 3/2004 | Mitchell et al. | |
| 2006/0134658 A1 | 6/2006 | Garcia-Blanco | |
| 2006/0194317 A1 | 8/2006 | Puttaraju et al. | |
| 2006/0234247 A1 | 10/2006 | Puttaraju et al. | |
| 2011/0212058 A1 | 9/2011 | Lamond et al. | |
| 2013/0059901 A1 | 3/2013 | Bauer et al. | |
| 2014/0186300 A1 | 7/2014 | Yu et al. | |
| 2015/0209448 A1 | 7/2015 | de Boer et al. | |
| 2022/0062437 A1 | 3/2022 | Bennett et al. | |
| 2022/0160898 A1 | 5/2022 | Michalakis et al. | |
| 2022/0213469 A1 | 7/2022 | Blainey et al. | |
| 2022/0243194 A1 | 8/2022 | Wei et al. | |
| 2023/0340469 A1 | 10/2023 | Nelles | |
| 2024/0011026 A1 | 1/2024 | Nelles | |
| 2024/0209366 A1 | 6/2024 | Nelles | |

FOREIGN PATENT DOCUMENTS

| | | |
|---|---|---|
| EP | 1521766 B1 | 11/2012 |
| EP | 2205739 B1 | 7/2014 |
| EP | 2627339 B1 | 5/2015 |
| EP | 2872632 A1 | 5/2015 |
| EP | 2320952 B1 | 5/2016 |
| EP | 3377116 A1 | 9/2018 |
| EP | 3781213 A1 | 2/2021 |
| EP | 3898996 A1 | 10/2021 |
| EP | 4217010 A1 | 8/2023 |
| EP | 4323391 A1 | 2/2024 |
| EP | 4370680 A2 | 5/2024 |
| WO | 95/13392 A1 | 5/1995 |
| WO | 96/17947 A1 | 10/1996 |
| WO | 97/06243 A1 | 2/1997 |
| WO | 97/08298 A1 | 3/1997 |
| WO | 97/09441 A2 | 3/1997 |
| WO | 97/21825 A1 | 6/1997 |

(Continued)

OTHER PUBLICATIONS

Coady et al., 2007, Molecular Therapy, vol. 15, No. 8, p. 1471-1478 (Year: 2007).*
Dooley et al., 2018, Molecular Therapy: Nucleic Acids, vol. 12, p. 294-308 (Year: 2018).*
Jorjani et al., 2016, Nucleic Acids Research, vol. 44, No. 11, p. 5068-5082 (Year: 2016).*
Monjaret et al., 2014, Molecular Therapy, vol. 22, No. 6, p. 1176-1187 (Year: 2014).*
Puttaraju et al., 1999, Nature Biotechnology, vol. 17, p. 246-252 (Year: 1999).*
Wally et al., 2012, Journal of Investigative Dermatology, vol. 132, p. 1959-1966 (Year: 2012).*
Reichow et al., 2007, Nucleic Acids Research, vol. 35, No. 5, p. 1452-1464 (Year: 2007).*

(Continued)

*Primary Examiner* — Soren Harward
*Assistant Examiner* — Jenna L Persons
(74) *Attorney, Agent, or Firm* — Morgan, Lewis & Bockius LLP

(57)     ABSTRACT

The present disclosure provides compositions and methods of use thereof for targeting trans-splicing of a pre-mRNA in a cell.

11 Claims, 22 Drawing Sheets

Specification includes a Sequence Listing.

(56) References Cited

FOREIGN PATENT DOCUMENTS

| WO | 99/11764 A2 | 3/1999 |
|---|---|---|
| WO | 2013151666 A2 | 10/2013 |
| WO | 2020181101 A1 | 9/2020 |
| WO | 2020181102 A1 | 9/2020 |
| WO | 2021034717 A1 | 2/2021 |
| WO | 2021133829 A1 | 7/2021 |
| WO | 2021216512 A1 | 10/2021 |
| WO | 2022055998 A1 | 3/2022 |
| WO | 2022067228 A1 | 3/2022 |
| WO | 2022220968 A1 | 10/2022 |
| WO | 2023039346 A1 | 3/2023 |
| WO | 2023039373 A2 | 3/2023 |
| WO | 2023064895 A1 | 4/2023 |
| WO | 2023130959 A1 | 7/2023 |
| WO | 2023201203 A2 | 10/2023 |
| WO | 2023215761 A1 | 11/2023 |
| WO | 2023220566 A1 | 11/2023 |
| WO | 2023237627 A1 | 12/2023 |
| WO | 2023237638 A1 | 12/2023 |
| WO | 2023250384 A2 | 12/2023 |
| WO | 2024019801 A1 | 1/2024 |
| WO | 2024068898 A1 | 4/2024 |
| WO | 2024102659 A1 | 5/2024 |
| WO | 2024112957 A1 | 5/2024 |
| WO | 2024118946 A1 | 6/2024 |
| WO | 2024124237 A2 | 6/2024 |
| WO | 2024124238 A1 | 6/2024 |

OTHER PUBLICATIONS

Bergeron, Sep. 27, 2022, Nucleic Acids Research, vol. 51, D291-D296; https://bioinfo-scottgroup.med.usherbrooke.ca/snoDB/ (Year: 2022).*

Zakov, et al., "Rich Parameterization Improves RNA Structure Prediction", Journal of Computational Biology, vol. 18, No. 11, pp. 1525-1542 (2011).

Zeng, et al., "Predicting RNA splicing from DNA sequence using Pangolin", Genome Biology, vol. 23, No. 103 (2022).

Zuker, et al., "Mfold web server for nucleic acid folding and hybridization prediction" Mfold web server for nucleic acid folding and hybridization prediction, Nucleic Acids Research, 2003, vol. 31, No. 13, 3406-3415.

Zuker, et al., "Optimal computer folding of lare RNA sequences using thermodynamics and auxiliary Information" Nucleic Acids Research, vol. 9, No. 1 (1981).

Akiyama, et al., "A max-margin training of RNA secondary structure prediction integrated with the thermodynamic model", Journal of Bioinformatics and Computational Biology, vol. 1, No. 6, published Dec. 19, 2018.

Andronescu, et al., "Computational approaches for RNA energy parameter estimation," Bioinformatics, vol. 16, No. 12, pp. 2304-2318 (2010).

Andronescu, et al., "Efficient parameter estimation for RNA secondary structure prediction", Bioinformatics, vol. 23, pp. i19-i28, (2007).

Black, et al., "U2 as well as U1 Small Nuclear Ribonucleoproteins are Involved in Premessenger RNA Splicing", (1985) Cell 42: 737-750.

Bratkovic, et al., "Functional diversity of small nucleolar RNAs", Nucleic Acids Res. Feb. 28, 2020; 48(4): 1627-1651.

Charenton, et al., "Mechanism of 5' splice site transfer for human spliceosome activation", (2019) Science 364:362-367.

Chen, et al., "RNA Secondary Structure Prediction by Learning Unrolled Algorithms", Published as a conference paper at International Conference on Learning Representations (ICLR) (2020) (arXiv:2002.05810).

Cotten, et al., "Specific contacts between mammalian U7 snRNA and histone precursor RNA are indispensable for the in vitro 3' RNA processing reaction", (1988) The EMBO Journal 7:801-808.

Dieci, et al., "Eukaryotic snoRNAs: A paradigm for gene expression flexibility", Elsevier, Genomics 94 (2009) 83-88.

Do, et al., "ONTRAfold: RNA secondary structure prediction without physics-based models", Bioinformatics, vol. 22, No. 14, 2006.

Eddy, et al., "RNA sequence analysis using convariance models", Nucleic Acids Research, 1994, vol. 22, No. 11, 2079-2088.

*Homo sapiens* small nucleolar RNA, H/ACA box 48 (SNORA48), small nucleolar RNA NCBI Reference Sequence: NR_002918.1 (Year: 2020).

Jaganathan, et al., "Predicting Splicing from Primary Sequence with Deep Learning", Cell, vol. 176, No. 3, pp. 535-548 (2019).

Kolossova, et al., "U11 snRNA interacts in vivo with the 5' splice site of U12-dependent (AU-AC) pre-mRNA introns", (1997) RNA 3: 227.

Lasda and Blumenthal, "Trans-splicing", Wiley Interdiscip Rev RNA, vol. 2, No. 3, pp. 417-434 (2011).

Laughlin, et al., "Cloning of infectious adeno-associated virus genomes in bacterial plasmids", Gene, vol. 23, No. 1, pp. 65-73 (1983).

Lebkowski, et al., "Adeno-Associated Virus: a Vector System for Efficient Introduction and Integration of DNA into a Variety of Mammalian Cell Types", Molecular and Cellular Biology. 1988, vol. 8, No. 10, p. 3988-399.

Liu, et al., "Partial correction of endogenous ΔF508 CFTR in human cystic fibrosis airway epithelia by spliceosome-mediated RNA trans-splicing", Nat Biotechnol, vol. 20, pp. 47-52 (2002).

Liu, et al., "Splicing inactivation generates hybrid mRNA-snoRNA transcripts targeted by cytoplasmic RNA decay", RNAS, Jul. 25, 2022. vol. 119, No. 31, pp. 1-9.

Lorenz, et al., "ViennaRNA Package 2.0", Algorithms for Molecular Biology Jun. 2011:26.

Ma, et al., "Pol III Promoters to Express Small RNAs: Delineation of Transcription Initiation", Mol Ther Nucleic Acids, vol. 3, No. 5, e161 (2014).

Mansfield, et al., "Repair of CFTR mRNA by spliceosome-mediated RNA trans-splicing", Gene Therapy (2000) 7, 1885-1895.

Markham & Zuker, "UNAFold Software for Nucleic Acid Folding and Hybridization," Methods Mol Biol, vol. 453, pp. 3-31 (2008).

Matera, et al., "A day in the life of the spliceosome", Nat Rev Mol Cell Biol, vol. 15, pp. 108-121 (2014).

McLaughlin, et al., "Adeno-Associated Virus General Transduction Vectors: Analysis of Proviral Structures", Journal of Virology, (1988) vol. 62, No. 6, p. 1963-1973.

Miyagishi, et al., "U6 promoter—driven siRNAs with four uridine 3' overhangs efficiently suppress targeted gene expression in mammalian cells", Nature Biotechnology, vol. 19 (2022).

Mosig, et al., "To code or not to code? That is the question for RNA in timekeeping", Biochem (Lond) (2020) vol. 42, No. 2: pp. 12-15.

Muzyczka, "Use of Adeno-Associated Virus as a General Transduction Vector for Mammalian Cells", Current Topics in Microbiology and Immunology, vol. 158, 1992.

Nguyen, et al., "The architecture of the spliceosomal U4/U6.U5 tri-snRNP", (2015), Nature 523:47-52.

Ni, et al., "Small Nucleolar RNAs Direct Site-Specific Synthesis of Pseudouridine in Ribosomal RNA", Cell. May 16, 1997;89(4):565-71.

Paul, et al., "Increased Viral Titer Through Concentration of Viral Harvests from Retroviral Packaging Lines", Human Gene Therapy 4:609-615 (1993).

Reuter, et al., "RNAstructure: software for RNA secondary structure prediction and analysis", Reuter and Mathews BMC Bioinformatics Nov. 2010:129.

Rindt, et al., "Replacement of huntingtin exon 1 by trans-splicing", Cell. Mol. Life Sci. (2012) 69:4191-4204.

Rivas, et al., "A range of complex probabilistic models for RNA secondary structure prediction that includes the nearest-neighbor model and more," RNA, vol. 18, No. 2: pp. 193-212 (2025).

Roithova, et al., "The Sm-core mediates the retention of partially-assembled spliceosomal snRNPs in Cajal bodies until their full maturation", Nucleic Acids Research, 2018, vol. 46, No. 7, 3774-3790.

(56)            References Cited

OTHER PUBLICATIONS

Rossi, et al., "Involvement of U1 Small Nuclear Ribonucleoproteins (snRNP) in 5* Splice Site-U1 snRNP Interaction", vol. 271, No. 39, Issue of Sep. 27, pp. 23985-23991, 1996.

Samulski, et al., "Cloning of adeno-associated virus into pBR322: Rescue of intact virus from the recombinant plasmid in human cells", Proc. Natt Acad. Sci. USA vol. 79, pp. 2077-2081, Mar. 1982, Microbiology.

Samulski, et al., "Helper-Free Stocks of Recombinant Adeno-Associated Viruses: Normal Integration Does Not Require Viral Gene Expression", Journal of Virology, (1989) pp. 3822-3828.

Schroeder, et al., "Optical Melting Measurements of Nucleic Acid Thermodynamics", Methods Enzymol. (2009) 468:371-387.

Semple, et al., "Rational design of cationic lipids for siRNA delivery", Nature Biotechnology, vol. 28, pp. 172-176 (2010).

Senapathy, et al., "Replication of Adeno-associated virus DNA", J. Mol. Kiol. (1984) 178, 179, 1-20.

Singh, et al., "RNA secondary structure prediction using an ensemble of two-dimensional deep neural networks and transfer learning", Nature Communications, vol. 10, No. 5407 (2019).

Soldati, et al., "Structural and Functional Characterization of Mouse U7 Small Nuclear RNA Active in 3' Processing of Histone Pre-mRNA", (1988), Molecular and Cellular Biology 8:1518-1524.

Strub, et al., "The cDNA sequences of the sea urchin U7 small nuclear RNAsuggest specific contacts between histone mRNA precursor andU7 RNA during RNA processing", (1984) EMBO journal 3:2801-2807.

The RNAcentral Consortium "RNAcentral: a comprehensive database of non-coding RNA sequences," Nucleic Acids Research, vol. 45, No. D1, pp. D128-D134 (2016).

Tratschin, et al., "A Human Parvovirus, Adeno-Associated Virus, as a Eucaryotic Vector: Transient Expression and Encapsidation of the Procaryotic Gene for Chloramphenicol Acetyltransferase", Molecular and Cellular Biology, Oct. 1984, p. 2072-2081.

Turner, et al., "NNDB: the nearest neighbor parameter database for predicting stability of nucleic acid secondary structure", Nucleic Acids Research, 2010, vol. 38, D280-D282.

Turunen, et al., "HnRNPH1/H2, U1 snRNP, and U11 snRNP cooperate to regulate the stability of the U11-48K pre-mRNA", (2013) RNA 4:61-76.

Wilkinson, et al., "RNA Splicing by the Spliceosome", Annual Review of Biochemistry, vol. 89, pp. 359-388 (2020).

Xia, et al., "An enhanced U6 promoter for synthesis of short hairpin RNA", Nucleic Acids Research, 2003, vol. 31, No. 17 e100.

Hirose, et al., "Splicing-Dependent and -Independent Modes of Assembly for Intron-Encoded Box C/D snoRNPs in Mammalian Cells," Molecular Cell, vol. 12, pp. 113-123, Jul. 2003.

Wang, et al. "The m6A Consensus Motif Provides a Paradigm of Epitranscriptomic Studies," Biochemistry 2021, 60, 3410-3412.

* cited by examiner cis-splicing trans-splicing

U1-based splice editor (U1-SE) examples

SEQ ID NO: 696

SEQ ID NO: 697

SEQ ID NO: 698 folded RNA

U1-SE schematic

U1-SE / target RNA-RNA interactions

U11-based splice editor (U11-SE)

SEQ ID NO: 699 binding domain     U11 snRNA (ncRNA)     intron     exon

SEQ ID NO: 700 binding domain     U11 snRNA (ncRNA)     intron     exon

SEQ ID NO: 701 binding domain     U11 snRNA (ncRNA)     intron     exon folded RNA

U11 snRNA (ncRNA)

intron binding domain

SA exon

U11-SE schematic

U11-SE / target RNA-RNA interactions

U7-based splice editor (U7-SE) examples

SEQ ID NO: 702

SEQ ID NO: 703

SEQ ID NO: 704

SEQ ID NO: 705

U7-SE schematic

U7-SE / target RNA-RNA interactions

Sm-based splice editor (Sm-SE) examples
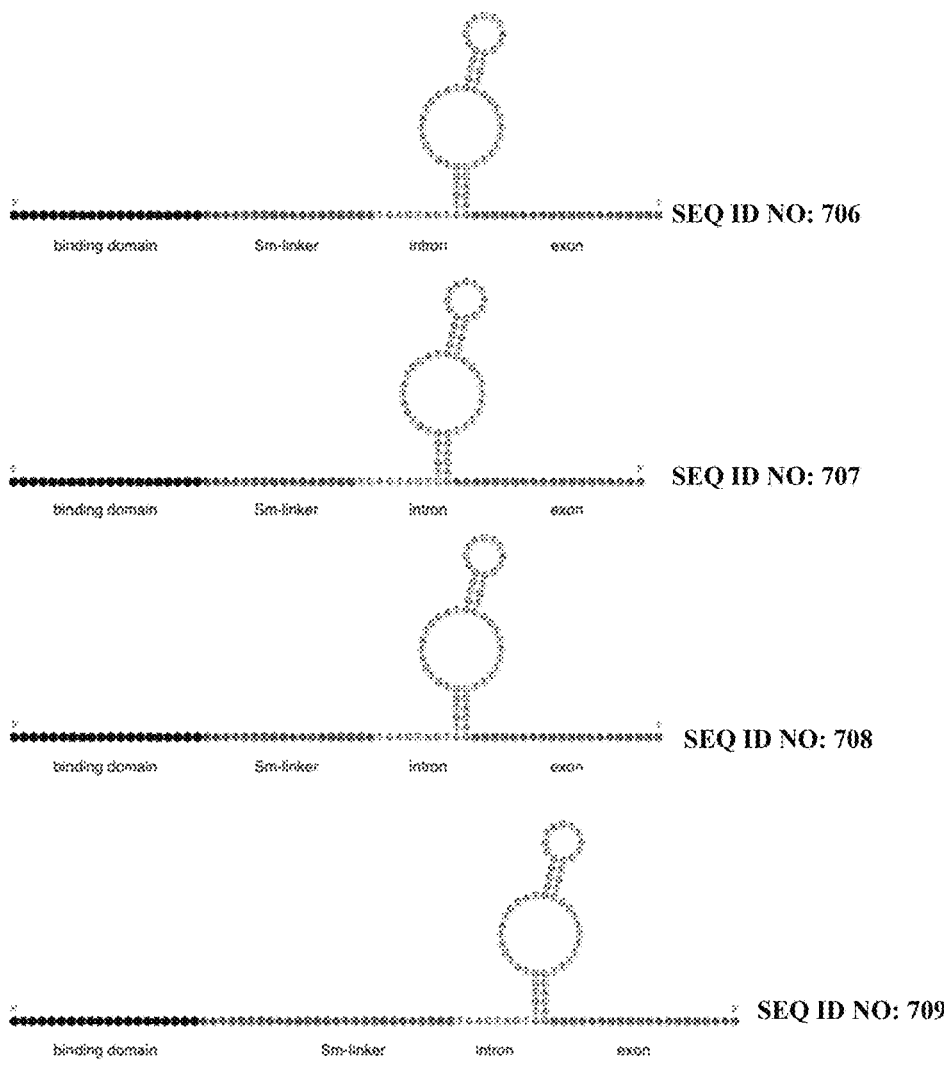
SEQ ID NO: 706
binding domain      Sm-linker      intron      exon
SEQ ID NO: 707
binding domain      Sm-linker      intron      exon
SEQ ID NO: 708
binding domain      Sm-linker      intron      exon
SEQ ID NO: 709
binding domain      Sm-linker      intron      exon
FIG. 5A
folded RNA
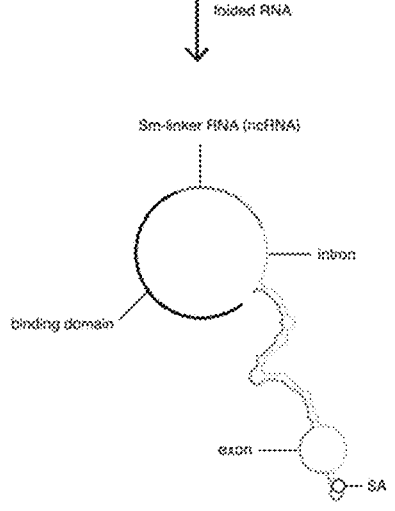
Sm-linker RNA (ncRNA)
intron
binding domain
exon
SA Sm-SE schematic Sm-SE / target RNA-RNA interactions engineered snoRNA (esnoRNA)-based splice editor (esnoRNA-SE) examples
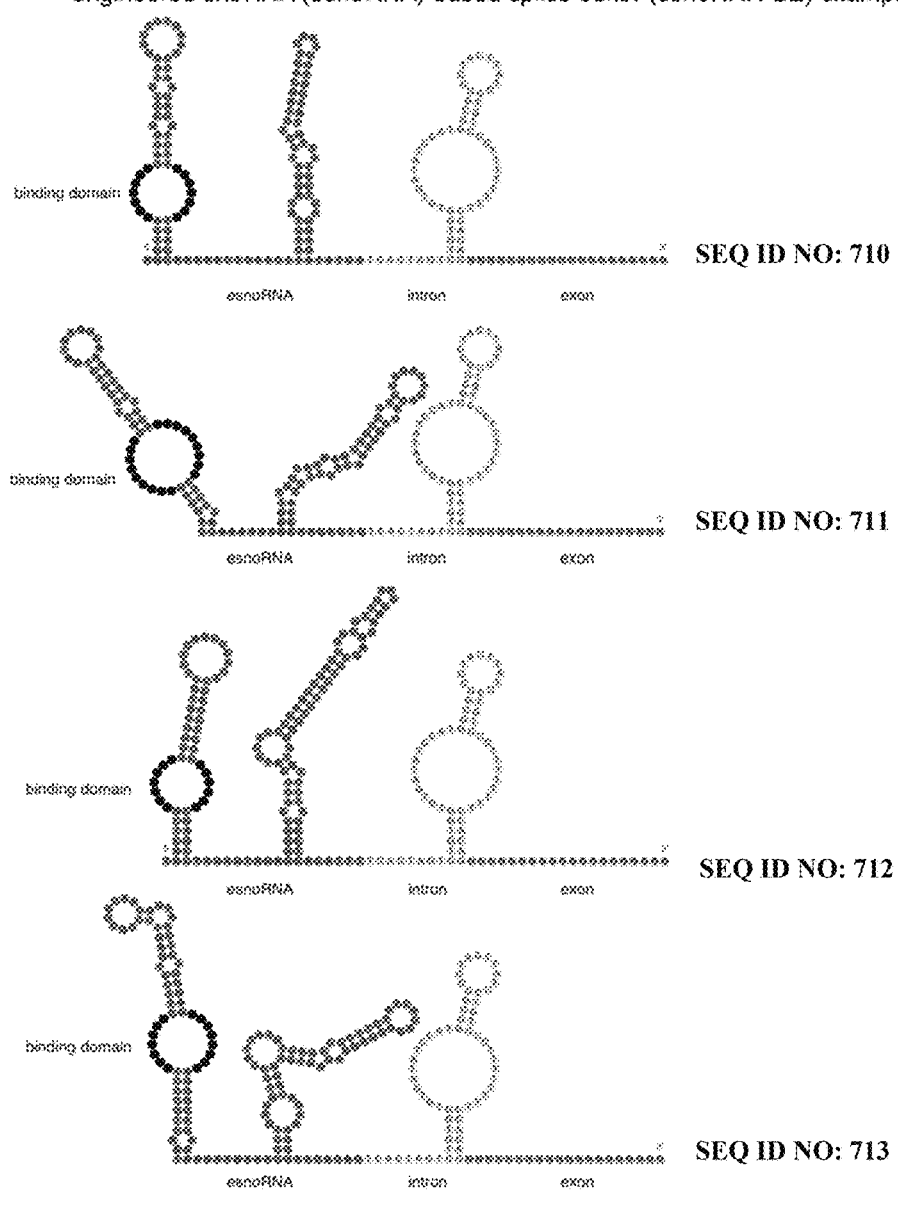
SEQ ID NO: 710
SEQ ID NO: 711
SEQ ID NO: 712
FIG. 6A
SEQ ID NO: 713
folded RNA
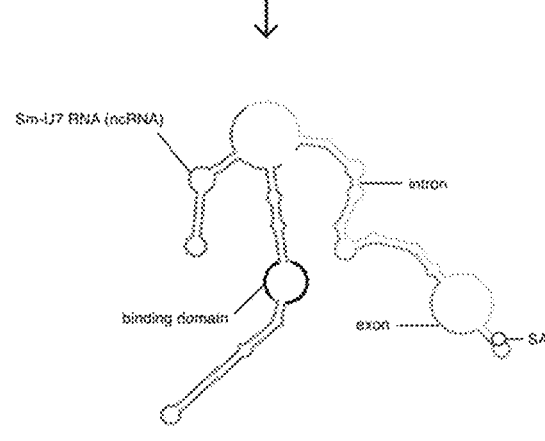

FIG. 6B    esnoRNA-SE schematic
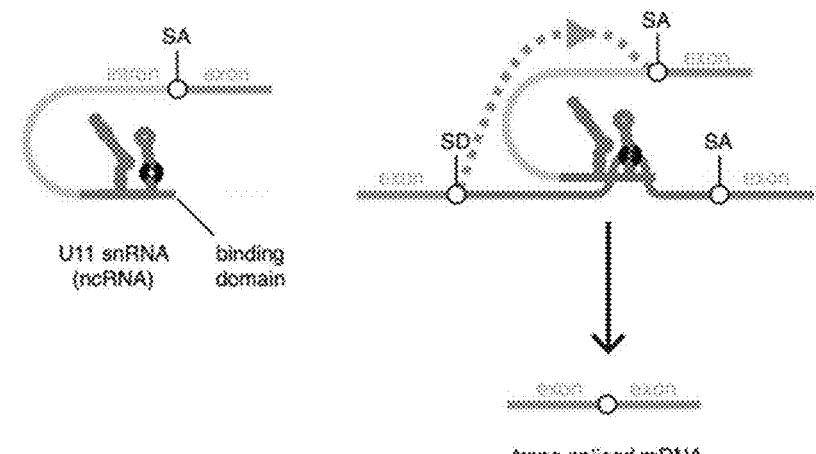
FIG. 6C    esnoRNA-SE / target RNA-RNA interactions
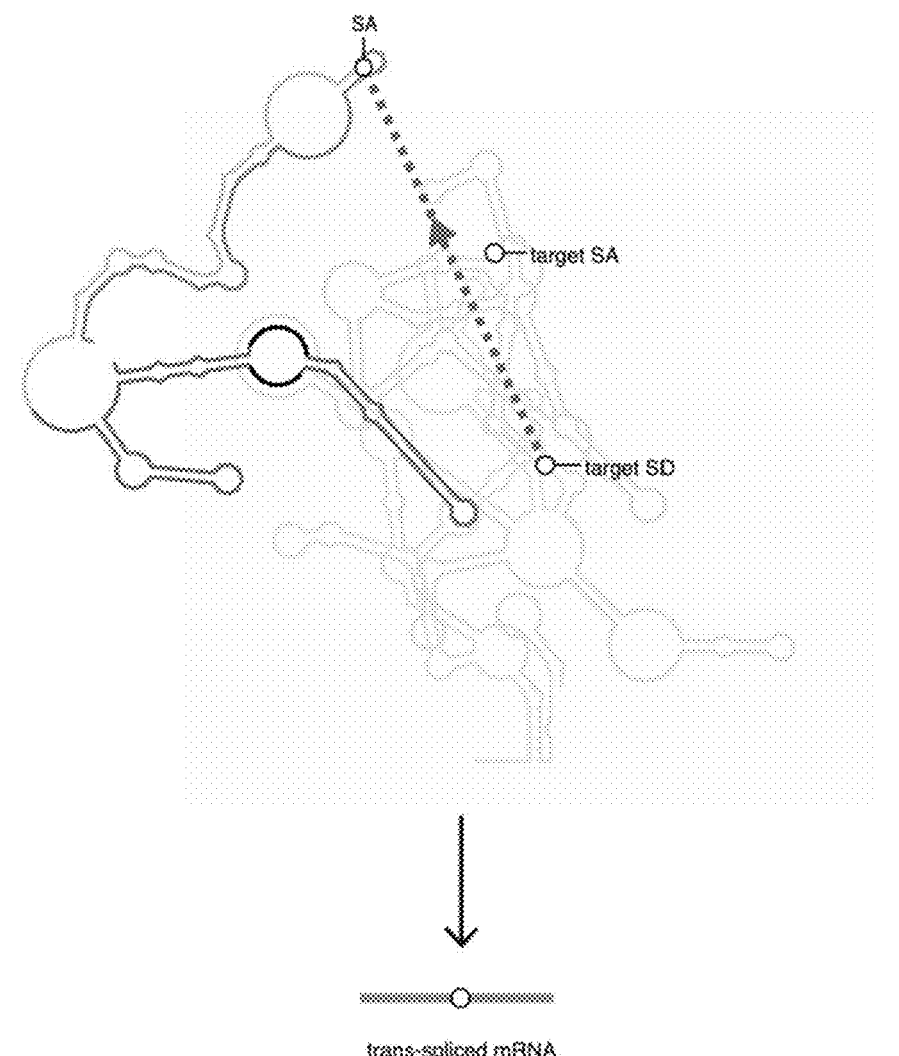

SEQUENCE LISTING

Sequence total quantity: 713

SEQ ID NO: 1          moltype =    length =
SEQUENCE: 1
000

SEQ ID NO: 2          moltype =    length =
SEQUENCE: 2
000

SEQ ID NO: 3          moltype =    length =
SEQUENCE: 3
000

SEQ ID NO: 4          moltype =    length =
SEQUENCE: 4
000

SEQ ID NO: 5          moltype =    length =
SEQUENCE: 5
000

SEQ ID NO: 6          moltype =    length =
SEQUENCE: 6
000

SEQ ID NO: 7          moltype =    length =
SEQUENCE: 7
000

SEQ ID NO: 8          moltype =    length =
SEQUENCE: 8

-continued

000

```
SEQ ID NO: 9              moltype = RNA   length = 154
FEATURE                  Location/Qualifiers
source                   1..154
                         mol_type = other RNA
                         organism = synthetic construct
SEQUENCE: 9
atacttacgt aacaggagaa aatacggcca tgaagttggt gtttctcggg ggcgatttct   60
ccattgtact cagtatgtgc tgactgactc ctgttacttc cacatgtggg gaaactggac  120
tgtaatttgt ggtggtgggg aattgcgttc gcgc                              154

SEQ ID NO: 10             moltype = RNA   length = 154
FEATURE                  Location/Qualifiers
source                   1..154
                         mol_type = other RNA
                         organism = synthetic construct
SEQUENCE: 10
tacttacgta acaggagaaa atacggccat gaagttggtg tttctcgggg gcgatttctc   60
cattgtactc agtatgtgct gactgactcc tgttacttcc acatgtgggg aaactggact  120
gtaatttgtg gtggtgggga attgcgttcg cgct                              154

SEQ ID NO: 11             moltype = RNA   length = 154
FEATURE                  Location/Qualifiers
source                   1..154
                         mol_type = other RNA
                         organism = synthetic construct
SEQUENCE: 11
acttacgtaa caggagaaaa tacggccatg aagttggtgt tctcgggggg cgatttctcc   60
attgtactca gtatgtgctg actgactcct gttacttcca catgtgggga aactggactg  120
taatttgtgg tggtggggaa ttgcgttcgc gctt                              154

SEQ ID NO: 12             moltype = RNA   length = 154
FEATURE                  Location/Qualifiers
source                   1..154
                         mol_type = other RNA
                         organism = synthetic construct
SEQUENCE: 12
cttacgtaac aggagaaaat acggccatga agttggtgtt tctcgggggc gatttctcca   60
ttgtactcag tatgtgctga ctgactcctg ttacttccac atgtggggaa actggactgt  120
aatttgtggt ggtggggaat tgcgttcgcg cttt                              154

SEQ ID NO: 13             moltype = RNA   length = 154
FEATURE                  Location/Qualifiers
source                   1..154
                         mol_type = other RNA
                         organism = synthetic construct
SEQUENCE: 13
ttacgtaaca ggagaaaata cggccatgaa gttggtgttt ctcgggggcg atttctccat   60
tgtactcagt atgtgctgac tgactcctgt tacttccaca tgtggggaaa ctggactgta  120
atttgtggtg gtggggaatt gcgttcgcgc tttc                              154

SEQ ID NO: 14             moltype = RNA   length = 154
FEATURE                  Location/Qualifiers
source                   1..154
                         mol_type = other RNA
                         organism = synthetic construct
SEQUENCE: 14
tacgtaacag gagaaaatac ggccatgaag ttggtgtttc tcgggggcga tttctccatt   60
gtactcagta tgtgctgact gactcctgtt acttccacat gtgggaaac tggactgtaa   120
tttgtggtgg tggggaattg cgttcgcgct ttct                              154

SEQ ID NO: 15             moltype = RNA   length = 154
FEATURE                  Location/Qualifiers
source                   1..154
                         mol_type = other RNA
                         organism = synthetic construct
SEQUENCE: 15
acgtaacagg agaaaatacg gccatgaagt tggtgtttct cgggggcgat tctccattg   60
tactcagtat gtgctgactg actcctgtta cttccacatg tgggaaact ggactgtaat   120
ttgtggtggt ggggaattgc gttcgcgctt tctt                              154

SEQ ID NO: 16             moltype = RNA   length = 154
FEATURE                  Location/Qualifiers
source                   1..154
                         mol_type = other RNA
                         organism = synthetic construct
SEQUENCE: 16
cgtaacagga gaaaatacgg ccatgaagtt ggtgtttctc ggggcgatt tctccattgt   60
```

-continued

```
actcagtatg tgctgactga ctcctgttac ttccacatgt ggggaaactg gactgtaatt   120
tgtggtggtg gggaattgcg ttcgcgcttt cttc                               154

SEQ ID NO: 17            moltype = RNA   length = 154
FEATURE                  Location/Qualifiers
source                   1..154
                         mol_type = other RNA
                         organism = synthetic construct
SEQUENCE: 17
gtaacaggag aaaatacggc catgaagttg gtgtttctcg ggggcgattt ctccattgta   60
ctcagtatgt gctgactgac tcctgttact tccacatgtg gggaaactgg actgtaatttt  120
gtggtggtgg ggaattgcgt tcgcgctttc ttct                              154

SEQ ID NO: 18            moltype = RNA   length = 153
FEATURE                  Location/Qualifiers
source                   1..153
                         mol_type = other RNA
                         organism = synthetic construct
SEQUENCE: 18
taacaggaga aaatacggcc atgaagttgg tgtttctcgg gggcgatttc tccattgtac   60
tcagtatgt ctgactgact cctgttactt ccacatgtgg ggaaactgga ctgtaatttg    120
tggtggtggg gaattgcgtt cgcgcttct tct                                153

SEQ ID NO: 19            moltype = RNA   length = 154
FEATURE                  Location/Qualifiers
source                   1..154
                         mol_type = other RNA
                         organism = synthetic construct
SEQUENCE: 19
atatttactt ggcaggggag ataacgtgac cacgaaggtg gttttcccag ggctgaggct   60
tattcattgt actccggatg tgctgacccc tgcgatttcc ccaaatgtgg gaaactcgac   120
tgcataattt gtggtagtgg ggggctgtgt ccgt                              154

SEQ ID NO: 20            moltype = RNA   length = 154
FEATURE                  Location/Qualifiers
source                   1..154
                         mol_type = other RNA
                         organism = synthetic construct
SEQUENCE: 20
tatttacttg gcaggggaga taacgtgacc acgaaggtgg ttttcccagg gctgaggctt   60
attcattgta ctccggatgt gctgacccct gcgatttccc caaatgtggg aaactcgact   120
gcataatttg tggtagtggg gggctgtgtc cgtg                              154

SEQ ID NO: 21            moltype = RNA   length = 154
FEATURE                  Location/Qualifiers
source                   1..154
                         mol_type = other RNA
                         organism = synthetic construct
SEQUENCE: 21
atttacttgg caggggagat aacgtgacca cgaaggtggt tttcccaggg ctgaggctta   60
ttcattgtac tccggatgtg ctgacccctg cgatttcccc aaatgtggga aactcgactg   120
cataatttgt ggtagtgggg ggctgtgtcc gtgc                              154

SEQ ID NO: 22            moltype = RNA   length = 154
FEATURE                  Location/Qualifiers
source                   1..154
                         mol_type = other RNA
                         organism = synthetic construct
SEQUENCE: 22
tttacttggc aggggagata acgtgaccac gaaggtggtt tcccagggc tgaggcttat    60
tcattgtact ccggatgtgc tgacccctgc gatttcccca aatgtgggaa actcgactgc   120
ataatttgtg gtagtggggg gctgtgtccg tgct                              154

SEQ ID NO: 23            moltype = RNA   length = 154
FEATURE                  Location/Qualifiers
source                   1..154
                         mol_type = other RNA
                         organism = synthetic construct
SEQUENCE: 23
ttacttggca ggggagataa cgtgaccacg aaggtggttt tcccagggct gaggcttatt   60
cattgtactc cggatgtgct gacccctgcg atttccccaa atgtgggaaa ctcgactgca   120
taatttgtgg tagtggggg ctgtgtccgt gctt                               154

SEQ ID NO: 24            moltype = RNA   length = 154
FEATURE                  Location/Qualifiers
source                   1..154
                         mol_type = other RNA
                         organism = synthetic construct
SEQUENCE: 24
```

-continued

```
tacttggcag gggagataac gtgaccacga aggtggtttt cccagggctg aggcttattc   60
attgtactcc ggatgtgctg acccctgcga tttccccaaa tgtgggaaac tcgactgcat   120
aatttgtggt agtgggggggc tgtgtccgtg cttt                                154

SEQ ID NO: 25            moltype = RNA   length = 154
FEATURE                  Location/Qualifiers
source                   1..154
                         mol_type = other RNA
                         organism = synthetic construct
SEQUENCE: 25
acttggcagg ggagataacg tgaccacgaa ggtggttttc ccagggctga ggcttattca   60
ttgtactccg gatgtgctga cccctgcgat ttccccaaat gtgggaaact cgactgcata   120
atttgtggta gtgggggggct gtgtccgtgc tttt                                154

SEQ ID NO: 26            moltype = RNA   length = 154
FEATURE                  Location/Qualifiers
source                   1..154
                         mol_type = other RNA
                         organism = synthetic construct
SEQUENCE: 26
cttggcaggg gagataacgt gaccacgaag gtggttttcc cagggctgag gcttattcat   60
tgtactccgg atgtgctgac ccctgcgatt tccccaaatg tgggaaactc gactgcataa   120
tttgtggtag tggggggctg tgtccgtgct tttc                                154

SEQ ID NO: 27            moltype = RNA   length = 154
FEATURE                  Location/Qualifiers
source                   1..154
                         mol_type = other RNA
                         organism = synthetic construct
SEQUENCE: 27
ttggcagggg agataacgtg accacgaagg tggttttccc agggctgagg cttattcatt   60
gtactccgga tgtgctgacc cctgcgattt ccccaaatgt gggaaactcg actgcataat   120
ttgtggtagt ggggggctgt gtccgtgctt ttcc                                154

SEQ ID NO: 28            moltype = RNA   length = 154
FEATURE                  Location/Qualifiers
source                   1..154
                         mol_type = other RNA
                         organism = synthetic construct
SEQUENCE: 28
tggcagggga gataacgtga ccacgaaggt ggttttccca gggctgaggc ttattcattg   60
tactccggat gtgctgaccc ctgcgatttc cccaaatgtg ggaaactcga ctgcataatt   120
tgtggtagtg ggggctgtg tccgtgcttt tccc                                154

SEQ ID NO: 29            moltype = RNA   length = 154
FEATURE                  Location/Qualifiers
source                   1..154
                         mol_type = other RNA
                         organism = synthetic construct
SEQUENCE: 29
atacttacct ggcagggcag ataccatgat cttaaaggca gttttcccag ggcaaggctt   60
atccattcca ctctggatcc attatagggg catgctgatc cctggaattg ccccaaatgt   120
gggaagctct actgcaaaat ttttggtagt gagc                                154

SEQ ID NO: 30            moltype = RNA   length = 154
FEATURE                  Location/Qualifiers
source                   1..154
                         mol_type = other RNA
                         organism = synthetic construct
SEQUENCE: 30
tacttacctg gcagggcaga taccatgatc ttaaaggcag ttttcccagg gcaaggctta   60
tccattccac tctggatcca ttataggggc atgctgatcc ctggaattgc cccaaatgtg   120
ggaagctcta ctgcaaaatt tttggtagtg agcg                                154

SEQ ID NO: 31            moltype = RNA   length = 154
FEATURE                  Location/Qualifiers
source                   1..154
                         mol_type = other RNA
                         organism = synthetic construct
SEQUENCE: 31
acttacctgg cagggcagat accatgatct aaaggcagt tttcccaggg caaggcttat   60
ccattccact ctggatccat tatagggca tgctgatccc tggaattgcc ccaaatgtgg   120
gaagctctac tgcaaaattt ttggtagtga gcga                                154

SEQ ID NO: 32            moltype = RNA   length = 154
FEATURE                  Location/Qualifiers
source                   1..154
                         mol_type = other RNA
                         organism = synthetic construct
```

```
SEQUENCE: 32
cttacctggc agggcagata ccatgatctt aaaggcagtt ttcccagggc aaggcttatc    60
cattccactc tggatccatt atagggggcat gctgatccct ggaattgccc caaatgtggg   120
aagctctact gcaaaatttt tggtagtgag cgat                                154

SEQ ID NO: 33           moltype = RNA   length = 154
FEATURE                 Location/Qualifiers
source                  1..154
                        mol_type = other RNA
                        organism = synthetic construct
SEQUENCE: 33
ttacctggca gggcagatac catgatctta aaggcagttt tcccagggca aggcttatcc    60
attccactct ggatccatta taggggcatg ctgatccctg gaattgcccc aaatgtggga   120
agctctactg caaaattttt ggtagtgagc gatg                                154

SEQ ID NO: 34           moltype = RNA   length = 154
FEATURE                 Location/Qualifiers
source                  1..154
                        mol_type = other RNA
                        organism = synthetic construct
SEQUENCE: 34
tacctggcag ggcagatacc atgatcttaa aggcagtttt cccagggcaa ggcttatcca    60
ttccactctg gatccattat aggggcatgc tgatccctgg aattgcccca aatgtgggaa   120
gctctactgc aaaatttttg gtagtgagcg atgg                                154

SEQ ID NO: 35           moltype = RNA   length = 154
FEATURE                 Location/Qualifiers
source                  1..154
                        mol_type = other RNA
                        organism = synthetic construct
SEQUENCE: 35
acctggcagg gcagatacca tgatcttaaa ggcagttttc ccagggcaag gcttatccat    60
tccactctgg atccattata ggggcatgct gatccctgga attgccccaa atgtgggaag   120
ctctactgca aaattttggg tagtgagcga tggc                                154

SEQ ID NO: 36           moltype = RNA   length = 154
FEATURE                 Location/Qualifiers
source                  1..154
                        mol_type = other RNA
                        organism = synthetic construct
SEQUENCE: 36
cctggcaggg cagataccat gatcttaaag gcagttttcc cagggcaagg cttatccatt    60
ccactctgga tccattatag gggcatgctg atccctggaa ttgccccaaa tgtgggaagc   120
tctactgcaa aattttttggt agtgagcgat ggca                               154

SEQ ID NO: 37           moltype = RNA   length = 154
FEATURE                 Location/Qualifiers
source                  1..154
                        mol_type = other RNA
                        organism = synthetic construct
SEQUENCE: 37
ctggcagggc agataccatg atcttaaagg cagttttccc agggcaaggc ttatccattc    60
cactctggat ccattatagg ggcatgctga tccctggaat tgccccaaat gtgggaagct   120
ctactgcaaa attttttggta gtgagcgatg gcat                               154

SEQ ID NO: 38           moltype = RNA   length = 154
FEATURE                 Location/Qualifiers
source                  1..154
                        mol_type = other RNA
                        organism = synthetic construct
SEQUENCE: 38
tggcagggca gataccatga tcttaaaggc agttttccca gggcaaggct tatccattcc    60
actctggatc cattataggg gcatgctgat ccctggaatt gccccaaatg tgggaagctc   120
tactgcaaaa ttttttggtag tgagcgatgg catt                               154

SEQ ID NO: 39           moltype = RNA   length = 154
FEATURE                 Location/Qualifiers
source                  1..154
                        mol_type = other RNA
                        organism = synthetic construct
SEQUENCE: 39
atacttacct ggcaggggag ataccatgat cacgaaggtg ttttcccag ggcgaggctt     60
atccattgca ctccggatgt gctgacccct gcgatttccc caaatgtggg aaactcgact   120
gcataatttg tggtagtggg ggactgcgtt cgcg                                154

SEQ ID NO: 40           moltype = RNA   length = 154
FEATURE                 Location/Qualifiers
source                  1..154
                        mol_type = other RNA
```

-continued

```
                               organism = synthetic construct
SEQUENCE: 40
tacttacctg gcaggggaga taccatgatc acgaaggtgg ttttcccagg gcgaggctta    60
tccattgcac tccggatgtg ctgacccctg cgatttcccc aaatgtggga aactcgactg   120
cataatttgt ggtagtgggg gactgcgttc gcgc                               154

SEQ ID NO: 41           moltype = RNA   length = 154
FEATURE                 Location/Qualifiers
source                  1..154
                        mol_type = other RNA
                        organism = synthetic construct
SEQUENCE: 41
acttacctgg caggggagat accatgatca cgaaggtggt tttcccaggg cgaggcttat    60
ccattgcact ccggatgtgc tgacccctgc gatttcccca aatgtgggaa actcgactgc   120
ataatttgtg gtagtggggg actgcgttcg cgct                               154

SEQ ID NO: 42           moltype = RNA   length = 154
FEATURE                 Location/Qualifiers
source                  1..154
                        mol_type = other RNA
                        organism = synthetic construct
SEQUENCE: 42
cttacctggc agggagata ccatgatcac gaaggtggtt ttcccagggc gaggcttatc    60
cattgcactc cggatgtgct gaccctgcg atttccccaa atgtgggaaa ctcgactgca   120
taatttgtgg tagtggggga ctgcgttcgc gctt                               154

SEQ ID NO: 43           moltype = RNA   length = 154
FEATURE                 Location/Qualifiers
source                  1..154
                        mol_type = other RNA
                        organism = synthetic construct
SEQUENCE: 43
ttacctggca ggggagatac catgatcacg aaggtggttt tcccagggcg aggcttatcc    60
attgcactcc ggatgtgctg acccctgcga tttccccaaa tgtgggaaac tcgactgcat   120
aatttgtggt agtgggggac tgcgttcgcg cttt                               154

SEQ ID NO: 44           moltype = RNA   length = 154
FEATURE                 Location/Qualifiers
source                  1..154
                        mol_type = other RNA
                        organism = synthetic construct
SEQUENCE: 44
tacctggcag gggagatacc atgatcacga aggtggtttt cccagggcga ggcttatcca    60
ttgcactccg gatgtgctga cccctgcgat tccccaaat gtgggaaact cgactgcata   120
atttgtggta gtgggggact gcgttcgcgc tttc                               154

SEQ ID NO: 45           moltype = RNA   length = 154
FEATURE                 Location/Qualifiers
source                  1..154
                        mol_type = other RNA
                        organism = synthetic construct
SEQUENCE: 45
acctggcagg ggagatacca tgatcacgaa ggtggttttc caggggcgag gcttatccat    60
tgcactccgg atgtgctgac ccctgcgatt tccccaaatg tgggaaactc gactgcataa   120
tttgtggtag tgggggactg cgttcgcgct ttcc                               154

SEQ ID NO: 46           moltype = RNA   length = 154
FEATURE                 Location/Qualifiers
source                  1..154
                        mol_type = other RNA
                        organism = synthetic construct
SEQUENCE: 46
cctggcaggg gagataccat gatcacgaag gtggttttcc cagggcgagg cttatccatt    60
gcactccgga tgtgctgacc cctgcgattt ccccaaatgt gggaaactcg actgcataat   120
ttgtggtagt gggggactgc gttcgcgctt tccc                               154

SEQ ID NO: 47           moltype = RNA   length = 154
FEATURE                 Location/Qualifiers
source                  1..154
                        mol_type = other RNA
                        organism = synthetic construct
SEQUENCE: 47
ctggcagggg agataccatg atcacgaagg tggttttccc agggcgaggc ttatccattg    60
cactccggat gtgctgaccc ctgcgatttc cccaaatgtg ggaaactcga ctgcataatt   120
tgtggtagtg ggggactgcg ttcgcgcttt cccc                               154

SEQ ID NO: 48           moltype = RNA   length = 154
FEATURE                 Location/Qualifiers
source                  1..154
```

-continued

```
                             mol_type = other RNA
                             organism = synthetic construct
SEQUENCE: 48
tggcagggga gataccatga tcacgaaggt ggttttccca gggcgaggct tatccattgc   60
actccggatg tgctgacccc tgcgatttcc ccaaatgtgg gaaactcgac tgcataattt  120
gtggtagtgg gggactgcgt tcgcgctttc ccct                              154

SEQ ID NO: 49          moltype = RNA   length = 154
FEATURE                Location/Qualifiers
source                 1..154
                       mol_type = other RNA
                       organism = synthetic construct
SEQUENCE: 49
atacttccct gacaggggag atacctagga atccaacttc ccagggcaag actgatctat   60
tgcactatgg atgtgccgac ccctgagatt tacaaaattg tgggaaactc aactgcataa  120
tttatggaaa tgaaggactg tgtttgcgct ttca                              154

SEQ ID NO: 50          moltype = RNA   length = 153
FEATURE                Location/Qualifiers
source                 1..153
                       mol_type = other RNA
                       organism = synthetic construct
SEQUENCE: 50
tacttccctg acaggggaga tacctaggaa tccaacttcc cagggcaaga ctgatctatt   60
gcactatgga tgtgccgacc cctgagattt acaaaattgt gggaaactca actgcataat  120
ttatggaaat gaaggactgt gtttgcgctt tca                               153

SEQ ID NO: 51          moltype = RNA   length = 152
FEATURE                Location/Qualifiers
source                 1..152
                       mol_type = other RNA
                       organism = synthetic construct
SEQUENCE: 51
acttccctga caggggagat acctaggaat ccaacttccc agggcaagac tgatctattg   60
cactatggat gtgccgaccc ctgagattta caaaattgtg ggaaactcaa ctgcataatt  120
tatggaaatg aaggactgtg tttgcgcttt ca                                152

SEQ ID NO: 52          moltype = RNA   length = 151
FEATURE                Location/Qualifiers
source                 1..151
                       mol_type = other RNA
                       organism = synthetic construct
SEQUENCE: 52
cttccctgac aggggagata cctaggaatc caacttccca gggcaagact gatctattgc   60
actatggatg tgccgacccc tgagatttac aaaattgtgg gaaactcaac tgcataattt  120
atggaaatga aggactgtgt ttgcgctttc a                                 151

SEQ ID NO: 53          moltype = RNA   length = 150
FEATURE                Location/Qualifiers
source                 1..150
                       mol_type = other RNA
                       organism = synthetic construct
SEQUENCE: 53
ttccctgaca ggggagatac ctaggaatcc aacttcccag gcaagactg atctattgca    60
ctatggatgt gccgacccct gagatttaca aaattgtggg aaactcaact gcataattta  120
tggaaatgaa ggactgtgtt tgcgctttca                                   150

SEQ ID NO: 54          moltype = RNA   length = 149
FEATURE                Location/Qualifiers
source                 1..149
                       mol_type = other RNA
                       organism = synthetic construct
SEQUENCE: 54
tccctgacag gggagatacc taggaatcca acttcccagg caagactga tctattgcac    60
tatggatgtg ccgacccctg agatttacaa aattgtggga aactcaactg cataatttat  120
ggaaatgaag gactgtgttt gcgctttca                                    149

SEQ ID NO: 55          moltype = RNA   length = 148
FEATURE                Location/Qualifiers
source                 1..148
                       mol_type = other RNA
                       organism = synthetic construct
SEQUENCE: 55
ccctgacagg ggagatacct aggaatccaa cttcccaggg caagactgat ctattgcact   60
atggatgtgc cgacccctga gatttacaaa attgtgggaa actcaactgc ataatttatg  120
gaaatgaagg actgtgtttg cgctttca                                     148

SEQ ID NO: 56          moltype = RNA   length = 147
FEATURE                Location/Qualifiers
```

-continued

```
source                    1..147
                          mol_type = other RNA
                          organism = synthetic construct
SEQUENCE: 56
cctgacaggg gagataccta ggaatccaac ttcccagggc aagactgatc tattgcacta   60
tggatgtgcc gacccctgag atttacaaaa ttgtgggaaa ctcaactgca taatttatgg   120
aaatgaagga ctgtgtttgc gctttca                                       147

SEQ ID NO: 57          moltype = RNA   length = 146
FEATURE                Location/Qualifiers
source                 1..146
                       mol_type = other RNA
                       organism = synthetic construct
SEQUENCE: 57
ctgacagggg agatacctag gaatccaact tcccagggca agactgatct attgcactat   60
ggatgtgccg acccctgaga tttacaaaat gtgggaaac tcaactgcat aatttatgga    120
aatgaaggac tgtgtttgcg ctttca                                        146

SEQ ID NO: 58          moltype = RNA   length = 145
FEATURE                Location/Qualifiers
source                 1..145
                       mol_type = other RNA
                       organism = synthetic construct
SEQUENCE: 58
tgacagggga gatacctagg aatccaactt cccagggcaa gactgatcta ttgcactatg   60
gatgtgccga ccctgagat ttacaaaatt gtgggaaact caactgcata atttatgaa     120
atgaaggact gtgtttgcgc tttca                                         145

SEQ ID NO: 59          moltype = RNA   length = 154
FEATURE                Location/Qualifiers
source                 1..154
                       mol_type = other RNA
                       organism = synthetic construct
SEQUENCE: 59
aaacttctct gccaggggag ataccatgat cacaaaggtg gctttctcag ggaaaggctg   60
atttattgca ctccagatgt gctgacccct gagatttctc caaatgtggg aaactcagct   120
gcataatttg tggaagcgaa ggactgtgtt tgtg                               154

SEQ ID NO: 60          moltype = RNA   length = 154
FEATURE                Location/Qualifiers
source                 1..154
                       mol_type = other RNA
                       organism = synthetic construct
SEQUENCE: 60
aacttctctg ccaggggaga taccatgatc acaaaggtgg ctttctcagg gaaaggctga   60
tttattgcac tccagatgtg ctgacccctg agatttctcc aaatgtggga aactcagctg   120
cataatttgt ggaagcgaag gactgtgttt gtgc                               154

SEQ ID NO: 61          moltype = RNA   length = 154
FEATURE                Location/Qualifiers
source                 1..154
                       mol_type = other RNA
                       organism = synthetic construct
SEQUENCE: 61
acttctctgc caggggagat accatgatca caaaggtggc tttctcaggg aaaggctgat   60
ttattgcact ccagatgtgc tgacccctga gatttctcca aatgtgggaa actcagctgc   120
ataatttgtg gaagcgaagg actgtgtttg tgct                               154

SEQ ID NO: 62          moltype = RNA   length = 154
FEATURE                Location/Qualifiers
source                 1..154
                       mol_type = other RNA
                       organism = synthetic construct
SEQUENCE: 62
cttctctgcc aggggagata ccatgatcac aaaggtggct ttctcaggga aaggctgatt   60
tattgcactc cagatgtgct gacccctgag atttctccaa atgtgggaaa ctcagctgca   120
taatttgtgg aagcgaagga ctgtgtttgt gctt                               154

SEQ ID NO: 63          moltype = RNA   length = 154
FEATURE                Location/Qualifiers
source                 1..154
                       mol_type = other RNA
                       organism = synthetic construct
SEQUENCE: 63
ttctctgcca ggggagatac catgatcaca aaggtggctt tctcaggaa aggctgattt     60
attgcactcc agatgtgctg acccctgaga tttctccaaa tgtgggaaac tcagctgcat    120
aatttgtgga agcgaaggac tgtgtttgtg cttt                               154

SEQ ID NO: 64          moltype = RNA   length = 154
```

```
FEATURE                 Location/Qualifiers
source                  1..154
                        mol_type = other RNA
                        organism = synthetic construct
SEQUENCE: 64
tctctgccag gggagatacc atgatcacaa aggtggcttt ctcagggaaa ggctgattta     60
ttgcactcca gatgtgctga cccctgagat ttctccaaat gtgggaaact cagctgcata    120
atttgtggaa gcgaaggact gtgtttgtgc tttc                                154

SEQ ID NO: 65           moltype = RNA   length = 154
FEATURE                 Location/Qualifiers
source                  1..154
                        mol_type = other RNA
                        organism = synthetic construct
SEQUENCE: 65
ctctgccagg ggagatacca tgatcacaaa ggtggctttc tcagggaaag gctgatttat     60
tgcactccag atgtgctgac ccctgagatt tctccaaatg tgggaaactc agctgcataa    120
tttgtggaag cgaaggactg tgtttgtgct ttca                                154

SEQ ID NO: 66           moltype = RNA   length = 154
FEATURE                 Location/Qualifiers
source                  1..154
                        mol_type = other RNA
                        organism = synthetic construct
SEQUENCE: 66
tctgccaggg gagataccat gatcacaaag gtggctttct cagggaaagg ctgatttatt     60
gcactccaga tgtgctgacc cctgagattc tccaaatgtg ggaaactcag ctgcataat    120
ttgtggaagc gaaggactgt gtttgtgctt tcat                                154

SEQ ID NO: 67           moltype = RNA   length = 154
FEATURE                 Location/Qualifiers
source                  1..154
                        mol_type = other RNA
                        organism = synthetic construct
SEQUENCE: 67
ctgccagggg agataccatg atcacaaagg tggctttctc agggaaaggc tgatttattg     60
cactccagat gtgctgaccc ctgagatttc tccaaatgtg ggaaactcag ctgcataatt    120
tgtggaagcg aaggactgtg tttgtgcttt catg                                154

SEQ ID NO: 68           moltype = RNA   length = 154
FEATURE                 Location/Qualifiers
source                  1..154
                        mol_type = other RNA
                        organism = synthetic construct
SEQUENCE: 68
tgccagggga gataccatga tcacaaaggt ggctttctca gggaaaggct gatttattgc     60
actccagatg tgctgacccc tgagatttct ccaaatgtgg gaaactcagc tgcataattt    120
gtggaagcga aggactgtgt ttgtgctttc atgt                                154

SEQ ID NO: 69           moltype = RNA   length = 154
FEATURE                 Location/Qualifiers
source                  1..154
                        mol_type = other RNA
                        organism = synthetic construct
SEQUENCE: 69
atacttctct gccaggggag atactgtgat catgaaggtg gctttcccag ggcaaggctg     60
atctattgca ttctggatgt gctgactcct acgatttccc caagtgtggg aaactcaact    120
gcataatttg tggaagtaat gactgtgttt gcac                                154

SEQ ID NO: 70           moltype = RNA   length = 154
FEATURE                 Location/Qualifiers
source                  1..154
                        mol_type = other RNA
                        organism = synthetic construct
SEQUENCE: 70
tacttctctg ccaggggaga tactgtgatc atgaaggtgg ctttcccagg gcaaggctga     60
tctattgcat ctggatgtg ctgactccta cgatttcccc aagtgtggga aactcaactg    120
cataatttgt ggaagtaatg actgtgtttg cact                                154

SEQ ID NO: 71           moltype = RNA   length = 154
FEATURE                 Location/Qualifiers
source                  1..154
                        mol_type = other RNA
                        organism = synthetic construct
SEQUENCE: 71
acttctctgc caggggagat actgtgatca tgaaggtggc tttcccaggg caaggctgat     60
ctattgcatt ctggatgtgc tgactcctac gatttcccca agtgtgggaa actcaactgc    120
ataatttgtg gaagtaatga ctgtgtttgc actt                                154
```

-continued

```
SEQ ID NO: 72          moltype = RNA   length = 154
FEATURE                Location/Qualifiers
source                 1..154
                       mol_type = other RNA
                       organism = synthetic construct
SEQUENCE: 72
cttctctgcc aggggagata ctgtgatcat gaaggtggct ttcccagggc aaggctgatc   60
tattgcattc tggatgtgct gactcctacg atttccccaa gtgtgggaaa ctcaactgca  120
taatttgtgg aagtaatgac tgtgtttgca cttt                             154

SEQ ID NO: 73          moltype = RNA   length = 154
FEATURE                Location/Qualifiers
source                 1..154
                       mol_type = other RNA
                       organism = synthetic construct
SEQUENCE: 73
ttctctgcca ggggagatac tgtgatcatg aaggtggctt tcccagggca aggctgatct   60
attgcattct ggatgtgctg actcctacga tttccccaag tgtgggaaac tcaactgcat  120
aatttgtgga agtaatgact gtgtttgcac tttc                             154

SEQ ID NO: 74          moltype = RNA   length = 154
FEATURE                Location/Qualifiers
source                 1..154
                       mol_type = other RNA
                       organism = synthetic construct
SEQUENCE: 74
tctctgccag gggagatact gtgatcatga aggtggcttt cccagggcaa ggctgatcta   60
ttgcattctg gatgtgctga ctcctacgat ttccccaagt gtgggaaact caactgcata  120
atttgtggaa gtaatgactg tgtttgcact ttca                             154

SEQ ID NO: 75          moltype = RNA   length = 154
FEATURE                Location/Qualifiers
source                 1..154
                       mol_type = other RNA
                       organism = synthetic construct
SEQUENCE: 75
ctctgccagg ggagatactg tgatcatgaa ggtggctttc ccagggcaag gctgatctat   60
tgcattctgg atgtgctgac tcctacgatt tccccaagtg tgggaaactc aactgcataa  120
tttgtggaag taatgactgt gtttgcactt tcac                             154

SEQ ID NO: 76          moltype = RNA   length = 154
FEATURE                Location/Qualifiers
source                 1..154
                       mol_type = other RNA
                       organism = synthetic construct
SEQUENCE: 76
tctgccaggg gagatactgt gatcatgaag gtggctttcc cagggcaagg ctgatctatt   60
gcattctgga tgtgctgact cctacgattt ccccaagtgt gggaaactca actgcataat  120
ttgtggaagt aatgactgtg tttgcacttt cacg                             154

SEQ ID NO: 77          moltype = RNA   length = 154
FEATURE                Location/Qualifiers
source                 1..154
                       mol_type = other RNA
                       organism = synthetic construct
SEQUENCE: 77
ctgccagggg agatactgtg atcatgaagg tggctttccc agggcaaggc tgatctattg   60
cattctggat gtgctgactc ctacgatttc cccaagtgtg ggaaactcaa ctgcataatt  120
tgtggaagta atgactgtgt ttgcactttc acgt                             154

SEQ ID NO: 78          moltype = RNA   length = 153
FEATURE                Location/Qualifiers
source                 1..153
                       mol_type = other RNA
                       organism = synthetic construct
SEQUENCE: 78
tgccagggga gatactgtga tcatgaaggt ggctttccca gggcaaggct gatctattgc   60
attctggatg tgctgactcc tacgatttcc caagtgtgg gaaactcaac tgcataattt  120
gtggaagtaa tgactgtgtt tgcactttca cgt                              153

SEQ ID NO: 79          moltype = RNA   length = 154
FEATURE                Location/Qualifiers
source                 1..154
                       mol_type = other RNA
                       organism = synthetic construct
SEQUENCE: 79
atacttccct gccaggggag ataccgtgat catgaaggtg gctttcccag ggaaaggccg   60
atatgttgca ctctagatgt gctgacccgt gagatttccc caaatgtggg acactcaaat  120
gcataattgg tggaagtgaa ggactgtgtt tgtg                             154
```

```
SEQ ID NO: 80            moltype = RNA   length = 154
FEATURE                  Location/Qualifiers
source                   1..154
                         mol_type = other RNA
                         organism = synthetic construct
SEQUENCE: 80
tacttccctg ccaggggaga taccgtgatc atgaaggtgg ctttcccagg gaaaggccga   60
tatgttgcac tctagatgtg ctgacccgtg agatttcccc aaatgtggga cactcaaatg  120
cataattggt ggaagtgaag gactgtgttt gtgc                              154

SEQ ID NO: 81            moltype = RNA   length = 154
FEATURE                  Location/Qualifiers
source                   1..154
                         mol_type = other RNA
                         organism = synthetic construct
SEQUENCE: 81
acttccctgc caggggagat accgtgatca tgaaggtggc tttcccaggg aaaggccgat   60
atgttgcact ctagatgtgc tgacccgtga gatttcccca aatgtgggac actcaaatgc  120
ataattggtg gaagtgaagg actgtgtttg tgct                              154

SEQ ID NO: 82            moltype = RNA   length = 154
FEATURE                  Location/Qualifiers
source                   1..154
                         mol_type = other RNA
                         organism = synthetic construct
SEQUENCE: 82
cttccctgcc aggggagata ccgtgatcat gaaggtggct ttcccaggga aaggccgata   60
tgttgcactc tagatgtgct gacccgtgag atttccccaa atgtgggaca ctcaaatgca  120
taattggtgg aagtgaagga ctgtgtttgt gctt                              154

SEQ ID NO: 83            moltype = RNA   length = 154
FEATURE                  Location/Qualifiers
source                   1..154
                         mol_type = other RNA
                         organism = synthetic construct
SEQUENCE: 83
ttccctgcca ggggagatac cgtgatcatg aaggtggctt tcccagggaa aggccgatat   60
gttgcactct agatgtgctg acccgtgaga tttccccaaa tgtgggacac tcaaatgcat  120
aattggtgga agtgaaggac tgtgtttgtg cttt                              154

SEQ ID NO: 84            moltype = RNA   length = 154
FEATURE                  Location/Qualifiers
source                   1..154
                         mol_type = other RNA
                         organism = synthetic construct
SEQUENCE: 84
tccctgccag gggagatacc gtgatcatga aggtggcttt cccagggaaa ggccgatatg   60
ttgcactcta gatgtgctga cccgtgagat tccccaaat gtgggacact caaatgcata  120
attggtggaa gtgaaggact gtgtttgtgc tttc                              154

SEQ ID NO: 85            moltype = RNA   length = 154
FEATURE                  Location/Qualifiers
source                   1..154
                         mol_type = other RNA
                         organism = synthetic construct
SEQUENCE: 85
ccctgccagg ggagataccg tgatcatgaa ggtggctttc cagggaaag ccgatatgt   60
tgcactctag atgtgctgac ccgtgagatt ccccaaatg tgggacactc aaatgcataa  120
ttggtggaag tgaaggactg tgtttgtgct ttca                              154

SEQ ID NO: 86            moltype = RNA   length = 153
FEATURE                  Location/Qualifiers
source                   1..153
                         mol_type = other RNA
                         organism = synthetic construct
SEQUENCE: 86
cctgccaggg gagataccgt gatcatgaag gtggctttcc caggaaagg ccgatatgtt   60
gcactctaga tgtgctgacc cgtgagattt ccccaaatgg gggacactca aatgcataat  120
tggtggaagt gaaggactgt gtttgtgctt tca                               153

SEQ ID NO: 87            moltype = RNA   length = 152
FEATURE                  Location/Qualifiers
source                   1..152
                         mol_type = other RNA
                         organism = synthetic construct
SEQUENCE: 87
ctgccagggg agataccgtg atcatgaagg tggctttccc aggaaaggc cgatatgttg   60
cactctagat gtgctgaccc gtgagatttc cccaaatgtg gacactcaa atgcataatt  120
```

```
ggtggaagtg aaggactgtg tttgtgcttt ca                                    152

SEQ ID NO: 88            moltype = RNA   length = 151
FEATURE                  Location/Qualifiers
source                   1..151
                         mol_type = other RNA
                         organism = synthetic construct
SEQUENCE: 88
tgccagggga gataccgtga tcatgaaggt ggctttccca gggaaaggcc gatatgttgc      60
actctagatg tgctgacccg tgagatttcc ccaaatgtgg gacactcaaa tgcataattg      120
gtggaagtga aggactgtgt ttgtgctttc a                                     151

SEQ ID NO: 89            moltype = RNA   length = 154
FEATURE                  Location/Qualifiers
source                   1..154
                         mol_type = other RNA
                         organism = synthetic construct
SEQUENCE: 89
ttaactacct gacagaggag atactgtgat catgaaagtg gttttcctag ggcaagactt      60
atccgttgca ctccagatgt gctgactcat gcaatttccc caaatgtggg aaactcgact      120
acataatttc tggtggtagg ggactgcgtt catg                                  154

SEQ ID NO: 90            moltype = RNA   length = 154
FEATURE                  Location/Qualifiers
source                   1..154
                         mol_type = other RNA
                         organism = synthetic construct
SEQUENCE: 90
taactacctg acagaggaga tactgtgatc atgaaagtgg ttttcctagg gcaagactta      60
tccgttgcac tccagatgtg ctgactcatg caatttcccc aaatgtggga aactcgacta      120
cataatttct ggtggtaggg gactgcgttc atgt                                  154

SEQ ID NO: 91            moltype = RNA   length = 154
FEATURE                  Location/Qualifiers
source                   1..154
                         mol_type = other RNA
                         organism = synthetic construct
SEQUENCE: 91
aactacctga cagaggagat actgtgatca tgaaagtggt tttcctaggg caagacttat      60
ccgttgcact ccagatgtgc tgactcatgc aatttcccca aatgtgggaa actcgactac      120
ataatttctg gtggtagggg actgcgttca tgtt                                  154

SEQ ID NO: 92            moltype = RNA   length = 154
FEATURE                  Location/Qualifiers
source                   1..154
                         mol_type = other RNA
                         organism = synthetic construct
SEQUENCE: 92
actacctgac agaggagata ctgtgatcat gaaagtggtt ttcctagggc aagacttatc      60
cgttgcactc cagatgtgct gactcatgca atttccccaa atgtgggaaa ctcgactaca      120
taatttctgg tggtagggga ctgcgttcat gttc                                  154

SEQ ID NO: 93            moltype = RNA   length = 154
FEATURE                  Location/Qualifiers
source                   1..154
                         mol_type = other RNA
                         organism = synthetic construct
SEQUENCE: 93
ctacctgaca gaggagatac tgtgatcatg aaagtggttt tcctagggca agacttatcc      60
gttgcactcc agatgtgctg actcatgcaa tttcccaaa tgtgggaaac tcgactacat       120
aatttctggt ggtaggggac tgcgttcatg ttct                                  154

SEQ ID NO: 94            moltype = RNA   length = 154
FEATURE                  Location/Qualifiers
source                   1..154
                         mol_type = other RNA
                         organism = synthetic construct
SEQUENCE: 94
tacctgacag aggagatact gtgatcatga aagtggtttt cctagggcaa gacttatccg      60
ttgcactcca gatgtgctga ctcatgcaat tccccaaat gtgggaaact cgactacata       120
atttctggtg gtaggggact gcgttcatgt tctc                                  154

SEQ ID NO: 95            moltype = RNA   length = 154
FEATURE                  Location/Qualifiers
source                   1..154
                         mol_type = other RNA
                         organism = synthetic construct
SEQUENCE: 95
acctgacaga ggagatactg tgatcatgaa agtggttttc ctagggcaag acttatccgt      60
```

```
tgcactccag atgtgctgac tcatgcaatt tccccaaatg tgggaaactc gactacataa   120
tttctggtgg tagggactg cgttcatgtt ctcc                                 154

SEQ ID NO: 96              moltype = RNA   length = 154
FEATURE                    Location/Qualifiers
source                     1..154
                           mol_type = other RNA
                           organism = synthetic construct
SEQUENCE: 96
cctgacagag gagatactgt gatcatgaaa gtggttttcc tagggcaaga cttatccgtt   60
gcactccaga tgtgctgact catgcaattt ccccaaatgt gggaaactcg actacataat   120
ttctggtggt aggggactgc gttcatgttc tccc                                154

SEQ ID NO: 97              moltype = RNA   length = 154
FEATURE                    Location/Qualifiers
source                     1..154
                           mol_type = other RNA
                           organism = synthetic construct
SEQUENCE: 97
ctgacagagg agatactgtg atcatgaaag tggttttcct agggcaagac ttatccgttg   60
cactccagat gtgctgactc atgcaatttc cccaaatgtg ggaaactcga ctacataatt   120
tctggtggta ggggactgcg ttcatgttct cccc                                154

SEQ ID NO: 98              moltype = RNA   length = 154
FEATURE                    Location/Qualifiers
source                     1..154
                           mol_type = other RNA
                           organism = synthetic construct
SEQUENCE: 98
tgacagagga gatactgtga tcatgaaagt ggttttccta gggcaagact tatccgttgc   60
actccagatg tgctgactca tgcaatttcc ccaaatgtgg gaaactcgac tacataattt   120
ctggtggtag gggactgcgt tcatgttctc ccct                                154

SEQ ID NO: 99              moltype = RNA   length = 147
FEATURE                    Location/Qualifiers
source                     1..147
                           mol_type = other RNA
                           organism = synthetic construct
SEQUENCE: 99
agacttatct ggcaggggag acaccatgaa catgaggata gttttcccaa ggcaagtttc   60
aacccttgca ctctagatga tgagattact taatgggtac aatgcatgtg atttgggtaa   120
tggatactgt agaaacactg acgtcac                                       147

SEQ ID NO: 100             moltype = RNA   length = 146
FEATURE                    Location/Qualifiers
source                     1..146
                           mol_type = other RNA
                           organism = synthetic construct
SEQUENCE: 100
gacttatctg gcaggggaga caccatgaac atgaggatag ttttcccaag gcaagtttca   60
acccttgcac tctagatgat gagattactt aatgggtaca atgcatgtga tttgggtaat   120
ggatactgta gaaacactga cgtcac                                        146

SEQ ID NO: 101             moltype = RNA   length = 145
FEATURE                    Location/Qualifiers
source                     1..145
                           mol_type = other RNA
                           organism = synthetic construct
SEQUENCE: 101
acttatctgg caggggagac accatgaaca tgaggatagt tttcccaagg caagtttcaa   60
cccttgcact ctagatgatg agattactta atgggtacaa tgcatgtgat ttgggtaatg   120
gatactgtag aaacactgac gtcac                                         145

SEQ ID NO: 102             moltype = RNA   length = 144
FEATURE                    Location/Qualifiers
source                     1..144
                           mol_type = other RNA
                           organism = synthetic construct
SEQUENCE: 102
cttatctggc aggggagaca ccatgaacat gaggatagtt ttcccaaggc aagtttcaac   60
ccttgcactc tagatgatga gattacttaa tgggtacaat gcatgtgatt tgggtaatgg   120
atactgtaga aacactgacg tcac                                          144

SEQ ID NO: 103             moltype = RNA   length = 143
FEATURE                    Location/Qualifiers
source                     1..143
                           mol_type = other RNA
                           organism = synthetic construct
SEQUENCE: 103
```

-continued

```
ttatctggca ggggagacac catgaacatg aggatagttt tcccaaggca agtttcaacc   60
cttgcactct agatgatgag attacttaat gggtacaatg catgtgattt gggtaatgga   120
tactgtagaa acactgacgt cac                                          143

SEQ ID NO: 104           moltype = RNA   length = 142
FEATURE                  Location/Qualifiers
source                   1..142
                         mol_type = other RNA
                         organism = synthetic construct
SEQUENCE: 104
tatctggcag gggagacacc atgaacatga ggatagtttt cccaaggcaa gtttcaaccc   60
ttgcactcta gatgatgaga ttacttaatg ggtacaatgc atgtgatttg ggtaatggat   120
actgtagaaa cactgacgtc ac                                           142

SEQ ID NO: 105           moltype = RNA   length = 141
FEATURE                  Location/Qualifiers
source                   1..141
                         mol_type = other RNA
                         organism = synthetic construct
SEQUENCE: 105
atctggcagg ggagacacca tgaacatgag gatagttttc ccaaggcaag tttcaaccct   60
tgcactctag atgatgagat tacttaatgg gtacaatgca tgtgatttgg gtaatggata   120
ctgtagaaac actgacgtca c                                            141

SEQ ID NO: 106           moltype = RNA   length = 140
FEATURE                  Location/Qualifiers
source                   1..140
                         mol_type = other RNA
                         organism = synthetic construct
SEQUENCE: 106
tctggcaggg gagacaccat gaacatgagg atagttttcc caaggcaagt ttcaaccctt   60
gcactctaga tgatgagatt acttaatggg tacaatgcat gtgatttggg taatggatac   120
tgtagaaaca ctgacgtcac                                              140

SEQ ID NO: 107           moltype = RNA   length = 139
FEATURE                  Location/Qualifiers
source                   1..139
                         mol_type = other RNA
                         organism = synthetic construct
SEQUENCE: 107
ctggcagggg agacaccatg aacatgagga tagttttccc aaggcaagtt tcaacccttg   60
cactctagat gatgagatta cttaatgggt acaatgcatg tgatttgggt aatggatact   120
gtagaaacac tgacgtcac                                               139

SEQ ID NO: 108           moltype = RNA   length = 138
FEATURE                  Location/Qualifiers
source                   1..138
                         mol_type = other RNA
                         organism = synthetic construct
SEQUENCE: 108
tggcagggga gacaccatga acatgaggat agttttccca aggcaagttt caacccttgc   60
actctagatg atgagattac ttaatgggta caatgcatgt gatttgggta atggatactg   120
tagaaacact gacgtcac                                                138

SEQ ID NO: 109           moltype = RNA   length = 149
FEATURE                  Location/Qualifiers
source                   1..149
                         mol_type = other RNA
                         organism = synthetic construct
SEQUENCE: 109
agactcatct ggcagcggag ataccatgaa catcacggta gttttcccaa agcaagtttc   60
caccttgca ctccggatga tgagacatta cttaatggat acaatgcatg tgatttgagt   120
gatggatact gtgaaacac cgacttcac                                     149

SEQ ID NO: 110           moltype = RNA   length = 148
FEATURE                  Location/Qualifiers
source                   1..148
                         mol_type = other RNA
                         organism = synthetic construct
SEQUENCE: 110
gactcatctg gcagcggaga taccatgaac atcacggtag ttttcccaaa gcaagtttcc   60
acccttgcac tccggatgat gagacattac ttaatggata caatgcatgt gatttgagtg   120
atggatactg tggaaacacc gacttcac                                     148

SEQ ID NO: 111           moltype = RNA   length = 147
FEATURE                  Location/Qualifiers
source                   1..147
                         mol_type = other RNA
                         organism = synthetic construct
```

```
SEQUENCE: 111
actcatctgg cagcggagat accatgaaca tcacggtagt tttcccaaag caagtttcca    60
cccttgcact ccggatgatg agacattact taatggatac aatgcatgtg atttgagtga   120
tggatactgt ggaaacaccg acttcac                                       147

SEQ ID NO: 112             moltype = RNA   length = 146
FEATURE                    Location/Qualifiers
source                     1..146
                           mol_type = other RNA
                           organism = synthetic construct
SEQUENCE: 112
ctcatctggc agcggagata ccatgaacat cacggtagtt ttcccaaagc aagtttccac    60
ccttgcactc cggatgatga gacattactt aatggataca atgcatgtga tttgagtgat   120
ggatactgtg gaaacaccga cttcac                                        146

SEQ ID NO: 113             moltype = RNA   length = 145
FEATURE                    Location/Qualifiers
source                     1..145
                           mol_type = other RNA
                           organism = synthetic construct
SEQUENCE: 113
tcatctggca gcggagatac catgaacatc acggtagttt tcccaaagca agtttccacc    60
cttgcactcc ggatgatgag acattactta atggatacaa tgcatgtgat ttgagtgatg   120
gatactgtgg aaacaccgac ttcac                                         145

SEQ ID NO: 114             moltype = RNA   length = 144
FEATURE                    Location/Qualifiers
source                     1..144
                           mol_type = other RNA
                           organism = synthetic construct
SEQUENCE: 114
catctggcag cggagatacc atgaacatca cggtagtttt cccaaagcaa gtttccaccc    60
ttgcactccg gatgatgaga cattacttaa tggatacaat gcatgtgatt tgagtgatgg   120
atactgtgga aacaccgact tcac                                          144

SEQ ID NO: 115             moltype = RNA   length = 143
FEATURE                    Location/Qualifiers
source                     1..143
                           mol_type = other RNA
                           organism = synthetic construct
SEQUENCE: 115
atctggcagc ggagatacca tgaacatcac ggtagttttc ccaaagcaag tttccaccct    60
tgcactccgg atgatgagac attacttaat ggatacaatg catgtgattt gagtgatgga   120
tactgtggaa acaccgactt cac                                           143

SEQ ID NO: 116             moltype = RNA   length = 142
FEATURE                    Location/Qualifiers
source                     1..142
                           mol_type = other RNA
                           organism = synthetic construct
SEQUENCE: 116
tctggcagcg gagataccat gaacatcacg gtagttttcc caaagcaagt ttcacccctt    60
gcactccgga tgatgagaca ttacttaatg gatacaatgc atgtgatttg agtgatggat   120
actgtggaaa caccgacttc ac                                            142

SEQ ID NO: 117             moltype = RNA   length = 141
FEATURE                    Location/Qualifiers
source                     1..141
                           mol_type = other RNA
                           organism = synthetic construct
SEQUENCE: 117
ctggcagcgg agataccatg aacatcacgg tagttttccc aaagcaagtt tccacccttg    60
cactccggat gatgagacat tacttaatgg atacaatgca tgtgatttga gtgatggata   120
ctgtggaaac accgacttca c                                             141

SEQ ID NO: 118             moltype = RNA   length = 140
FEATURE                    Location/Qualifiers
source                     1..140
                           mol_type = other RNA
                           organism = synthetic construct
SEQUENCE: 118
tggcagcgga gataccatga acatcacggt agttttccca aagcaagttt ccacccttgc    60
actccggatg atgagacatt acttaatgga tacaatgcat gtgatttgag tgatggatac   120
tgtggaaaca ccgacttcac                                               140

SEQ ID NO: 119             moltype = RNA   length = 154
FEATURE                    Location/Qualifiers
source                     1..154
                           mol_type = other RNA
```

-continued

```
                              organism = synthetic construct
SEQUENCE: 119
agacttggca ggggagatag catgatcacg aaggtggttt tcccaaggca agatttattc    60
actgcactct ggatgtgctg acccctacga tttccgccca atggggaagc ttgactgctt   120
agtttgttgt ggcaggggac tgtgttcaca cttt                               154

SEQ ID NO: 120        moltype = RNA   length = 154
FEATURE               Location/Qualifiers
source                1..154
                      mol_type = other RNA
                      organism = synthetic construct
SEQUENCE: 120
gacttggcag gggagatagc atgatcacga aggtggtttt cccaaggcaa gatttattca    60
ctgcactctg gatgtgctga cccctacgat ttccgcccaa tggggaagct tgactgctta   120
gtttgttgtg gcaggggact gtgttcacac tttt                               154

SEQ ID NO: 121        moltype = RNA   length = 154
FEATURE               Location/Qualifiers
source                1..154
                      mol_type = other RNA
                      organism = synthetic construct
SEQUENCE: 121
acttggcagg ggagatagca tgatcacgaa ggtggttttc ccaaggcaag atttattcac    60
tgcactctgg atgtgctgac ccctacgatt tccgcccaat ggggaagctt gactgcttag   120
tttgttgtgg cagggggactg tgttcacact tttc                              154

SEQ ID NO: 122        moltype = RNA   length = 154
FEATURE               Location/Qualifiers
source                1..154
                      mol_type = other RNA
                      organism = synthetic construct
SEQUENCE: 122
cttggcaggg gagatagcat gatcacgaag gtggttttcc caaggcaaga tttattcact    60
gcactctgga tgtgctgacc cctacgattt ccgcccaatg gggaagcttg actgcttagt   120
ttgttgtggc aggggactgt gttcacactt ttcc                               154

SEQ ID NO: 123        moltype = RNA   length = 154
FEATURE               Location/Qualifiers
source                1..154
                      mol_type = other RNA
                      organism = synthetic construct
SEQUENCE: 123
ttggcagggg agatagcatg atcacgaagg tggttttccc aaggcaagat ttattcactg    60
cactctggat gtgctgaccc ctacgatttc cgcccaatgg ggaagcttga ctgcttagtt   120
tgttgtggca ggggactgtg ttcacacttt tccc                               154

SEQ ID NO: 124        moltype = RNA   length = 154
FEATURE               Location/Qualifiers
source                1..154
                      mol_type = other RNA
                      organism = synthetic construct
SEQUENCE: 124
tggcagggga gatagcatga tcacgaaggt ggttttccca aggcaagatt tattcactgc    60
actctggatg tgctgacccc tacgatttcc gcccaatggg gaagcttgac tgcttagttt   120
gttgtggcag gggactgtgt tcacactttt cccg                               154

SEQ ID NO: 125        moltype = RNA   length = 154
FEATURE               Location/Qualifiers
source                1..154
                      mol_type = other RNA
                      organism = synthetic construct
SEQUENCE: 125
ggcagggga gatagcatgat cacgaaggtg gttttcccaa ggcaagattt attcactgca    60
ctctggatgt gctgacccct acgatttccg cccaatgggg aagcttgact gcttagtttg   120
ttgtggcagg ggactgtgtt cacacttttc cgg                                154

SEQ ID NO: 126        moltype = RNA   length = 153
FEATURE               Location/Qualifiers
source                1..153
                      mol_type = other RNA
                      organism = synthetic construct
SEQUENCE: 126
gcagggga ga tagcatgatc acgaaggtgg ttttcccaag gcaagattta ttcactgcac    60
tctggatgtg ctgacccta cgatttccgc ccaatgggga gcttgactg cttagtttgt     120
tgtggcaggg gactgtgttc actttttcc cgg                                 153

SEQ ID NO: 127        moltype = RNA   length = 152
FEATURE               Location/Qualifiers
source                1..152
```

```
                          mol_type = other RNA
                          organism = synthetic construct
SEQUENCE: 127
caggggagat agcatgatca cgaaggtggt tttcccaagg caagatttat tcactgcact    60
ctggatgtgc tgacccctac gatttccgcc caatggggaa gcttgactgc ttagtttgtt   120
gtggcagggg actgtgttca cactttttccc gg                                 152

SEQ ID NO: 128       moltype = RNA   length = 151
FEATURE              Location/Qualifiers
source               1..151
                     mol_type = other RNA
                     organism = synthetic construct
SEQUENCE: 128
aggggagata gcatgatcac gaaggtggtt ttcccaaggc aagatttatt cactgcactc    60
tggatgtgct gacccctacg atttccgccc aatggggaag cttgactgct tagtttgttg   120
tggcaggggga ctgtgttcac acttttttcccg g                                151

SEQ ID NO: 129       moltype = RNA   length = 154
FEATURE              Location/Qualifiers
source               1..154
                     mol_type = other RNA
                     organism = synthetic construct
SEQUENCE: 129
atacttaaca tggcagagga gatatcataa tcacaaaggt agttttccca gggcaagcct    60
tatccactgc attccagatg tgctcacctc tgtggtttcc ccaaatgtgg aaaactggac   120
tgcataattt gtggtagcgg gggactgcat taat                               154

SEQ ID NO: 130       moltype = RNA   length = 154
FEATURE              Location/Qualifiers
source               1..154
                     mol_type = other RNA
                     organism = synthetic construct
SEQUENCE: 130
tacttaacat ggcagaggag atatcataat cacaaaggta gttttccag ggcaagcctt    60
atccactgca ttccagatgt gctcacctct gtggtttccc caaatgtgga aaactggact   120
gcataatttg tggtagcggg ggactgcatt aata                               154

SEQ ID NO: 131       moltype = RNA   length = 154
FEATURE              Location/Qualifiers
source               1..154
                     mol_type = other RNA
                     organism = synthetic construct
SEQUENCE: 131
acttaacatg gcagaggaga tatcataatc acaaaggtag ttttcccagg gcaagcctta    60
tccactgcat tccagatgtg ctcacctctg tggtttcccc aaatgtggaa aactggactg   120
cataatttgt ggtagcgggg gactgcatta atac                               154

SEQ ID NO: 132       moltype = RNA   length = 154
FEATURE              Location/Qualifiers
source               1..154
                     mol_type = other RNA
                     organism = synthetic construct
SEQUENCE: 132
cttaacatgg cagaggagat cataatca caaaggtagt tttcccaggg caagccttat    60
ccactgcatt ccagatgtgc tcacctctgt ggtttcccca atgtggaaa actggactgc   120
ataatttgtg gtagcggggg actgcattaa tacc                               154

SEQ ID NO: 133       moltype = RNA   length = 154
FEATURE              Location/Qualifiers
source               1..154
                     mol_type = other RNA
                     organism = synthetic construct
SEQUENCE: 133
ttaacatggc agaggagata tcataatcac aaaggtagtt ttcccagggc aagccttatc    60
cactgcattc cagatgtgct cacctctgtg gtttccccaa atgtggaaaa ctggactgca   120
taatttgtgg tagcggggga ctgcattaat acct                               154

SEQ ID NO: 134       moltype = RNA   length = 154
FEATURE              Location/Qualifiers
source               1..154
                     mol_type = other RNA
                     organism = synthetic construct
SEQUENCE: 134
taacatggca gaggagatat cataatcaca aaggtagttt cccagggca agccttatcc    60
actgcattcc agatgtgctc acctctgtgt ttccccaaa tgtggaaaac tggactgcat   120
aatttgtggt agcgggggac tgcattaata cctt                               154

SEQ ID NO: 135       moltype = RNA   length = 154
FEATURE              Location/Qualifiers
```

-continued

```
source                    1..154
                          mol_type = other RNA
                          organism = synthetic construct
SEQUENCE: 135
aacatggcag aggagatatc ataatcacaa aggtagtttt cccagggcaa gccttatcca    60
ctgcattcca gatgtgctca cctctgtggt ttccccaaat gtggaaaact ggactgcata   120
atttgtggta gcggggggact gcattaatac cttc                               154

SEQ ID NO: 136           moltype = RNA   length = 154
FEATURE                  Location/Qualifiers
source                   1..154
                         mol_type = other RNA
                         organism = synthetic construct
SEQUENCE: 136
acatggcaga ggagatatca taatcacaaa ggtagttttc ccagggcaag ccttatccac    60
tgcattccag atgtgctcac ctctgtggtt tccccaaatg tggaaaactg gactgcataa   120
tttgtggtag cggggggactg cattaatacc ttcc                              154

SEQ ID NO: 137           moltype = RNA   length = 154
FEATURE                  Location/Qualifiers
source                   1..154
                         mol_type = other RNA
                         organism = synthetic construct
SEQUENCE: 137
catggcagag gagatatcat aatcacaaag gtagttttcc cagggcaagc cttatccact    60
gcattccaga tgtgctcacc tctgtggttt ccccaaatgt ggaaaactgg actgcataat   120
ttgtggtagc ggggggactgc attaataccct tcct                             154

SEQ ID NO: 138           moltype = RNA   length = 154
FEATURE                  Location/Qualifiers
source                   1..154
                         mol_type = other RNA
                         organism = synthetic construct
SEQUENCE: 138
atggcagagg agatatcata atcacaaagg tagttttccc agggcaagcc ttatccactg    60
cattccagat gtgctcacct ctgtggtttc cccaaatgtg gaaaactgga ctgcataatt   120
tgtggtagcg gggactgca ttaataccctt cctc                               154

SEQ ID NO: 139           moltype = RNA   length = 133
FEATURE                  Location/Qualifiers
source                   1..133
                         mol_type = other RNA
                         organism = synthetic construct
SEQUENCE: 139
aaaaagggct tctgctgtga gtggcacaca tagggcatcg tttgctcttg gtgccagaat    60
caacatcaag agatttcaga agcataattt tttggtactt gggcagctgg tgatcattgg   120
tcctgtagcc ctt                                                      133

SEQ ID NO: 140           moltype = RNA   length = 132
FEATURE                  Location/Qualifiers
source                   1..132
                         mol_type = other RNA
                         organism = synthetic construct
SEQUENCE: 140
aaaagggctt ctgctgtgag tggcacacat agggcatcgt ttgctcttgg tgccagaatc    60
aacatcaaga gatttcagaa gcataatttt ttggtacttg ggcagctggt gatcattggt   120
cctgtagccc tt                                                       132

SEQ ID NO: 141           moltype = RNA   length = 131
FEATURE                  Location/Qualifiers
source                   1..131
                         mol_type = other RNA
                         organism = synthetic construct
SEQUENCE: 141
aaagggcttc tgctgtgagt ggcacacata gggcatcgtt tgctcttggt gccagaatca    60
acatcaagag atttcagaag cataattttt tggtacttgg gcagctggtg atcattggtc   120
ctgtagccct t                                                        131

SEQ ID NO: 142           moltype = RNA   length = 130
FEATURE                  Location/Qualifiers
source                   1..130
                         mol_type = other RNA
                         organism = synthetic construct
SEQUENCE: 142
aagggcttct gctgtgagtg gcacacatag ggcatcgttt gctcttggtg ccagaatcaa    60
catcaagaga tttcagaagc ataatttttt ggtacttggg cagctggtga tcattggtcc   120
tgtagccctt                                                          130

SEQ ID NO: 143           moltype = RNA   length = 129
```

-continued

```
FEATURE                 Location/Qualifiers
source                  1..129
                        mol_type = other RNA
                        organism = synthetic construct
SEQUENCE: 143
agggcttctg ctgtgagtgg cacacatagg gcatcgtttg ctcttggtgc cagaatcaac   60
atcaagagat ttcagaagca taattttttg gtacttgggc agctggtgat cattggtcct  120
gtagccctt                                                           129

SEQ ID NO: 144          moltype = RNA   length = 128
FEATURE                 Location/Qualifiers
source                  1..128
                        mol_type = other RNA
                        organism = synthetic construct
SEQUENCE: 144
gggcttctgc tgtgagtggc acacataggg catcgtttgc tcttggtgcc agaatcaaca   60
tcaagagatt tcagaagcat aatttttttgg tacttgggca gctggtgatc attggtcctg  120
tagcccctt                                                           128

SEQ ID NO: 145          moltype = RNA   length = 127
FEATURE                 Location/Qualifiers
source                  1..127
                        mol_type = other RNA
                        organism = synthetic construct
SEQUENCE: 145
ggcttctgct gtgagtggca cacatagggc atcgtttgct cttggtgcca gaatcaacat   60
caagagattt cagaagcata atttttttggt acttgggcag ctggtgatca ttggtcctgt  120
agcccctt                                                            127

SEQ ID NO: 146          moltype = RNA   length = 126
FEATURE                 Location/Qualifiers
source                  1..126
                        mol_type = other RNA
                        organism = synthetic construct
SEQUENCE: 146
gcttctgctg tgagtggcac acatagggca tcgtttgctc ttggtgccag aatcaacatc   60
aagagatttc agaagcataa tttttttggta cttgggcagc tggtgatcat tggtcctgta  120
gcccctt                                                             126

SEQ ID NO: 147          moltype = RNA   length = 125
FEATURE                 Location/Qualifiers
source                  1..125
                        mol_type = other RNA
                        organism = synthetic construct
SEQUENCE: 147
cttctgctgt gagtggcaca catagggcat cgtttgctct tggtgccaga atcaacatca   60
agagatttca gaagcataat tttttggtac ttgggcagct ggtgatcatt ggtcctgtag  120
ccctt                                                               125

SEQ ID NO: 148          moltype = RNA   length = 124
FEATURE                 Location/Qualifiers
source                  1..124
                        mol_type = other RNA
                        organism = synthetic construct
SEQUENCE: 148
ttctgctgtg agtggcacac atagggcatc gtttgctctt ggtgccagaa tcaacatcaa   60
gagatttcag aagcataatt ttttggtact gggcagctg gtgatcattg gtcctgtagc  120
cctt                                                                124

SEQ ID NO: 149          moltype = RNA   length = 129
FEATURE                 Location/Qualifiers
source                  1..129
                        mol_type = other RNA
                        organism = synthetic construct
SEQUENCE: 149
aaaaaaagct gctgttgtga gtgatacatg caggcaact tgattgctct tagtgcagaa   60
ttgacatcaa ggaattttgg aagtataatt ttttggcagg tggatagctg gttgtattag  120
tccattctc                                                           129

SEQ ID NO: 150          moltype = RNA   length = 128
FEATURE                 Location/Qualifiers
source                  1..128
                        mol_type = other RNA
                        organism = synthetic construct
SEQUENCE: 150
aaaaaagctg ctgttgtgag tgatacatgc agggcaactt gattgctct agtgcagaat   60
tgacatcaag gaattttgga agtataattt tttggcaggt ggatagctgg ttgtattagt  120
ccattctc                                                            128
```

-continued

```
SEQ ID NO: 151        moltype = RNA   length = 127
FEATURE               Location/Qualifiers
source                1..127
                      mol_type = other RNA
                      organism = synthetic construct
SEQUENCE: 151
aaaaagctgc tgttgtgagt gatacatgca gggcaacttg attgctctta gtgcagaatt   60
gacatcaagg aattttggaa gtataatttt ttggcaggtg gatagctggt tgtattagtc   120
cattctc                                                             127

SEQ ID NO: 152        moltype = RNA   length = 126
FEATURE               Location/Qualifiers
source                1..126
                      mol_type = other RNA
                      organism = synthetic construct
SEQUENCE: 152
aaaagctgct gttgtgagtg atacatgcag ggcaacttga ttgctcttag tgcagaattg   60
acatcaagga attttggaag tataattttt tggcaggtgg atagctggtt gtattagtcc   120
attctc                                                              126

SEQ ID NO: 153        moltype = RNA   length = 125
FEATURE               Location/Qualifiers
source                1..125
                      mol_type = other RNA
                      organism = synthetic construct
SEQUENCE: 153
aaagctgctg ttgtgagtga tacatgcagg gcaacttgat tgctcttagt gcagaattga   60
catcaaggaa ttttggaagt ataatttttt ggcaggtgga tagctggttg tattagtcca   120
ttctc                                                               125

SEQ ID NO: 154        moltype = RNA   length = 124
FEATURE               Location/Qualifiers
source                1..124
                      mol_type = other RNA
                      organism = synthetic construct
SEQUENCE: 154
aagctgctgt tgtgagtgat acatgcaggg caacttgatt gctcttagtg cagaattgac   60
atcaaggaat tttggaagta taattttttg gcaggtggat agctggttgt attagtccat   120
tctc                                                                124

SEQ ID NO: 155        moltype = RNA   length = 123
FEATURE               Location/Qualifiers
source                1..123
                      mol_type = other RNA
                      organism = synthetic construct
SEQUENCE: 155
agctgctgtt gtgagtgata catgcagggc aacttgattg ctcttagtgc agaattgaca   60
tcaaggaatt ttggaagtat aattttttgg caggtggata gctggttgta ttagtccatt   120
ctc                                                                 123

SEQ ID NO: 156        moltype = RNA   length = 122
FEATURE               Location/Qualifiers
source                1..122
                      mol_type = other RNA
                      organism = synthetic construct
SEQUENCE: 156
gctgctgttg tgagtgatac atgcagggca acttgattgc tcttagtgca gaattgacat   60
caaggaattt ggaagtata atttttggc aggtggatag ctggttgtat tagtccattc   120
tc                                                                  122

SEQ ID NO: 157        moltype = RNA   length = 121
FEATURE               Location/Qualifiers
source                1..121
                      mol_type = other RNA
                      organism = synthetic construct
SEQUENCE: 157
ctgctgttgt gagtgataca tgcagggcaa cttgattgct cttagtgcag aattgacatc   60
aaggaatttt ggaagtataa ttttttggca ggtggatagc tggttgtatt agtccattct   120
c                                                                   121

SEQ ID NO: 158        moltype = RNA   length = 120
FEATURE               Location/Qualifiers
source                1..120
                      mol_type = other RNA
                      organism = synthetic construct
SEQUENCE: 158
tgctgttgtg agtgatacat gcagggcaac ttgattgctc ttagtgcaga attgacatca   60
aggaattttg gaagtataat tttttggcag gtggatagct ggttgtatta gtccattctc   120
```

-continued

```
SEQ ID NO: 159          moltype = RNA   length = 133
FEATURE                 Location/Qualifiers
source                  1..133
                        mol_type = other RNA
                        organism = synthetic construct
SEQUENCE: 159
aaaaagggct tctgtcatga gtggcacaca taggacaact caatttctct tcatgcagaa    60
taaacatcaa gagattttgg aagcgtaatt tttggtagtt gggcagctgg tgatcactgg   120
tgccagcacc ctt                                                       133

SEQ ID NO: 160          moltype = RNA   length = 132
FEATURE                 Location/Qualifiers
source                  1..132
                        mol_type = other RNA
                        organism = synthetic construct
SEQUENCE: 160
aaaagggctt ctgtcatgag tggcacacat aggacaactc aatttctctt catgcagaat    60
aaacatcaag agattttgga agcgtaattt ttggtagttg ggcagctggt gatcactggt   120
gccagcaccc tt                                                        132

SEQ ID NO: 161          moltype = RNA   length = 131
FEATURE                 Location/Qualifiers
source                  1..131
                        mol_type = other RNA
                        organism = synthetic construct
SEQUENCE: 161
aaagggcttc tgtcatgagt ggcacacata ggacaactca atttctcttc atgcagaata    60
aacatcaaga gattttggaa gcgtaatttt tggtagttgg gcagctggtg atcactggtg   120
ccagcaccct t                                                         131

SEQ ID NO: 162          moltype = RNA   length = 130
FEATURE                 Location/Qualifiers
source                  1..130
                        mol_type = other RNA
                        organism = synthetic construct
SEQUENCE: 162
aagggcttct gtcatgagtg gcacacatag gacaactcaa tttctcttca tgcagaataa    60
acatcaagag attttggaag cgtaattttt ggtagttggg cagctggtga tcactggtgc   120
cagcaccctt                                                           130

SEQ ID NO: 163          moltype = RNA   length = 129
FEATURE                 Location/Qualifiers
source                  1..129
                        mol_type = other RNA
                        organism = synthetic construct
SEQUENCE: 163
agggcttctg tcatgagtgg cacacatagg acaactcaat ttctcttcat gcagaataaa    60
catcaagaga ttttggaagc gtaatttttg gtagttgggc agctggtgat cactggtgcc   120
agcaccctt                                                            129

SEQ ID NO: 164          moltype = RNA   length = 128
FEATURE                 Location/Qualifiers
source                  1..128
                        mol_type = other RNA
                        organism = synthetic construct
SEQUENCE: 164
gggcttctgt catgagtggc acacatagga caactcaatt tctcttcatg cagaataaac    60
atcaagagat tttggaagcg taattttttg gtagttgggca gctggtgatc actggtgcca   120
gcacccctt                                                            128

SEQ ID NO: 165          moltype = RNA   length = 127
FEATURE                 Location/Qualifiers
source                  1..127
                        mol_type = other RNA
                        organism = synthetic construct
SEQUENCE: 165
ggcttctgtc atgagtggca cacataggac aactcaattt ctcttcatgc agaataaaca    60
tcaagagatt ttggaagcgt aattttttggt agttgggcag ctggtgatca ctggtgccag   120
caccctt                                                              127

SEQ ID NO: 166          moltype = RNA   length = 126
FEATURE                 Location/Qualifiers
source                  1..126
                        mol_type = other RNA
                        organism = synthetic construct
SEQUENCE: 166
gcttctgtca tgagtggcac acataggaca actcaatttc tcttcatgca gaataaacat    60
caagagattt tggaagcgta attttttggta gttgggcagc tggtgatcac tggtgccagc   120
accctt                                                               126
```

-continued

```
SEQ ID NO: 167            moltype = RNA   length = 125
FEATURE                   Location/Qualifiers
source                    1..125
                          mol_type = other RNA
                          organism = synthetic construct
SEQUENCE: 167
cttctgtcat gagtggcaca cataggacaa ctcaatttct cttcatgcag aataaacatc    60
aagagatttt ggaagcgtaa tttttggtag ttgggcagct ggtgatcact ggtgccagca   120
ccctt                                                               125

SEQ ID NO: 168            moltype = RNA   length = 124
FEATURE                   Location/Qualifiers
source                    1..124
                          mol_type = other RNA
                          organism = synthetic construct
SEQUENCE: 168
ttctgtcatg agtggcacac ataggacaac tcaatttctc ttcatgcaga ataaacatca    60
agagattttg gaagcgtaat ttttggtagt tgggcagctg gtgatcactg gtgccagcac   120
cctt                                                                124

SEQ ID NO: 169            moltype = RNA   length = 133
FEATURE                   Location/Qualifiers
source                    1..133
                          mol_type = other RNA
                          organism = synthetic construct
SEQUENCE: 169
aaaaagggct tctgtcatga gtggcctatg tagggcaacc agattgctct tcatgtggaa    60
ttgacatcaa gagctttcag aagtgtattt tttggaagtt gggcagctgg taatcattgg   120
tcttggcatc ctt                                                      133

SEQ ID NO: 170            moltype = RNA   length = 132
FEATURE                   Location/Qualifiers
source                    1..132
                          mol_type = other RNA
                          organism = synthetic construct
SEQUENCE: 170
aaaagggctt ctgtcatgag tggcctatgt agggcaacca gattgctctt catgtggaat    60
tgacatcaag agctttcaga agtgtatttt ttggaagttg ggcagctggt aatcattggt   120
cttggcatcc tt                                                       132

SEQ ID NO: 171            moltype = RNA   length = 131
FEATURE                   Location/Qualifiers
source                    1..131
                          mol_type = other RNA
                          organism = synthetic construct
SEQUENCE: 171
aaagggcttc tgtcatgagt ggcctatgta gggcaaccag attgctcttc atgtggaatt    60
gacatcaaga gctttcagaa gtgtattttt tggaagttgg gcagctggta atcattggtc   120
ttggcatcct t                                                        131

SEQ ID NO: 172            moltype = RNA   length = 130
FEATURE                   Location/Qualifiers
source                    1..130
                          mol_type = other RNA
                          organism = synthetic construct
SEQUENCE: 172
aagggcttct gtcatgagtg gcctatgtag ggcaaccaga ttgctcttca tgtggaattg    60
acatcaagag ctttcagaag tgtatttttt ggaagttggg cagctggtaa tcattggtct   120
tggcatcctt                                                          130

SEQ ID NO: 173            moltype = RNA   length = 129
FEATURE                   Location/Qualifiers
source                    1..129
                          mol_type = other RNA
                          organism = synthetic construct
SEQUENCE: 173
agggcttctg tcatgagtgg cctatgtagg gcaaccagat tgctcttcat gtggaattga    60
catcaagagc tttcagaagt gtattttttg gaagttgggc agctggtaat cattggtctt   120
ggcatcctt                                                           129

SEQ ID NO: 174            moltype = RNA   length = 128
FEATURE                   Location/Qualifiers
source                    1..128
                          mol_type = other RNA
                          organism = synthetic construct
SEQUENCE: 174
gggcttctgt catgagtggc ctatgtaggg caaccagatt gctcttcatg tggaattgac    60
atcaagagct tcagaagtg tatttttgg aagttgggca gctggtaatc attggtcttg   120
```

-continued

```
gcatcctt                                                            128

SEQ ID NO: 175          moltype = RNA  length = 127
FEATURE                 Location/Qualifiers
source                  1..127
                        mol_type = other RNA
                        organism = synthetic construct
SEQUENCE: 175
ggcttctgtc atgagtggcc tatgtagggc aaccagattg ctcttcatgt ggaattgaca   60
tcaagagctt tcagaagtgt attttttgga agttgggcag ctggtaatca ttggtcttgg   120
catcctt                                                             127

SEQ ID NO: 176          moltype = RNA  length = 126
FEATURE                 Location/Qualifiers
source                  1..126
                        mol_type = other RNA
                        organism = synthetic construct
SEQUENCE: 176
gcttctgtca tgagtggcct atgtagggca accagattgc tcttcatgtg gaattgacat   60
caagagcttt cagaagtgta ttttttggaa gttgggcagc tggtaatcat tggtcttggc   120
atcctt                                                              126

SEQ ID NO: 177          moltype = RNA  length = 125
FEATURE                 Location/Qualifiers
source                  1..125
                        mol_type = other RNA
                        organism = synthetic construct
SEQUENCE: 177
cttctgtcat gagtggccta tgtagggcaa ccagattgct cttcatgtgg aattgacatc   60
aagagctttc agaagtgtat ttttggaag ttgggcagct ggtaatcatt ggtcttggca   120
tcctt                                                               125

SEQ ID NO: 178          moltype = RNA  length = 124
FEATURE                 Location/Qualifiers
source                  1..124
                        mol_type = other RNA
                        organism = synthetic construct
SEQUENCE: 178
ttctgtcatg agtggcctat gtagggcaac cagattgctc ttcatgtgga attgacatca   60
agagctttca gaagtgtatt ttttggaagt tgggcagctg gtaatcattg gtcttggcat   120
cctt                                                                124

SEQ ID NO: 179          moltype = RNA  length = 142
FEATURE                 Location/Qualifiers
source                  1..142
                        mol_type = other RNA
                        organism = synthetic construct
SEQUENCE: 179
aaagggggct tctgtcatga gtggcacaca ttgggcaact caactgctct tcatgaggaa   60
tcaacatcag gaggttttgg aagaatgatt tttttggtag ttgggcagct tgtgagaaaa   120
aaatgttttc aggcaaatcc tc                                            142

SEQ ID NO: 180          moltype = RNA  length = 141
FEATURE                 Location/Qualifiers
source                  1..141
                        mol_type = other RNA
                        organism = synthetic construct
SEQUENCE: 180
aaggggctt ctgtcatgag tggcacacat tgggcaactc aactgctctt catgaggaat   60
caacatcagg aggttttgga agaatgattt ttttggtagt tgggcagctt gtgagaaaaa   120
aatgttttca ggcaaatcct c                                             141

SEQ ID NO: 181          moltype = RNA  length = 140
FEATURE                 Location/Qualifiers
source                  1..140
                        mol_type = other RNA
                        organism = synthetic construct
SEQUENCE: 181
aggggcttc tgtcatgagt ggcacacatt gggcaactca actgctcttc atgaggaatc   60
aacatcagga ggttttggaa gaatgatttt tttggtagtt gggcagcttg tgagaaaaaa   120
atgttttcag gcaaatcctc                                               140

SEQ ID NO: 182          moltype = RNA  length = 139
FEATURE                 Location/Qualifiers
source                  1..139
                        mol_type = other RNA
                        organism = synthetic construct
SEQUENCE: 182
gggggcttct gtcatgagtg gcacacattg ggcaactcaa ctgctcttca tgaggaatca   60
```

```
acatcaggag gttttggaag aatgattttt ttggtagttg ggcagcttgt gagaaaaaaa    120
tgttttcagg caaatcctc                                                 139

SEQ ID NO: 183         moltype = RNA   length = 138
FEATURE                Location/Qualifiers
source                 1..138
                       mol_type = other RNA
                       organism = synthetic construct
SEQUENCE: 183
ggggcttctg tcatgagtgg cacacattgg gcaactcaac tgctcttcat gaggaatcaa    60
catcaggagg ttttggaaga atgatttttt tggtagttgg gcagcttgtg agaaaaaaat    120
gttttcaggc aaatcctc                                                  138

SEQ ID NO: 184         moltype = RNA   length = 137
FEATURE                Location/Qualifiers
source                 1..137
                       mol_type = other RNA
                       organism = synthetic construct
SEQUENCE: 184
gggcttctgt catgagtggc acacattggg caactcaact gctcttcatg aggaatcaac    60
atcaggaggt tttggaagaa tgattttttt ggtagttggg cagcttgtga gaaaaaaatg    120
ttttcaggca aatcctc                                                   137

SEQ ID NO: 185         moltype = RNA   length = 136
FEATURE                Location/Qualifiers
source                 1..136
                       mol_type = other RNA
                       organism = synthetic construct
SEQUENCE: 185
ggcttctgtc atgagtggca cacattgggc aactcaactg ctcttcatga ggaatcaaca    60
tcaggaggtt ttggaagaat gatttttttg gtagttgggc agcttgtgag aaaaaaatgt    120
tttcaggcaa atcctc                                                    136

SEQ ID NO: 186         moltype = RNA   length = 135
FEATURE                Location/Qualifiers
source                 1..135
                       mol_type = other RNA
                       organism = synthetic construct
SEQUENCE: 186
gcttctgtca tgagtggcac acattgggca actcaactgc tcttcatgag gaatcaacat    60
caggaggttt tggaagaatg atttttttgg tagttgggca gcttgtgaga aaaaatgtt    120
ttcaggcaaa tcctc                                                     135

SEQ ID NO: 187         moltype = RNA   length = 134
FEATURE                Location/Qualifiers
source                 1..134
                       mol_type = other RNA
                       organism = synthetic construct
SEQUENCE: 187
cttctgtcat gagtggcaca cattgggcaa ctcaactgct cttcatgagg aatcaacatc    60
aggaggtttt ggaagaatga ttttttggt agttgggcag cttgtgagaa aaaatgttt    120
tcaggcaaat cctc                                                      134

SEQ ID NO: 188         moltype = RNA   length = 133
FEATURE                Location/Qualifiers
source                 1..133
                       mol_type = other RNA
                       organism = synthetic construct
SEQUENCE: 188
ttctgtcatg agtggcacac attgggcaac tcaactgctc ttcatgagga atcaacatca    60
ggaggttttg gaagaatgat ttttttggta gttgggcagc ttgtgagaaa aaatgtttt    120
caggcaaatc ctc                                                       133

SEQ ID NO: 189         moltype = RNA   length = 134
FEATURE                Location/Qualifiers
source                 1..134
                       mol_type = other RNA
                       organism = synthetic construct
SEQUENCE: 189
aaaaagggct tctgtcgtga gtggcacacg tagggcaact cgattgctct gcgtgcggaa    60
tcgacatcaa gagatttcgg aagcataatt ttttggtatt tgggcagctg gtgatcgttg    120
gtcccggcgc cctt                                                      134

SEQ ID NO: 190         moltype = RNA   length = 133
FEATURE                Location/Qualifiers
source                 1..133
                       mol_type = other RNA
                       organism = synthetic construct
SEQUENCE: 190
```

```
aaaagggctt ctgtcgtgag tggcacacgt agggcaactc gattgctctg cgtgcggaat    60
cgacatcaag agatttcgga agcataattt tttggtattt gggcagctgg tgatcgttgg   120
tcccggcgcc ctt                                                       133

SEQ ID NO: 191            moltype = RNA   length = 132
FEATURE                   Location/Qualifiers
source                    1..132
                          mol_type = other RNA
                          organism = synthetic construct
SEQUENCE: 191
aaagggcttc tgtcgtgagt ggcacacgta gggcaactcg attgctctgc gtgcggaatc    60
gacatcaaga gatttcggaa gcataatttt ttggtatttg gcagctggt gatcgttggt    120
cccggcgccc tt                                                        132

SEQ ID NO: 192            moltype = RNA   length = 131
FEATURE                   Location/Qualifiers
source                    1..131
                          mol_type = other RNA
                          organism = synthetic construct
SEQUENCE: 192
aagggcttct gtcgtgagtg gcacacgtag ggcaactcga ttgctctgcg tgcggaatcg    60
acatcaagag atttcggaag cataattttt tggtatttgg gcagctggtg atcgttggtc   120
ccggcgccct t                                                         131

SEQ ID NO: 193            moltype = RNA   length = 130
FEATURE                   Location/Qualifiers
source                    1..130
                          mol_type = other RNA
                          organism = synthetic construct
SEQUENCE: 193
agggcttctg tcgtgagtgg cacacgtagg gcaactcgat tgctctgcgt gcggaatcga    60
catcaagaga tttcggaagc ataatttttt ggtatttggg cagctggtga tcgttggtcc   120
cggcgccctt                                                           130

SEQ ID NO: 194            moltype = RNA   length = 129
FEATURE                   Location/Qualifiers
source                    1..129
                          mol_type = other RNA
                          organism = synthetic construct
SEQUENCE: 194
gggcttctgt cgtgagtggc acacgtaggg caactcgatt gctctgcgtg cggaatcgac    60
atcaagagat ttcggaagca taattttttg gtatttgggc agctggtgat cgttggtccc   120
ggcgccctt                                                            129

SEQ ID NO: 195            moltype = RNA   length = 128
FEATURE                   Location/Qualifiers
source                    1..128
                          mol_type = other RNA
                          organism = synthetic construct
SEQUENCE: 195
ggcttctgtc gtgagtggca cacgtagggc aactcgattg ctctgcgtgc ggaatcgaca    60
tcaagagatt tcggaagcat aattttttgg tatttgggca gctggtgatc gttggtcccg   120
gcgccctt                                                             128

SEQ ID NO: 196            moltype = RNA   length = 127
FEATURE                   Location/Qualifiers
source                    1..127
                          mol_type = other RNA
                          organism = synthetic construct
SEQUENCE: 196
gcttctgtcg tgagtggcac acgtagggca actcgattgc tctgcgtgcg gaatcgacat    60
caagagattt cggaagcata attttttggt atttgggcag ctggtgatcg ttggtcccgg   120
cgccctt                                                              127

SEQ ID NO: 197            moltype = RNA   length = 126
FEATURE                   Location/Qualifiers
source                    1..126
                          mol_type = other RNA
                          organism = synthetic construct
SEQUENCE: 197
cttctgtcgt gagtggcaca cgtagggcaa ctcgattgct ctgcgtgcgg aatcgacatc    60
aagagatttc ggaagcataa ttttttggta tttgggcagc tggtgatcgt tggtcccggc   120
gccctt                                                               126

SEQ ID NO: 198            moltype = RNA   length = 125
FEATURE                   Location/Qualifiers
source                    1..125
                          mol_type = other RNA
                          organism = synthetic construct
```

```
SEQUENCE: 198
ttctgtcgtg agtggcacac gtagggcaac tcgattgctc tgcgtgcgga atcgacatca    60
agagatttcg gaagcataat tttttggtat ttgggcagct ggtgatcgtt ggtcccggcg   120
ccctt                                                               125

SEQ ID NO: 199           moltype = RNA   length = 131
FEATURE                  Location/Qualifiers
source                   1..131
                         mol_type = other RNA
                         organism = synthetic construct
SEQUENCE: 199
aaaaagggct tctgtcgtga gtggcacacg tagggcaact cgattgctct gcgtgcggaa    60
tcgacatcaa gagatttcgg aagcataatt ttttggtatt tgggcagctg gtgatcgttg   120
gtcccggcgc c                                                        131

SEQ ID NO: 200           moltype = RNA   length = 130
FEATURE                  Location/Qualifiers
source                   1..130
                         mol_type = other RNA
                         organism = synthetic construct
SEQUENCE: 200
aaaagggctt ctgtcgtgag tggcacacgt agggcaactc gattgctctg cgtgcggaat    60
cgacatcaag agatttcgga agcataattt tttggtattt gggcagctgg tgatcgttgg   120
tcccggcgcc                                                          130

SEQ ID NO: 201           moltype = RNA   length = 129
FEATURE                  Location/Qualifiers
source                   1..129
                         mol_type = other RNA
                         organism = synthetic construct
SEQUENCE: 201
aaagggcttc tgtcgtgagt ggcacacgta gggcaactcg attgctctgc gtgcggaatc    60
gacatcaaga gatttcggaa gcataatttt ttggtatttg gcagctggt gatcgttggt    120
cccggcgcc                                                           129

SEQ ID NO: 202           moltype = RNA   length = 128
FEATURE                  Location/Qualifiers
source                   1..128
                         mol_type = other RNA
                         organism = synthetic construct
SEQUENCE: 202
aagggcttct gtcgtgagtg gcacacgtag ggcaactcga ttgctctgcg tgcggaatcg    60
acatcaagag atttcggaag cataattttt tggtatttgg gcagctggtg atcgttggtc   120
ccggcgcc                                                            128

SEQ ID NO: 203           moltype = RNA   length = 127
FEATURE                  Location/Qualifiers
source                   1..127
                         mol_type = other RNA
                         organism = synthetic construct
SEQUENCE: 203
agggcttctg tcgtgagtgg cacacgtagg gcaactcgat tgctctgcgt gcggaatcga    60
catcaagaga tttcggaagc ataatttttt ggtatttggg cagctggtga tcgttggtcc   120
cggcgcc                                                             127

SEQ ID NO: 204           moltype = RNA   length = 126
FEATURE                  Location/Qualifiers
source                   1..126
                         mol_type = other RNA
                         organism = synthetic construct
SEQUENCE: 204
gggcttctgt cgtgagtggc acacgtaggg caactcgatt gctctgcgtg cggaatcgac    60
atcaagagat tcggaagca taattttttg gtatttgggc agctggtgat cgttggtccc    120
ggcgcc                                                              126

SEQ ID NO: 205           moltype = RNA   length = 125
FEATURE                  Location/Qualifiers
source                   1..125
                         mol_type = other RNA
                         organism = synthetic construct
SEQUENCE: 205
ggcttctgtc gtgagtggca cacgtagggc aactcgattg ctctgcgtgc ggaatcgaca    60
tcaagagatt tcggaagcat aattttttgg tatttgggca gctggtgatc gttggtcccg   120
gcgcc                                                               125

SEQ ID NO: 206           moltype = RNA   length = 124
FEATURE                  Location/Qualifiers
source                   1..124
                         mol_type = other RNA
```

-continued

```
                              organism = synthetic construct
SEQUENCE: 206
gcttctgtcg tgagtggcac acgtagggca actcgattgc tctgcgtgcg gaatcgacat    60
caagagattt cggaagcata attttttggt atttgggcag ctggtgatcg ttggtcccgg   120
cgcc                                                                124

SEQ ID NO: 207          moltype = RNA   length = 123
FEATURE                 Location/Qualifiers
source                  1..123
                        mol_type = other RNA
                        organism = synthetic construct
SEQUENCE: 207
cttctgtcgt gagtggcaca cgtagggcaa ctcgattgct ctgcgtgcgg aatcgacatc    60
aagagatttc ggaagcataa ttttttggta tttgggcagc tggtgatcgt tggtcccggc   120
gcc                                                                 123

SEQ ID NO: 208          moltype = RNA   length = 122
FEATURE                 Location/Qualifiers
source                  1..122
                        mol_type = other RNA
                        organism = synthetic construct
SEQUENCE: 208
ttctgtcgtg agtggcacac gtagggcaac tcgattgctc tgcgtgcgga atcgacatca    60
agagatttcg gaagcataat tttttggtat ttgggcagct ggtgatcgtt ggtcccggcg   120
cc                                                                  122

SEQ ID NO: 209          moltype = RNA   length = 11
FEATURE                 Location/Qualifiers
source                  1..11
                        mol_type = other RNA
                        organism = synthetic construct
SEQUENCE: 209
aatttttgga g                                                         11

SEQ ID NO: 210          moltype = RNA   length = 11
FEATURE                 Location/Qualifiers
source                  1..11
                        mol_type = other RNA
                        organism = synthetic construct
SEQUENCE: 210
aatttttgga g                                                         11

SEQ ID NO: 211          moltype = RNA   length = 11
FEATURE                 Location/Qualifiers
source                  1..11
                        mol_type = other RNA
                        organism = synthetic construct
SEQUENCE: 211
tatttttgga g                                                         11

SEQ ID NO: 212          moltype = RNA   length = 11
FEATURE                 Location/Qualifiers
source                  1..11
                        mol_type = other RNA
                        organism = synthetic construct
SEQUENCE: 212
gatttttgga g                                                         11

SEQ ID NO: 213          moltype = RNA   length = 11
FEATURE                 Location/Qualifiers
source                  1..11
                        mol_type = other RNA
                        organism = synthetic construct
SEQUENCE: 213
catttttgga g                                                         11

SEQ ID NO: 214          moltype = RNA   length = 11
FEATURE                 Location/Qualifiers
source                  1..11
                        mol_type = other RNA
                        organism = synthetic construct
SEQUENCE: 214
attttttgga g                                                         11

SEQ ID NO: 215          moltype = RNA   length = 11
FEATURE                 Location/Qualifiers
source                  1..11
                        mol_type = other RNA
                        organism = synthetic construct
```

-continued

```
SEQUENCE: 215
agttttttgga g                                                        11

SEQ ID NO: 216          moltype = RNA   length = 11
FEATURE                 Location/Qualifiers
source                  1..11
                        mol_type = other RNA
                        organism = synthetic construct
SEQUENCE: 216
actttttgga g                                                         11

SEQ ID NO: 217          moltype = RNA   length = 11
FEATURE                 Location/Qualifiers
source                  1..11
                        mol_type = other RNA
                        organism = synthetic construct
SEQUENCE: 217
aaattttgga g                                                         11

SEQ ID NO: 218          moltype = RNA   length = 11
FEATURE                 Location/Qualifiers
source                  1..11
                        mol_type = other RNA
                        organism = synthetic construct
SEQUENCE: 218
aagttttgga g                                                         11

SEQ ID NO: 219          moltype = RNA   length = 11
FEATURE                 Location/Qualifiers
source                  1..11
                        mol_type = other RNA
                        organism = synthetic construct
SEQUENCE: 219
aacttttgga g                                                         11

SEQ ID NO: 220          moltype = RNA   length = 11
FEATURE                 Location/Qualifiers
source                  1..11
                        mol_type = other RNA
                        organism = synthetic construct
SEQUENCE: 220
aatatttgga g                                                         11

SEQ ID NO: 221          moltype = RNA   length = 11
FEATURE                 Location/Qualifiers
source                  1..11
                        mol_type = other RNA
                        organism = synthetic construct
SEQUENCE: 221
aatgtttgga g                                                         11

SEQ ID NO: 222          moltype = RNA   length = 11
FEATURE                 Location/Qualifiers
source                  1..11
                        mol_type = other RNA
                        organism = synthetic construct
SEQUENCE: 222
aatctttgga g                                                         11

SEQ ID NO: 223          moltype = RNA   length = 11
FEATURE                 Location/Qualifiers
source                  1..11
                        mol_type = other RNA
                        organism = synthetic construct
SEQUENCE: 223
aattattgga g                                                         11

SEQ ID NO: 224          moltype = RNA   length = 11
FEATURE                 Location/Qualifiers
source                  1..11
                        mol_type = other RNA
                        organism = synthetic construct
SEQUENCE: 224
aattgttgga g                                                         11

SEQ ID NO: 225          moltype = RNA   length = 11
FEATURE                 Location/Qualifiers
source                  1..11
                        mol_type = other RNA
```

-continued

```
                                  organism = synthetic construct
SEQUENCE: 225
aattcttgga g                                                                      11

SEQ ID NO: 226          moltype = RNA   length = 11
FEATURE                 Location/Qualifiers
source                  1..11
                        mol_type = other RNA
                        organism = synthetic construct
SEQUENCE: 226
aatttatgga g                                                                      11

SEQ ID NO: 227          moltype = RNA   length = 11
FEATURE                 Location/Qualifiers
source                  1..11
                        mol_type = other RNA
                        organism = synthetic construct
SEQUENCE: 227
aatttgtgga g                                                                      11

SEQ ID NO: 228          moltype = RNA   length = 11
FEATURE                 Location/Qualifiers
source                  1..11
                        mol_type = other RNA
                        organism = synthetic construct
SEQUENCE: 228
aatttctgga g                                                                      11

SEQ ID NO: 229          moltype = RNA   length = 11
FEATURE                 Location/Qualifiers
source                  1..11
                        mol_type = other RNA
                        organism = synthetic construct
SEQUENCE: 229
aattttagga g                                                                      11

SEQ ID NO: 230          moltype = RNA   length = 11
FEATURE                 Location/Qualifiers
source                  1..11
                        mol_type = other RNA
                        organism = synthetic construct
SEQUENCE: 230
aattttggga g                                                                      11

SEQ ID NO: 231          moltype = RNA   length = 11
FEATURE                 Location/Qualifiers
source                  1..11
                        mol_type = other RNA
                        organism = synthetic construct
SEQUENCE: 231
aattttcgga g                                                                      11

SEQ ID NO: 232          moltype = RNA   length = 11
FEATURE                 Location/Qualifiers
source                  1..11
                        mol_type = other RNA
                        organism = synthetic construct
SEQUENCE: 232
aatttttaga g                                                                      11

SEQ ID NO: 233          moltype = RNA   length = 11
FEATURE                 Location/Qualifiers
source                  1..11
                        mol_type = other RNA
                        organism = synthetic construct
SEQUENCE: 233
aattttttga g                                                                      11

SEQ ID NO: 234          moltype = RNA   length = 11
FEATURE                 Location/Qualifiers
source                  1..11
                        mol_type = other RNA
                        organism = synthetic construct
SEQUENCE: 234
aatttttcga g                                                                      11

SEQ ID NO: 235          moltype = RNA   length = 11
FEATURE                 Location/Qualifiers
source                  1..11
```

-continued

```
                              mol_type = other RNA
                              organism = synthetic construct
SEQUENCE: 235
aatttttgaa g                                               11

SEQ ID NO: 236          moltype = RNA   length = 11
FEATURE                 Location/Qualifiers
source                  1..11
                        mol_type = other RNA
                        organism = synthetic construct
SEQUENCE: 236
aatttttgta g                                               11

SEQ ID NO: 237          moltype = RNA   length = 11
FEATURE                 Location/Qualifiers
source                  1..11
                        mol_type = other RNA
                        organism = synthetic construct
SEQUENCE: 237
aatttttgca g                                               11

SEQ ID NO: 238          moltype = RNA   length = 11
FEATURE                 Location/Qualifiers
source                  1..11
                        mol_type = other RNA
                        organism = synthetic construct
SEQUENCE: 238
aatttttggt g                                               11

SEQ ID NO: 239          moltype = RNA   length = 11
FEATURE                 Location/Qualifiers
source                  1..11
                        mol_type = other RNA
                        organism = synthetic construct
SEQUENCE: 239
aatttttggg g                                               11

SEQ ID NO: 240          moltype = RNA   length = 11
FEATURE                 Location/Qualifiers
source                  1..11
                        mol_type = other RNA
                        organism = synthetic construct
SEQUENCE: 240
aatttttggc g                                               11

SEQ ID NO: 241          moltype = RNA   length = 11
FEATURE                 Location/Qualifiers
source                  1..11
                        mol_type = other RNA
                        organism = synthetic construct
SEQUENCE: 241
aatttttgga a                                               11

SEQ ID NO: 242          moltype = RNA   length = 11
FEATURE                 Location/Qualifiers
source                  1..11
                        mol_type = other RNA
                        mol_type = other RNA
                        organism = synthetic construct
                        organism = synthetic construct
SEQUENCE: 242
aatttttgga t                                               11

SEQ ID NO: 243          moltype = RNA   length = 11
FEATURE                 Location/Qualifiers
source                  1..11
                        mol_type = other RNA
                        organism = synthetic construct
SEQUENCE: 243
aatttttgga c                                               11

SEQ ID NO: 244          moltype = RNA   length = 11
FEATURE                 Location/Qualifiers
source                  1..11
                        mol_type = other RNA
                        mol_type = other RNA
                        organism = synthetic construct
                        organism = synthetic construct
SEQUENCE: 244
```

-continued

```
aatgttttga g                                                     11

SEQ ID NO: 245          moltype = RNA   length = 11
FEATURE                 Location/Qualifiers
source                  1..11
                        mol_type = other RNA
                        mol_type = other RNA
                        organism = synthetic construct
                        organism = synthetic construct
SEQUENCE: 245
aatttgtgta g                                                     11

SEQ ID NO: 246          moltype = RNA   length = 11
FEATURE                 Location/Qualifiers
source                  1..11
                        mol_type = other RNA
                        mol_type = other RNA
                        organism = synthetic construct
                        organism = synthetic construct
SEQUENCE: 246
agtttttgga a                                                     11

SEQ ID NO: 247          moltype = RNA   length = 11
FEATURE                 Location/Qualifiers
source                  1..11
                        mol_type = other RNA
                        mol_type = other RNA
                        organism = synthetic construct
                        organism = synthetic construct
SEQUENCE: 247
attttgtgga g                                                     11

SEQ ID NO: 248          moltype = RNA   length = 11
FEATURE                 Location/Qualifiers
source                  1..11
                        mol_type = other RNA
                        mol_type = other RNA
                        organism = synthetic construct
                        organism = synthetic construct
SEQUENCE: 248
aatgtttgca g                                                     11

SEQ ID NO: 249          moltype = RNA   length = 11
FEATURE                 Location/Qualifiers
source                  1..11
                        mol_type = other RNA
                        mol_type = other RNA
                        organism = synthetic construct
                        organism = synthetic construct
SEQUENCE: 249
aatgttggga g                                                     11

SEQ ID NO: 250          moltype = RNA   length = 11
FEATURE                 Location/Qualifiers
source                  1..11
                        mol_type = other RNA
                        mol_type = other RNA
                        organism = synthetic construct
                        organism = synthetic construct
SEQUENCE: 250
aattgctgga g                                                     11

SEQ ID NO: 251          moltype = RNA   length = 11
FEATURE                 Location/Qualifiers
source                  1..11
                        mol_type = other RNA
                        mol_type = other RNA
                        organism = synthetic construct
                        organism = synthetic construct
SEQUENCE: 251
aattttagca g                                                     11

SEQ ID NO: 252          moltype = RNA   length = 11
FEATURE                 Location/Qualifiers
source                  1..11
                        mol_type = other RNA
                        mol_type = other RNA
                        organism = synthetic construct
                        organism = synthetic construct
```

-continued

```
SEQUENCE: 252
aaggtttgga g                                                        11

SEQ ID NO: 253           moltype = RNA   length = 11
FEATURE                  Location/Qualifiers
source                   1..11
                         mol_type = other RNA
                         mol_type = other RNA
                         organism = synthetic construct
                         organism = synthetic construct
SEQUENCE: 253
gatttgtgga g                                                        11

SEQ ID NO: 254           moltype = RNA   length = 11
FEATURE                  Location/Qualifiers
source                   1..11
                         mol_type = other RNA
                         mol_type = other RNA
                         organism = synthetic construct
                         organism = synthetic construct
SEQUENCE: 254
actttttgga a                                                        11

SEQ ID NO: 255           moltype = RNA   length = 11
FEATURE                  Location/Qualifiers
source                   1..11
                         mol_type = other RNA
                         mol_type = other RNA
                         organism = synthetic construct
                         organism = synthetic construct
SEQUENCE: 255
aaattatgga g                                                        11

SEQ ID NO: 256           moltype = RNA   length = 11
FEATURE                  Location/Qualifiers
source                   1..11
                         mol_type = other RNA
                         mol_type = other RNA
                         organism = synthetic construct
                         organism = synthetic construct
SEQUENCE: 256
aattttgcga g                                                        11

SEQ ID NO: 257           moltype = RNA   length = 11
FEATURE                  Location/Qualifiers
source                   1..11
                         mol_type = other RNA
                         mol_type = other RNA
                         organism = synthetic construct
                         organism = synthetic construct
SEQUENCE: 257
aatttctgga a                                                        11

SEQ ID NO: 258           moltype = RNA   length = 11
FEATURE                  Location/Qualifiers
source                   1..11
                         mol_type = other RNA
                         mol_type = other RNA
                         organism = synthetic construct
                         organism = synthetic construct
SEQUENCE: 258
tatttttggt g                                                        11

SEQ ID NO: 259           moltype = RNA   length = 11
FEATURE                  Location/Qualifiers
source                   1..11
                         mol_type = other RNA
                         mol_type = other RNA
                         organism = synthetic construct
                         organism = synthetic construct
SEQUENCE: 259
gatttttagga g                                                       11

SEQ ID NO: 260           moltype = RNA   length = 11
FEATURE                  Location/Qualifiers
source                   1..11
                         mol_type = other RNA
                         mol_type = other RNA
                         organism = synthetic construct
```

-continued

```
                          organism = synthetic construct
SEQUENCE: 260
aatctgtgga g                                                                  11

SEQ ID NO: 261            moltype = RNA   length = 11
FEATURE                   Location/Qualifiers
source                    1..11
                          mol_type = other RNA
                          mol_type = other RNA
                          organism = synthetic construct
                          organism = synthetic construct
SEQUENCE: 261
aaattttaga g                                                                  11

SEQ ID NO: 262            moltype = RNA   length = 11
FEATURE                   Location/Qualifiers
source                    1..11
                          mol_type = other RNA
                          mol_type = other RNA
                          organism = synthetic construct
                          organism = synthetic construct
SEQUENCE: 262
aatttttcga c                                                                  11

SEQ ID NO: 263            moltype = RNA   length = 11
FEATURE                   Location/Qualifiers
source                    1..11
                          mol_type = other RNA
                          mol_type = other RNA
                          organism = synthetic construct
                          organism = synthetic construct
SEQUENCE: 263
aatttttggg t                                                                  11

SEQ ID NO: 264            moltype = RNA   length = 11
FEATURE                   Location/Qualifiers
source                    1..11
                          mol_type = other RNA
                          mol_type = other RNA
                          organism = synthetic construct
                          organism = synthetic construct
SEQUENCE: 264
aatctttgga a                                                                  11

SEQ ID NO: 265            moltype = RNA   length = 11
FEATURE                   Location/Qualifiers
source                    1..11
                          mol_type = other RNA
                          mol_type = other RNA
                          organism = synthetic construct
                          organism = synthetic construct
SEQUENCE: 265
aattattggt g                                                                  11

SEQ ID NO: 266            moltype = RNA   length = 11
FEATURE                   Location/Qualifiers
source                    1..11
                          mol_type = other RNA
                          mol_type = other RNA
                          organism = synthetic construct
                          organism = synthetic construct
SEQUENCE: 266
aattttaaga g                                                                  11

SEQ ID NO: 267            moltype = RNA   length = 11
FEATURE                   Location/Qualifiers
source                    1..11
                          mol_type = other RNA
                          mol_type = other RNA
                          organism = synthetic construct
                          organism = synthetic construct
SEQUENCE: 267
aatgttagga g                                                                  11

SEQ ID NO: 268            moltype = RNA   length = 11
FEATURE                   Location/Qualifiers
source                    1..11
                          mol_type = other RNA
                          mol_type = other RNA
```

-continued

```
                            organism = synthetic construct
                            organism = synthetic construct
SEQUENCE: 268
aattttagaa g                                                    11

SEQ ID NO: 269             moltype = RNA   length = 11
FEATURE                    Location/Qualifiers
source                     1..11
                           mol_type = other RNA
                           mol_type = other RNA
                           organism = synthetic construct
                           organism = synthetic construct
SEQUENCE: 269
attttttggc g                                                    11

SEQ ID NO: 270             moltype = RNA   length = 11
FEATURE                    Location/Qualifiers
source                     1..11
                           mol_type = other RNA
                           mol_type = other RNA
                           organism = synthetic construct
                           organism = synthetic construct
SEQUENCE: 270
aacttttggt g                                                    11

SEQ ID NO: 271             moltype = RNA   length = 11
FEATURE                    Location/Qualifiers
source                     1..11
                           mol_type = other RNA
                           mol_type = other RNA
                           organism = synthetic construct
                           organism = synthetic construct
SEQUENCE: 271
aatgtttgga t                                                    11

SEQ ID NO: 272             moltype = RNA   length = 11
FEATURE                    Location/Qualifiers
source                     1..11
                           mol_type = other RNA
                           mol_type = other RNA
                           organism = synthetic construct
                           organism = synthetic construct
SEQUENCE: 272
aattttagga t                                                    11

SEQ ID NO: 273             moltype = RNA   length = 11
FEATURE                    Location/Qualifiers
source                     1..11
                           mol_type = other RNA
                           mol_type = other RNA
                           organism = synthetic construct
                           organism = synthetic construct
SEQUENCE: 273
aattttgat g                                                     11

SEQ ID NO: 274             moltype = RNA   length = 11
FEATURE                    Location/Qualifiers
source                     1..11
                           mol_type = other RNA
                           mol_type = other RNA
                           organism = synthetic construct
                           organism = synthetic construct
SEQUENCE: 274
aattcttggt g                                                    11

SEQ ID NO: 275             moltype = RNA   length = 11
FEATURE                    Location/Qualifiers
source                     1..11
                           mol_type = other RNA
                           mol_type = other RNA
                           organism = synthetic construct
                           organism = synthetic construct
SEQUENCE: 275
aatccttgga g                                                    11

SEQ ID NO: 276             moltype = RNA   length = 11
FEATURE                    Location/Qualifiers
source                     1..11
                           mol_type = other RNA
```

-continued

```
                              mol_type = other RNA
                              organism = synthetic construct
                              organism = synthetic construct
SEQUENCE: 276
aatttttcaa g                                                                        11

SEQ ID NO: 277          moltype = RNA   length = 11
FEATURE                 Location/Qualifiers
source                  1..11
                        mol_type = other RNA
                        mol_type = other RNA
                        organism = synthetic construct
                        organism = synthetic construct
SEQUENCE: 277
catttttgca g                                                                        11

SEQ ID NO: 278          moltype = RNA   length = 11
FEATURE                 Location/Qualifiers
source                  1..11
                        mol_type = other RNA
                        mol_type = other RNA
                        organism = synthetic construct
                        organism = synthetic construct
SEQUENCE: 278
catttttcga g                                                                        11

SEQ ID NO: 279          moltype = RNA   length = 11
FEATURE                 Location/Qualifiers
source                  1..11
                        mol_type = other RNA
                        mol_type = other RNA
                        organism = synthetic construct
                        organism = synthetic construct
SEQUENCE: 279
aattttgggc g                                                                        11

SEQ ID NO: 280          moltype = RNA   length = 11
FEATURE                 Location/Qualifiers
source                  1..11
                        mol_type = other RNA
                        mol_type = other RNA
                        organism = synthetic construct
                        organism = synthetic construct
SEQUENCE: 280
agtttttgca g                                                                        11

SEQ ID NO: 281          moltype = RNA   length = 11
FEATURE                 Location/Qualifiers
source                  1..11
                        mol_type = other RNA
                        mol_type = other RNA
                        organism = synthetic construct
                        organism = synthetic construct
SEQUENCE: 281
aaaatttgga g                                                                        11

SEQ ID NO: 282          moltype = RNA   length = 11
FEATURE                 Location/Qualifiers
source                  1..11
                        mol_type = other RNA
                        mol_type = other RNA
                        organism = synthetic construct
                        organism = synthetic construct
SEQUENCE: 282
aactcttgga g                                                                        11

SEQ ID NO: 283          moltype = RNA   length = 11
FEATURE                 Location/Qualifiers
source                  1..11
                        mol_type = other RNA
                        mol_type = other RNA
                        organism = synthetic construct
                        organism = synthetic construct
SEQUENCE: 283
aatttgtgga c                                                                        11

SEQ ID NO: 284          moltype = RNA   length = 11
FEATURE                 Location/Qualifiers
source                  1..11
```

-continued

```
                         mol_type = other RNA
                         mol_type = other RNA
                         organism = synthetic construct
                         organism = synthetic construct
SEQUENCE: 284
acttttttggt g                                                            11

SEQ ID NO: 285           moltype = RNA   length = 11
FEATURE                  Location/Qualifiers
source                   1..11
                         mol_type = other RNA
                         mol_type = other RNA
                         organism = synthetic construct
                         organism = synthetic construct
SEQUENCE: 285
atttttttgaa g                                                            11

SEQ ID NO: 286           moltype = RNA   length = 11
FEATURE                  Location/Qualifiers
source                   1..11
                         mol_type = other RNA
                         mol_type = other RNA
                         organism = synthetic construct
                         organism = synthetic construct
SEQUENCE: 286
atttttttgga a                                                            11

SEQ ID NO: 287           moltype = RNA   length = 11
FEATURE                  Location/Qualifiers
source                   1..11
                         mol_type = other RNA
                         mol_type = other RNA
                         organism = synthetic construct
                         organism = synthetic construct
SEQUENCE: 287
aagttatgga g                                                             11

SEQ ID NO: 288           moltype = RNA   length = 11
FEATURE                  Location/Qualifiers
source                   1..11
                         mol_type = other RNA
                         mol_type = other RNA
                         organism = synthetic construct
                         organism = synthetic construct
SEQUENCE: 288
catttctgga g                                                             11

SEQ ID NO: 289           moltype = RNA   length = 11
FEATURE                  Location/Qualifiers
source                   1..11
                         mol_type = other RNA
                         mol_type = other RNA
                         organism = synthetic construct
                         organism = synthetic construct
SEQUENCE: 289
agttcttgga g                                                             11

SEQ ID NO: 290           moltype = RNA   length = 11
FEATURE                  Location/Qualifiers
source                   1..11
                         mol_type = other RNA
                         mol_type = other RNA
                         organism = synthetic construct
                         organism = synthetic construct
SEQUENCE: 290
aattttggaa g                                                             11

SEQ ID NO: 291           moltype = RNA   length = 11
FEATURE                  Location/Qualifiers
source                   1..11
                         mol_type = other RNA
                         mol_type = other RNA
                         organism = synthetic construct
                         organism = synthetic construct
SEQUENCE: 291
agtatttgga g                                                             11

SEQ ID NO: 292           moltype = RNA   length = 11
FEATURE                  Location/Qualifiers
```

-continued

```
source                  1..11
                        mol_type = other RNA
                        mol_type = other RNA
                        organism = synthetic construct
                        organism = synthetic construct
SEQUENCE: 292
aatttttggg c                                                                       11

SEQ ID NO: 293          moltype = RNA   length = 11
FEATURE                 Location/Qualifiers
source                  1..11
                        mol_type = other RNA
                        mol_type = other RNA
                        organism = synthetic construct
                        organism = synthetic construct
SEQUENCE: 293
aattcttgta g                                                                       11

SEQ ID NO: 294          moltype = RNA   length = 11
FEATURE                 Location/Qualifiers
source                  1..11
                        mol_type = other RNA
                        mol_type = other RNA
                        organism = synthetic construct
                        organism = synthetic construct
SEQUENCE: 294
aattttggga a                                                                       11

SEQ ID NO: 295          moltype = RNA   length = 11
FEATURE                 Location/Qualifiers
source                  1..11
                        mol_type = other RNA
                        mol_type = other RNA
                        organism = synthetic construct
                        organism = synthetic construct
SEQUENCE: 295
tatttttga g                                                                        11

SEQ ID NO: 296          moltype = RNA   length = 11
FEATURE                 Location/Qualifiers
source                  1..11
                        mol_type = other RNA
                        mol_type = other RNA
                        organism = synthetic construct
                        organism = synthetic construct
SEQUENCE: 296
aacttttgta g                                                                       11

SEQ ID NO: 297          moltype = RNA   length = 11
FEATURE                 Location/Qualifiers
source                  1..11
                        mol_type = other RNA
                        mol_type = other RNA
                        organism = synthetic construct
                        organism = synthetic construct
SEQUENCE: 297
aattattgca g                                                                       11

SEQ ID NO: 298          moltype = RNA   length = 11
FEATURE                 Location/Qualifiers
source                  1..11
                        mol_type = other RNA
                        mol_type = other RNA
                        organism = synthetic construct
                        organism = synthetic construct
SEQUENCE: 298
aattttggt a                                                                        11

SEQ ID NO: 299          moltype = RNA   length = 11
FEATURE                 Location/Qualifiers
source                  1..11
                        mol_type = other RNA
                        mol_type = other RNA
                        organism = synthetic construct
                        organism = synthetic construct
SEQUENCE: 299
aattttcgaa g                                                                       11

SEQ ID NO: 300          moltype = RNA   length = 11
```

-continued

```
FEATURE                 Location/Qualifiers
source                  1..11
                        mol_type = other RNA
                        mol_type = other RNA
                        organism = synthetic construct
                        organism = synthetic construct
SEQUENCE: 300
tatctttgga g                                                        11

SEQ ID NO: 301          moltype = RNA  length = 11
FEATURE                 Location/Qualifiers
source                  1..11
                        mol_type = other RNA
                        mol_type = other RNA
                        organism = synthetic construct
                        organism = synthetic construct
SEQUENCE: 301
aatttttcgt g                                                        11

SEQ ID NO: 302          moltype = RNA  length = 11
FEATURE                 Location/Qualifiers
source                  1..11
                        mol_type = other RNA
                        mol_type = other RNA
                        organism = synthetic construct
                        organism = synthetic construct
SEQUENCE: 302
aatctttggc g                                                        11

SEQ ID NO: 303          moltype = RNA  length = 11
FEATURE                 Location/Qualifiers
source                  1..11
                        mol_type = other RNA
                        mol_type = other RNA
                        organism = synthetic construct
                        organism = synthetic construct
SEQUENCE: 303
gatttatgga g                                                        11

SEQ ID NO: 304          moltype = RNA  length = 11
FEATURE                 Location/Qualifiers
source                  1..11
                        mol_type = other RNA
                        mol_type = other RNA
                        organism = synthetic construct
                        organism = synthetic construct
SEQUENCE: 304
aatttttcga a                                                        11

SEQ ID NO: 305          moltype = RNA  length = 11
FEATURE                 Location/Qualifiers
source                  1..11
                        mol_type = other RNA
                        mol_type = other RNA
                        organism = synthetic construct
                        organism = synthetic construct
SEQUENCE: 305
cctttttgga g                                                        11

SEQ ID NO: 306          moltype = RNA  length = 11
FEATURE                 Location/Qualifiers
source                  1..11
                        mol_type = other RNA
                        mol_type = other RNA
                        organism = synthetic construct
                        organism = synthetic construct
SEQUENCE: 306
tattttttgaa g                                                       11

SEQ ID NO: 307          moltype = RNA  length = 11
FEATURE                 Location/Qualifiers
source                  1..11
                        mol_type = other RNA
                        mol_type = other RNA
                        organism = synthetic construct
                        organism = synthetic construct
SEQUENCE: 307
aatttttgta a                                                        11
```

-continued

```
SEQ ID NO: 308          moltype = RNA   length = 11
FEATURE                 Location/Qualifiers
source                  1..11
                        mol_type = other RNA
                        mol_type = other RNA
                        organism = synthetic construct
                        organism = synthetic construct
SEQUENCE: 308
aattttgaga g                                                        11

SEQ ID NO: 309          moltype = RNA   length = 11
FEATURE                 Location/Qualifiers
source                  1..11
                        mol_type = other RNA
                        mol_type = other RNA
                        organism = synthetic construct
                        organism = synthetic construct
SEQUENCE: 309
aagtattgga g                                                        11

SEQ ID NO: 310          moltype = RNA   length = 11
FEATURE                 Location/Qualifiers
source                  1..11
                        mol_type = other RNA
                        mol_type = other RNA
                        organism = synthetic construct
                        organism = synthetic construct
SEQUENCE: 310
aattttagga c                                                        11

SEQ ID NO: 311          moltype = RNA   length = 11
FEATURE                 Location/Qualifiers
source                  1..11
                        mol_type = other RNA
                        mol_type = other RNA
                        organism = synthetic construct
                        organism = synthetic construct
SEQUENCE: 311
aatttttaaa g                                                        11

SEQ ID NO: 312          moltype = RNA   length = 11
FEATURE                 Location/Qualifiers
source                  1..11
                        mol_type = other RNA
                        mol_type = other RNA
                        organism = synthetic construct
                        organism = synthetic construct
SEQUENCE: 312
aattcttgga t                                                        11

SEQ ID NO: 313          moltype = RNA   length = 11
FEATURE                 Location/Qualifiers
source                  1..11
                        mol_type = other RNA
                        mol_type = other RNA
                        organism = synthetic construct
                        organism = synthetic construct
SEQUENCE: 313
aatttgtggt g                                                        11

SEQ ID NO: 314          moltype = RNA   length = 11
FEATURE                 Location/Qualifiers
source                  1..11
                        mol_type = other RNA
                        mol_type = other RNA
                        organism = synthetic construct
                        organism = synthetic construct
SEQUENCE: 314
aattttcggg g                                                        11

SEQ ID NO: 315          moltype = RNA   length = 11
FEATURE                 Location/Qualifiers
source                  1..11
                        mol_type = other RNA
                        mol_type = other RNA
                        organism = synthetic construct
                        organism = synthetic construct
SEQUENCE: 315
acttttttga g                                                        11
```

```
SEQ ID NO: 316        moltype = RNA  length = 11
FEATURE               Location/Qualifiers
source                1..11
                      mol_type = other RNA
                      mol_type = other RNA
                      organism = synthetic construct
                      organism = synthetic construct
SEQUENCE: 316
aagtttcgga g                                              11

SEQ ID NO: 317        moltype = RNA  length = 11
FEATURE               Location/Qualifiers
source                1..11
                      mol_type = other RNA
                      mol_type = other RNA
                      organism = synthetic construct
                      organism = synthetic construct
SEQUENCE: 317
acttttggga g                                             11

SEQ ID NO: 318        moltype = RNA  length = 11
FEATURE               Location/Qualifiers
source                1..11
                      mol_type = other RNA
                      mol_type = other RNA
                      organism = synthetic construct
                      organism = synthetic construct
SEQUENCE: 318
gacttttgga g                                             11

SEQ ID NO: 319        moltype = RNA  length = 11
FEATURE               Location/Qualifiers
source                1..11
                      mol_type = other RNA
                      mol_type = other RNA
                      organism = synthetic construct
                      organism = synthetic construct
SEQUENCE: 319
cttttttgga g                                             11

SEQ ID NO: 320        moltype = RNA  length = 11
FEATURE               Location/Qualifiers
source                1..11
                      mol_type = other RNA
                      mol_type = other RNA
                      organism = synthetic construct
                      organism = synthetic construct
SEQUENCE: 320
cattgttgga g                                             11

SEQ ID NO: 321        moltype = RNA  length = 11
FEATURE               Location/Qualifiers
source                1..11
                      mol_type = other RNA
                      mol_type = other RNA
                      organism = synthetic construct
                      organism = synthetic construct
SEQUENCE: 321
aatattttga g                                             11

SEQ ID NO: 322        moltype = RNA  length = 11
FEATURE               Location/Qualifiers
source                1..11
                      mol_type = other RNA
                      mol_type = other RNA
                      organism = synthetic construct
                      organism = synthetic construct
SEQUENCE: 322
aagttttggc g                                             11

SEQ ID NO: 323        moltype = RNA  length = 11
FEATURE               Location/Qualifiers
source                1..11
                      mol_type = other RNA
                      mol_type = other RNA
                      organism = synthetic construct
                      organism = synthetic construct
SEQUENCE: 323
```

-continued

```
aattttagga a                                                11

SEQ ID NO: 324       moltype = RNA   length = 11
FEATURE              Location/Qualifiers
source               1..11
                     mol_type = other RNA
                     mol_type = other RNA
                     organism = synthetic construct
                     organism = synthetic construct
SEQUENCE: 324
aacttgtgga g                                                11

SEQ ID NO: 325       moltype = RNA   length = 11
FEATURE              Location/Qualifiers
source               1..11
                     mol_type = other RNA
                     mol_type = other RNA
                     organism = synthetic construct
                     organism = synthetic construct
SEQUENCE: 325
atttttgggg g                                                11

SEQ ID NO: 326       moltype = RNA   length = 11
FEATURE              Location/Qualifiers
source               1..11
                     mol_type = other RNA
                     mol_type = other RNA
                     organism = synthetic construct
                     organism = synthetic construct
SEQUENCE: 326
aattttaga t                                                 11

SEQ ID NO: 327       moltype = RNA   length = 11
FEATURE              Location/Qualifiers
source               1..11
                     mol_type = other RNA
                     mol_type = other RNA
                     organism = synthetic construct
                     organism = synthetic construct
SEQUENCE: 327
tattttggga g                                                11

SEQ ID NO: 328       moltype = RNA   length = 11
FEATURE              Location/Qualifiers
source               1..11
                     mol_type = other RNA
                     mol_type = other RNA
                     organism = synthetic construct
                     organism = synthetic construct
SEQUENCE: 328
aatttgtggg g                                                11

SEQ ID NO: 329       moltype = RNA   length = 11
FEATURE              Location/Qualifiers
source               1..11
                     mol_type = other RNA
                     mol_type = other RNA
                     organism = synthetic construct
                     organism = synthetic construct
SEQUENCE: 329
aattttagg g                                                 11

SEQ ID NO: 330       moltype = RNA   length = 11
FEATURE              Location/Qualifiers
source               1..11
                     mol_type = other RNA
                     mol_type = other RNA
                     organism = synthetic construct
                     organism = synthetic construct
SEQUENCE: 330
aattttcgta g                                                11

SEQ ID NO: 331       moltype = RNA   length = 11
FEATURE              Location/Qualifiers
source               1..11
                     mol_type = other RNA
                     mol_type = other RNA
                     organism = synthetic construct
                     organism = synthetic construct
```

-continued

```
SEQUENCE: 331
aattttctga g                                                            11

SEQ ID NO: 332        moltype = RNA   length = 11
FEATURE               Location/Qualifiers
source                1..11
                      mol_type = other RNA
                      mol_type = other RNA
                      organism = synthetic construct
                      organism = synthetic construct
SEQUENCE: 332
gattcttgga g                                                            11

SEQ ID NO: 333        moltype = RNA   length = 11
FEATURE               Location/Qualifiers
source                1..11
                      mol_type = other RNA
                      mol_type = other RNA
                      organism = synthetic construct
                      organism = synthetic construct
SEQUENCE: 333
aatctttgga t                                                            11

SEQ ID NO: 334        moltype = RNA   length = 11
FEATURE               Location/Qualifiers
source                1..11
                      mol_type = other RNA
                      mol_type = other RNA
                      organism = synthetic construct
                      organism = synthetic construct
SEQUENCE: 334
aaattttggc g                                                            11

SEQ ID NO: 335        moltype = RNA   length = 11
FEATURE               Location/Qualifiers
source                1..11
                      mol_type = other RNA
                      mol_type = other RNA
                      organism = synthetic construct
                      organism = synthetic construct
SEQUENCE: 335
aatcattgga g                                                            11

SEQ ID NO: 336        moltype = RNA   length = 11
FEATURE               Location/Qualifiers
source                1..11
                      mol_type = other RNA
                      mol_type = other RNA
                      organism = synthetic construct
                      organism = synthetic construct
SEQUENCE: 336
aacttttggc g                                                            11

SEQ ID NO: 337        moltype = RNA   length = 11
FEATURE               Location/Qualifiers
source                1..11
                      mol_type = other RNA
                      mol_type = other RNA
                      organism = synthetic construct
                      organism = synthetic construct
SEQUENCE: 337
aatttttggg a                                                            11

SEQ ID NO: 338        moltype = RNA   length = 11
FEATURE               Location/Qualifiers
source                1..11
                      mol_type = other RNA
                      mol_type = other RNA
                      organism = synthetic construct
                      organism = synthetic construct
SEQUENCE: 338
aatgtttggt g                                                            11

SEQ ID NO: 339        moltype = RNA   length = 11
FEATURE               Location/Qualifiers
source                1..11
                      mol_type = other RNA
                      mol_type = other RNA
                      organism = synthetic construct
```

-continued

```
                           organism = synthetic construct
SEQUENCE: 339
aatttatgca g                                                        11

SEQ ID NO: 340             moltype = RNA  length = 11
FEATURE                    Location/Qualifiers
source                     1..11
                           mol_type = other RNA
                           mol_type = other RNA
                           organism = synthetic construct
                           organism = synthetic construct
SEQUENCE: 340
aatctctgga g                                                        11

SEQ ID NO: 341             moltype = RNA  length = 11
FEATURE                    Location/Qualifiers
source                     1..11
                           mol_type = other RNA
                           mol_type = other RNA
                           organism = synthetic construct
                           organism = synthetic construct
SEQUENCE: 341
agtttgtgga g                                                        11

SEQ ID NO: 342             moltype = RNA  length = 11
FEATURE                    Location/Qualifiers
source                     1..11
                           mol_type = other RNA
                           mol_type = other RNA
                           organism = synthetic construct
                           organism = synthetic construct
SEQUENCE: 342
aagttttgga t                                                        11

SEQ ID NO: 343             moltype = RNA  length = 11
FEATURE                    Location/Qualifiers
source                     1..11
                           mol_type = other RNA
                           mol_type = other RNA
                           organism = synthetic construct
                           organism = synthetic construct
SEQUENCE: 343
tatttttggc g                                                        11

SEQ ID NO: 344             moltype = RNA  length = 11
FEATURE                    Location/Qualifiers
source                     1..11
                           mol_type = other RNA
                           mol_type = other RNA
                           organism = synthetic construct
                           organism = synthetic construct
SEQUENCE: 344
aatttctgaa g                                                        11

SEQ ID NO: 345             moltype = RNA  length = 11
FEATURE                    Location/Qualifiers
source                     1..11
                           mol_type = other RNA
                           mol_type = other RNA
                           organism = synthetic construct
                           organism = synthetic construct
SEQUENCE: 345
tatttctgga g                                                        11

SEQ ID NO: 346             moltype = RNA  length = 11
FEATURE                    Location/Qualifiers
source                     1..11
                           mol_type = other RNA
                           mol_type = other RNA
                           organism = synthetic construct
                           organism = synthetic construct
SEQUENCE: 346
aatttttgct g                                                        11

SEQ ID NO: 347             moltype = RNA  length = 11
FEATURE                    Location/Qualifiers
source                     1..11
                           mol_type = other RNA
                           mol_type = other RNA
```

-continued

```
                             organism = synthetic construct
                             organism = synthetic construct
SEQUENCE: 347
aaatcttgga g                                                              11

SEQ ID NO: 348              moltype = RNA   length = 11
FEATURE                     Location/Qualifiers
source                      1..11
                            mol_type = other RNA
                            mol_type = other RNA
                            organism = synthetic construct
                            organism = synthetic construct
SEQUENCE: 348
aaatttttga g                                                              11

SEQ ID NO: 349              moltype = RNA   length = 11
FEATURE                     Location/Qualifiers
source                      1..11
                            mol_type = other RNA
                            mol_type = other RNA
                            organism = synthetic construct
                            organism = synthetic construct
SEQUENCE: 349
tatttttgta g                                                              11

SEQ ID NO: 350              moltype = RNA   length = 11
FEATURE                     Location/Qualifiers
source                      1..11
                            mol_type = other RNA
                            mol_type = other RNA
                            organism = synthetic construct
                            organism = synthetic construct
SEQUENCE: 350
gattattgga g                                                              11

SEQ ID NO: 351              moltype = RNA   length = 11
FEATURE                     Location/Qualifiers
source                      1..11
                            mol_type = other RNA
                            mol_type = other RNA
                            organism = synthetic construct
                            organism = synthetic construct
SEQUENCE: 351
aagttctgga g                                                              11

SEQ ID NO: 352              moltype = RNA   length = 11
FEATURE                     Location/Qualifiers
source                      1..11
                            mol_type = other RNA
                            mol_type = other RNA
                            organism = synthetic construct
                            organism = synthetic construct
SEQUENCE: 352
aatctttgaa g                                                              11

SEQ ID NO: 353              moltype = RNA   length = 11
FEATURE                     Location/Qualifiers
source                      1..11
                            mol_type = other RNA
                            mol_type = other RNA
                            organism = synthetic construct
                            organism = synthetic construct
SEQUENCE: 353
aaatattgga g                                                              11

SEQ ID NO: 354              moltype = RNA   length = 11
FEATURE                     Location/Qualifiers
source                      1..11
                            mol_type = other RNA
                            mol_type = other RNA
                            organism = synthetic construct
                            organism = synthetic construct
SEQUENCE: 354
aactattgga g                                                              11

SEQ ID NO: 355              moltype = RNA   length = 11
FEATURE                     Location/Qualifiers
source                      1..11
                            mol_type = other RNA
```

```
                              mol_type = other RNA
                              organism = synthetic construct
                              organism = synthetic construct
SEQUENCE: 355
aatatatgga g                                                                11

SEQ ID NO: 356               moltype = RNA   length = 11
FEATURE                      Location/Qualifiers
source                       1..11
                             mol_type = other RNA
                             mol_type = other RNA
                             organism = synthetic construct
                             organism = synthetic construct
SEQUENCE: 356
attctttgga g                                                                11

SEQ ID NO: 357               moltype = RNA   length = 11
FEATURE                      Location/Qualifiers
source                       1..11
                             mol_type = other RNA
                             mol_type = other RNA
                             organism = synthetic construct
                             organism = synthetic construct
SEQUENCE: 357
gatttttgaa g                                                                11

SEQ ID NO: 358               moltype = RNA   length = 11
FEATURE                      Location/Qualifiers
source                       1..11
                             mol_type = other RNA
                             mol_type = other RNA
                             organism = synthetic construct
                             organism = synthetic construct
SEQUENCE: 358
aagttttggt g                                                                11

SEQ ID NO: 359               moltype = RNA   length = 11
FEATURE                      Location/Qualifiers
source                       1..11
                             mol_type = other RNA
                             mol_type = other RNA
                             organism = synthetic construct
                             organism = synthetic construct
SEQUENCE: 359
aatctttgca g                                                                11

SEQ ID NO: 360               moltype = RNA   length = 11
FEATURE                      Location/Qualifiers
source                       1..11
                             mol_type = other RNA
                             mol_type = other RNA
                             organism = synthetic construct
                             organism = synthetic construct
SEQUENCE: 360
acttttggc g                                                                 11

SEQ ID NO: 361               moltype = RNA   length = 11
FEATURE                      Location/Qualifiers
source                       1..11
                             mol_type = other RNA
                             mol_type = other RNA
                             organism = synthetic construct
                             organism = synthetic construct
SEQUENCE: 361
gattttggga g                                                                11

SEQ ID NO: 362               moltype = RNA   length = 11
FEATURE                      Location/Qualifiers
source                       1..11
                             mol_type = other RNA
                             mol_type = other RNA
                             organism = synthetic construct
                             organism = synthetic construct
SEQUENCE: 362
cattttgga a                                                                 11

SEQ ID NO: 363               moltype = RNA   length = 11
FEATURE                      Location/Qualifiers
source                       1..11
```

-continued

```
                           mol_type = other RNA
                           mol_type = other RNA
                           organism = synthetic construct
                           organism = synthetic construct
SEQUENCE: 363
aattttttga c                                                            11

SEQ ID NO: 364            moltype = RNA  length = 11
FEATURE                   Location/Qualifiers
source                    1..11
                           mol_type = other RNA
                           mol_type = other RNA
                           organism = synthetic construct
                           organism = synthetic construct
SEQUENCE: 364
aaattttgca g                                                            11

SEQ ID NO: 365            moltype = RNA  length = 11
FEATURE                   Location/Qualifiers
source                    1..11
                           mol_type = other RNA
                           mol_type = other RNA
                           organism = synthetic construct
                           organism = synthetic construct
SEQUENCE: 365
actttttgaa g                                                            11

SEQ ID NO: 366            moltype = RNA  length = 11
FEATURE                   Location/Qualifiers
source                    1..11
                           mol_type = other RNA
                           mol_type = other RNA
                           organism = synthetic construct
                           organism = synthetic construct
SEQUENCE: 366
agtctttgga g                                                            11

SEQ ID NO: 367            moltype = RNA  length = 11
FEATURE                   Location/Qualifiers
source                    1..11
                           mol_type = other RNA
                           mol_type = other RNA
                           organism = synthetic construct
                           organism = synthetic construct
SEQUENCE: 367
agtttatgga g                                                            11

SEQ ID NO: 368            moltype = RNA  length = 11
FEATURE                   Location/Qualifiers
source                    1..11
                           mol_type = other RNA
                           mol_type = other RNA
                           organism = synthetic construct
                           organism = synthetic construct
SEQUENCE: 368
acttcttgga g                                                            11

SEQ ID NO: 369            moltype = RNA  length = 11
FEATURE                   Location/Qualifiers
source                    1..11
                           mol_type = other RNA
                           mol_type = other RNA
                           organism = synthetic construct
                           organism = synthetic construct
SEQUENCE: 369
aattttttca g                                                            11

SEQ ID NO: 370            moltype = RNA  length = 11
FEATURE                   Location/Qualifiers
source                    1..11
                           mol_type = other RNA
                           mol_type = other RNA
                           organism = synthetic construct
                           organism = synthetic construct
SEQUENCE: 370
aattttcgga t                                                            11

SEQ ID NO: 371            moltype = RNA  length = 11
FEATURE                   Location/Qualifiers
```

-continued

```
source                    1..11
                          mol_type = other RNA
                          mol_type = other RNA
                          organism = synthetic construct
                          organism = synthetic construct
SEQUENCE: 371
aatttttgta t                                                                    11

SEQ ID NO: 372            moltype = RNA   length = 11
FEATURE                   Location/Qualifiers
source                    1..11
                          mol_type = other RNA
                          organism = synthetic construct
SEQUENCE: 372
aatgtctgga g                                                                    11

SEQ ID NO: 373            moltype = RNA   length = 11
FEATURE                   Location/Qualifiers
source                    1..11
                          mol_type = other RNA
                          mol_type = other RNA
                          organism = synthetic construct
                          organism = synthetic construct
SEQUENCE: 373
aattgttggg g                                                                    11

SEQ ID NO: 374            moltype = RNA   length = 11
FEATURE                   Location/Qualifiers
source                    1..11
                          mol_type = other RNA
                          mol_type = other RNA
                          organism = synthetic construct
                          organism = synthetic construct
SEQUENCE: 374
aatttatgga c                                                                    11

SEQ ID NO: 375            moltype = RNA   length = 11
FEATURE                   Location/Qualifiers
source                    1..11
                          mol_type = other RNA
                          mol_type = other RNA
                          organism = synthetic construct
                          organism = synthetic construct
SEQUENCE: 375
aatttatgaa g                                                                    11

SEQ ID NO: 376            moltype = RNA   length = 11
FEATURE                   Location/Qualifiers
source                    1..11
                          mol_type = other RNA
                          mol_type = other RNA
                          organism = synthetic construct
                          organism = synthetic construct
SEQUENCE: 376
aatttatggg g                                                                    11

SEQ ID NO: 377            moltype = RNA   length = 11
FEATURE                   Location/Qualifiers
source                    1..11
                          mol_type = other RNA
                          mol_type = other RNA
                          organism = synthetic construct
                          organism = synthetic construct
SEQUENCE: 377
aatttgtcga g                                                                    11

SEQ ID NO: 378            moltype = RNA   length = 11
FEATURE                   Location/Qualifiers
source                    1..11
                          mol_type = other RNA
                          mol_type = other RNA
                          organism = synthetic construct
                          organism = synthetic construct
SEQUENCE: 378
aattgttgga a                                                                    11

SEQ ID NO: 379            moltype = RNA   length = 11
FEATURE                   Location/Qualifiers
source                    1..11
```

-continued

```
                        mol_type = other RNA
                        mol_type = other RNA
                        organism = synthetic construct
                        organism = synthetic construct
SEQUENCE: 379
tgttttttgga g                                                        11

SEQ ID NO: 380         moltype = RNA   length = 11
FEATURE                Location/Qualifiers
source                 1..11
                        mol_type = other RNA
                        mol_type = other RNA
                        organism = synthetic construct
                        organism = synthetic construct
SEQUENCE: 380
aaatttagga g                                                         11

SEQ ID NO: 381         moltype = RNA   length = 11
FEATURE                Location/Qualifiers
source                 1..11
                        mol_type = other RNA
                        mol_type = other RNA
                        organism = synthetic construct
                        organism = synthetic construct
SEQUENCE: 381
aattttttgt g                                                         11

SEQ ID NO: 382         moltype = RNA   length = 11
FEATURE                Location/Qualifiers
source                 1..11
                        mol_type = other RNA
                        mol_type = other RNA
                        organism = synthetic construct
                        organism = synthetic construct
SEQUENCE: 382
cattcttgga g                                                         11

SEQ ID NO: 383         moltype = RNA   length = 11
FEATURE                Location/Qualifiers
source                 1..11
                        mol_type = other RNA
                        mol_type = other RNA
                        organism = synthetic construct
                        organism = synthetic construct
SEQUENCE: 383
aattctcgga g                                                         11

SEQ ID NO: 384         moltype = RNA   length = 11
FEATURE                Location/Qualifiers
source                 1..11
                        mol_type = other RNA
                        mol_type = other RNA
                        organism = synthetic construct
                        organism = synthetic construct
SEQUENCE: 384
aatttttata g                                                         11

SEQ ID NO: 385         moltype = RNA   length = 11
FEATURE                Location/Qualifiers
source                 1..11
                        mol_type = other RNA
                        mol_type = other RNA
                        organism = synthetic construct
                        organism = synthetic construct
SEQUENCE: 385
actttttaga g                                                         11

SEQ ID NO: 386         moltype = RNA   length = 11
FEATURE                Location/Qualifiers
source                 1..11
                        mol_type = other RNA
                        mol_type = other RNA
                        organism = synthetic construct
                        organism = synthetic construct
SEQUENCE: 386
aattgttaga g                                                         11

SEQ ID NO: 387         moltype = RNA   length = 11
FEATURE                Location/Qualifiers
```

-continued

```
source                  1..11
                        mol_type = other RNA
                        mol_type = other RNA
                        organism = synthetic construct
                        organism = synthetic construct
SEQUENCE: 387
cgtttttgga g                                                            11

SEQ ID NO: 388          moltype = RNA   length = 11
FEATURE                 Location/Qualifiers
source                  1..11
                        mol_type = other RNA
                        mol_type = other RNA
                        organism = synthetic construct
                        organism = synthetic construct
SEQUENCE: 388
aatttttgcg g                                                            11

SEQ ID NO: 389          moltype = RNA   length = 11
FEATURE                 Location/Qualifiers
source                  1..11
                        mol_type = other RNA
                        mol_type = other RNA
                        organism = synthetic construct
                        organism = synthetic construct
SEQUENCE: 389
aagttttgaa g                                                            11

SEQ ID NO: 390          moltype = RNA   length = 11
FEATURE                 Location/Qualifiers
source                  1..11
                        mol_type = other RNA
                        mol_type = other RNA
                        organism = synthetic construct
                        organism = synthetic construct
SEQUENCE: 390
aattttcgga a                                                            11

SEQ ID NO: 391          moltype = RNA   length = 11
FEATURE                 Location/Qualifiers
source                  1..11
                        mol_type = other RNA
                        mol_type = other RNA
                        organism = synthetic construct
                        organism = synthetic construct
SEQUENCE: 391
aatttttcca g                                                            11

SEQ ID NO: 392          moltype = RNA   length = 11
FEATURE                 Location/Qualifiers
source                  1..11
                        mol_type = other RNA
                        mol_type = other RNA
                        organism = synthetic construct
                        organism = synthetic construct
SEQUENCE: 392
attttttgta g                                                            11

SEQ ID NO: 393          moltype = RNA   length = 11
FEATURE                 Location/Qualifiers
source                  1..11
                        mol_type = other RNA
                        mol_type = other RNA
                        organism = synthetic construct
                        organism = synthetic construct
SEQUENCE: 393
aatctttaga g                                                            11

SEQ ID NO: 394          moltype = RNA   length = 11
FEATURE                 Location/Qualifiers
source                  1..11
                        mol_type = other RNA
                        mol_type = other RNA
                        organism = synthetic construct
                        organism = synthetic construct
SEQUENCE: 394
aatttttacga g                                                           11

SEQ ID NO: 395          moltype = RNA   length = 11
```

-continued

```
FEATURE              Location/Qualifiers
source               1..11
                     mol_type = other RNA
                     mol_type = other RNA
                     organism = synthetic construct
                     organism = synthetic construct
SEQUENCE: 395
catttttggc g                                                   11

SEQ ID NO: 396       moltype = RNA   length = 11
FEATURE              Location/Qualifiers
source               1..11
                     mol_type = other RNA
                     mol_type = other RNA
                     organism = synthetic construct
                     organism = synthetic construct
SEQUENCE: 396
aatttgcgga g                                                   11

SEQ ID NO: 397       moltype = RNA   length = 11
FEATURE              Location/Qualifiers
source               1..11
                     mol_type = other RNA
                     mol_type = other RNA
                     organism = synthetic construct
                     organism = synthetic construct
SEQUENCE: 397
catctttgga g                                                   11

SEQ ID NO: 398       moltype = RNA   length = 11
FEATURE              Location/Qualifiers
source               1..11
                     mol_type = other RNA
                     mol_type = other RNA
                     organism = synthetic construct
                     organism = synthetic construct
SEQUENCE: 398
aacttttgaa g                                                   11

SEQ ID NO: 399       moltype = RNA   length = 11
FEATURE              Location/Qualifiers
source               1..11
                     mol_type = other RNA
                     mol_type = other RNA
                     organism = synthetic construct
                     organism = synthetic construct
SEQUENCE: 399
aatttttcta g                                                   11

SEQ ID NO: 400       moltype = RNA   length = 33
FEATURE              Location/Qualifiers
source               1..33
                     mol_type = other RNA
                     mol_type = other RNA
                     organism = synthetic construct
                     organism = synthetic construct
SEQUENCE: 400
caggtttttcc agtgttcact gaaatttgtc tct                          33

SEQ ID NO: 401       moltype = RNA   length = 31
FEATURE              Location/Qualifiers
source               1..31
                     mol_type = other RNA
                     mol_type = other RNA
                     organism = synthetic construct
                     organism = synthetic construct
SEQUENCE: 401
aaggtttttct ggtctttatc agaaagcctc c                            31

SEQ ID NO: 402       moltype = RNA   length = 31
FEATURE              Location/Qualifiers
source               1..31
                     mol_type = other RNA
                     mol_type = other RNA
                     organism = synthetic construct
                     organism = synthetic construct
SEQUENCE: 402
caggtttttct ggttttcact gcaaaacccc a                            31
```

-continued

```
SEQ ID NO: 403          moltype = RNA   length = 31
FEATURE                 Location/Qualifiers
source                  1..31
                        mol_type = other RNA
                        mol_type = other RNA
                        organism = synthetic construct
                        organism = synthetic construct
SEQUENCE: 403
cagactttac ggtgcttacc agaaagctcc c                                   31

SEQ ID NO: 404          moltype = RNA   length = 45
FEATURE                 Location/Qualifiers
source                  1..45
                        mol_type = other RNA
                        mol_type = other RNA
                        organism = synthetic construct
                        organism = synthetic construct
SEQUENCE: 404
cacgttttcc ggttgtcact cccaggtagg ctggggaaga ggcat                    45

SEQ ID NO: 405          moltype = RNA   length = 31
FEATURE                 Location/Qualifiers
source                  1..31
                        mol_type = other RNA
                        mol_type = other RNA
                        organism = synthetic construct
                        organism = synthetic construct
SEQUENCE: 405
cagtctttcc agtttttgcc ggaaagcccc t                                   31

SEQ ID NO: 406          moltype = RNA   length = 31
FEATURE                 Location/Qualifiers
source                  1..31
                        mol_type = other RNA
                        mol_type = other RNA
                        organism = synthetic construct
                        organism = synthetic construct
SEQUENCE: 406
caggctttct ggttttgcc agaaagcccc c                                    31

SEQ ID NO: 407          moltype = RNA   length = 31
FEATURE                 Location/Qualifiers
source                  1..31
                        mol_type = other RNA
                        mol_type = other RNA
                        organism = synthetic construct
                        organism = synthetic construct
SEQUENCE: 407
caggttttc agttttcacc agaatgccca c                                    31

SEQ ID NO: 408          moltype = RNA   length = 31
FEATURE                 Location/Qualifiers
source                  1..31
                        mol_type = other RNA
                        mol_type = other RNA
                        organism = synthetic construct
                        organism = synthetic construct
SEQUENCE: 408
caggttttct ggtctttact ggaaagccca a                                   31

SEQ ID NO: 409          moltype = RNA   length = 31
FEATURE                 Location/Qualifiers
source                  1..31
                        mol_type = other RNA
                        mol_type = other RNA
                        organism = synthetic construct
                        organism = synthetic construct
SEQUENCE: 409
caggctttcc ggtttttacc agaaagcccc c                                   31

SEQ ID NO: 410          moltype = RNA   length = 31
FEATURE                 Location/Qualifiers
source                  1..31
                        mol_type = other RNA
                        mol_type = other RNA
                        organism = synthetic construct
                        organism = synthetic construct
SEQUENCE: 410
caggtttttc ggtttttact ggaaagcccc a                                   31
```

```
SEQ ID NO: 411            moltype = RNA   length = 31
FEATURE                   Location/Qualifiers
source                    1..31
                          mol_type = other RNA
                          mol_type = other RNA
                          organism = synthetic construct
                          organism = synthetic construct
SEQUENCE: 411
caggctttcc agtaaataca ggaaagccct c                                      31

SEQ ID NO: 412            moltype = RNA   length = 31
FEATURE                   Location/Qualifiers
source                    1..31
                          mol_type = other RNA
                          mol_type = other RNA
                          organism = synthetic construct
                          organism = synthetic construct
SEQUENCE: 412
caggctttcc ggtttttgct ggaaagactc c                                      31

SEQ ID NO: 413            moltype = RNA   length = 31
FEATURE                   Location/Qualifiers
source                    1..31
                          mol_type = other RNA
                          mol_type = other RNA
                          organism = synthetic construct
                          organism = synthetic construct
SEQUENCE: 413
aaggttttct ggtctttact gaaaagcccc a                                      31

SEQ ID NO: 414            moltype = RNA   length = 31
FEATURE                   Location/Qualifiers
source                    1..31
                          mol_type = other RNA
                          mol_type = other RNA
                          organism = synthetic construct
                          organism = synthetic construct
SEQUENCE: 414
tgggctttct gttttttacg agaaagtcct c                                      31

SEQ ID NO: 415            moltype = RNA   length = 30
FEATURE                   Location/Qualifiers
source                    1..30
                          mol_type = other RNA
                          mol_type = other RNA
                          organism = synthetic construct
                          organism = synthetic construct
SEQUENCE: 415
cagatttctc agttttcact ggaaaccctt                                        30

SEQ ID NO: 416            moltype = RNA   length = 31
FEATURE                   Location/Qualifiers
source                    1..31
                          mol_type = other RNA
                          mol_type = other RNA
                          organism = synthetic construct
                          organism = synthetic construct
SEQUENCE: 416
caggttttcc tgtcttcacc ggaactcccc a                                      31

SEQ ID NO: 417            moltype = RNA   length = 32
FEATURE                   Location/Qualifiers
source                    1..32
                          mol_type = other RNA
                          mol_type = other RNA
                          organism = synthetic construct
                          organism = synthetic construct
SEQUENCE: 417
caggttttct ggtttgcact agaaaaacca ta                                     32

SEQ ID NO: 418            moltype = RNA   length = 31
FEATURE                   Location/Qualifiers
source                    1..31
                          mol_type = other RNA
                          mol_type = other RNA
                          organism = synthetic construct
                          organism = synthetic construct
SEQUENCE: 418
```

-continued

```
cagattttct ggttttttacc agaaaattta a                                     31

SEQ ID NO: 419            moltype = RNA   length = 31
FEATURE                  Location/Qualifiers
source                   1..31
                         mol_type = other RNA
                         mol_type = other RNA
                         organism = synthetic construct
                         organism = synthetic construct
SEQUENCE: 419
caggtcttct tgttttttact ggaaaatcct c                                     31

SEQ ID NO: 420            moltype = RNA   length = 31
FEATURE                  Location/Qualifiers
source                   1..31
                         mol_type = other RNA
                         mol_type = other RNA
                         organism = synthetic construct
                         organism = synthetic construct
SEQUENCE: 420
caggttttcc ggtcttcacc agaaaacccc t                                      31

SEQ ID NO: 421            moltype = RNA   length = 31
FEATURE                  Location/Qualifiers
source                   1..31
                         mol_type = other RNA
                         mol_type = other RNA
                         organism = synthetic construct
                         organism = synthetic construct
SEQUENCE: 421
caggttttcc gatttttact ggaaagccct t                                      31

SEQ ID NO: 422            moltype = RNA   length = 29
FEATURE                  Location/Qualifiers
source                   1..29
                         mol_type = other RNA
                         mol_type = other RNA
                         organism = synthetic construct
                         organism = synthetic construct
SEQUENCE: 422
caggttttct ggttttccag aaaacctcc                                         29

SEQ ID NO: 423            moltype = RNA   length = 29
FEATURE                  Location/Qualifiers
source                   1..29
                         mol_type = other RNA
                         mol_type = other RNA
                         organism = synthetic construct
                         organism = synthetic construct
SEQUENCE: 423
caggttttcc agttttcact ggaacctct                                         29

SEQ ID NO: 424            moltype = RNA   length = 30
FEATURE                  Location/Qualifiers
source                   1..30
                         mol_type = other RNA
                         mol_type = other RNA
                         organism = synthetic construct
                         organism = synthetic construct
SEQUENCE: 424
ccggctttcc agttttgccg gaaagccccc                                        30

SEQ ID NO: 425            moltype = RNA   length = 29
FEATURE                  Location/Qualifiers
source                   1..29
                         mol_type = other RNA
                         mol_type = other RNA
                         organism = synthetic construct
                         organism = synthetic construct
SEQUENCE: 425
caggttttct ggttttttacc agaacttaa                                        29

SEQ ID NO: 426            moltype = RNA   length = 45
FEATURE                  Location/Qualifiers
source                   1..45
                         mol_type = other RNA
                         mol_type = other RNA
                         organism = synthetic construct
                         organism = synthetic construct
```

```
SEQUENCE: 426
cacgttttcc ggttgtcact cccaggtggg ctcgggaaga ggcat                          45

SEQ ID NO: 427        moltype = RNA   length = 31
FEATURE               Location/Qualifiers
source                1..31
                      mol_type = other RNA
                      mol_type = other RNA
                      organism = synthetic construct
                      organism = synthetic construct
SEQUENCE: 427
caggctttcc ggtctttacc ggaaagccta t                                         31

SEQ ID NO: 428        moltype = RNA   length = 31
FEATURE               Location/Qualifiers
source                1..31
                      mol_type = other RNA
                      mol_type = other RNA
                      organism = synthetic construct
                      organism = synthetic construct
SEQUENCE: 428
caggctttct ggtttttgcc ggaaagccct c                                         31

SEQ ID NO: 429        moltype = RNA   length = 31
FEATURE               Location/Qualifiers
source                1..31
                      mol_type = other RNA
                      mol_type = other RNA
                      organism = synthetic construct
                      organism = synthetic construct
SEQUENCE: 429
caggctttca ggtctttgcc agaaagcccc a                                         31

SEQ ID NO: 430        moltype = RNA   length = 30
FEATURE               Location/Qualifiers
source                1..30
                      mol_type = other RNA
                      mol_type = other RNA
                      organism = synthetic construct
                      organism = synthetic construct
SEQUENCE: 430
caggctttct tgttttcact ggaagcctcc                                           30

SEQ ID NO: 431        moltype = RNA   length = 31
FEATURE               Location/Qualifiers
source                1..31
                      mol_type = other RNA
                      mol_type = other RNA
                      organism = synthetic construct
                      organism = synthetic construct
SEQUENCE: 431
caggtttttc agtcttcacc ggaaagctcc c                                         31

SEQ ID NO: 432        moltype = RNA   length = 37
FEATURE               Location/Qualifiers
source                1..37
                      mol_type = other RNA
                      mol_type = other RNA
                      organism = synthetic construct
                      organism = synthetic construct
SEQUENCE: 432
cagattttct ggttttcacc acgaaagaaa tgtcatt                                   37

SEQ ID NO: 433        moltype = RNA   length = 30
FEATURE               Location/Qualifiers
source                1..30
                      mol_type = other RNA
                      mol_type = other RNA
                      organism = synthetic construct
                      organism = synthetic construct
SEQUENCE: 433
cagttctcct ggattttaca ggaaaacccc                                           30

SEQ ID NO: 434        moltype = RNA   length = 31
FEATURE               Location/Qualifiers
source                1..31
                      mol_type = other RNA
                      mol_type = other RNA
                      organism = synthetic construct
```

-continued

```
                            organism = synthetic construct
SEQUENCE: 434
caggctttct ggcatttgcc agaaagccct g                                 31

SEQ ID NO: 435            moltype = RNA   length = 31
FEATURE                   Location/Qualifiers
source                    1..31
                          mol_type = other RNA
                          mol_type = other RNA
                          organism = synthetic construct
                          organism = synthetic construct
SEQUENCE: 435
cagactttcc tgttttttaac agaaagcccc c                                31

SEQ ID NO: 436            moltype = RNA   length = 31
FEATURE                   Location/Qualifiers
source                    1..31
                          mol_type = other RNA
                          mol_type = other RNA
                          organism = synthetic construct
                          organism = synthetic construct
SEQUENCE: 436
caggctttcc ggttttgct ggaaagctcc c                                  31

SEQ ID NO: 437            moltype = RNA   length = 28
FEATURE                   Location/Qualifiers
source                    1..28
                          mol_type = other RNA
                          mol_type = other RNA
                          organism = synthetic construct
                          organism = synthetic construct
SEQUENCE: 437
cagcttttcc agttttcact gaggtaaa                                     28

SEQ ID NO: 438            moltype = RNA   length = 31
FEATURE                   Location/Qualifiers
source                    1..31
                          mol_type = other RNA
                          organism = synthetic construct
SEQUENCE: 438
taggttttct ggttttttatt gggaaatcac a                                31

SEQ ID NO: 439            moltype = RNA   length = 32
FEATURE                   Location/Qualifiers
source                    1..32
                          mol_type = other RNA
                          organism = synthetic construct
SEQUENCE: 439
cagggtttct ggtggtacca gcagactcca ca                                32

SEQ ID NO: 440            moltype = RNA   length = 30
FEATURE                   Location/Qualifiers
source                    1..30
                          mol_type = other RNA
                          organism = synthetic construct
SEQUENCE: 440
caagtttccc agttttcact ggaacctccg                                   30

SEQ ID NO: 441            moltype = RNA   length = 31
FEATURE                   Location/Qualifiers
source                    1..31
                          mol_type = other RNA
                          organism = synthetic construct
SEQUENCE: 441
cagattttcc agtttttact agaaacccccc c                                31

SEQ ID NO: 442            moltype = RNA   length = 31
FEATURE                   Location/Qualifiers
source                    1..31
                          mol_type = other RNA
                          organism = synthetic construct
SEQUENCE: 442
cagggtttcc agttttcact gtataccatc c                                 31

SEQ ID NO: 443            moltype = RNA   length = 31
FEATURE                   Location/Qualifiers
source                    1..31
                          mol_type = other RNA
                          organism = synthetic construct
```

-continued

```
SEQUENCE: 443
caagttctct ggtcttcact ggaaaaccca t                                    31

SEQ ID NO: 444          moltype = RNA   length = 31
FEATURE                 Location/Qualifiers
source                  1..31
                        mol_type = other RNA
                        organism = synthetic construct
SEQUENCE: 444
tagattttct ggtctttacc agaaagactc c                                    31

SEQ ID NO: 445          moltype = RNA   length = 32
FEATURE                 Location/Qualifiers
source                  1..32
                        mol_type = other RNA
                        organism = synthetic construct
SEQUENCE: 445
gcaggttttc tggttttttat tggaaaacct tc                                  32

SEQ ID NO: 446          moltype = RNA   length = 33
FEATURE                 Location/Qualifiers
source                  1..33
                        mol_type = other RNA
                        organism = synthetic construct
SEQUENCE: 446
caggttttcc acttttcacc agaaactgcc tct                                  33

SEQ ID NO: 447          moltype = RNA   length = 31
FEATURE                 Location/Qualifiers
source                  1..31
                        mol_type = other RNA
                        organism = synthetic construct
SEQUENCE: 447
taggctttcc ggttttttgca ggaaagcccc c                                   31

SEQ ID NO: 448          moltype = RNA   length = 31
FEATURE                 Location/Qualifiers
source                  1..31
                        mol_type = other RNA
                        organism = synthetic construct
SEQUENCE: 448
caggttttcc agtctttacc agaaagccac t                                    31

SEQ ID NO: 449          moltype = RNA   length = 33
FEATURE                 Location/Qualifiers
source                  1..33
                        mol_type = other RNA
                        organism = synthetic construct
SEQUENCE: 449
caggtttttt ggtcttcaca ggaaacttcc cct                                  33

SEQ ID NO: 450          moltype = RNA   length = 31
FEATURE                 Location/Qualifiers
source                  1..31
                        mol_type = other RNA
                        organism = synthetic construct
SEQUENCE: 450
caggttttct gcttttcact ggaagactcc c                                    31

SEQ ID NO: 451          moltype = RNA   length = 31
FEATURE                 Location/Qualifiers
source                  1..31
                        mol_type = other RNA
                        organism = synthetic construct
SEQUENCE: 451
cagactttcc agtttttgcc agaaagcccc c                                    31

SEQ ID NO: 452          moltype = RNA   length = 31
FEATURE                 Location/Qualifiers
source                  1..31
                        mol_type = other RNA
                        organism = synthetic construct
SEQUENCE: 452
caggctttct ggttttttgcc caaaagcctc t                                   31

SEQ ID NO: 453          moltype = RNA   length = 31
FEATURE                 Location/Qualifiers
source                  1..31
                        mol_type = other RNA
```

-continued

```
                              organism = synthetic construct
SEQUENCE: 453
caggttttcc aatcttcact gaaaagcttt a                              31

SEQ ID NO: 454          moltype = RNA   length = 31
FEATURE                 Location/Qualifiers
source                  1..31
                        mol_type = other RNA
                        organism = synthetic construct
SEQUENCE: 454
ctggttccta gtcttcactg gaagcaccct c                              31

SEQ ID NO: 455          moltype = RNA   length = 29
FEATURE                 Location/Qualifiers
source                  1..29
                        mol_type = other RNA
                        organism = synthetic construct
SEQUENCE: 455
ggctttccgc tcttcattgg aaagcccat                                 29

SEQ ID NO: 456          moltype = RNA   length = 31
FEATURE                 Location/Qualifiers
source                  1..31
                        mol_type = other RNA
                        organism = synthetic construct
SEQUENCE: 456
caggtttttc agtttttagc agaaaacctc c                              31

SEQ ID NO: 457          moltype = RNA   length = 29
FEATURE                 Location/Qualifiers
source                  1..29
                        mol_type = other RNA
                        organism = synthetic construct
SEQUENCE: 457
caggttctct ggttttttact gaaaccaaa                                29

SEQ ID NO: 458          moltype = RNA   length = 31
FEATURE                 Location/Qualifiers
source                  1..31
                        mol_type = other RNA
                        organism = synthetic construct
SEQUENCE: 458
caggttttcc agtcttcact ggaaagccct t                              31

SEQ ID NO: 459          moltype = RNA   length = 31
FEATURE                 Location/Qualifiers
source                  1..31
                        mol_type = other RNA
                        organism = synthetic construct
SEQUENCE: 459
caggctttct ggttttttgcc ggaaggcctc c                             31

SEQ ID NO: 460          moltype = RNA   length = 32
FEATURE                 Location/Qualifiers
source                  1..32
                        mol_type = other RNA
                        organism = synthetic construct
SEQUENCE: 460
caggttttct gttttttaac tagaaaactc cc                             32

SEQ ID NO: 461          moltype = RNA   length = 31
FEATURE                 Location/Qualifiers
source                  1..31
                        mol_type = other RNA
                        organism = synthetic construct
SEQUENCE: 461
taggctttct ggttttttgct ggaaagcccc c                             31

SEQ ID NO: 462          moltype = RNA   length = 32
FEATURE                 Location/Qualifiers
source                  1..32
                        mol_type = other RNA
                        organism = synthetic construct
SEQUENCE: 462
caggtttccc ggtttttacc agaaaaatct aa                             32

SEQ ID NO: 463          moltype = RNA   length = 32
FEATURE                 Location/Qualifiers
source                  1..32
```

-continued

```
                              mol_type = other RNA
                              organism = synthetic construct
SEQUENCE: 463
caggtttttcc agtctttacc agaaatgccc cc                                    32

SEQ ID NO: 464          moltype = RNA   length = 30
FEATURE                 Location/Qualifiers
source                  1..30
                        mol_type = other RNA
                        organism = synthetic construct
SEQUENCE: 464
ggttttctgg tcatcgctgg aaacaccctc                                        30

SEQ ID NO: 465          moltype = RNA   length = 31
FEATURE                 Location/Qualifiers
source                  1..31
                        mol_type = other RNA
                        organism = synthetic construct
SEQUENCE: 465
caacctttct ggttttttgct agaaagttct c                                     31

SEQ ID NO: 466          moltype = RNA   length = 31
FEATURE                 Location/Qualifiers
source                  1..31
                        mol_type = other RNA
                        organism = synthetic construct
SEQUENCE: 466
caggcctttg ggtctttact ggaaaacccc t                                      31

SEQ ID NO: 467          moltype = RNA   length = 35
FEATURE                 Location/Qualifiers
source                  1..35
                        mol_type = other RNA
                        organism = synthetic construct
SEQUENCE: 467
tatgttttcc ggttttcact cccaggtagg ctcgg                                  35

SEQ ID NO: 468          moltype = RNA   length = 31
FEATURE                 Location/Qualifiers
source                  1..31
                        mol_type = other RNA
                        organism = synthetic construct
SEQUENCE: 468
caaattttct ggcttttcca ggaaaatccc c                                      31

SEQ ID NO: 469          moltype = RNA   length = 28
FEATURE                 Location/Qualifiers
source                  1..28
                        mol_type = other RNA
                        organism = synthetic construct
SEQUENCE: 469
taggttttcc agtgaccaga aaatcctc                                          28

SEQ ID NO: 470          moltype = RNA   length = 31
FEATURE                 Location/Qualifiers
source                  1..31
                        mol_type = other RNA
                        organism = synthetic construct
SEQUENCE: 470
caggtcttcg ggtttttaac tggaaacctt c                                      31

SEQ ID NO: 471          moltype = RNA   length = 32
FEATURE                 Location/Qualifiers
source                  1..32
                        mol_type = other RNA
                        organism = synthetic construct
SEQUENCE: 471
gcaggctttc cagttttttc tggaaagcct ca                                     32

SEQ ID NO: 472          moltype = RNA   length = 29
FEATURE                 Location/Qualifiers
source                  1..29
                        mol_type = other RNA
                        organism = synthetic construct
SEQUENCE: 472
ggctttctgg tttttactgg aaagccccc                                         29

SEQ ID NO: 473          moltype = RNA   length = 31
FEATURE                 Location/Qualifiers
```

-continued

```
source                  1..31
                        mol_type = other RNA
                        organism = synthetic construct
SEQUENCE: 473
caggtttccc agtattcacc ggaaagctcc a                              31

SEQ ID NO: 474          moltype = RNA   length = 43
FEATURE                 Location/Qualifiers
source                  1..43
                        mol_type = other RNA
                        organism = synthetic construct
SEQUENCE: 474
caggctttct agttttccca cactaagaaa caaaaaaacc tgt                 43

SEQ ID NO: 475          moltype = RNA   length = 32
FEATURE                 Location/Qualifiers
source                  1..32
                        mol_type = other RNA
                        organism = synthetic construct
SEQUENCE: 475
gcaagctttc tggttttggc caaaaagcca cc                             32

SEQ ID NO: 476          moltype = RNA   length = 24
FEATURE                 Location/Qualifiers
source                  1..24
                        mol_type = other RNA
                        organism = synthetic construct
SEQUENCE: 476
ttctggtttt caccagaaac cact                                     24

SEQ ID NO: 477          moltype = RNA   length = 32
FEATURE                 Location/Qualifiers
source                  1..32
                        mol_type = other RNA
                        organism = synthetic construct
SEQUENCE: 477
gcaagttttc tagcctgtac ctgaaagcct ca                            32

SEQ ID NO: 478          moltype = RNA   length = 30
FEATURE                 Location/Qualifiers
source                  1..30
                        mol_type = other RNA
                        organism = synthetic construct
SEQUENCE: 478
aagttttctt gttttttacca gaaaactcct                              30

SEQ ID NO: 479          moltype = RNA   length = 29
FEATURE                 Location/Qualifiers
source                  1..29
                        mol_type = other RNA
                        organism = synthetic construct
SEQUENCE: 479
ggctttccaa tttttgccag aaagccccc                                29

SEQ ID NO: 480          moltype = RNA   length = 33
FEATURE                 Location/Qualifiers
source                  1..33
                        mol_type = other RNA
                        organism = synthetic construct
SEQUENCE: 480
agctggtttt ctggttttca ccggaagacc cat                           33

SEQ ID NO: 481          moltype = RNA   length = 32
FEATURE                 Location/Qualifiers
source                  1..32
                        mol_type = other RNA
                        organism = synthetic construct
SEQUENCE: 481
caggccttct ggttttttgct gggaagtccc ca                           32

SEQ ID NO: 482          moltype = RNA   length = 31
FEATURE                 Location/Qualifiers
source                  1..31
                        mol_type = other RNA
                        organism = synthetic construct
SEQUENCE: 482
caggttttcc agtttgtacc agaaaaccc t                              31

SEQ ID NO: 483          moltype = RNA   length = 22
```

```
FEATURE              Location/Qualifiers
source               1..22
                     mol_type = other RNA
                     organism = synthetic construct
SEQUENCE: 483
caggtttcac ccaaaaaccc ac                                        22

SEQ ID NO: 484       moltype = RNA   length = 32
FEATURE              Location/Qualifiers
source               1..32
                     mol_type = other RNA
                     organism = synthetic construct
SEQUENCE: 484
taggctttct ggctttttac cggaaagccc ct                             32

SEQ ID NO: 485       moltype = RNA   length = 31
FEATURE              Location/Qualifiers
source               1..31
                     mol_type = other RNA
                     organism = synthetic construct
SEQUENCE: 485
cagggtttct ggttttcacc aggaaacaaa a                              31

SEQ ID NO: 486       moltype = RNA   length = 31
FEATURE              Location/Qualifiers
source               1..31
                     mol_type = other RNA
                     organism = synthetic construct
SEQUENCE: 486
caggtttttc tgtctttact agaaacccct c                              31

SEQ ID NO: 487       moltype = RNA   length = 31
FEATURE              Location/Qualifiers
source               1..31
                     mol_type = other RNA
                     organism = synthetic construct
SEQUENCE: 487
caggtttttat aggtttttacc agaaaacttc c                            31

SEQ ID NO: 488       moltype = RNA   length = 31
FEATURE              Location/Qualifiers
source               1..31
                     mol_type = other RNA
                     organism = synthetic construct
SEQUENCE: 488
caggcttccc aatttttgct ggaaagcccc t                              31

SEQ ID NO: 489       moltype = RNA   length = 31
FEATURE              Location/Qualifiers
source               1..31
                     mol_type = other RNA
                     organism = synthetic construct
SEQUENCE: 489
caggcttttt gggttaggtc agaaagtccc c                              31

SEQ ID NO: 490       moltype = RNA   length = 29
FEATURE              Location/Qualifiers
source               1..29
                     mol_type = other RNA
                     organism = synthetic construct
SEQUENCE: 490
caggtttttg gttttttagc gaaaccctc                                 29

SEQ ID NO: 491       moltype = RNA   length = 33
FEATURE              Location/Qualifiers
source               1..33
                     mol_type = other RNA
                     organism = synthetic construct
SEQUENCE: 491
caggctttct ggttttcacc ataaaatgcc cca                            33

SEQ ID NO: 492       moltype = RNA   length = 43
FEATURE              Location/Qualifiers
source               1..43
                     mol_type = other RNA
                     organism = synthetic construct
SEQUENCE: 492
caggtcttcg gggtttttaca aaaagaagaa gaaatccacc ccc                43
```

-continued

```
SEQ ID NO: 493            moltype = RNA   length = 32
FEATURE                   Location/Qualifiers
source                    1..32
                          mol_type = other RNA
                          organism = synthetic construct
SEQUENCE: 493
caagttctct ggtctcccaa caagaaaccc cc                                  32

SEQ ID NO: 494            moltype = RNA   length = 33
FEATURE                   Location/Qualifiers
source                    1..33
                          mol_type = other RNA
                          organism = synthetic construct
SEQUENCE: 494
caggatttct ggtttctggt ggaaagctcc cat                                 33

SEQ ID NO: 495            moltype = RNA   length = 30
FEATURE                   Location/Qualifiers
source                    1..30
                          mol_type = other RNA
                          organism = synthetic construct
SEQUENCE: 495
aggctttcca gttttttgctg gaaagcccct                                    30

SEQ ID NO: 496            moltype = RNA   length = 30
FEATURE                   Location/Qualifiers
source                    1..30
                          mol_type = other RNA
                          organism = synthetic construct
SEQUENCE: 496
caggttttcc agtctttgtc aaatgccttc                                     30

SEQ ID NO: 497            moltype = RNA   length = 34
FEATURE                   Location/Qualifiers
source                    1..34
                          mol_type = other RNA
                          organism = synthetic construct
SEQUENCE: 497
caggctttca gttttttgcc agtgtgaacc caaa                                34

SEQ ID NO: 498            moltype = RNA   length = 31
FEATURE                   Location/Qualifiers
source                    1..31
                          mol_type = other RNA
                          organism = synthetic construct
SEQUENCE: 498
caggctttct ggtttttatc agaaagcctc c                                   31

SEQ ID NO: 499            moltype = RNA   length = 33
FEATURE                   Location/Qualifiers
source                    1..33
                          mol_type = other RNA
                          organism = synthetic construct
SEQUENCE: 499
gaggttttct ggttttcacc agaaccaacc ctt                                 33

SEQ ID NO: 500            moltype = RNA   length = 31
FEATURE                   Location/Qualifiers
source                    1..31
                          mol_type = other RNA
                          organism = synthetic construct
SEQUENCE: 500
cagattttcc agcttttact ggaagccccc t                                   31

SEQ ID NO: 501            moltype = RNA   length = 33
FEATURE                   Location/Qualifiers
source                    1..33
                          mol_type = other RNA
                          organism = synthetic construct
SEQUENCE: 501
caggttttct ggttttcact ggaaaatacc tca                                 33

SEQ ID NO: 502            moltype = RNA   length = 33
FEATURE                   Location/Qualifiers
source                    1..33
                          mol_type = other RNA
                          organism = synthetic construct
SEQUENCE: 502
catgttttttt ggtgttaata aaaacccgca cac                               33
```

-continued

```
SEQ ID NO: 503             moltype = RNA   length = 31
FEATURE                    Location/Qualifiers
source                     1..31
                           mol_type = other RNA
                           organism = synthetic construct
SEQUENCE: 503
aaggctttcc ggttttgca ggaaagcaac c                               31

SEQ ID NO: 504             moltype = RNA   length = 30
FEATURE                    Location/Qualifiers
source                     1..30
                           mol_type = other RNA
                           organism = synthetic construct
SEQUENCE: 504
agtctttccg ggttttgtca gaaaggccct                                30

SEQ ID NO: 505             moltype = RNA   length = 31
FEATURE                    Location/Qualifiers
source                     1..31
                           mol_type = other RNA
                           organism = synthetic construct
SEQUENCE: 505
gcaggttttc tggtttctac tggaagcttc t                              31

SEQ ID NO: 506             moltype = RNA   length = 31
FEATURE                    Location/Qualifiers
source                     1..31
                           mol_type = other RNA
                           organism = synthetic construct
SEQUENCE: 506
caggctttct ggtttttact ggaaagcccc t                              31

SEQ ID NO: 507             moltype = RNA   length = 31
FEATURE                    Location/Qualifiers
source                     1..31
                           mol_type = other RNA
                           organism = synthetic construct
SEQUENCE: 507
caggctttcc aatttttgcc agaaagctcc c                              31

SEQ ID NO: 508             moltype = RNA   length = 31
FEATURE                    Location/Qualifiers
source                     1..31
                           mol_type = other RNA
                           organism = synthetic construct
SEQUENCE: 508
caggttttct ggttctcacc agaaaacgcc a                              31

SEQ ID NO: 509             moltype = RNA   length = 31
FEATURE                    Location/Qualifiers
source                     1..31
                           mol_type = other RNA
                           organism = synthetic construct
SEQUENCE: 509
caggttttct ggtcttcact ggaagaccac t                              31

SEQ ID NO: 510             moltype = RNA   length = 34
FEATURE                    Location/Qualifiers
source                     1..34
                           mol_type = other RNA
                           organism = synthetic construct
SEQUENCE: 510
caggtggttt tccggtcttt accagtaagc cccc                           34

SEQ ID NO: 511             moltype = RNA   length = 31
FEATURE                    Location/Qualifiers
source                     1..31
                           mol_type = other RNA
                           organism = synthetic construct
SEQUENCE: 511
caggttttcc agtttctacc agaaacccct a                              31

SEQ ID NO: 512             moltype = RNA   length = 32
FEATURE                    Location/Qualifiers
source                     1..32
                           mol_type = other RNA
                           mol_type = other RNA
                           organism = synthetic construct
```

-continued

```
                         organism = synthetic construct
SEQUENCE: 512
caggtttttct ggtctttacc agaaaagtct cc                                    32

SEQ ID NO: 513          moltype = RNA   length = 32
FEATURE                 Location/Qualifiers
source                  1..32
                        mol_type = other RNA
                        mol_type = other RNA
                        organism = synthetic construct
                        organism = synthetic construct
SEQUENCE: 513
ccaggctttc tggtttttac cggaaagccc cg                                     32

SEQ ID NO: 514          moltype = RNA   length = 32
FEATURE                 Location/Qualifiers
source                  1..32
                        mol_type = other RNA
                        mol_type = other RNA
                        organism = synthetic construct
                        organism = synthetic construct
SEQUENCE: 514
caggtttttc acttttttact agaaaaacca gt                                    32

SEQ ID NO: 515          moltype = RNA   length = 35
FEATURE                 Location/Qualifiers
source                  1..35
                        mol_type = other RNA
                        mol_type = other RNA
                        organism = synthetic construct
                        organism = synthetic construct
SEQUENCE: 515
taggctttct gggaggtctt taccagaaag cctcc                                  35

SEQ ID NO: 516          moltype = RNA   length = 32
FEATURE                 Location/Qualifiers
source                  1..32
                        mol_type = other RNA
                        mol_type = other RNA
                        organism = synthetic construct
                        organism = synthetic construct
SEQUENCE: 516
tacattttcc agttttcacc aggaatctgc ct                                     32

SEQ ID NO: 517          moltype = RNA   length = 31
FEATURE                 Location/Qualifiers
source                  1..31
                        mol_type = other RNA
                        mol_type = other RNA
                        organism = synthetic construct
                        organism = synthetic construct
SEQUENCE: 517
taggtttttcc agttttcacc agaaaatccc g                                     31

SEQ ID NO: 518          moltype = RNA   length = 31
FEATURE                 Location/Qualifiers
source                  1..31
                        mol_type = other RNA
                        mol_type = other RNA
                        organism = synthetic construct
                        organism = synthetic construct
SEQUENCE: 518
caggtttttct ggtttttacg agactccccc a                                     31

SEQ ID NO: 519          moltype = RNA   length = 30
FEATURE                 Location/Qualifiers
source                  1..30
                        mol_type = other RNA
                        mol_type = other RNA
                        organism = synthetic construct
                        organism = synthetic construct
SEQUENCE: 519
caggctttct gttttttgct aaaatcctcc                                        30

SEQ ID NO: 520          moltype = RNA   length = 32
FEATURE                 Location/Qualifiers
source                  1..32
                        mol_type = other RNA
                        mol_type = other RNA
```

-continued

```
                             organism = synthetic construct
                             organism = synthetic construct
SEQUENCE: 520
ctgggcgtac tggctcacgc ctataatccc aa                                32

SEQ ID NO: 521          moltype = RNA   length = 29
FEATURE                 Location/Qualifiers
source                  1..29
                        mol_type = other RNA
                        mol_type = other RNA
                        organism = synthetic construct
                        organism = synthetic construct
SEQUENCE: 521
ggctctccgg tttttgccag aatgcccac                                    29

SEQ ID NO: 522          moltype = RNA   length = 31
FEATURE                 Location/Qualifiers
source                  1..31
                        mol_type = other RNA
                        mol_type = other RNA
                        organism = synthetic construct
                        organism = synthetic construct
SEQUENCE: 522
tgggtttttct ggtgaaaact agactgcccc c                                31

SEQ ID NO: 523          moltype = RNA   length = 31
FEATURE                 Location/Qualifiers
source                  1..31
                        mol_type = other RNA
                        mol_type = other RNA
                        organism = synthetic construct
                        organism = synthetic construct
SEQUENCE: 523
caggctttct ggtttttaca ggaaggcccc t                                 31

SEQ ID NO: 524          moltype = RNA   length = 29
FEATURE                 Location/Qualifiers
source                  1..29
                        mol_type = other RNA
                        mol_type = other RNA
                        organism = synthetic construct
                        organism = synthetic construct
SEQUENCE: 524
ggttttctgg ttctcactgg aaaaccccc                                    29

SEQ ID NO: 525          moltype = RNA   length = 31
FEATURE                 Location/Qualifiers
source                  1..31
                        mol_type = other RNA
                        mol_type = other RNA
                        organism = synthetic construct
                        organism = synthetic construct
SEQUENCE: 525
caggctttcc ggtaaagact ggaaagcccc t                                 31

SEQ ID NO: 526          moltype = RNA   length = 31
FEATURE                 Location/Qualifiers
source                  1..31
                        mol_type = other RNA
                        mol_type = other RNA
                        organism = synthetic construct
                        organism = synthetic construct
SEQUENCE: 526
caggtttttcc agtttttacc agaaaactct c                                31

SEQ ID NO: 527          moltype = RNA   length = 31
FEATURE                 Location/Qualifiers
source                  1..31
                        mol_type = other RNA
                        mol_type = other RNA
                        organism = synthetic construct
                        organism = synthetic construct
SEQUENCE: 527
aaggtttttct ggtcttcact ggaagaccac t                                31

SEQ ID NO: 528          moltype = RNA   length = 31
FEATURE                 Location/Qualifiers
source                  1..31
                        mol_type = other RNA
```

-continued

```
                            mol_type = other RNA
                            organism = synthetic construct
                            organism = synthetic construct
SEQUENCE: 528
gaggtttct ggtcttcact ggaagaccac t                                  31

SEQ ID NO: 529          moltype = RNA  length = 31
FEATURE                 Location/Qualifiers
source                  1..31
                        mol_type = other RNA
                        mol_type = other RNA
                        organism = synthetic construct
                        organism = synthetic construct
SEQUENCE: 529
taggtttct ggtcttcact ggaagaccac t                                  31

SEQ ID NO: 530          moltype = RNA  length = 31
FEATURE                 Location/Qualifiers
source                  1..31
                        mol_type = other RNA
                        mol_type = other RNA
                        organism = synthetic construct
                        organism = synthetic construct
SEQUENCE: 530
ccggtttct ggtcttcact ggaagaccac t                                  31

SEQ ID NO: 531          moltype = RNA  length = 31
FEATURE                 Location/Qualifiers
source                  1..31
                        mol_type = other RNA
                        mol_type = other RNA
                        organism = synthetic construct
                        organism = synthetic construct
SEQUENCE: 531
cgggtttct ggtcttcact ggaagaccac t                                  31

SEQ ID NO: 532          moltype = RNA  length = 31
FEATURE                 Location/Qualifiers
source                  1..31
                        mol_type = other RNA
                        mol_type = other RNA
                        organism = synthetic construct
                        organism = synthetic construct
SEQUENCE: 532
ctggtttct ggtcttcact ggaagaccac t                                  31

SEQ ID NO: 533          moltype = RNA  length = 31
FEATURE                 Location/Qualifiers
source                  1..31
                        mol_type = other RNA
                        mol_type = other RNA
                        organism = synthetic construct
                        organism = synthetic construct
SEQUENCE: 533
catgtttct ggtcttcact ggaagacaac t                                  31

SEQ ID NO: 534          moltype = RNA  length = 31
FEATURE                 Location/Qualifiers
source                  1..31
                        mol_type = other RNA
                        mol_type = other RNA
                        organism = synthetic construct
                        organism = synthetic construct
SEQUENCE: 534
cacgtttct ggtcttcact ggaagacgac t                                  31

SEQ ID NO: 535          moltype = RNA  length = 31
FEATURE                 Location/Qualifiers
source                  1..31
                        mol_type = other RNA
                        mol_type = other RNA
                        organism = synthetic construct
                        organism = synthetic construct
SEQUENCE: 535
caagtttct ggtcttcact ggaagactac t                                  31

SEQ ID NO: 536          moltype = RNA  length = 31
FEATURE                 Location/Qualifiers
source                  1..31
```

-continued

```
                              mol_type = other RNA
                              mol_type = other RNA
                              organism = synthetic construct
                              organism = synthetic construct
SEQUENCE: 536
cagctttct ggtcttcact ggaagagcac t                                  31

SEQ ID NO: 537         moltype = RNA   length = 31
FEATURE                Location/Qualifiers
source                 1..31
                       mol_type = other RNA
                       mol_type = other RNA
                       organism = synthetic construct
                       organism = synthetic construct
SEQUENCE: 537
cagattttct ggtcttcact ggaagatcac t                                  31

SEQ ID NO: 538         moltype = RNA   length = 31
FEATURE                Location/Qualifiers
source                 1..31
                       mol_type = other RNA
                       mol_type = other RNA
                       organism = synthetic construct
                       organism = synthetic construct
SEQUENCE: 538
cagttttct ggtcttcact ggaagaacac t                                   31

SEQ ID NO: 539         moltype = RNA   length = 31
FEATURE                Location/Qualifiers
source                 1..31
                       mol_type = other RNA
                       mol_type = other RNA
                       organism = synthetic construct
                       organism = synthetic construct
SEQUENCE: 539
cagggtttct ggtcttcact ggaagcccac t                                  31

SEQ ID NO: 540         moltype = RNA   length = 31
FEATURE                Location/Qualifiers
source                 1..31
                       mol_type = other RNA
                       mol_type = other RNA
                       organism = synthetic construct
                       organism = synthetic construct
SEQUENCE: 540
caggattttct ggtcttcact ggaagtccac t                                 31

SEQ ID NO: 541         moltype = RNA   length = 31
FEATURE                Location/Qualifiers
source                 1..31
                       mol_type = other RNA
                       mol_type = other RNA
                       organism = synthetic construct
                       organism = synthetic construct
SEQUENCE: 541
caggctttct ggtcttcact ggaaggccac t                                  31

SEQ ID NO: 542         moltype = RNA   length = 31
FEATURE                Location/Qualifiers
source                 1..31
                       mol_type = other RNA
                       mol_type = other RNA
                       organism = synthetic construct
                       organism = synthetic construct
SEQUENCE: 542
caggtgttct ggtcttcact ggaacaccac t                                  31

SEQ ID NO: 543         moltype = RNA   length = 31
FEATURE                Location/Qualifiers
source                 1..31
                       mol_type = other RNA
                       mol_type = other RNA
                       organism = synthetic construct
                       organism = synthetic construct
SEQUENCE: 543
caggtattct ggtcttcact ggaataccac t                                  31

SEQ ID NO: 544         moltype = RNA   length = 31
FEATURE                Location/Qualifiers
```

-continued

```
source                   1..31
                         mol_type = other RNA
                         mol_type = other RNA
                         organism = synthetic construct
                         organism = synthetic construct
SEQUENCE: 544
caggtcttct ggtcttcact ggaagaccac t                                            31

SEQ ID NO: 545           moltype = RNA   length = 31
FEATURE                  Location/Qualifiers
source                   1..31
                         mol_type = other RNA
                         mol_type = other RNA
                         organism = synthetic construct
                         organism = synthetic construct
SEQUENCE: 545
caggttttct ggtcttcact ggaaaaccac t                                            31

SEQ ID NO: 546           moltype = RNA   length = 31
FEATURE                  Location/Qualifiers
source                   1..31
                         mol_type = other RNA
                         mol_type = other RNA
                         organism = synthetic construct
                         organism = synthetic construct
SEQUENCE: 546
caggttctct ggtcttcact ggaggaccac t                                            31

SEQ ID NO: 547           moltype = RNA   length = 31
FEATURE                  Location/Qualifiers
source                   1..31
                         mol_type = other RNA
                         mol_type = other RNA
                         organism = synthetic construct
                         organism = synthetic construct
SEQUENCE: 547
caggttgtct ggtcttcact ggacgaccac t                                            31

SEQ ID NO: 548           moltype = RNA   length = 31
FEATURE                  Location/Qualifiers
source                   1..31
                         mol_type = other RNA
                         mol_type = other RNA
                         organism = synthetic construct
                         organism = synthetic construct
SEQUENCE: 548
caggttatct ggtcttcact ggatgaccac t                                            31

SEQ ID NO: 549           moltype = RNA   length = 31
FEATURE                  Location/Qualifiers
source                   1..31
                         mol_type = other RNA
                         mol_type = other RNA
                         organism = synthetic construct
                         organism = synthetic construct
SEQUENCE: 549
caggtttact ggtcttcact ggtagaccac t                                            31

SEQ ID NO: 550           moltype = RNA   length = 31
FEATURE                  Location/Qualifiers
source                   1..31
                         mol_type = other RNA
                         mol_type = other RNA
                         organism = synthetic construct
                         organism = synthetic construct
SEQUENCE: 550
caggtttgct ggtcttcact ggcagaccac t                                            31

SEQ ID NO: 551           moltype = RNA   length = 31
FEATURE                  Location/Qualifiers
source                   1..31
                         mol_type = other RNA
                         mol_type = other RNA
                         organism = synthetic construct
                         organism = synthetic construct
SEQUENCE: 551
caggtttcct ggtcttcact gggagaccac t                                            31

SEQ ID NO: 552           moltype = RNA   length = 31
```

-continued

```
FEATURE              Location/Qualifiers
source               1..31
                     mol_type = other RNA
                     mol_type = other RNA
                     organism = synthetic construct
                     organism = synthetic construct
SEQUENCE: 552
caggtttttt ggtcttcact gaaagaccac t                                    31

SEQ ID NO: 553       moltype = RNA   length = 31
FEATURE              Location/Qualifiers
source               1..31
                     mol_type = other RNA
                     mol_type = other RNA
                     organism = synthetic construct
                     organism = synthetic construct
SEQUENCE: 553
caggttttgt ggtcttcact gcaagaccac t                                    31

SEQ ID NO: 554       moltype = RNA   length = 31
FEATURE              Location/Qualifiers
source               1..31
                     mol_type = other RNA
                     mol_type = other RNA
                     organism = synthetic construct
                     organism = synthetic construct
SEQUENCE: 554
caggtttttat ggtcttcact gtaagaccac t                                   31

SEQ ID NO: 555       moltype = RNA   length = 31
FEATURE              Location/Qualifiers
source               1..31
                     mol_type = other RNA
                     mol_type = other RNA
                     organism = synthetic construct
                     organism = synthetic construct
SEQUENCE: 555
caggtttttcc ggtcttcact ggaagaccac t                                   31

SEQ ID NO: 556       moltype = RNA   length = 31
FEATURE              Location/Qualifiers
source               1..31
                     mol_type = other RNA
                     mol_type = other RNA
                     organism = synthetic construct
                     organism = synthetic construct
SEQUENCE: 556
caggtttttca ggtcttcact tgaagaccac t                                   31

SEQ ID NO: 557       moltype = RNA   length = 31
FEATURE              Location/Qualifiers
source               1..31
                     mol_type = other RNA
                     mol_type = other RNA
                     organism = synthetic construct
                     organism = synthetic construct
SEQUENCE: 557
caggtttttct ggtcttcact agaagaccac t                                   31

SEQ ID NO: 558       moltype = RNA   length = 31
FEATURE              Location/Qualifiers
source               1..31
                     mol_type = other RNA
                     mol_type = other RNA
                     organism = synthetic construct
                     organism = synthetic construct
SEQUENCE: 558
caggtttttcg ggtcttcact cgaagaccac t                                   31

SEQ ID NO: 559       moltype = RNA   length = 31
FEATURE              Location/Qualifiers
source               1..31
                     mol_type = other RNA
                     mol_type = other RNA
                     organism = synthetic construct
                     organism = synthetic construct
SEQUENCE: 559
caggtttttct tgtcttcaca ggaagaccac t                                   31
```

-continued

```
SEQ ID NO: 560          moltype = RNA   length = 31
FEATURE                 Location/Qualifiers
source                  1..31
                        mol_type = other RNA
                        mol_type = other RNA
                        organism = synthetic construct
                        organism = synthetic construct
SEQUENCE: 560
caggttttct agtcttcact ggaagaccac t                              31

SEQ ID NO: 561          moltype = RNA   length = 31
FEATURE                 Location/Qualifiers
source                  1..31
                        mol_type = other RNA
                        mol_type = other RNA
                        organism = synthetic construct
                        organism = synthetic construct
SEQUENCE: 561
caggttttct ggtcttcacc ggaagaccac t                              31

SEQ ID NO: 562          moltype = RNA   length = 31
FEATURE                 Location/Qualifiers
source                  1..31
                        mol_type = other RNA
                        mol_type = other RNA
                        organism = synthetic construct
                        organism = synthetic construct
SEQUENCE: 562
caggttttct cgtcttcacg ggaagaccac t                              31

SEQ ID NO: 563          moltype = RNA   length = 31
FEATURE                 Location/Qualifiers
source                  1..31
                        mol_type = other RNA
                        mol_type = other RNA
                        organism = synthetic construct
                        organism = synthetic construct
SEQUENCE: 563
caggttttct gttcttcaat ggaagaccac t                              31

SEQ ID NO: 564          moltype = RNA   length = 31
FEATURE                 Location/Qualifiers
source                  1..31
                        mol_type = other RNA
                        mol_type = other RNA
                        organism = synthetic construct
                        organism = synthetic construct
SEQUENCE: 564
caggttttct gatcttcatt ggaagaccac t                              31

SEQ ID NO: 565          moltype = RNA   length = 31
FEATURE                 Location/Qualifiers
source                  1..31
                        mol_type = other RNA
                        mol_type = other RNA
                        organism = synthetic construct
                        organism = synthetic construct
SEQUENCE: 565
caggttttct gctcttcagt ggaagaccac t                              31

SEQ ID NO: 566          moltype = RNA   length = 31
FEATURE                 Location/Qualifiers
source                  1..31
                        mol_type = other RNA
                        mol_type = other RNA
                        organism = synthetic construct
                        organism = synthetic construct
SEQUENCE: 566
caggttttct ggccttcgct ggaagaccac t                              31

SEQ ID NO: 567          moltype = RNA   length = 31
FEATURE                 Location/Qualifiers
source                  1..31
                        mol_type = other RNA
                        mol_type = other RNA
                        organism = synthetic construct
                        organism = synthetic construct
SEQUENCE: 567
caggttttct gggcttccct ggaagaccac t                              31
```

```
SEQ ID NO: 568          moltype = RNA   length = 31
FEATURE                 Location/Qualifiers
source                  1..31
                        mol_type = other RNA
                        mol_type = other RNA
                        organism = synthetic construct
                        organism = synthetic construct
SEQUENCE: 568
caggttttct ggacttctct ggaagaccac t                                   31

SEQ ID NO: 569          moltype = RNA   length = 31
FEATURE                 Location/Qualifiers
source                  1..31
                        mol_type = other RNA
                        mol_type = other RNA
                        organism = synthetic construct
                        organism = synthetic construct
SEQUENCE: 569
caggttttct ggttttcact ggaagaccac t                                   31

SEQ ID NO: 570          moltype = RNA   length = 31
FEATURE                 Location/Qualifiers
source                  1..31
                        mol_type = other RNA
                        mol_type = other RNA
                        organism = synthetic construct
                        organism = synthetic construct
SEQUENCE: 570
caggttttct ggtattcact ggaagaccac t                                   31

SEQ ID NO: 571          moltype = RNA   length = 31
FEATURE                 Location/Qualifiers
source                  1..31
                        mol_type = other RNA
                        mol_type = other RNA
                        organism = synthetic construct
                        organism = synthetic construct
SEQUENCE: 571
caggttttct ggtgttcact ggaagaccac t                                   31

SEQ ID NO: 572          moltype = RNA   length = 31
FEATURE                 Location/Qualifiers
source                  1..31
                        mol_type = other RNA
                        mol_type = other RNA
                        organism = synthetic construct
                        organism = synthetic construct
SEQUENCE: 572
caggttttct ggtcatcact ggaagaccac t                                   31

SEQ ID NO: 573          moltype = RNA   length = 31
FEATURE                 Location/Qualifiers
source                  1..31
                        mol_type = other RNA
                        organism = synthetic construct
SEQUENCE: 573
caggttttct ggtcgtcact ggaagaccac t                                   31

SEQ ID NO: 574          moltype = RNA   length = 31
FEATURE                 Location/Qualifiers
source                  1..31
                        mol_type = other RNA
                        organism = synthetic construct
SEQUENCE: 574
caggttttct ggtcctcact ggaagaccac t                                   31

SEQ ID NO: 575          moltype = RNA   length = 31
FEATURE                 Location/Qualifiers
source                  1..31
                        mol_type = other RNA
                        mol_type = other RNA
                        organism = synthetic construct
                        organism = synthetic construct
SEQUENCE: 575
caggttttct ggtctacact ggaagaccac t                                   31

SEQ ID NO: 576          moltype = RNA   length = 31
FEATURE                 Location/Qualifiers
```

-continued

```
source                  1..31
                        mol_type = other RNA
                        mol_type = other RNA
                        organism = synthetic construct
                        organism = synthetic construct
SEQUENCE: 576
caggttttct ggtctgcact ggaagaccac t                                  31

SEQ ID NO: 577          moltype = RNA   length = 31
FEATURE                 Location/Qualifiers
source                  1..31
                        mol_type = other RNA
                        mol_type = other RNA
                        organism = synthetic construct
                        organism = synthetic construct
SEQUENCE: 577
caggttttct ggtctccact ggaagaccac t                                  31

SEQ ID NO: 578          moltype = RNA   length = 31
FEATURE                 Location/Qualifiers
source                  1..31
                        mol_type = other RNA
                        mol_type = other RNA
                        organism = synthetic construct
                        organism = synthetic construct
SEQUENCE: 578
caggttttct ggtcttaact ggaagaccac t                                  31

SEQ ID NO: 579          moltype = RNA   length = 31
FEATURE                 Location/Qualifiers
source                  1..31
                        mol_type = other RNA
                        mol_type = other RNA
                        organism = synthetic construct
                        organism = synthetic construct
SEQUENCE: 579
caggttttct ggtcttgact ggaagaccac t                                  31

SEQ ID NO: 580          moltype = RNA   length = 31
FEATURE                 Location/Qualifiers
source                  1..31
                        mol_type = other RNA
                        mol_type = other RNA
                        organism = synthetic construct
                        organism = synthetic construct
SEQUENCE: 580
caggttttct ggtctttact ggaagaccac t                                  31

SEQ ID NO: 581          moltype = RNA   length = 31
FEATURE                 Location/Qualifiers
source                  1..31
                        mol_type = other RNA
                        mol_type = other RNA
                        organism = synthetic construct
                        organism = synthetic construct
SEQUENCE: 581
caggttttct ggtcttcact ggaagaccgc t                                  31

SEQ ID NO: 582          moltype = RNA   length = 31
FEATURE                 Location/Qualifiers
source                  1..31
                        mol_type = other RNA
                        mol_type = other RNA
                        organism = synthetic construct
                        organism = synthetic construct
SEQUENCE: 582
caggttttct ggtcttcact ggaagacccc t                                  31

SEQ ID NO: 583          moltype = RNA   length = 31
FEATURE                 Location/Qualifiers
source                  1..31
                        mol_type = other RNA
                        mol_type = other RNA
                        organism = synthetic construct
                        organism = synthetic construct
SEQUENCE: 583
caggttttct ggtcttcact ggaagacctc t                                  31

SEQ ID NO: 584          moltype = RNA   length = 31
```

-continued

```
FEATURE                  Location/Qualifiers
source                   1..31
                         mol_type = other RNA
                         mol_type = other RNA
                         organism = synthetic construct
                         organism = synthetic construct
SEQUENCE: 584
caggttttct ggtcttcact ggaagaccag t                          31

SEQ ID NO: 585           moltype = RNA   length = 31
FEATURE                  Location/Qualifiers
source                   1..31
                         mol_type = other RNA
                         organism = synthetic construct
SEQUENCE: 585
caggttttct ggtcttcact ggaagaccat t                          31

SEQ ID NO: 586           moltype = RNA   length = 31
FEATURE                  Location/Qualifiers
source                   1..31
                         mol_type = other RNA
                         organism = synthetic construct
SEQUENCE: 586
caggttttct ggtcttcact ggaagaccaa t                          31

SEQ ID NO: 587           moltype = RNA   length = 31
FEATURE                  Location/Qualifiers
source                   1..31
                         mol_type = other RNA
                         organism = synthetic construct
SEQUENCE: 587
caggttttct ggtcttcact ggaagaccac a                          31

SEQ ID NO: 588           moltype = RNA   length = 31
FEATURE                  Location/Qualifiers
source                   1..31
                         mol_type = other RNA
                         organism = synthetic construct
SEQUENCE: 588
caggttttct ggtcttcact ggaagaccac g                          31

SEQ ID NO: 589           moltype = RNA   length = 31
FEATURE                  Location/Qualifiers
source                   1..31
                         mol_type = other RNA
                         organism = synthetic construct
SEQUENCE: 589
caggttttct ggtcttcact ggaagaccac c                          31

SEQ ID NO: 590           moltype = RNA   length = 132
FEATURE                  Location/Qualifiers
source                   1..132
                         mol_type = other RNA
                         organism = synthetic construct
SEQUENCE: 590
tcctcctaca aaggcgtgtc tgtggttccc tgtctttgga cacgtaagaa ttggaggaaa   60
ataaatgtgg atttgggaaa ctttgaggcc agcttgcttc ttgcaggctc atgatcaacc  120
aatctcacat aa                                               132

SEQ ID NO: 591           moltype = RNA   length = 131
FEATURE                  Location/Qualifiers
source                   1..131
                         mol_type = other RNA
                         mol_type = other RNA
                         organism = synthetic construct
                         organism = synthetic construct
SEQUENCE: 591
ctccatgtat ctttgggacc tgtcagccgt ggcagtctcc cttcctagcc atggaagagc   60
atatccttgt ttattggcaa agctgtcacc atttaattgg tatcagattc tgacttgcac  120
aagtaacatt c                                                131

SEQ ID NO: 592           moltype = RNA   length = 132
FEATURE                  Location/Qualifiers
source                   1..132
                         mol_type = other RNA
                         mol_type = other RNA
                         organism = synthetic construct
                         organism = synthetic construct
SEQUENCE: 592
```

-continued

```
ctgcgaatat tctcgctgtt ctgattttgt aatagtcagg acaggctaaa cattcgctat   60
attaagacca tgcatgtgtc cccaaaccta gttctttccc taggtctggt ttcataaatg   120
ctggtgataa ac                                                        132

SEQ ID NO: 593          moltype = RNA   length = 133
FEATURE                 Location/Qualifiers
source                  1..133
                        mol_type = other RNA
                        mol_type = other RNA
                        organism = synthetic construct
                        organism = synthetic construct
SEQUENCE: 593
gcatggccga atactgtgtt tttatcagta gtttacacag ccagacacca tgcaaaagca   60
gtcttccctt tagaatgact gatggtatgc taaggttttt catagcatat cattattaaa   120
ggtgaataca aat                                                       133

SEQ ID NO: 594          moltype = RNA   length = 139
FEATURE                 Location/Qualifiers
source                  1..139
                        mol_type = other RNA
                        mol_type = other RNA
                        organism = synthetic construct
                        organism = synthetic construct
SEQUENCE: 594
tgcactgcat ggtatctgca ctcagcagtt tacacctgct agggtgttca aaggtcagtg   60
ctatagaaat tcagtatctg gcatcgttgg ttttcttggc tttgtgcttg ttaaacctgg   120
tatttctact gatacagta                                                 139

SEQ ID NO: 595          moltype = RNA   length = 134
FEATURE                 Location/Qualifiers
source                  1..134
                        mol_type = other RNA
                        mol_type = other RNA
                        organism = synthetic construct
                        organism = synthetic construct
SEQUENCE: 595
tggtccatcc taatccctgc cggtccatct gtggcctgcc aggtttcgct tgtggaccag   60
agcaccctag aagcctcacc cgaggagtga gcagggctcc agtgggctca cgtcatgggc   120
acttctagac actc                                                      134

SEQ ID NO: 596          moltype = RNA   length = 136
FEATURE                 Location/Qualifiers
source                  1..136
                        mol_type = other RNA
                        mol_type = other RNA
                        organism = synthetic construct
                        organism = synthetic construct
SEQUENCE: 596
cacctgcatt caaaaatgat cacgggctgc ctgtgctctg gtcatcaata acgcagggag   60
aggaattgct gaaagccgtt tcccgtgttt ggagggttca cacctgtccc tttcaaatgc   120
tggcgctttc acacac                                                    136

SEQ ID NO: 597          moltype = RNA   length = 134
FEATURE                 Location/Qualifiers
source                  1..134
                        mol_type = other RNA
                        mol_type = other RNA
                        organism = synthetic construct
                        organism = synthetic construct
SEQUENCE: 597
tgcattctta aaccctcttg gtggcttccc tgtaaatgct tccaagatat gagcgaatgc   60
tatagaaatt gcaggaaagt ccaaagggct gcgcgtctcc tgtggctcag tcttatttca   120
tacctgcaac atct                                                      134

SEQ ID NO: 598          moltype = RNA   length = 133
FEATURE                 Location/Qualifiers
source                  1..133
                        mol_type = other RNA
                        mol_type = other RNA
                        organism = synthetic construct
                        organism = synthetic construct
SEQUENCE: 598
attgcaccta aacccaagaa tcactgtttc ttatagcggt ggtttaaaca gaggtgcaaa   60
cagcaagcgg atcttgtcgc ctttgggggg ctgtggccgt gcccctcaaa gtgaatttgg   120
aggttccaca act                                                       133

SEQ ID NO: 599          moltype = RNA   length = 132
FEATURE                 Location/Qualifiers
source                  1..132
```

-continued

```
                              mol_type = other RNA
                              mol_type = other RNA
                              organism = synthetic construct
                              organism = synthetic construct
SEQUENCE: 599
cttcccattt atttgctgct tgtagtctca cagtgatacg agcagttata cgcatgggat    60
aaaataacat tgggccactg taaattgaga tgaagtaacc attttcatct cttctgcagg   120
gactagacat tg                                                        132

SEQ ID NO: 600           moltype = RNA   length = 135
FEATURE                  Location/Qualifiers
source                   1..135
                         mol_type = other RNA
                         mol_type = other RNA
                         organism = synthetic construct
                         organism = synthetic construct
SEQUENCE: 600
ctgcattctt aaaccctctt ggtagcttcg ttctaagtgc ttccaagata tgagtgaatg    60
ctatagaaat tgcaggggag tccaaagggc tgcgcttctc ccgtggctca gtcttatttc   120
atacctgcga catct                                                     135

SEQ ID NO: 601           moltype = RNA   length = 131
FEATURE                  Location/Qualifiers
source                   1..131
                         mol_type = other RNA
                         mol_type = other RNA
                         organism = synthetic construct
                         organism = synthetic construct
SEQUENCE: 601
aggcaggatc tagttacatt gtagctgtga agtgctgcat tgtctttgcc ccctgctcaa    60
aataaaactg ttacctttca agccctgtct gccatggtgc tgtagcagca gggatgtttg   120
gtctcataca t                                                         131

SEQ ID NO: 602           moltype = RNA   length = 123
FEATURE                  Location/Qualifiers
source                   1..123
                         mol_type = other RNA
                         mol_type = other RNA
                         organism = synthetic construct
                         organism = synthetic construct
SEQUENCE: 602
actggaggac taaggaggct gggtctgatg aggcaagatt ttgctgatac attgctccta    60
gaaaaaaggg ttggcaagag cagccctgga gactcacacg gctgactgtt ctacccaaca   120
ctc                                                                  123

SEQ ID NO: 603           moltype = RNA   length = 129
FEATURE                  Location/Qualifiers
source                   1..129
                         mol_type = other RNA
                         mol_type = other RNA
                         organism = synthetic construct
                         organism = synthetic construct
SEQUENCE: 603
aagcaggatt cagactacaa tatagctgtt aagtgctgta ttgtcattcc ccctgctcaa    60
attaaagttg tttcttaact atacccatct gctattctgt agcagccagg gatgcttggt   120
cacatacat                                                            129

SEQ ID NO: 604           moltype = RNA   length = 132
FEATURE                  Location/Qualifiers
source                   1..132
                         mol_type = other RNA
                         organism = synthetic construct
SEQUENCE: 604
ggcttcctag tacttaccat ggtctgtgtt cttacgctga ctgtatagaa acaggaggca    60
gagtaaaccg accccacata tacctcagcc caggccctgt gctgcgtctg tattgtgaat   120
caggagacat gg                                                        132

SEQ ID NO: 605           moltype = RNA   length = 139
FEATURE                  Location/Qualifiers
source                   1..139
                         mol_type = other RNA
                         mol_type = other RNA
                         organism = synthetic construct
                         organism = synthetic construct
SEQUENCE: 605
tggctcgatt tcctgggggg tggtctcagc ccactccacc tcccctcagc cgagcctaga    60
gtagaggggc caggcatcct ccccagggga ggggcgttga agcaaggagc ctctcctggg   120
ctgtcctagc ctcacattt                                                 139
```

-continued

```
SEQ ID NO: 606            moltype = RNA   length = 132
FEATURE                   Location/Qualifiers
source                    1..132
                          mol_type = other RNA
                          mol_type = other RNA
                          organism = synthetic construct
                          organism = synthetic construct
SEQUENCE: 606
gttgaggtct atcccgatag gtcttttcct gtagcctgca cgttgttgga aatgcctcat   60
agagtaactc tgtgatttta ctttacttac aggactattg ttacatctgt gggaaggaac  120
cacaagacag tt                                                       132

SEQ ID NO: 607            moltype = RNA   length = 133
FEATURE                   Location/Qualifiers
source                    1..133
                          mol_type = other RNA
                          mol_type = other RNA
                          organism = synthetic construct
                          organism = synthetic construct
SEQUENCE: 607
ttctcaccta aacccaagaa tcactgtttc ttatagcggt ggtttaaaca gaggtgcaaa   60
cagcaagtga atctcgtcgc ctttgcgggg ctgtggccag gccctcaaa  ggaaatttgg  120
aggctctaca gcc                                                      133

SEQ ID NO: 608            moltype = RNA   length = 128
FEATURE                   Location/Qualifiers
source                    1..128
                          mol_type = other RNA
                          mol_type = other RNA
                          organism = synthetic construct
                          organism = synthetic construct
SEQUENCE: 608
aggtcatttc aaagaggtct tgtgaggctg tgaaaccaag agctcttaac actgcgacca   60
aagatggaag ttctctatag gatgccatgg catttgatgg tgctatgttt tcttgaggag  120
atataaga                                                            128

SEQ ID NO: 609            moltype = RNA   length = 131
FEATURE                   Location/Qualifiers
source                    1..131
                          mol_type = other RNA
                          mol_type = other RNA
                          organism = synthetic construct
                          organism = synthetic construct
SEQUENCE: 609
ccctcctaca aaggcatgtc tatagttcct tgtctttgga catgtaagaa ttggaggcaa   60
agaaatgtgg acttggagaa atctgggggcc agcttgctct ccgcaggctc aagatcaacc  120
atcccacata g                                                        131

SEQ ID NO: 610            moltype = RNA   length = 125
FEATURE                   Location/Qualifiers
source                    1..125
                          mol_type = other RNA
                          mol_type = other RNA
                          organism = synthetic construct
                          organism = synthetic construct
SEQUENCE: 610
gcagactcac tatgcacctg actgtacttc caggcaggtg ctttttctgt ctgccagaga   60
aacattccag ggtgctgtgg ctgcctcacc tatccagggc gatgcagctc cctggggaca  120
caggt                                                               125

SEQ ID NO: 611            moltype = RNA   length = 125
FEATURE                   Location/Qualifiers
source                    1..125
                          mol_type = other RNA
                          mol_type = other RNA
                          organism = synthetic construct
                          organism = synthetic construct
SEQUENCE: 611
gcagactcac tctgcatctg actatacttc caggcgggtg ctttttctgt ctgccagata   60
aacattccag ggtgctgtgg ccgcctcacg tatccagagt gatgcagctc cctggggaca  120
caggt                                                               125

SEQ ID NO: 612            moltype = RNA   length = 148
FEATURE                   Location/Qualifiers
source                    1..148
                          mol_type = other RNA
                          mol_type = other RNA
                          organism = synthetic construct
                          organism = synthetic construct
```

```
SEQUENCE: 612
tgatggctgt tcctctcact gcttgaagcc ttaggcagtg ggattttgat ccatcatata    60
tcaaaaatgg cttatcttca ctcagggcac catgaggatg ggctggctgt ccgttagtgc   120
cttctgattt ttgcggagtc aaacaatt                                      148

SEQ ID NO: 613          moltype = RNA   length = 127
FEATURE                 Location/Qualifiers
source                  1..127
                        mol_type = other RNA
                        mol_type = other RNA
                        organism = synthetic construct
                        organism = synthetic construct
SEQUENCE: 613
ctggggaatt caaacttgtg ttaagaaat gtgtcccagt gtgcaatggc tgcaaacagc     60
agcttccttg gtagtgtatg cagcctgttt gttgtacggg ttgctctaaa gggccttgga   120
gacagtc                                                             127

SEQ ID NO: 614          moltype = RNA   length = 126
FEATURE                 Location/Qualifiers
source                  1..126
                        mol_type = other RNA
                        mol_type = other RNA
                        organism = synthetic construct
                        organism = synthetic construct
SEQUENCE: 614
aggtcacttc aaagagggct tgtggggctg tgaaaccaag aggtcttaac agtatgacca    60
aaaactgaag ttctctatag gatgctgtag cactcaatgg tgctatgttt tcctcaggag   120
atatga                                                              126

SEQ ID NO: 615          moltype = RNA   length = 139
FEATURE                 Location/Qualifiers
source                  1..139
                        mol_type = other RNA
                        mol_type = other RNA
                        organism = synthetic construct
                        organism = synthetic construct
SEQUENCE: 615
ctgtccgttg ctggcttcac aagtactagt ataatttta aaatgtttta ttattttgaa     60
aataatgttg taattcatgc cagggactga caaaaagactt gagacaggat ggttattctt   120
gtcagctaag gtcacattg                                                139

SEQ ID NO: 616          moltype = RNA   length = 113
FEATURE                 Location/Qualifiers
source                  1..113
                        mol_type = other RNA
                        mol_type = other RNA
                        organism = synthetic construct
                        organism = synthetic construct
SEQUENCE: 616
tccaaacaga cactgatggc accttctgcc atttaggaat ttgttttaaa acagacattt    60
gtctagatat ttcctttgtg gcctcctccc catcaaaagt caatcaaaca tcg          113

SEQ ID NO: 617          moltype = RNA   length = 143
FEATURE                 Location/Qualifiers
source                  1..143
                        mol_type = other RNA
                        mol_type = other RNA
                        organism = synthetic construct
                        organism = synthetic construct
SEQUENCE: 617
gccctatgtt aaaattttaa ttctgcactt actaactatc ttgggaacct tgggcaagta    60
accaacctct tgtgctttgg tttcctcatt ggtaaaatgg ggataacagt acttacctca   120
cagagttgtt gagaggaaca aat                                           143

SEQ ID NO: 618          moltype = RNA   length = 125
FEATURE                 Location/Qualifiers
source                  1..125
                        mol_type = other RNA
                        mol_type = other RNA
                        organism = synthetic construct
                        organism = synthetic construct
SEQUENCE: 618
atgcaggtac tgttacaata caactgatgt gttttgttgt cgttccccct gcttaaagca    60
cttgatgcat aactctgtct accttcattc cgtagtaaga cagagacgct tggcttcaga   120
cattt                                                               125

SEQ ID NO: 619          moltype = RNA   length = 147
FEATURE                 Location/Qualifiers
source                  1..147
```

-continued

```
                              mol_type = other RNA
                              organism = synthetic construct
SEQUENCE: 619
tcactgccct gctcaccctt cctgagtccg gcggcaaggg taactctggg agcatcgtag    60
agggcagaga agaagaaacc ctgaggtccc attatgtcag ccccttctat cacacgggag   120
gagactgagg acagaaaggg aacagag                                       147

SEQ ID NO: 620           moltype = RNA   length = 147
FEATURE                  Location/Qualifiers
source                   1..147
                         mol_type = other RNA
                         organism = synthetic construct
SEQUENCE: 620
cttttctcag tggtgcaaga agattaagcc acattctggc tttagagagg catttctgag    60
agagatgaag gacacttcgt tccccagccc caacctaagc atgtgactgt actcaccttg   120
tcagatgctg ttggaacctg gctgaca                                       147

SEQ ID NO: 621           moltype = RNA   length = 122
FEATURE                  Location/Qualifiers
source                   1..122
                         mol_type = other RNA
                         mol_type = other RNA
                         organism = synthetic construct
                         organism = synthetic construct
SEQUENCE: 621
ctggaggact aaggaggctg ggtctgatga ggcaagattt tgctgataca ttgctcctag    60
aaaaaagggt tggcaagagc agccctggag actcacacgg ctgactgttc tacccaacac   120
tc                                                                  122

SEQ ID NO: 622           moltype = RNA   length = 118
FEATURE                  Location/Qualifiers
source                   1..118
                         mol_type = other RNA
                         mol_type = other RNA
                         organism = synthetic construct
                         organism = synthetic construct
SEQUENCE: 622
tagtgtggaa ctgtctactc ctcattcctg tggaagcagg aatacattca taacatgctc    60
cattaaaaaa ggagttctag gccaggcagc gtgcctcatg cctggaatcc cagcactt     118

SEQ ID NO: 623           moltype = RNA   length = 126
FEATURE                  Location/Qualifiers
source                   1..126
                         mol_type = other RNA
                         mol_type = other RNA
                         organism = synthetic construct
                         organism = synthetic construct
SEQUENCE: 623
atacctaaac ccaagaatca ctttcttata gtgatgattt aaacagatgc aaacagcgag    60
cacatcttgt cacctttgcg ggactgtggc tgtgcccctc gcagtaaatt tggaggttct   120
acatcc                                                              126

SEQ ID NO: 624           moltype = RNA   length = 133
FEATURE                  Location/Qualifiers
source                   1..133
                         mol_type = other RNA
                         mol_type = other RNA
                         organism = synthetic construct
                         organism = synthetic construct
SEQUENCE: 624
aggcaggatc tagttacatt gtagctgtga agtgctgcat tgtctttgcc ccctgctcaa    60
aataaaactg ttacctttca agccctgtct gccatggtgc tgtagcagca gggatgtttg   120
gtctcataca tgt                                                      133

SEQ ID NO: 625           moltype = RNA   length = 81
FEATURE                  Location/Qualifiers
source                   1..81
                         mol_type = other RNA
                         mol_type = other RNA
                         organism = synthetic construct
                         organism = synthetic construct
SEQUENCE: 625
cactagaaga cagaattcac agaagtagca tttcaccttt tgcctttaca gaagtatatt    60
tggctgtttt gtgagacatt c                                              81

SEQ ID NO: 626           moltype = RNA   length = 112
FEATURE                  Location/Qualifiers
source                   1..112
                         mol_type = other RNA
```

```
                              mol_type = other RNA
                              organism = synthetic construct
                              organism = synthetic construct
SEQUENCE: 626
acttttacag gtagaatagt aaagcacagt gttgattgcc caagatttat tttactttga  60
aaaaattaga aatttattac tatagcaaat gtctagaact ttggaaacaa gt           112

SEQ ID NO: 627           moltype = RNA   length = 134
FEATURE                  Location/Qualifiers
source                   1..134
                         mol_type = other RNA
                         mol_type = other RNA
                         organism = synthetic construct
                         organism = synthetic construct
SEQUENCE: 627
atgcatctat ttgacagacc tggagcagtt gctatctgct gctatggttt ccaccacaga  60
tgcaagaaga acatgtcctt gcgctttccg tctgtctaat tgtggcagct gagattgaat  120
agaggaatac agga                                                     134

SEQ ID NO: 628           moltype = RNA   length = 136
FEATURE                  Location/Qualifiers
source                   1..136
                         mol_type = other RNA
                         mol_type = other RNA
                         organism = synthetic construct
                         organism = synthetic construct
SEQUENCE: 628
aagcactgcc tttgaacctg atgtgtcttg tttgtagctt cacgggccaa gcaacagtgc  60
tagagcataa cgacttgtta taactggggc tcttcagctc tcaactgaac tgctctttta  120
aaaacaaggt acattt                                                   136

SEQ ID NO: 629           moltype = RNA   length = 136
FEATURE                  Location/Qualifiers
source                   1..136
                         mol_type = other RNA
                         mol_type = other RNA
                         organism = synthetic construct
                         organism = synthetic construct
SEQUENCE: 629
aagcactgcc tttgaacctg atgtgtcttg tttgtagctt cacgggccaa gcaacagtgc  60
tagagcataa cgacttgtta taactggggc tcttcagctc tcaactgaac tgctctttta  120
aaaacaaggt acattt                                                   136

SEQ ID NO: 630           moltype = RNA   length = 133
FEATURE                  Location/Qualifiers
source                   1..133
                         mol_type = other RNA
                         mol_type = other RNA
                         organism = synthetic construct
                         organism = synthetic construct
SEQUENCE: 630
agcctttgtg ttgcccattc actttggaaa ctagtgaatg tggtgtcaaa aaaggcgtaa  60
attaaacgct ttgcagcctt ttcctgccct taaatttgat acctttggtg taggagctgc  120
ataagtaaca gtt                                                      133

SEQ ID NO: 631           moltype = RNA   length = 132
FEATURE                  Location/Qualifiers
source                   1..132
                         mol_type = other RNA
                         mol_type = other RNA
                         organism = synthetic construct
                         organism = synthetic construct
SEQUENCE: 631
ttccaaagtg ttgagttcag tccagggcag cttccctgtt ctgttaatta aactttggga  60
cattaaaatg ggctaaggga gatgattggg tagaaagtat tattctattc atttgcctcc  120
cagcctacaa aa                                                       132

SEQ ID NO: 632           moltype = RNA   length = 126
FEATURE                  Location/Qualifiers
source                   1..126
                         mol_type = other RNA
                         mol_type = other RNA
                         organism = synthetic construct
                         organism = synthetic construct
SEQUENCE: 632
aagcaacact ctgtggcaga tgatcaaaac tgtctgacac aatttgagct tgctatagca  60
agaaagtcta accattccg gtgttctctc tcccatgaga caagccgtta tatagactta  120
aacagt                                                              126
```

```
SEQ ID NO: 633            moltype = RNA   length = 126
FEATURE                   Location/Qualifiers
source                    1..126
                          mol_type = other RNA
                          mol_type = other RNA
                          organism = synthetic construct
                          organism = synthetic construct
SEQUENCE: 633
aagcaacact ctgtggcaga tgatcaaaac tgtctgacac aatttgagct tgctatagca   60
agaaagtcta acctattccg gtgttctctc tcccatgaga caagccgtta tatagactta   120
aacagt                                                              126

SEQ ID NO: 634            moltype = RNA   length = 132
FEATURE                   Location/Qualifiers
source                    1..132
                          mol_type = other RNA
                          mol_type = other RNA
                          organism = synthetic construct
                          organism = synthetic construct
SEQUENCE: 634
ttccacagct actggtctgc agctgttctt atggtagcag ttgtggcatt cctctgtggg   60
aaagaaactg ttaacacaaa cacctctttc ttagcaaaac agaaagtggg tatatatgtg   120
tgacagacac aa                                                       132

SEQ ID NO: 635            moltype = RNA   length = 134
FEATURE                   Location/Qualifiers
source                    1..134
                          mol_type = other RNA
                          mol_type = other RNA
                          organism = synthetic construct
                          organism = synthetic construct
SEQUENCE: 635
tgcagccgtg tcaaattcag tacctgtcct atgcatggta ggcactggcc cagaaggctg   60
ccacagaaac actgtgactc atgggccctg ttcctgtgtc ccaggctcag ggataaattt   120
ggttacagac atca                                                     134

SEQ ID NO: 636            moltype = RNA   length = 139
FEATURE                   Location/Qualifiers
source                    1..139
                          mol_type = other RNA
                          mol_type = other RNA
                          organism = synthetic construct
                          organism = synthetic construct
SEQUENCE: 636
tgcactgcat ggtatctgca ctcagcagtt tacacctgct agggtgttca aaggtcagtg   60
ctatagaaat tcagtatctg gcatcgttgg ttttcttggc tttgtgcttg ttaaacctgg   120
tatttctact gatacagta                                                139

SEQ ID NO: 637            moltype = RNA   length = 139
FEATURE                   Location/Qualifiers
source                    1..139
                          mol_type = other RNA
                          mol_type = other RNA
                          organism = synthetic construct
                          organism = synthetic construct
SEQUENCE: 637
tgcactgcat ggtatctgca ctcagcagtt tacacctgct agggtgttca aaggtcagtg   60
ctatagaaat tcagtatctg gcatcgttgg ttttcttggc tttgtgcttg ttaaacctgg   120
tatttctact gatacagta                                                139

SEQ ID NO: 638            moltype = RNA   length = 133
FEATURE                   Location/Qualifiers
source                    1..133
                          mol_type = other RNA
                          organism = synthetic construct
SEQUENCE: 638
tgcagccgtg tcaattcagt acctgtccta tgcatggtag gcactggccc agaaggctgc   60
cacagaaaca ctgtgactca tgggccctgt tcctgtgtcc caggctcagg gataaatttg   120
gttacagaca tca                                                      133

SEQ ID NO: 639            moltype = RNA   length = 132
FEATURE                   Location/Qualifiers
source                    1..132
                          mol_type = other RNA
                          organism = synthetic construct
SEQUENCE: 639
ttccaaagtg ttgagttcag tccagggcag cttccctgtt ctgttaatta aactttggga   60
cattaaaatg ggctaaggga gatgattggg tagaaagtat tattctattc atttgcctcc   120
cagcctacaa aa                                                       132
```

-continued

```
SEQ ID NO: 640            moltype = RNA   length = 134
FEATURE                   Location/Qualifiers
source                    1..134
                          mol_type = other RNA
                          mol_type = other RNA
                          organism = synthetic construct
                          organism = synthetic construct
SEQUENCE: 640
tggtaatgga tttatggtgg gtccttctct gtgggcctct catagtgtac ccatgccata   60
gcaaatggca gcctcgaacc attgcccagt ccccttacct gtgggctgtg agcactgaag  120
ggggttgcac agtg                                                    134

SEQ ID NO: 641            moltype = RNA   length = 134
FEATURE                   Location/Qualifiers
source                    1..134
                          mol_type = other RNA
                          mol_type = other RNA
                          organism = synthetic construct
                          organism = synthetic construct
SEQUENCE: 641
tggtaatgga tttatggtgg gtccttctct gtgggcctct catagtgtac ccatgccata   60
gcaaatggca gcctcgaacc attgcccagt ccccttacct gtgggctgtg agcactgaag  120
ggggttgcac agtg                                                    134

SEQ ID NO: 642            moltype = RNA   length = 132
FEATURE                   Location/Qualifiers
source                    1..132
                          mol_type = other RNA
                          mol_type = other RNA
                          organism = synthetic construct
                          organism = synthetic construct
SEQUENCE: 642
cagcatgttt ccaagggctg tggctggtca tagccatggg atctccaact gcatgcaaga   60
gcaacctgga aagactttga cagcgcaggt cagtacaata cctgcaagct gccactcagc  120
tttcctataa tg                                                     132

SEQ ID NO: 643            moltype = RNA   length = 132
FEATURE                   Location/Qualifiers
source                    1..132
                          mol_type = other RNA
                          mol_type = other RNA
                          organism = synthetic construct
                          organism = synthetic construct
SEQUENCE: 643
cagcatgttt ccaagggctg tggctggtca tagccatggg atctccaact gcatgcaaga   60
gcaacctgga aagactttga cagcgcaggt cagtacaata cctgcaagct gccactcagc  120
tttcctataa tg                                                     132

SEQ ID NO: 644            moltype = RNA   length = 133
FEATURE                   Location/Qualifiers
source                    1..133
                          mol_type = other RNA
                          mol_type = other RNA
                          organism = synthetic construct
                          organism = synthetic construct
SEQUENCE: 644
ggtctctcag ctccgcttaa ccacacgggt ccagtgtgtg cttggcgtgt tttcagggag   60
gcagagaaag gctctcctaa tgcacgacag acccgcccag aatggcctct ctgttcctag  120
gagtgcgaca att                                                    133

SEQ ID NO: 645            moltype = RNA   length = 135
FEATURE                   Location/Qualifiers
source                    1..135
                          mol_type = other RNA
                          mol_type = other RNA
                          organism = synthetic construct
                          organism = synthetic construct
SEQUENCE: 645
agcactatat ttaaacctgt ggatgggaat attccccatt cttggttacg ctgtagtgca   60
aaagaattcc tggctctctg ttgcacagct gacttgtgcc attctgctgt tgctgtatag  120
agttaaggaa catgg                                                  135

SEQ ID NO: 646            moltype = RNA   length = 133
FEATURE                   Location/Qualifiers
source                    1..133
                          mol_type = other RNA
                          mol_type = other RNA
                          organism = synthetic construct
```

-continued

```
                              organism = synthetic construct
SEQUENCE: 646
ggtctctcag ctccgcttaa ccacacgggt ccagtgtgtg cttggcgtgt tttcagggag    60
gcagagaaag gctctcctaa tgcacgacag acccgcccag aatggcctct ctgttcctag   120
gagtgcgaca att                                                      133

SEQ ID NO: 647           moltype = RNA   length = 130
FEATURE                  Location/Qualifiers
source                   1..130
                         mol_type = other RNA
                         mol_type = other RNA
                         organism = synthetic construct
                         organism = synthetic construct
SEQUENCE: 647
tgcctcattc tagagaatgg gcactgttga tcatggtgtc caaaaatagt taatgtggct    60
aaattgagac aggttatgct tccatcacag tatgcatatt gcagtggtga caatgagacc   120
tgtaacattt                                                          130

SEQ ID NO: 648           moltype = RNA   length = 135
FEATURE                  Location/Qualifiers
source                   1..135
                         mol_type = other RNA
                         mol_type = other RNA
                         organism = synthetic construct
                         organism = synthetic construct
SEQUENCE: 648
taggccctga atcaagacca atggtttgct gtagctgttg gtttcaaaca ggagctaaga    60
gtgatgtctt ccttgtggtc tgttggctat tcagtattcc agtgcgaatt gccaattcag   120
ttggaagaaa catag                                                    135

SEQ ID NO: 649           moltype = RNA   length = 135
FEATURE                  Location/Qualifiers
source                   1..135
                         mol_type = other RNA
                         mol_type = other RNA
                         organism = synthetic construct
                         organism = synthetic construct
SEQUENCE: 649
taggccctga atcaagacca atggtttgct gtagctgttg gtttcaaaca ggagctaaga    60
gtgatgtctt ccttgtggtc tgttggctat tcagtattcc agtgcgaatt gccaattcag   120
ttggaagaaa catag                                                    135

SEQ ID NO: 650           moltype = RNA   length = 130
FEATURE                  Location/Qualifiers
source                   1..130
                         mol_type = other RNA
                         mol_type = other RNA
                         organism = synthetic construct
                         organism = synthetic construct
SEQUENCE: 650
atcgaggcta gagtcacgct tgggtatcgg ctattgcctg agtgtgctag agtcctcgaa    60
gagtaactgc tgaccttatt cactggctgt gggccttatg gcacagtcag tcaccaggtt   120
agagacatgc                                                          130

SEQ ID NO: 651           moltype = RNA   length = 130
FEATURE                  Location/Qualifiers
source                   1..130
                         mol_type = other RNA
                         mol_type = other RNA
                         organism = synthetic construct
                         organism = synthetic construct
SEQUENCE: 651
atcgaggcta gagtcacgct tgggtatcgg ctattgcctg agtgtgctag agtcctcgaa    60
gagtaactgc tgaccttatt cactggctgt gggccttatg gcacagtcag tcaccaggtt   120
agagacatgc                                                          130

SEQ ID NO: 652           moltype = RNA   length = 149
FEATURE                  Location/Qualifiers
source                   1..149
                         mol_type = other RNA
                         mol_type = other RNA
                         organism = synthetic construct
                         organism = synthetic construct
SEQUENCE: 652
tgcacactat taaagctcag ggtggaggcc agtcttggct catgaacttc tgagtgtcgg    60
aagtgtgcta tatcaatggc aggattttcg ctaacaccag tagagcttgc ctctatgact   120
ggagtttggt agtactcgct gccacatag                                     149

SEQ ID NO: 653           moltype = RNA   length = 139
```

```
FEATURE            Location/Qualifiers
source             1..139
                   mol_type = other RNA
                   mol_type = other RNA
                   organism = synthetic construct
                   organism = synthetic construct
SEQUENCE: 653
gacctcctgg gatcgcatct ggagagtgcc tagtattctg ccagcttcgg aaagggaggg   60
aaagcaagcc tggcagaggc acccattcca ttcccagctt gctccgtagc tggcgattgg  120
aagacactct gcgacagtg                                                139

SEQ ID NO: 654    moltype = RNA  length = 139
FEATURE            Location/Qualifiers
source             1..139
                   mol_type = other RNA
                   mol_type = other RNA
                   organism = synthetic construct
                   organism = synthetic construct
SEQUENCE: 654
gacctcctgg gatcgcatct ggagagtgcc tagtattctg ccagcttcgg aaagggaggg   60
aaagcaagcc tggcagaggc acccattcca ttcccagctt gctccgtagc tggcgattgg  120
aagacactct gcgacagtg                                                139

SEQ ID NO: 655    moltype = RNA  length = 133
FEATURE            Location/Qualifiers
source             1..133
                   mol_type = other RNA
                   mol_type = other RNA
                   organism = synthetic construct
                   organism = synthetic construct
SEQUENCE: 655
tagcaagcct ccagcgtgct tgggtctgcg gtgaccctat gcattccttc agtgcttgct   60
agaacagttt tgaaacggtt tgaggccttg ccctgctcca tccagagcaa ggttatagaa  120
atttcagaca atg                                                      133

SEQ ID NO: 656    moltype = RNA  length = 133
FEATURE            Location/Qualifiers
source             1..133
                   mol_type = other RNA
                   mol_type = other RNA
                   organism = synthetic construct
                   organism = synthetic construct
SEQUENCE: 656
tagcaagcct ccagcgtgct tgggtctgcg gtgaccctat gcattccttc agtgcttgct   60
agaacagttt tgaaacggtt tgaggccttg ccctgctcca tccagagcaa ggttatagaa  120
atttcagaca atg                                                      133

SEQ ID NO: 657    moltype = RNA  length = 134
FEATURE            Location/Qualifiers
source             1..134
                   mol_type = other RNA
                   mol_type = other RNA
                   organism = synthetic construct
                   organism = synthetic construct
SEQUENCE: 657
ttggccctta tcgaagctgc agctgcttcc gcatagctgc tgtggtcaaa aaggagccca   60
gagtgacagt tttccttgac ggtcgccgtt ctgtttgttg taactgatct gcaacatttt  120
gggaaaatac agtt                                                     134

SEQ ID NO: 658    moltype = RNA  length = 31
FEATURE            Location/Qualifiers
source             1..31
                   mol_type = other RNA
                   mol_type = other RNA
                   organism = synthetic construct
                   organism = synthetic construct
SEQUENCE: 658
acacaggcac tggccactga aatttttgga g                                   31

SEQ ID NO: 659    moltype = RNA  length = 47
FEATURE            Location/Qualifiers
source             1..47
                   mol_type = other RNA
                   mol_type = other RNA
                   organism = synthetic construct
                   organism = synthetic construct
SEQUENCE: 659
taggctttct ggcttttcac cggaaagccc ctaaatgatt aaattaa                  47
```

-continued

```
SEQ ID NO: 660           moltype = RNA   length = 31
FEATURE                  Location/Qualifiers
source                   1..31
                         mol_type = other RNA
                         mol_type = other RNA
                         organism = synthetic construct
                         organism = synthetic construct
SEQUENCE: 660
gattaggcac acacaggcac aatttttgga g                                    31

SEQ ID NO: 661           moltype = RNA   length = 47
FEATURE                  Location/Qualifiers
source                   1..47
                         mol_type = other RNA
                         mol_type = other RNA
                         organism = synthetic construct
                         organism = synthetic construct
SEQUENCE: 661
taggctttct ggcttttcac cggaaagccc ctaaatgatt aaattaa                   47

SEQ ID NO: 662           moltype = RNA   length = 31
FEATURE                  Location/Qualifiers
source                   1..31
                         mol_type = other RNA
                         mol_type = other RNA
                         organism = synthetic construct
                         organism = synthetic construct
SEQUENCE: 662
cttccttgac gattaggcac aatttttgga g                                    31

SEQ ID NO: 663           moltype = RNA   length = 47
FEATURE                  Location/Qualifiers
source                   1..47
                         mol_type = other RNA
                         mol_type = other RNA
                         organism = synthetic construct
                         organism = synthetic construct
SEQUENCE: 663
taggctttct ggcttttcac cggaaagccc ctaaatgatt aaattaa                   47

SEQ ID NO: 664           moltype = RNA   length = 31
FEATURE                  Location/Qualifiers
source                   1..31
                         mol_type = other RNA
                         mol_type = other RNA
                         organism = synthetic construct
                         organism = synthetic construct
SEQUENCE: 664
accttcttcc ttgacgatta aatttttgga g                                    31

SEQ ID NO: 665           moltype = RNA   length = 47
FEATURE                  Location/Qualifiers
source                   1..47
                         mol_type = other RNA
                         mol_type = other RNA
                         organism = synthetic construct
                         organism = synthetic construct
SEQUENCE: 665
taggctttct ggcttttcac cggaaagccc ctaaatgatt aaattaa                   47

SEQ ID NO: 666           moltype = RNA   length = 31
FEATURE                  Location/Qualifiers
source                   1..31
                         mol_type = other RNA
                         mol_type = other RNA
                         organism = synthetic construct
                         organism = synthetic construct
SEQUENCE: 666
acacaggcac tggccactga tgcgtgtcat t                                    31

SEQ ID NO: 667           moltype = RNA   length = 47
FEATURE                  Location/Qualifiers
source                   1..47
                         mol_type = other RNA
                         mol_type = other RNA
                         organism = synthetic construct
                         organism = synthetic construct
SEQUENCE: 667
taggctttct ggcttttcac cggaaagccc ctaaatgatt aaattaa                   47
```

-continued

```
SEQ ID NO: 668          moltype = DNA   length = 31
FEATURE                 Location/Qualifiers
source                  1..31
                        mol_type = other DNA
                        mol_type = other DNA
                        organism = synthetic construct
                        organism = synthetic construct
SEQUENCE: 668
ggcacacaca ggcactggcc tgcgtgtcat t                                31

SEQ ID NO: 669          moltype = DNA   length = 47
FEATURE                 Location/Qualifiers
source                  1..47
                        mol_type = other DNA
                        mol_type = other DNA
                        organism = synthetic construct
                        organism = synthetic construct
SEQUENCE: 669
taggctttct ggcttttcac cggaaagccc ctaaatgatt aaattaa             47

SEQ ID NO: 670          moltype = DNA   length = 31
FEATURE                 Location/Qualifiers
source                  1..31
                        mol_type = other DNA
                        mol_type = other DNA
                        organism = synthetic construct
                        organism = synthetic construct
SEQUENCE: 670
acgagctcag cctatgcgag aatttttgga g                                31

SEQ ID NO: 671          moltype = DNA   length = 47
FEATURE                 Location/Qualifiers
source                  1..47
                        mol_type = other DNA
                        mol_type = other DNA
                        organism = synthetic construct
                        organism = synthetic construct
SEQUENCE: 671
taggctttct ggcttttcac cggaaagccc ctaaatgatt aaattaa             47

SEQ ID NO: 672          moltype = DNA   length = 31
FEATURE                 Location/Qualifiers
source                  1..31
                        mol_type = other DNA
                        mol_type = other DNA
                        organism = synthetic construct
                        organism = synthetic construct
SEQUENCE: 672
ccacctaccc tatcgtgcgg aatttttgga g                                31

SEQ ID NO: 673          moltype = DNA   length = 47
FEATURE                 Location/Qualifiers
source                  1..47
                        mol_type = other DNA
                        mol_type = other DNA
                        organism = synthetic construct
                        organism = synthetic construct
SEQUENCE: 673
taggctttct ggcttttcac cggaaagccc ctaaatgatt aaattaa             47

SEQ ID NO: 674          moltype = DNA   length = 83
FEATURE                 Location/Qualifiers
source                  1..83
                        mol_type = other DNA
                        mol_type = other DNA
                        organism = synthetic construct
                        organism = synthetic construct
SEQUENCE: 674
ggtcaatgat gtgttggcat gtatcaggta ttcctgtggc tgatgtgtaa taacactgga  60
tgaagggaca cacactgaga cct                                        83

SEQ ID NO: 675          moltype = DNA   length = 103
FEATURE                 Location/Qualifiers
source                  1..103
                        mol_type = other DNA
                        mol_type = other DNA
                        organism = synthetic construct
                        organism = synthetic construct
```

-continued

```
SEQUENCE: 675
tatgatagggg acttagggtg ggtcaatgat gtgttggcat gtatcaggta ttcctgtggc   60
tgatgtgtaa taacactgga tgaagggaca cacactgaga cct                     103

SEQ ID NO: 676          moltype = DNA  length = 103
FEATURE                 Location/Qualifiers
source                  1..103
                        mol_type = other DNA
                        mol_type = other DNA
                        organism = synthetic construct
                        organism = synthetic construct
SEQUENCE: 676
ggtcaatgat gtgttggcat gtatcaggta ttcctgtggc tgatgtgtaa taacactgga   60
tgaagggaca cacactgaga ccttatgata gggacttagg gtg                     103

SEQ ID NO: 677          moltype = DNA  length = 83
FEATURE                 Location/Qualifiers
source                  1..83
                        mol_type = other DNA
                        mol_type = other DNA
                        organism = synthetic construct
                        organism = synthetic construct
SEQUENCE: 677
ggtcaatgat gtgttggcat gtatggtaca ggtattcctc tgatgtgtaa taacactctg   60
tggatgaagg gacactgaga cct                                           83

SEQ ID NO: 678          moltype = DNA  length = 103
FEATURE                 Location/Qualifiers
source                  1..103
                        mol_type = other DNA
                        mol_type = other DNA
                        organism = synthetic construct
                        organism = synthetic construct
SEQUENCE: 678
tatgatagggg acttagggtg ggtcaatgat gtgttggcat gtatggtaca ggtattcctc   60
tgatgtgtaa taacactctg tggatgaagg gacactgaga cct                     103

SEQ ID NO: 679          moltype = DNA  length = 103
FEATURE                 Location/Qualifiers
source                  1..103
                        mol_type = other DNA
                        mol_type = other DNA
                        organism = synthetic construct
                        organism = synthetic construct
SEQUENCE: 679
ggtcaatgat gtgttggcat gtatggtaca ggtattcctc tgatgtgtaa taacactctg   60
tggatgaagg gacactgaga ccttatgata gggacttagg gtg                     103

SEQ ID NO: 680          moltype = DNA  length = 135
FEATURE                 Location/Qualifiers
source                  1..135
                        mol_type = other DNA
                        mol_type = other DNA
                        organism = synthetic construct
                        organism = synthetic construct
SEQUENCE: 680
agcactataa agggacctgt ggatgggaat attccccatt cttggtacac acatagtgca   60
aaagaattcc tggctctctg ttgcacagct gacttgtgcc attctgctgt tgctgtatag   120
agttaaggaa catgg                                                    135

SEQ ID NO: 681          moltype = DNA  length = 155
FEATURE                 Location/Qualifiers
source                  1..155
                        mol_type = other DNA
                        mol_type = other DNA
                        organism = synthetic construct
                        organism = synthetic construct
SEQUENCE: 681
tatgatagggg acttagggtg agcactataa agggacctgt ggatgggaat attccccatt   60
cttggtacac acatagtgca aaagaattcc tggctctctg ttgcacagct gacttgtgcc   120
attctgctgt tgctgtatag agttaaggaa catgg                              155

SEQ ID NO: 682          moltype = DNA  length = 155
FEATURE                 Location/Qualifiers
source                  1..155
                        mol_type = other DNA
                        mol_type = other DNA
                        organism = synthetic construct
                        organism = synthetic construct
```

-continued

```
SEQUENCE: 682
agcactataa agggacctgt ggatgggaat attccccatt cttggtacac acatagtgca    60
aaagaattcc tggctctctg ttgcacagct gacttgtgcc attctgctgt tgctgtatag    120
agttaaggaa catggtatga tagggactta gggtg                              155

SEQ ID NO: 683        moltype = DNA   length = 132
FEATURE               Location/Qualifiers
source                1..132
                      mol_type = other DNA
                      mol_type = other DNA
                      organism = synthetic construct
                      organism = synthetic construct
SEQUENCE: 683
cagcatgttt ccaagggctg tggctggtca tagccatggg atctccaact gcatgcaaga    60
gcaacctgga aagacacaca cagcgcaggt cagtacaata cctgcaagct gcatgccagc    120
tttcctataa tg                                                        132

SEQ ID NO: 684        moltype = DNA   length = 152
FEATURE               Location/Qualifiers
source                1..152
                      mol_type = other DNA
                      mol_type = other DNA
                      organism = synthetic construct
                      organism = synthetic construct
SEQUENCE: 684
tatgataggg acttagggtg cagcatgttt ccaagggctg tggctggtca tagccatggg    60
atctccaact gcatgcaaga gcaacctgga aagacacaca cagcgcaggt cagtacaata    120
cctgcaagct gcatgccagc tttcctataa tg                                  152

SEQ ID NO: 685        moltype = DNA   length = 152
FEATURE               Location/Qualifiers
source                1..152
                      mol_type = other DNA
                      mol_type = other DNA
                      organism = synthetic construct
                      organism = synthetic construct
SEQUENCE: 685
cagcatgttt ccaagggctg tggctggtca tagccatggg atctccaact gcatgcaaga    60
gcaacctgga aagacacaca cagcgcaggt cagtacaata cctgcaagct gcatgccagc    120
tttcctataa tgtatgatag ggacttaggg tg                                  152

SEQ ID NO: 686        moltype = DNA   length = 103
FEATURE               Location/Qualifiers
source                1..103
                      mol_type = other DNA
                      mol_type = other DNA
                      organism = synthetic construct
                      organism = synthetic construct
SEQUENCE: 686
ggtcaatgat gtgttggcat gtatcaggta ttcctgtggc tgatgtgtaa taacactgga    60
tgaagggaca cacactgaga ccttatgata gggacttagg gtg                      103

SEQ ID NO: 687        moltype = DNA   length = 83
FEATURE               Location/Qualifiers
source                1..83
                      mol_type = other DNA
                      mol_type = other DNA
                      organism = synthetic construct
                      organism = synthetic construct
SEQUENCE: 687
ggtcaatgat gtgttggcat gtatggtaca ggtattcctc tgatgtgtaa taacactctg    60
tggatgaagg gacactgaga cct                                            83

SEQ ID NO: 688        moltype = DNA   length = 103
FEATURE               Location/Qualifiers
source                1..103
                      mol_type = other DNA
                      mol_type = other DNA
                      organism = synthetic construct
                      organism = synthetic construct
SEQUENCE: 688
tatgataggg acttagggtg ggtcaatgat gtgttggcat gtatggtaca ggtattcctc    60
tgatgtgtaa taacactctg tggatgaagg gacactgaga cct                      103

SEQ ID NO: 689        moltype = DNA   length = 103
FEATURE               Location/Qualifiers
source                1..103
                      mol_type = other DNA
                      organism = synthetic construct
```

```
SEQUENCE: 689
ggtcaatgat gtgttggcat gtatggtaca ggtattcctc tgatgtgtaa taacactctg   60
tggatgaagg gacactgaga ccttatgata gggacttagg gtg                     103

SEQ ID NO: 690          moltype = DNA   length = 135
FEATURE                 Location/Qualifiers
source                  1..135
                        mol_type = other DNA
                        organism = synthetic construct
SEQUENCE: 690
agcactataa agggacctgt ggatgggaat attccccatt cttggtacac acatagtgca   60
aaagaattcc tggctctctg ttgcacagct gacttgtgcc attctgctgt tgctgtatag  120
agttaaggaa catgg                                                    135

SEQ ID NO: 691          moltype = DNA   length = 155
FEATURE                 Location/Qualifiers
source                  1..155
                        mol_type = other DNA
                        organism = synthetic construct
SEQUENCE: 691
tatgataggg acttagggtg agcactataa agggacctgt ggatgggaat attccccatt   60
cttggtacac acatagtgca aaagaattcc tggctctctg ttgcacagct gacttgtgcc  120
attctgctgt tgctgtatag agttaaggaa catgg                              155

SEQ ID NO: 692          moltype = DNA   length = 155
FEATURE                 Location/Qualifiers
source                  1..155
                        mol_type = other DNA
                        organism = synthetic construct
SEQUENCE: 692
agcactataa agggacctgt ggatgggaat attccccatt cttggtacac acatagtgca   60
aaagaattcc tggctctctg ttgcacagct gacttgtgcc attctgctgt tgctgtatag  120
agttaaggaa catggtatga tagggactta gggtg                              155

SEQ ID NO: 693          moltype = DNA   length = 132
FEATURE                 Location/Qualifiers
source                  1..132
                        mol_type = other DNA
                        organism = synthetic construct
SEQUENCE: 693
cagcatgttt ccaagggctg tggctggtca tagccatggg atctccaact gcatgcaaga   60
gcaacctgga aagacacaca cagcgcaggt cagtacaata cctgcaagct gcatgccagc  120
tttcctataa tg                                                       132

SEQ ID NO: 694          moltype = DNA   length = 152
FEATURE                 Location/Qualifiers
source                  1..152
                        mol_type = other DNA
                        organism = synthetic construct
SEQUENCE: 694
tatgataggg acttagggtg cagcatgttt ccaagggctg tggctggtca tagccatggg   60
atctccaact gcatgcaaga gcaacctgga aagacacaca cagcgcaggt cagtacaata  120
cctgcaagct gcatgccagc tttcctataa tg                                 152

SEQ ID NO: 695          moltype = DNA   length = 152
FEATURE                 Location/Qualifiers
source                  1..152
                        mol_type = other DNA
                        organism = synthetic construct
SEQUENCE: 695
cagcatgttt ccaagggctg tggctggtca tagccatggg atctccaact gcatgcaaga   60
gcaacctgga aagacacaca cagcgcaggt cagtacaata cctgcaagct gcatgccagc  120
tttcctataa tgtatgatag ggacttaggg tg                                 152

SEQ ID NO: 696          moltype = DNA   length = 247
FEATURE                 Location/Qualifiers
source                  1..247
                        mol_type = other DNA
                        organism = synthetic construct
SEQUENCE: 696
tacttacctg gcaggggaga taccatgatc acgaaggtgg ttttttcccag ggcgaggctt   60
atccattgca ctccggatgt gctgacccct gcgattccc caaatgtggg aaactcgact   120
gcataatttg tggtagtggg ggactgcgtt cgcgctttcc cctgtcacta gtctgtggtg  180
tgatatccat ggcggcctac ttatcctgtc cctttttttt ccacagnnnn nnnnnnnnnn  240
nnnnnnn                                                             247

SEQ ID NO: 697          moltype = DNA   length = 242
FEATURE                 Location/Qualifiers
source                  1..242
```

-continued

```
                            mol_type = other DNA
                            organism = synthetic construct
SEQUENCE: 697
acctggcagg ggagatacca tgatcacgaa ggtggttttc ccagggcgag gcttatccat    60
tgcactccgg atgtgctgac ccctgcgatt tccccaaatg tgggaaactc gactgcataa    120
ttttgtggta gtgggggact gcgttcgcgc tttccctgt cactagtctg tggtgtgata    180
tccatggcgg cctacttatc ctgtcccttt ttttttccaca gnnnnnnnnn nnnnnnnnnn    240
nn                                                                  242

SEQ ID NO: 698          moltype = DNA   length = 237
FEATURE                 Location/Qualifiers
source                  1..237
                        mol_type = other DNA
                        organism = synthetic construct
SEQUENCE: 698
ggcaggggag ataccatgat cacgaaggtg gttttcccag ggcgaggctt atccattgca    60
ctccggatgt gctgacccct gcgatttccc caaatgtggg aaactcgact gcataatttg    120
tggtagtggg ggactgcgtt cgcgcttcc cctgtcacta gtctgtggtg tgatatccat    180
ggcggcctac ttatcctgtc cctttttttt ccacagnnnn nnnnnnnnnn nnnnnn       237

SEQ ID NO: 699          moltype = DNA   length = 216
FEATURE                 Location/Qualifiers
source                  1..216
                        mol_type = other DNA
                        organism = synthetic construct
SEQUENCE: 699
aaaaagggct tctgtcgtga gtggcacacg tagggcaact cgattgctct gcgtgcggaa    60
tcgacatcaa gagatttcgg aagcataatt ttttggtatt tgggcagctg gtgatcgttc    120
gtcccggcgc cctttcacta gtctgtggtg tgctatccat ggcggcctac ttatcctgtc    180
cctttttttt ccacagnnnn nnnnnnnnnn nnnnn                              216

SEQ ID NO: 700          moltype = DNA   length = 213
FEATURE                 Location/Qualifiers
source                  1..213
                        mol_type = other DNA
                        organism = synthetic construct
SEQUENCE: 700
agggcttctg tcgtgagtgg cacacgtagg gcaactcgat tgctctgcgt gcggaatcga    60
catcaagaga tttcggaagc ataatttttt ggtatttggg cagctggtga tcgttcgtcc    120
cggcgccctt tcactagtct gtggtgtgac tatccatggc ggcctactta tcctgtccct    180
ttttttttcca cagnnnnnnn nnnnnnnnnn nnn                               213

SEQ ID NO: 701          moltype = DNA   length = 208
FEATURE                 Location/Qualifiers
source                  1..208
                        mol_type = other DNA
                        organism = synthetic construct
SEQUENCE: 701
gcttctgtcg tgagtggcac acgtagggca actgattgct ctgcgtgcgg aatcgacatc    60
aagagatttc ggaagcataa ttttttggta tttgggcagc tggtgatcgt tcgtcccggc    120
gccctttcac tagtctgtgg tgtgatatcc atggcggcct acttatcctg tccctttttt    180
ttccacagnn nnnnnnnnnn nnnnnnnn                                      208

SEQ ID NO: 702          moltype = DNA   length = 127
FEATURE                 Location/Qualifiers
source                  1..127
                        mol_type = other DNA
                        organism = synthetic construct
SEQUENCE: 702
aatttttgga gcaggttttc cagtgttcac tgaaatttgt ctcttcacta gtctgtggtg    60
tgatatccca tggcggccta cttatcctgt ccctttttttt tccacagnnn nnnnnnnnnn    120
nnnnnnn                                                             127

SEQ ID NO: 703          moltype = DNA   length = 124
FEATURE                 Location/Qualifiers
source                  1..124
                        mol_type = other DNA
                        organism = synthetic construct
SEQUENCE: 703
aatttttgga gaaggttttc tggtctttat cagaaagcct cctcactagt ctgtggtgtg    60
atatccatgg cggcctactt atcctgtccc ttttttttcc acagnnnnnn nnnnnnnnnn    120
nnnn                                                                124

SEQ ID NO: 704          moltype = DNA   length = 125
FEATURE                 Location/Qualifiers
source                  1..125
                        mol_type = other DNA
                        organism = synthetic construct
SEQUENCE: 704
```

-continued

```
aatttttgga gcaggttttc tggtttcact gcaaaacccc atcactagtc tgtggtgtga   60
tatccatggc ggcctactgg atcctgtccc ttttttttttc cacagnnnnn nnnnnnnnnn   120
nnnnn                                                               125

SEQ ID NO: 705          moltype = DNA   length = 138
FEATURE                 Location/Qualifiers
source                  1..138
                        mol_type = other DNA
                        organism = synthetic construct
SEQUENCE: 705
aatttttgga gcacgttttc cggttgtcac tcccaggtag gctggggaag aggcattcac   60
tagtctgtgg tgtgatatcc atggcggcct acttatcctg tccctttttt ttccacagnn   120
nnnnnnnnnn nnnnnnnn                                                  138

SEQ ID NO: 706          moltype = DNA   length = 101
FEATURE                 Location/Qualifiers
source                  1..101
                        mol_type = other DNA
                        organism = synthetic construct
SEQUENCE: 706
aatttttgg agcgtctctt cactagtctg tggtgtgata tccatggcgg cctacttatc   60
ctgtcccttt tttttccaca gnnnnnnnnn nnnnnnnnnn n                       101

SEQ ID NO: 707          moltype = DNA   length = 98
FEATURE                 Location/Qualifiers
source                  1..98
                        mol_type = other DNA
                        organism = synthetic construct
SEQUENCE: 707
aatttttgga gaatcctcac tagtctgtgg tgtgatatcc atggcggcct acttatcctg   60
tccctttttt ttccacagnn nnnnnnnnnn nnnnnnn                            98

SEQ ID NO: 708          moltype = DNA   length = 102
FEATURE                 Location/Qualifiers
source                  1..102
                        mol_type = other DNA
                        organism = synthetic construct
SEQUENCE: 708
aatttttgga gcagcccatc actagtctgt ggtgtgatat ccatggcgtg cctacttatc   60
ctgtcccttt tttttccac agnnnnnnnn nnnnnnnnnn nn                        102

SEQ ID NO: 709          moltype = DNA   length = 109
FEATURE                 Location/Qualifiers
source                  1..109
                        mol_type = other DNA
                        organism = synthetic construct
SEQUENCE: 709
aatttttgga gcacgttttc cggttattca ctagtctgtg gtgtgatatc catggcggcc   60
tacttatcct gtcccttttt tttccacagn nnnnnnnnnn nnnnnnnnn                 109

SEQ ID NO: 710          moltype = DNA   length = 195
FEATURE                 Location/Qualifiers
source                  1..195
                        mol_type = other DNA
                        organism = synthetic construct
SEQUENCE: 710
aggtcagagg gcttgtgggg ctgtgaaacc aagaggtctt tgaccaaaaa ctgaagttct   60
ctataggatg ctgtagcact caatggtgct atgtttttcct caggagatat gatcactagt   120
ctgtggtgtg atatccatgg cggcctactt atcctgtccc ttttttttttc cacagnnnnn   180
nnnnnnnnnn nnnnn                                                     195

SEQ ID NO: 711          moltype = DNA   length = 186
FEATURE                 Location/Qualifiers
source                  1..186
                        mol_type = other DNA
                        organism = synthetic construct
SEQUENCE: 711
ctggagggct gggtctgatg aggcaagatt ttgctctcct agaaaaaagg gttggcaaga   60
gcagccctgg agactcacac ggctgactgt tctacccaac actctcacta gtctgtggtg   120
tgatatccat ggcggcctac ttatcctgtc ccttttttttt ccacagnnnn nnnnnnnnnn   180
nnnnnn                                                               186

SEQ ID NO: 712          moltype = DNA   length = 209
FEATURE                 Location/Qualifiers
source                  1..209
                        mol_type = other DNA
                        organism = synthetic construct
SEQUENCE: 712
tggctcgggg gggtggtctc agcccactcc acctccccga gcctagagta gagggggccag   60
```

-continued

```
gcatcctccc caggggaggg gcgttgaagc aaggagcctc tcctgggctg tcctagcctc  120
acattttcac tagtctgtgg tgtgatatcc atggcggcct acttatcctg tccctttttt  180
tttccacagn nnnnnnnnnn nnnnnnnnn                                    209

SEQ ID NO: 713            moltype = DNA   length = 214
FEATURE                   Location/Qualifiers
source                    1..214
                          mol_type = other DNA
                          organism = synthetic construct
SEQUENCE: 713
tcactgccct cttcctgagt ccggcggcaa gggtaactct gggagagggc agagaagaag   60
aaaccctgag gtcccattat gtcagcccct tctatcacac gggaggagac tgaggacaga  120
aagggaacag agtcactagt ctgtggtgtg atatccatgg cggcctactt atcctgtccc  180
ttttttttcc acagnnnnnn nnnnnnnnnn nnnn                              214
```

METHODS AND COMPOSITIONS FOR TARGETED TRANS-SPLICING

CROSS-REFERENCE TO RELATED APPLICATIONS

This application is a U.S. National Phase Application under 35 U.S.C. § 371 of International Application No. PCT/US2023/081868, filed Nov. 30, 2023, which claims priority to U.S. Provisional Application No. 63/429,031, filed on Nov. 30, 2022, the entire contents of which are incorporated herein.

FIELD

The disclosure relates to a nucleic acid composition for targeting trans-splicing of a pre-mRNA in a cell, and related methods.

SEQUENCE LISTING SUBMISSION VIA EFS-WEB

The instant application contains a sequence listing, which has been submitted in XML format via PatentCenter. The contents of the XML copy named "AMR-014_134241-5014_Sequence_Listing.xml," which was created on Dec. 23, 2025 and is 789,481 bytes in size, the contents of which are incorporated herein by reference in their entirety.

BACKGROUND

Gene editing is widely recognized as a promising approach to treat numerous diseases associated with viral infection, enzymatic deficiency, and hereditary myopathies. For example, gene-editing using a CRISPR/Cas system can introduce a double-stranded break in a gene of interest that is repaired by endogenous DNA repair pathways to introduce a gene knockout or a correction of a mutation. Appropriate gene edits can function to eliminate a mutation in, decrease expression of, or alter function or activity of an encoded protein in order to provide desirable therapeutic outcomes. However, despite significant progress, gene editing approaches remain problematic due to the risk of introducing deleterious off-target edits to the genome and packaging constraints for delivery of system components. An alternative approach to introduce genetic information to a cell that avoids the risk of introducing permanent changes to the genome is by regulating splicing of endogenous nucleic acids (e.g., RNA transcripts).

Splicing is a reaction that occurs in the nucleus of eukaryotic cells and is catalyzed by the spliceosome, a large ribonucleoprotein (RNP) complex. Splicing removes non-coding sequences (introns) from RNA transcripts (pre-mRNA) and ligates coding sequences (exons) together. The spliceosome typically mediates cis-splicing of endogenous RNA transcripts, in which a lariat is formed in an intron and then excised in order to join two exons in the same RNA transcript (see, e.g., Matera, et al (2014) Nat Rev Mol Cell Biol 15(2):108-21; Wilkinson, et al (2020) Annu Rev Biochem 89:359). The spliceosome can also perform trans-splicing, in which exons from two different primary RNA transcripts are joined end-to-end and ligated (Lasda, et al (2011) Wiley Interdiscip Rev RNA 2:417-34). Trans-splicing yields a chimeric molecule comprising one or more exonic regions from the first RNA molecule and one or more exonic regions from the second RNA molecule.

Trans-splicing using an exogenous nucleic acid encoding desired genetic information is a promising avenue for therapeutic nucleic acid editing and other biotechnology applications. For example, it has been demonstrated that introducing an artificial RNA introduced to a cell can undergo trans-splicing with an endogenous pre-mRNA (see, e.g., Puttaraju, et al (1999) Nat Biotech 17:246). Such trans-splicing efforts have focused on spliceosome-mediated RNA trans-splicing (SMaRT), where activity of a pre-mRNA trans-splicing molecule (PTM) is achieved by RNA-RNA interactions between a binding domain that hybridizes to a target pre-mRNA (Puttaraju, 1999). While some groups have been able to demonstrate in vitro and in vivo activity with SMaRT technology (Mansfield, et al (2000) Gene therapy 7: 1885-1895; Liu, et al (2002) *Nat. Biotechnol.* 20:47), it is a relatively inefficient process that has not yet progressed to the clinic (Berger, et al (2016) *Wiley Interdisciplinary Reviews: RNA* 7:487-98).

Thus, new approaches are needed to enable targeted and efficient trans-splicing to introduce desired genetic information to a cell.

SUMMARY OF THE DISCLOSURE

In some aspects, the disclosure provides a nucleic acid for targeting trans-splicing of a pre-mRNA in a cell, the nucleic acid comprising a nucleotide sequence comprising (a) at least one intronic sequence comprising (i) one or more binding domain sequences of about 4 to about 300 nucleotides each with complementarity to a pre-mRNA target sequence; and (ii) a non-coding RNA (ncRNA) sequence of about 7 to about 300 nucleotides in length which forms a secondary structure and/or comprises a sequence motif to direct the one or more binding domains to the pre-mRNA target sequence; (b) a splice acceptor and/or splice donor sequence; and (c) at least one exonic sequence.

In some embodiments, the one or more binding domain sequences is at least about 5 to about 10, about 5 to about 15, about 5 to about 20, about 10 to about 15, about 10 to about 20, about 15 to about 20, or about 20, 19, 18, 17, 16, 15, 14, 13, 12, 11, 10, 9, 8, 7, 6, or 5 nucleotides in length. In some embodiments, the one or more binding domain sequences is less than about 250 to about 300, about 200 to about 300, about 150 to about 300, about 100 to about 300, about 50 to about 300, about 100 to about 250, about 100 to about 200, about 100 to about 150, about 50 to about 250, about 50 to about 200, about 50 to about 150, about 50 to about 100, or about 300, 250, 200, 150, 100, or 50 nucleotides in length. In some embodiments, the one or more binding domain sequences is about 5 to about 20, about 5 to about 30, about 5 to about 40, about 5 to about 50, about 10 to about 50, about 10 to about 100, about 20 to about 100, about 30 to about 100, about 40 to about 100, about 50 to about 100, about 50 to about 150, about 50 to about 200, about 50 to about 250, about 100 to about 150, about 100 to about 200, about 100 to about 250, or about 100 to about 300 nucleotides in length.

In some embodiments, the at least one intronic sequence comprises one binding domain sequence. In some embodiments, the at least one intronic sequence comprises at least two binding domain sequences. In some embodiments, the at least one intronic sequence comprises 3, 4, 5, 6, 7, 8, 9, or 10 binding domain sequences.

In some embodiments, when the nucleic acid is introduced to the cell an exon in the pre-mRNA is targeted for trans-splicing. In some embodiments, the target sequence is positioned in a region of the pre-mRNA comprising the exon targeted for trans-splicing. In some embodiments, the target sequence is positioned proximal to a splice site. In some embodiments, the target sequence is positioned proximal to a splice donor or a splice acceptor.

In some embodiments, the ncRNA sequence is selected from an snRNA, a snoRNA, a lncRNA, an rRNA, a ribozyme, an sRNA, a scaRNA, and a vault RNA. In some embodiments, the ncRNA sequence is an snRNA. In some embodiments, the snRNA is selected from a U1 snRNA, a U2 snRNA, a U4 snRNA, a U4atac snRNA, a U5 snRNA, a U6 snRNA, a U6atac snRNA, a U11 snRNA, a U12 snRNA, and a U7 snRNA. In some embodiments, the ncRNA sequence is a snoRNA. In some embodiments, the snoRNA comprises an H/ACA box or C/D box.

In some embodiments, the ncRNA sequence assembles into an RNP. In some embodiments, the ncRNA sequence comprises a sequence motif that assembles into an RNP. In some embodiments, the ncRNA sequence comprises a secondary structure that assembles into an RNP. In some embodiments, the ncRNA sequence comprises a sequence motif and a secondary structure that assembles into an RNP. In some embodiments, the secondary structure comprises one or more stem loops. In some embodiments, the RNP is selected from a small nuclear RNP (snRNP), a small nucleolar RNP (snoRNP), a small cajal body RNP (scaRNP), and a combination thereof. In some embodiments, the RNP is a snRNP. In some embodiments, the RNP is selected from U1, U2, U4, U4atac, U5, U6, U6atac, U7, U11, and U12. In some embodiments, the RNP is a snoRNP. In some embodiments, the RNP is selected from a C/D box snoRNP and a H/ACA box snoRNP.

In some embodiments, the ncRNA comprises an Sm sequence motif. In some embodiments, the Sm sequence motif assembles with an Sm or Lsm protein into an RNP. In some embodiments, the Sm or Lsm proteins are selected from a B/B', D3, D2, D1, E, F, G, LSm5, LSm7, LSm4, LSm8, LSm2, LSm3, LSm6 and LSm10 proteins.

In some embodiments, the at least one intronic sequence comprises a splice acceptor. In some embodiments, the at least one intronic sequence comprises a splice donor. In some embodiments, the at least one intronic sequences comprises one or more splicing signals. In some embodiments, the one or more splicing signals are selected from an exonic splicing enhancer (ESE), an intronic splicing enhancer (ISE), an exonic splicing silencer (ESS), intronic splicing silencer (ISS), a polypyrimidine tract, a branch point, and a combination thereof. In some embodiments, the at least one intronic sequences comprises a branch point and a polypyrimidine tract. In some embodiments, the nucleic acid comprising a nucleotide sequence comprises 1, 2, 3, 4, 5, 6, 7, 8, 9, or 10 exons.

In some aspects, the disclosure provides a nucleic acid for targeting trans-splicing of a pre-mRNA in a cell, the nucleic acid comprising a nucleotide sequence comprising from 5' to 3': (a) at least one intronic sequences comprising (i) one or more binding domain sequences of about 4 to about 300 nucleotides each with complementarity to a pre-mRNA target sequence; (ii) a non-coding RNA (ncRNA) sequence of about 7 to about 300 nucleotides in length which forms a secondary structure and/or comprises a sequence motif to direct the one or more binding domains to the pre-mRNA target sequence; and (iii) one or more splicing signals; (b) a splice acceptor; and (c) at least one exonic sequences. In some embodiments, when the nucleic acid is introduced to the cell an exon in the pre-mRNA is targeted for trans-splicing. In some embodiments, the target sequence is positioned upstream the exon in the pre-mRNA targeted for trans-splicing. In some embodiments, the target sequence is positioned proximal to a splice site (e.g., a splice acceptor or splice donor). In some embodiments, the target sequence is positioned proximal to a splice acceptor. In some embodiments, the target sequence is positioned proximal to a splice donor. In some embodiments, trans-splicing occurs between a splice donor upstream the exon in the pre-mRNA and the splice acceptor of the nucleic acid. In some embodiments, trans-splicing results in ligation of the 3'end of an exon upstream the splice donor in the pre-mRNA with the 5'end of the at least one exonic sequence of the nucleic acid. In some embodiments, the one or more splicing signals comprises a branch point and a polypyrimidine tract.

In some aspects, the disclosure provides a nucleic acid for targeting trans-splicing a pre-mRNA in a cell, the nucleic acid comprising a nucleotide sequence comprising from 5' to 3': (a) at least one exonic sequence; (b) a splice donor; (c) at least one intronic sequence comprising (i) a non-coding RNA (ncRNA) sequence of about 7 to about 300 nucleotides in length, and (ii) one or more binding domain sequences of about 4 to about 300 nucleotides each with complementarity to a pre-mRNA target sequence, wherein the ncRNA forms a secondary structure and/or comprises a sequence motif to direct the one or more binding domains to the pre-mRNA target sequence. In some embodiments, when the nucleic acid is introduced to the cell an exon in the pre-mRNA is targeted for trans-splicing. In some embodiments, the target sequence is positioned downstream the exon in the pre-mRNA. In some embodiments, the target sequence is positioned proximal to a splice site (e.g., a splice donor or splice acceptor). In some embodiments, the target sequence is positioned proximal to a splice donor. In some embodiments, the target sequence is positioned proximal to a splice acceptor. In some embodiments, trans-splicing occurs between the splice donor of the nucleic acid and a splice acceptor downstream the exon in the pre-mRNA. In some embodiments, trans-splicing results in ligation of the 3'end of the at least one exonic sequence of the nucleic acid with the 5'end of an exon downstream the splice acceptor in the pre-mRNA.

In some embodiments, the ncRNA sequence is an snRNA. In some embodiments, the snRNA is selected from a U1 snRNA, a U2 snRNA, a U4 snRNA, a U4atac snRNA, a U5 snRNA, a U6 snRNA, a U6atac snRNA, a U11 snRNA, a U12 snRNA, and a U7 snRNA. In some embodiments, the snRNA assembles into an snRNP. In some embodiments, the snRNA is a U1 snRNA. In some embodiments, the U1 snRNA assembles into a U1 RNP. In some embodiments, the snRNA is a U11 snRNA. In some embodiments, the U11 snRNA assembles into a U11 RNP. In some embodiments, the snRNA is a U7 snRNA. In some embodiments, the U7 snRNA assembles into a U7 RNP. In some embodiments, the ncRNA sequence comprises an Sm sequence motif. In some embodiments, the ncRNA sequence comprises an Sm sequence motif and a U7 snRNA. In some embodiments, the Sm sequence motif comprises a sequence set forth in SEQ ID NOs: 3 and 4. In some embodiments, the Sm sequence motif assembles with an Sm protein into an RNP. In some embodiments, the Sm protein is selected from a B/B', D3, D2, D1, E, F, and G Sm protein.

In some embodiments, the ncRNA sequence comprises a sequence having at least 80% sequence identity to a sequence selected from SEQ ID NOs: 9-589 or a portion thereof (e.g., a contiguous portion thereof). In some embodiments, the ncRNA sequence comprises a region of about 7 to about 40 nucleotides in length, wherein the region comprises an Sm sequence motif. In some embodiments, the ncRNA sequence comprises a region of about 40 to about 300 nucleotides in length, wherein the region comprises a secondary structure and/or an Sm sequence motif. In some embodiments, the Sm sequence motif comprises a sequence selected from SEQ ID NOs: 209-399.

In some embodiments, the at least one intronic sequences comprises one binding domain sequence. In some embodiments, the one binding domain sequence is about 5 to about 20, about 5 to about 30, about 5 to about 40, about 5 to about 50, about 10 to about 50, about 10 to about 100, about 20 to about 100, about 30 to about 100, about 40 to about 100, about 50 to about 100, about 50 to about 150, about 50 to about 200, about 50 to about 250, about 100 to about 150, about 100 to about 200, about 100 to about 250, or about 100 to about 300 nucleotides in length.

In some embodiments, the at least one intronic sequences more than one binding domain sequence. In some embodiments, more than one binding domain sequences are each about 5 to about 20, about 5 to about 30, about 5 to about 40, about 5 to about 50, about 10 to about 50, about 10 to about 100, about 20 to about 100, about 30 to about 100, about 40 to about 100, about 50 to about 100, about 50 to about 150, about 50 to about 200, about 50 to about 250, about 100 to about 150, about 100 to about 200, about 100 to about 250, or about 100 to about 300 nucleotides in length.

In some aspects, the disclosure provides a nucleic acid for targeting trans-splicing of a pre-mRNA in a cell, the nucleic acid comprising a nucleotide sequence comprising from 5' to 3' (a) at least one intronic sequence comprising (i) a ncRNA sequence comprising an H/ACA box or a C/D box and one or more binding domain sequences of about 4 to about 30 nucleotides each with complementarity to a pre-mRNA target sequence; and (ii) one or more splicing signals; (b) a splice acceptor; and (c) at least one exonic sequence. In some embodiments, when the nucleic acid is introduced to the cell an exon in the pre-mRNA is targeted for trans-splicing. In some embodiments, the target sequence is positioned upstream the exon in the pre-mRNA. In some embodiments, the target sequence is positioned proximal to a splice site. In some embodiments, the target sequence is positioned proximal to a splice donor or splice acceptor. In some embodiments, trans-splicing occurs between a splice donor upstream the exon in the pre-mRNA and the splice acceptor of the nucleic acid. In some embodiments, trans-splicing results in ligation of the 3' end of an exon upstream the splice donor in the pre-mRNA with the 5'end of the at least one exonic sequence of the nucleic acid. In some embodiments, the one or more splicing signals comprises a branch point and a polypyrimidine tract.

In some aspects, the disclosure provides a nucleic acid for targeting trans-splicing of a pre-mRNA in a cell, the nucleic acid comprising a nucleotide sequence comprising from 5' to 3' (a) at least one exonic sequence; (b) a splice donor; and (c) at least one intronic sequence comprising a ncRNA sequence comprising an H/ACA box or a C/D box and one or more binding domain sequences of about 4 to about 30 nucleotides each with complementarity to a pre-mRNA target sequence. In some embodiments, when the nucleic acid is introduced to the cell an exon in the pre-mRNA is targeted for trans-splicing. In some embodiments, the target sequence is positioned downstream the exon in the pre-mRNA. In some embodiments, the target sequence is positioned proximal to a splice site. In some embodiments, the target sequence is positioned proximal to a splice donor or a splice acceptor. In some embodiments, trans-splicing occurs between the splice donor of the nucleic acid and a splice acceptor downstream the exon in the pre-mRNA. In some embodiments, trans-splicing results in ligation of the 3'end of the at least one exonic sequence of the nucleic acid with the 5'end of an exon downstream the splice acceptor in the pre-mRNA.

In some embodiments, the ncRNA sequence comprises an H/ACA box comprising 5' to 3' an H consensus sequence and an ACA consensus sequence. In some embodiments, the ncRNA sequence comprises the at least one binding domain sequence positioned (i) upstream the H consensus sequence; (ii) downstream the ACA consensus sequence; (iii) between the H consensus sequence and the ACA consensus sequence; or (iv) a combination of (i)-(iii).

In some embodiments, the ncRNA sequence comprises C/D box comprising 5' to 3' a C consensus sequence, a D' consensus sequence, a C' consensus sequence, and a D consensus sequence. In some embodiments, the ncRNA sequence comprises the at least one binding domain positioned (i) upstream the C consensus sequence; (ii) between the C consensus sequence and the D' consensus sequence; (iii) between the C' consensus sequence and the D consensus sequence; (iv) downstream the D consensus sequence; or (iv) a combination of (i)-(iii).

In some embodiments, the ncRNA sequence comprises a sequence having at least 80% sequence identity to a sequence selected from SEQ ID NOs: 590-657 or a portion thereof (e.g., a contiguous portion thereof). In some embodiments, the ncRNA sequence comprises a region of about 40 to about 300 nucleotides in length and comprising an H consensus sequence and an ACA consensus sequence.

In some embodiments, the ncRNA sequence comprises one binding domain sequence. In some embodiments, the ncRNA sequence comprises more than one binding domain sequence.

In some embodiments, the at least one intronic sequence comprises at least one binding domain sequence with full complementarity to the pre-mRNA target sequence. In some embodiments, the at least one intronic sequence comprises at least one binding domain sequence with partial complementarity to the pre-mRNA target sequence. In some embodiments, the at least one binding domain sequence comprises one or more mismatches relative to the pre-mRNA target sequence. In some embodiments, the at least one binding domain sequence has at least 95% complementarity to the pre-mRNA target sequence.

In some embodiments, the nucleic acid comprises a sequence up to about 20,000 nucleotides in length. In some embodiments, the nucleic acid comprises a sequence of about 50 to about 500, about 50 to about 1000, about 100 to about 500, about 100 to about 1000, about 500 to about 1000, about 500 to about 2000, about 500 to about 3,000, about 500 to about 4,000, about 500 to about 5,000, about 1,000 to about 5,000, about 1,000 to about 10,000, about 5,000 to about 15,000, or about 5,000 to about 20,000 nucleotides in length.

In some embodiments, the nucleic acid is introduced to the cell as an RNA. In some embodiments, the nucleic acid is introduced to the cell as a DNA. In some embodiments, the nucleic acid is introduced to the cell by a viral vector. In some embodiments, the viral vector is an AAV. In some embodiments, the nucleic acid is introduced to the cell by a non-viral vector.

In some embodiments, introduction of the nucleic acid to the cell results in an efficiency of trans-splicing that is greater than a nucleic acid lacking the ncRNA sequence. In some embodiments, the efficiency of trans-splicing is greater than about 10%, about 20%, about 30%, about 40%, about 50%, about 60%, about 70%, about 80%, about 90%, or about 99%.

In some embodiments, the nucleic acid is formulated as a lipid nanoparticle.

In some aspects, the disclosure provides a viral vector comprising a nucleic acid described herein.

In some aspects, the disclosure provides a lipid nanoparticle comprising a nucleic acid described herein.

In some aspects, the disclosure provides a cell comprising a nucleic acid described herein, a viral vector described herein, or a lipid nanoparticle described herein.

In some aspects, the disclosure provides a pharmaceutical composition comprising a nucleic acid described herein, a viral vector described herein, or a lipid nanoparticle described herein, and a pharmaceutically acceptable carrier.

In some aspects, the disclosure provides a pharmaceutical composition comprising a cell described herein, and a pharmaceutically acceptable carrier.

In some aspects, the disclosure provides a method of targeting trans-splicing of a pre-mRNA in a cell, the method comprising contacting the cell with a nucleic acid described herein, a viral vector described herein, a lipid nanoparticle described herein, or a pharmaceutical composition described herein, wherein when the nucleic acid, the viral vector, the lipid nanoparticle, or the pharmaceutical composition contacts the cell, the one or more binding domain sequences bind to the pre-mRNA, thereby targeting the pre-mRNA for trans-splicing.

In some aspects, the disclosure provides a method of correcting a mutation in a pre-mRNA in a cell, the method comprising contacting the cell with a nucleic acid described herein, a viral vector described herein, a lipid nanoparticle described herein, or a pharmaceutical composition described herein, wherein when the nucleic acid, the viral vector, the lipid nanoparticle, or the pharmaceutical composition contacts the cell, the one or more binding domain sequences bind to the pre-mRNA at a location proximal to the mutation, and wherein trans-splicing replaces one or more exons in the pre-mRNA comprising the mutation, thereby correcting the mutation.

In some aspects, the disclosure provides a method of treating a patient with a disease or disorder associated with a mutation in a pre-mRNA, the method comprising administering to the patient an effective amount of a nucleic acid described herein, a viral vector described herein, a lipid nanoparticle described herein, or a pharmaceutical composition described herein, wherein when the nucleic acid, the viral vector, the lipid nanoparticle, or the pharmaceutical composition is administered, the one or more binding domain sequences bind to the pre-mRNA at a location proximal to the mutation, and wherein trans-splicing replaces one or more exons in the pre-mRNA comprising the mutation, thereby correcting the mutation. In some embodiments, the trans-splicing results in an mRNA that alleviates the disease or does not cause or contribute to the disease.

In some aspects, the disclosure provides a nucleic acid of any one of the embodiments disclosed herein, the viral vector of any one of the embodiments disclosed herein, the lipid nanoparticle of any one of the embodiments disclosed herein, or the pharmaceutical composition of any one of the embodiments disclosed herein for use in treating a patient with a disease or disorder associated with a mutation in a pre-mRNA, the treatment comprising administering to the patient the nucleic acid, the viral vector, the lipid nanoparticle, or the pharmaceutical composition, wherein when the nucleic acid, the viral vector, the lipid nanoparticle, or the pharmaceutical composition is administered, the one or more binding domain sequences bind to the pre-mRNA at a location proximal to the mutation, and wherein trans-splicing replaces one or more exons in the pre-mRNA comprising the mutation, thereby correcting the mutation.

In some aspects, the disclosure provides a nucleic acid of any one of the embodiments disclosed herein, the viral vector of any one of the embodiments disclosed herein, the lipid nanoparticle of any one of the embodiments disclosed herein, or the pharmaceutical composition of any one of the embodiments disclosed herein for the manufacture of a medicament for use in treating a patient with a disease or disorder associated with a mutation in a pre-mRNA, the treatment comprising administering to the patient the medicament, wherein when the medicament is administered, the one or more binding domain sequences of the nucleic acid binds to the pre-mRNA at a location proximal to the mutation, and wherein trans-splicing replaces one or more exons in the pre-mRNA comprising the mutation, thereby correcting the mutation.

In some aspects, the disclosure provides a kit comprising a container comprising a nucleic acid described herein, a viral vector described herein, a lipid nanoparticle described herein, or a pharmaceutical composition described herein, with instructions for use in correcting a mutation in a pre-mRNA.

BRIEF DESCRIPTION OF THE FIGURES

FIG. 5A, FIG. 5B, and FIG. 5C provides a schematic, without wishing to be bound by theory, depicting the extended and folded secondary structure of an exemplary splice editor nucleic acid molecule of the disclosure having 5' to 3' an RNA binding domain, an ncRNA having an Sm sequence motif, intron, SA, and exon (SEQ ID NO: 706, SEQ ID NO: 707, SEQ ID NO: 708, and SEQ ID NO: 709) (FIG. 5A) and the interaction of the exemplary splice editor with a target pre-mRNA that initiates a trans-splicing event between the SD of the pre-mRNA and the SA of the exemplary splice editor (FIG. 5B, and FIG. 5C).

FIG. 6A, FIG. 6B, and FIG. 6C provides a schematic, without wishing to be bound by theory, depicting the extended and folded secondary structure of an exemplary splice editor nucleic acid molecule of the disclosure having 5' to 3' a snoRNA having an insertion of two RNA binding domains, intron, SA, and exon (SEQ ID NO: 710, SEQ ID NO: 711, SEQ ID NO: 712, and SEQ ID NO: 713) (FIG. 6A) and the interaction of the exemplary splice editor with a target pre-mRNA that initiates a trans-splicing event between the SD of the pre-mRNA and the SA of the exemplary splice editor (FIG. 6B, and FIG. 6C).

DETAILED DESCRIPTION

Figure 1A:
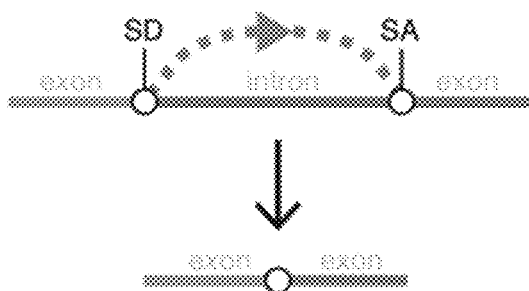
FIG. 1A and FIG. 1B provide schematics, without wishing to be bound by theory, depicting cis-splicing of a pre-mRNA (FIG. 1A) and trans-splicing between two pre-mRNA molecules (FIG. 1B). "SD" refers to a splice donor. "SA" refers to a splice acceptor.

The present disclosure provides nucleic acid molecules for targeting trans-splicing of a target RNA (e.g., a pre-mRNA) in a cell. In some embodiments, the nucleic acid molecules are engineered to comprise a nucleotide sequence comprising (i) at least one noncoding sequence (an intronic sequence) comprising an RNA-guided domain that binds to one or more target sequences in the target RNA (e.g., the pre-mRNA), (ii) a splice acceptor and/or splice donor, and (iii) at least one coding sequence (an exonic sequence). The nucleic acid molecules of the disclosure are referred to herein as "splice editor nucleic acids" or "splice editor nucleic acid molecules." Without being bound by theory, the binding event brings the splice editor nucleic acid into proximity of a region of the target RNA (e.g., pre-mRNA) selected for trans-splicing and recruits the spliceosome to the target RNA (e.g., pre-mRNA) such that efficient trans-splicing occurs. In some embodiments, the target RNA is a pre-mRNA. In some embodiments, the pre-mRNA comprises a nucleotide sequence comprising a disease-causing mutation. In some embodiments, the trans-splicing generates a mRNA comprising a desired alteration compared to an mRNA generated by cis-splicing of the pre-mRNA. For example, in some embodiments, the desired alteration is correction of a disease-causing mutation in the pre-mRNA.

In some embodiments, the RNA-guided domain comprises (i) one or more binding domains each having complementarity to a target sequence in the target RNA (e.g., pre-mRNA), and (ii) a non-coding RNA (ncRNA) sequence. In some embodiments, the ncRNA sequence comprises a secondary structure and/or a sequence motif that assembles into a ribonucleoprotein (RNP). Without being bound by theory, assembly of the ncRNA to form an RNP endows the trans-splicing nucleic acid molecule with one or more desirable properties that enable efficient trans-splicing. For example, in some embodiments, the RNP functions to (i) stabilize RNA secondary structures present in the splice editor nucleic acid molecule, the pre-mRNA, or both; (ii) stabilize RNA-RNA interactions formed between the splice editor nucleic acid molecule and the pre-mRNA; (iii) protect the splice editor nucleic acid molecule and/or the pre-mRNA from degradation; (iv) localize the splice editor nucleic acid molecule to a subcellular compartment where pre-mRNA is present; and (v) a combination of (i)-(iv).

In some embodiments, the disclosure provides methods of targeting trans-splicing of a target RNA (e.g., pre-mRNA) in a cell, comprising introducing to the cell a splice editor nucleic acid molecule described herein. In some embodiments, the disclosure provides methods of correcting a mutation in at target RNA (e.g., a pre-mRNA) in a cell, comprising introducing to the cell a splice editor nucleic acid molecule described herein. In some aspects, the introducing is performed in vivo. In some embodiments, the introducing is performed ex vivo. In some embodiments, the methods described herein are used to introduce a desired edit to a target nucleic acid edit in a manner that avoids certain disadvantages of gene-editing, e.g., gene-editing performed using a CRISPR/Cas system. Whereas gene-editing is associated with a risk of introducing a permanent and disease-causing off-target edit to the genome, the present disclosure provides methods of trans-splicing that avoid altering genomic DNA and enable transient editing. Thus, and without being bound by theory, the methods of the disclosure are used to introduce edits to nucleic acids in a cell in a manner that is safer than gene-editing. Additionally, in some embodiments, the methods of the disclosure are used to inactivate an undesirable off-target gene edit introduced to the genome, thereby preventing or ameliorating deleterious phenotypes associated with gene editing approaches.

In some embodiments, the disclosure provides methods for treating a disease or disorder in a subject in need thereof, the disease or disorder associated with (i) one or more genetic mutations, and/or (ii) an aberrant expression level and/or activity of a gene, or a transcriptional or translational product thereof, comprising administering to a subject one or more splice editor nucleic acid molecules described herein.

In some embodiments, the disclosure provides methods and compositions for delivery of the splice editor nucleic acid molecule to a cell or a subject. In some embodiments, the splice editor nucleic acid molecule is delivered as a DNA. In some embodiments, the splice editor nucleic acid molecule is delivered as an RNA. In some aspects, the delivery comprises administering a recombinant expression vector (e.g., a viral vector, e.g., an AAV) comprising the splice editor nucleic acid molecule. In some aspects, the delivery comprises administering a non-viral vector (e.g., a lipid particle) comprising the splice editor nucleic acid molecule.

Splice Editor Nucleic Acid Molecules for Targeted Trans-Splicing

Accurate pre-mRNA splicing is critical for proper protein expression. Nuclear pre-mRNA splicing is catalyzed by the spliceosome. Vertebrate gene architecture often consists of relatively long introns and short internal exons. The exon-intron boundaries are defined by a splice donor (the 5' splice site or splice site at the 3'end of an exon) and a splice acceptor (the 3'splice site or splice site at the 5'end of an exon). In addition to recognizing splice sites, the spliceosome relies on various splicing signals to mediate a splicing event, including a branch point sequence and a polypyrimidine tract. Typically, the branch point sequence comprises an adenosine situated within a consensus sequence and is situated about 18-40 nucleotides upstream of the 3' splice site. The polypyrimidine tract comprises a repetitive sequence of uracils and is proximal the 3'splice site. Alternative signals can enhance or decrease splicing activity, including exonic splicing enhancers (ESEs), exonic splicing silencers (ESSs), intronic splicing enhancers (ISEs), and intronic splicing silencers (ISSs). Splicing in cis ("cis-splicing") occurs when the 2'OH group of the branch adenosine of the intron carries out a nucleophilic attack on the 5'splice site (splice donor). This results in cleavage at this site and ligation of the 5'end of the intron to the branch adenosine, forming a lariat structure. The 3'splice site (splice acceptor) is attacked by the 3'OH of the 5'exon, resulting in ligation of the 5' and 3' exons to form the mRNA and release of the intron lariat (see, e.g., FIG. 1A).

Figure 1B:
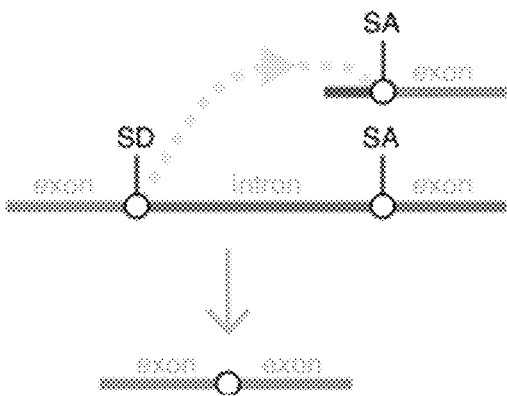
Figure 1C:
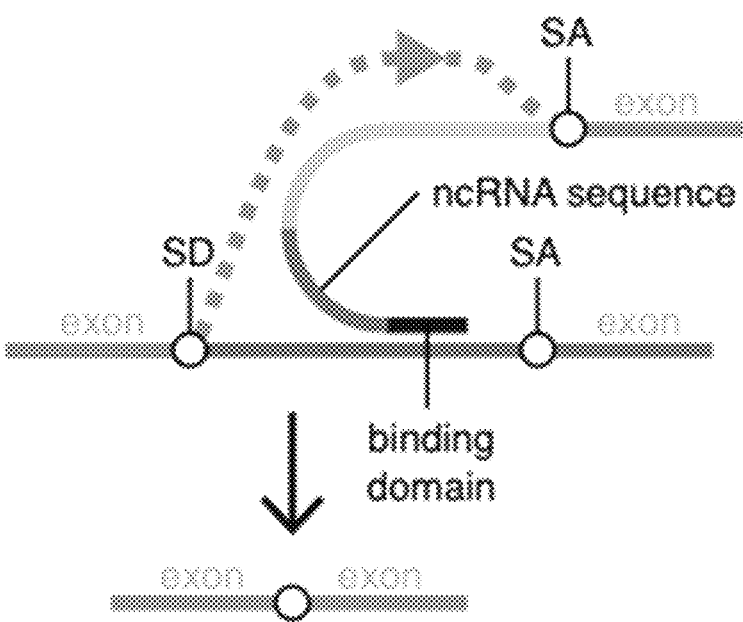
FIG. 1C provides a schematic, without wishing to be bound by theory, depicting an exemplary splice editor nucleic acid molecule of the disclosure for targeted trans-splicing of a pre-mRNA. Labeling of the splice editor indicates the segments corresponding to an RNA binding domain, a non-coding RNA (ncRNA), SA, and exon. Labeling of the pre-mRNA indicates segments of the pre-mRNA corresponding to the 5'exon, SD, SA, and 3'exon.
Figure 1D:
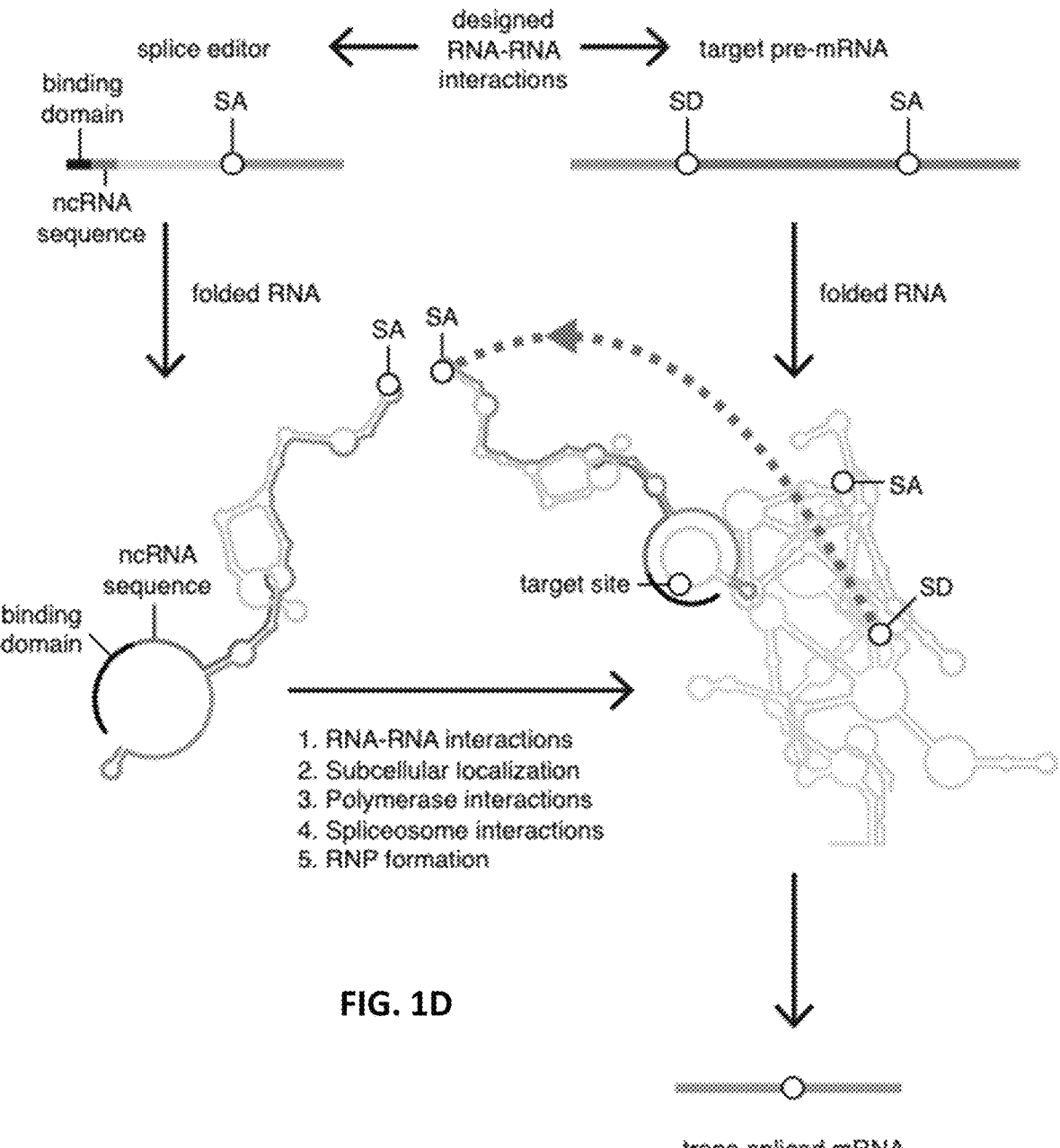
FIG. 1D provides a schematic, without wishing to be bound by theory, depicting a predicted secondary structure of an exemplary splice editor nucleic acid molecule of the disclosure and pre-mRNA and the interactions between the splice editor and pre-mRNA that yield a trans-splicing mRNA product.

In contrast, splicing in trans ("trans-splicing") occurs between two different RNA molecules, wherein the 3'splice site (splice acceptor) of a second RNA is attacked by the 3'OH of the 5'exon of a first RNA, resulting in ligation of the 5'exon of the first RNA and the 3'exon of the second RNA, thereby forming a chimeric RNA (see, e.g., FIG. 1B).

The present disclosure provides splice editor nucleic acid molecules for targeting trans-splicing of a target RNA (e.g., pre-mRNA) in a cell, the splice editor nucleic acid molecule comprising a nucleotide sequence comprising (i) at least one intronic sequence comprising an RNA-guided domain; (ii) one or more splice sites (e.g., a splice acceptor and/or splice donor); and (iii) at least one exonic sequence. In some embodiments, the RNA-guided domain is designed to bind to a specific region of a target RNA (e.g., pre-mRNA), thereby enabling splicing between the one or more splice sites of the splice editor nucleic acid molecule and one or more splice sites of the target RNA (e.g., pre-mRNA). In some embodiments, the trans-splicing results in a chimeric mRNA comprising the at least one exonic sequence of the splice editor nucleic acid and one or more exons of the target RNA (e.g., pre-mRNA).

In humans, exon definition is determined by splice sites paired across an exon (e.g., a splice acceptor (3'splice site) at the 5'end of the exon and a splice donor (5'splice site) at the 3'end of the exon). Other splicing signals (e.g., branch point sequences, polypyrimidine tracts, exonic (or intronic) splicing enhancers and silencers) contribute to proper splicing together of exons to form a mature mRNA. During pre-mRNA splicing, the spliceosome searches for a pair of closely spaced splice sites. Without being bound by theory, the splice editor nucleic acid molecules described herein mediate efficient trans-splicing by bringing a splice site of the target RNA (e.g., pre-mRNA, e.g., a splice acceptor or splice donor of the target pre-mRNA) into close proximity with a splice site of the splice editor nucleic acid molecule (e.g., a splice acceptor or splice donor of the splice editor nucleic acid molecule), such that the spliceosome mediates splicing between the splice site of the target pre-mRNA and the splice site of the splice editor nucleic acid molecule.

In some embodiments, the splice editor nucleic acid molecule comprises a nucleotide sequence comprising from 5' to 3' (i) at least one intronic sequence comprising an RNA-guided domain; (ii) a splice acceptor; and (iii) at least one exonic sequence.

In some embodiments, the splice editor nucleic acid molecule comprises a nucleotide sequence comprising from 5' to 3' (i) at least one exonic sequence; (ii) a splice donor; and (iii) at least one intronic sequence comprising an RNA-guided domain.

In some embodiments, the at least one intronic sequences comprises one or more splicing signals (e.g., a branch point sequence, a polypyrimidine tract, an ISE, and/or an ISS). In some embodiments, the at least one exonic sequences comprises one or more splicing signals (e.g., an ESE and/or an ESS).

RNA Guided Domain

In some embodiments, the RNA guided domain comprises a nucleotide sequence comprising (i) one or more binding domains, each having complementarity to a target sequence in the target RNA (e.g., pre-mRNA); and (ii) a ncRNA. In some embodiments, the one or more binding domains mediate binding of the trans-splicing nucleic acid molecules to a target RNA (e.g., pre-mRNA) in a cell. In some embodiments, the ncRNA mediates assembly into an RNP.

In some embodiments, the RNA guided domain comprises a nucleotide sequence having from 5' to 3': (i) one or more binding domains, each having complementarity to a target sequence in the target RNA (e.g., pre-mRNA); and (ii) a ncRNA.

In some embodiments, the RNA guided domain comprises a nucleotide sequence having from 5' to 3': (i) a ncRNA; and (ii) one or more binding domains, each having complementarity to a target sequence in the target RNA (e.g., pre-mRNA).

In some embodiments, the RNA guided domain comprises a nucleotide sequence having a ncRNA, wherein the one or more binding domains are inserted into the ncRNA or exchanged for contiguous nucleotides of the ncRNA.

Target Sequence

In some embodiments, the one or more binding domains of the RNA guided domain are each complementary to a target sequence in a target RNA (e.g., pre-mRNA) targeted for trans-splicing.

As used herein, the term "target sequence" refers to a sequence of contiguous nucleotides present in a target RNA (e.g., pre-mRNA) targeted for trans-splicing. As used herein, the term "contiguous nucleotides" refers to a string of nucleotides that are covalently linked and immediately adjacent to one another. In some embodiments, the target sequence is at least about 4, 5, 6, 7, 8, 9, 10, 11, 12, 13, 14, 15, 16, 17, 18, 19, or 20 nucleotides in length. In some embodiments, the target sequence is less than about 300, 250, 200, 100, 150, or 50 nucleotides in length. In some embodiments, the target sequence is about 5-10, about 5-15, about 5-20, about 10-20, about 10-30, about 10-40, about 10-50, about 10-60, about 10-70, about 10-80, about 10-90, about 10-100, about 50-100, about 50-150, about 50-200, about 50-250, about 50-300, about 100-200, about 100-300, or about 200-300 nucleotides in length.

In some embodiments, the target sequence is in a region comprising a splice site in the target RNA (e.g., pre-mRNA) targeted for trans-splicing. As used herein, "a splice site in the target RNA (e.g., pre-mRNA) targeted for trans-splicing" refers to a splice site in the target RNA (e.g., pre-mRNA) selected for trans-splicing, wherein upon introducing a splice editor nucleic acid molecule described herein to a cell comprising the target RNA (e.g., pre-mRNA), a trans-splicing event mediates ligation between the splice site of the target RNA (e.g., pre-mRNA) and a splice site of the splice editor nucleic acid molecule. In some embodiments, the target sequence is upstream the splice site in the target RNA (e.g., pre-mRNA) targeted for trans-splicing. In some embodiments, the target sequence is downstream the splice site in the target RNA (e.g., pre-mRNA) targeted for trans-splicing. In some embodiments, the target sequence is in a region comprising the splice site in the target RNA (e.g., pre-mRNA) targeted for trans-splicing, wherein the region spans at least about 50, about 100, about 150, about 200, about 300, about 400, about 500, about 1,000, about 2,000, about 3,000, about 4,000, about 5,000 nucleotides.

In some embodiments, the target sequence is proximal to the splice site in the target RNA (e.g., pre-mRNA) targeted for trans-splicing. As used herein, the term "proximal to the splice site" refers to a region of less than about 500 nucleotides extending upstream and/or downstream of the splice site in the target RNA (e.g., pre-mRNA) targeted for trans-splicing.

In some embodiments, the target sequence is proximal to a splice acceptor targeted for trans-splicing. In some embodiments, the target sequence is upstream a splice acceptor targeted for trans-splicing. In some embodiments, the target sequence is downstream of a splice acceptor targeted for trans-splicing. In some embodiments, the target sequence overlaps a splice acceptor targeted for trans-splicing.

In some embodiments, the target sequence is proximal to a splice donor targeted for trans-splicing. In some embodiments, the target sequence is upstream a splice donor targeted for trans-splicing. In some embodiments, the target sequence is downstream of a splice donor targeted for trans-splicing. In some embodiments, the target sequence overlaps a splice donor targeted for trans-splicing.

In some embodiments, the target sequence is in a region of the target RNA (e.g., pre-mRNA) comprising an exon targeted for trans-splicing. As used herein, an "exon targeted for trans-splicing" refers to an exon in the target RNA that is selected for removal following trans-splicing between the target RNA and a splice editor nucleic acid described herein, wherein the trans-splicing results in ligation between one or more exons of the target RNA (e.g., pre-mRNA) and the at least one exonic sequence of the splice editor nucleic acid to form a chimeric RNA molecule, and wherein the exon targeted for trans-splicing is present in the target RNA, but absent in the chimeric RNA molecule formed by the trans-splicing event.

In some embodiments, the target sequence is upstream the exon targeted for trans-splicing. In some embodiments, the target sequence is downstream the exon targeted for trans-splicing. In some embodiments, the target sequence is within the exon targeted for trans-splicing.

In some embodiments, the target sequence is proximal to a splice acceptor of the exon targeted for trans-splicing. In some embodiments, the target sequence is upstream the splice acceptor of the exon targeted for trans-splicing. In some embodiments, the target sequence is downstream the splice acceptor of the exon targeted for trans-splicing. In some embodiments, the target sequence overlaps the splice acceptor of the exon targeted for trans-splicing.

In some embodiments, the target sequence is proximal to a splice donor of the exon targeted for trans-splicing. In some embodiments, the target sequence is upstream the splice donor of the exon targeted for trans-splicing. In some embodiments, the target sequence is downstream the splice donor of the exon targeted for trans-splicing. In some embodiments, the target sequence overlaps the splice donor of the exon targeted for trans-splicing.

RNA Binding Domain

In some embodiments, the binding domain complementary to a target sequence in the target RNA (e.g., pre-mRNA) is at least 4 nucleotides in length. In some embodiments, the binding domain is less than about 300 nucleotides in length. In some embodiments, the binding domain is at least about 5, about 6, about 7, about 8, about 9, about 10, about 11, about 12, about 13, about 14, about 15, about 16, about 17, about 18, about 19 or about 20 nucleotides in length. In some embodiments, the binding domain about 250 to about 300, about 200 to about 300, about 150 to about 300, about 100 to about 300, about 50 to about 300, about 100 to about 250, about 100 to about 200, about 100 to about 150, about 50 to about 250, about 50 to about 200, about 50 to about 150, about 50 to about 100, or about 300, 250, 200, 150, 100, or 50 nucleotides in length.

In some embodiments, the binding domain is about 5 to about 20, about 5 to about 30, about 5 to about 40, about 5 to about 50, about 10 to about 50, about 10 to about 100, about 20 to about 100, about 30 to about 100, about 40 to about 100, about 50 to about 100, about 50 to about 150, about 50 to about 200, about 50 to about 250, about 100 to about 150, about 100 to about 200, about 100 to about 250, or about 100 to about 300 nucleotides in length.

In some embodiments, the binding domain is 10-50 nucleotides in length, e.g., 10-45, 10-40, 10-35, 10-30, 10-20, 11-45, 11-40, 11-35, 11-30, 11-20, 12-45, 12-40, 12-35, 12-30, 12-25, 12-20, 13-45, 13-40, 13-35, 13-30, 13-25, 13-20, 14-45, 14-40, 14-35, 14-30, 14-25, 14-20, 15-45, 15-40, 15-35, 15-30, 15-25, 15-20, 16-45, 16-40, 16-35, 16-30, 16-25, 16-20, 17-45, 17-40, 17-35, 17-30, 17-25, 17-20, 18-45, 18-40, 18-35, 18-30, 18-25, 18-20, 19-45, 19-40, 19-35, 19-30, 19-25, 19-20, e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length.

In some embodiments, the RNA-guided domain comprises one binding domain. In some embodiments, the RNA-guided domain comprises more than one binding domain. In some embodiments, the RNA-guided domain comprises 2, 3, 4, 5, 6, 7, 8, 9, or 10 binding domains. In some embodiments, the more than one binding domains are immediately adjacent to one another. In some embodiments, the more than one binding domains are linked by an intervening nucleotide spacer sequence.

In some embodiments, the one or more binding domains each comprise a sequence that is sufficiently complementary to its target sequence to enable the splice editor nucleic acid molecule to specifically bind to the target sequence by forming base pairs. As used herein, the term "base pair" refers to two nucleobases on opposite complementary nucleic acid strands that interact by formation of specific hydrogen bonding (e.g., Watson-Crick, Hoogsteen, or reversed Hoogsteen hydrogen bonding). In some embodiments, the base pair is formed by Watson-Crick base pairing. As understood by the skilled artisan, Watson-Crick base pairing refers to the set of base pairing rules wherein a purine nucleobase binds to a pyrimidine nucleobase to form a complementary base pair. The nature of the hydrogen bonding depends upon the particular base pair. For example, a guanosine-cytosine base pair is formed by three hydrogen bonds and the adenine-thymine or adenine-uracil base pair is formed by two hydrogen bonds. It is understood that analogs or derivatives of canonical nucleobases will form base pair interactions via Watson Crick base pairing or non-canonical base pairing.

A binding domain that "specifically binds to" a target sequence in a target RNA (e.g., pre-mRNA) refers to one that will not appreciably bind to a reference sequence, e.g., a nucleic acid lacking the target sequence. For example, a splice editor nucleic acid molecule comprising a binding domain that specifically binds a target sequence will exhibit substantially higher binding affinity for a target RNA (e.g., pre-mRNA) comprising a nucleotide sequence comprising the target sequence compared to a target RNA (e.g., pre-mRNA) lacking the target sequence. As is understood by the skilled artisan, the binding affinity between a first nucleic acid strand and a second nucleic acid strand is measured as the melting temperature (Tm), which is the temperature at which half the first nucleic acid strand is duplexed to the second nucleic acid strand.

In some embodiments, a binding domain is complementary to a target sequence in the target RNA (e.g., pre-mRNA) if it base-pairs to the target sequence under conditions suitable for modulating trans-splicing. Such conditions can be stringent conditions, e.g., combination of the target RNA (e.g., pre-mRNA) and splice editor nucleic acid molecule in buffer comprising 400 mM NaCl, 40 mM PIPES pH 6.4, 1 mM EDTA at a temperature of 50° C.-70° C. for 12-16 hours, followed by washing (see, e.g., "Molecular Cloning: A Laboratory Manual, Sambrook, et al. (1989) Cold Spring Harbor Laboratory Press). Other conditions include physiologically relevant conditions as can be encountered inside an organism. The skilled person will be able to determine the set of conditions most appropriate for a test of complementarity of two sequences in accordance with the ultimate application of the hybridized nucleotides.

Non-Coding RNAs

In some embodiments, the RNA-guided domain comprises a ncRNA. As used herein, a "ncRNA" refers to an RNA sequence that does not encode a protein and functions in one or more cellular regulatory processes (e.g., RNA splicing, histone modification, translation, RNA pseudouridylation, RNA methylation, RNA cleavage, RNA processing and RNA modification).

For example, certain ncRNAs function in RNA-guided systems that have evolved to (i) stabilize RNA secondary structures and RNA-RNA interactions (Rossi 1996 Journal of Biological Chemistry 271.39 (1996): 23985-23991, Sabath, et al (2013) RNA 19:1726-1744; Skrajna, et al (2017) RNA 23:938-951); (ii) assemble into ribonucleoproteins (RNPs) to envelope and protect RNA from degradation (Darzacq 2006); and (iii) localize to relevant subcellular compartments (Roithovi, et al (2018) Nucleic acids research 46:3774-3790). In some embodiments, the ncRNA is identified according to a method described herein.

In some embodiments, the method comprises identifying a ncRNA sequence from a database. Databases listing ncRNA sequences are known in the art. For example, in some embodiments, the database is RNAcentral (see, e.g., Nucleic Acids Res 45:D128 (2017). RNAcentral is a searchable database that provides ncRNA sequences annotated with unique identifiers and information regarding the one or more species in which the RNA sequence has been observed.

In some embodiments, the method comprises identifying a ncRNA expressed by a cell or organism. Methods to identify ncRNAs are known in the art (see, e.g., Huttenhofer, et al (2006) *Nucleic Acids Res* 34:635). In some embodiments, cellular RNA is extracted from a cell or organism, separated by PAGE and elution from the gel, and ncRNAs are identified by sequence analysis (e.g., via 2D RNA fingerprinting or enzymatic or chemical RNA sequencing). In some embodiments, a cDNA library is generated by reverse transcription of ncRNAs obtained from a cell or organism through a selection process based on size or antibody-binding that is then subjected to sequence analysis. In some embodiments, total RNA is harvested from a cell or organism and microarray hybridization is used to detect ncRNAs. In some embodiments, genomic SELEX is used to identify ncRNAs obtained from a cell or organism. In some embodiments, the ncRNA sequence is identified from any known organism. In some embodiments, the organism is a bacteria. In some embodiments, the organism is a archaebacteria. In some embodiments, the organism is a metazoan. In some embodiments, the organism is a vertebrate. In some embodiments, the organism is a mammal, amphibian, reptile, fish, or bird. In some embodiments, the organism is a human.

In some embodiments, ncRNA functions to modify, alter, inhibit, or promote RNP formation and/or canonical processing. In some embodiments, the ncRNA assembles into an RNP. In some embodiments, the RNP functions to stabilize the RNA secondary structure of the splice editor nucleic acid. In some embodiments, the RNP functions in to stabilize RNA-RNA interactions within the splice editor nucleic acid and/or with a target RNA (e.g., pre-mRNA). In some embodiments, the RNP functions in to protect the splice editor nucleic acid from degradation. In some embodiments, the RNP functions in to localize the splice editor nucleic acid to a subcellular compartment comprising a target pre-mRNA. Methods to measure assembly of one or more nucleic acids (e.g., RNA or DNA) and one or more proteins to form an RNP are known in the art. Such methods include, but are not limited to, electrophoretic mobility shift assay (EMSA), DNA or RNA pull-down assays, oligonucleotide-targeted RNase H protection assays, fluorescent in situ hybridization co-localization, co-immunoprecipitation assays, and RNA sequencing and cross-linking methods such as high throughput sequencing crosslinking immuno-precipitation (HITS-CLIP).

In some embodiments, a ncRNA sequence identified according to a method described herein is incorporated into a splice editor nucleic acid of the disclosure. In some embodiments, the entire ncRNA sequence is incorporated into the splice editor nucleic acid. In some embodiments, a portion of the ncRNA sequence is incorporated into the splice editor nucleic acid.

In some embodiments, a splice editor of the disclosure comprises an ncRNA sequence or portion thereof, wherein the ncRNA is selected from an snRNA, a snoRNA, a lncRNA, a an rRNA, a ribozyme, an sRNA, a scaRNA, a vault RNA, and a combination thereof.

In some embodiments, the ncRNA sequence or portion thereof is less than about 500 nucleotides in length. In some embodiments, the ncRNA sequence or portion thereof is less than about 400 nucleotides in length. In some embodiments, the ncRNA sequence or portion thereof is less than about 300 nucleotides in length. In some embodiments, the ncRNA sequence or portion thereof is about 250 to about 300, about 200 to about 300, about 150 to about 300, about 100 to about 300, about 50 to about 300, about 100 to about 250, about 100 to about 200, about 100 to about 150, about 50 to about 250, about 50 to about 200, about 50 to about 150, about 50 to about 100, or about 300, 250, 200, 150, 100, or 50 nucleotides in length.

In some embodiments, the ncRNA sequence or portion thereof is at least about 5, about 6, about 7, about 8, about 9, about 10, about 11, about 12, about 13, about 14, about 15, about 16, about 17, about 18, about 19 or about 20 nucleotides in length.

In some embodiments, the ncRNA sequence or portion thereof is about 5 to about 20, about 5 to about 30, about 5 to about 40, about 5 to about 50, about 10 to about 50, about 10 to about 100, about 20 to about 100, about 30 to about 100, about 40 to about 100, about 50 to about 100, about 50 to about 150, about 50 to about 200, about 50 to about 250, about 100 to about 150, about 100 to about 200, about 100 to about 250, or about 100 to about 300 nucleotides in length.

In some embodiments, the ncRNA sequence or portion thereof comprises one or more RNA secondary structures that assembles into an RNP. Methods to determine the secondary structure formed by an RNA sequence are known in the art. In some embodiments, the method comprises an experimental assay, e.g., nuclear magnetic resonance, cryo-electron microscopy, or X-ray crystal structure analysis. In some embodiments, the method comprises a computational prediction, e.g., based on a thermodynamic model such as Turner's nearest-neighbor model (Schroeder, et al, Methods Enzymol. 468, 371-387 (2009); Turner, et al Nucleic Acids Res. 38, D280-2 (2010)) or the Zuker algorithm (Zuker, et al Nucleic Acids Res. 9, 133-148 (1981); Zuker, et al Nucleic Acids Res. 31, 3406-3415 (2003); Markham, et al Methods Mol. Biol. 453, 3-31 (2008); Hofacker, et al Nucleic Acids Res. 31, 3429-3431 (2003); Lorenz, Algorithms Mol. Biol. 6, 26 (2011); Matthews, et al Molecular Modeling of Nucleic Acids. Vol. 682 of ACS Symposium Series. 246-257; Reuther, et al BMC Bioinform. 11, 129 (2010)); a machine learning technique such as CON- TRAfold (Do, et al Bioinformatics 22, e90-8 (2006); Foo, et al Advances in Neural Information Processing Systems 20, 377-384), ContextFold (Zakov, et al J. Comput. Biol. 18, 1525-1542 (2011)); a probabilistic generative model such as stochastic context-free grammars (Rivas, et al RNA 18, 193-212 (2012)); a hybrid model such as SimFold (Andronescu, et al Bioinformatics 23, i19-28 (2007); Andronescu et al RNA 16, 2304-2318 (2010)) or MXfold (Akiyama, et al J. Bioinform. Comput. Biol. 16, 1840025 (2018)); a deep learning approach such as SPOT-RNA (Singh, et al Nat. Commun. 10, 5407 (2019)) or E2Efold (Chen et al Proceedings of the 8th International Conference on Learning Representations; arXiv:2002.05810 (2020)).

In some embodiments, the one or more RNA secondary structures comprises a single-stranded RNA sequence, a double-stranded RNA sequence, or a combination thereof. In some embodiments, the one or more RNA secondary structure comprises a duplex structure, a stem-loop, a pseudo-knot, an internal loop, a multi-branch loop, a bulge loop, an external loop, or a combination thereof. In some embodiments, the ncRNA sequence or portion thereof comprises a sequence motif that assembles into an RNP. In some embodiments, the sequence motif comprises a single-stranded RNA sequence that assembles into an RNP. In some embodiments, the ncRNA sequence or portion thereof comprises a sequence motif and one or more RNA secondary structures that assemble into an RNP. In some embodiments, the secondary structure and/or a sequence motif assembles with one or more proteins in a human cell to form an RNP.

In some embodiments, the ncRNA sequence or portion thereof comprises one or more RNA secondary structures. In some embodiments, the ncRNA sequence or portion thereof comprises one or more sequence motifs. In some embodiments, the ncRNA sequence or portion thereof comprises one or more RNA secondary structures and one or more sequence motifs. In some embodiments, the sequence motif comprises a sequence selected from Table 1. In some embodiments, the sequence motif comprises an H consensus sequence comprising or consisting of a sequence set forth in Table 1. In some embodiments, the H consensus sequence comprises or consists of ANANNA, where N=A, C, G, or U. In some embodiments, the sequence motif comprises an ACA consensus sequence comprising or consisting of a sequence set forth in Table 1. In some embodiments, the ACA consensus sequence comprises or consists of ACA. In some embodiments, the sequence motif comprises an H/ACA box, wherein the H/ACA box comprises a sequence comprising an H consensus sequence and an ACA consensus sequence, each comprising a sequence set forth in Table 1. In some embodiments, the H/ACA box comprises a sequence comprising ANANNA, where N=A, C, G, or U and ACA. In some embodiments, the sequence motif comprises a C consensus sequence comprising or consisting of a sequence set forth in Table 1. In some embodiments, the C consensus sequence comprises or consists of RUGAUGA, where R=A or G. In some embodiments, the sequence motif comprises a D consensus sequence comprising or consisting of a sequence set forth in Table 1. In some embodiments, the D consensus sequence comprises or consists of CUGA. In some embodiments, the sequence motif comprises a C/D box, wherein the C/D box comprises a C consensus sequence and a D consensus sequence, each comprising a sequence set forth in Table 1. In some embodiments, the C/D box comprises RUGAUGA, where R=A or G and CUGA. In some embodiments, the sequence motif comprises an Sm motif comprising a sequence set forth in Table 1. In some embodiments, the Sm motif comprises AAUUUUUGG. In some embodiments, the Sm motif comprises AAUUUGUCU.

TABLE 1 ncRNA Sequence Motifs

| Name/Identifier | RNA Sequence |
|---|---|
| H box | ANANNA<br>N = A, C, G, or U |
| ACA box | ACA |
| Sm motif | AAUUUUUGG |
| Sm U7 motif | AAUUUGUCU |
| C box | RUGAUGA<br>R = A or G |
| D box | CUGA |
| C' box | RUGAUGA |
| D' box | CUGA |

In some embodiments, a splice editor of the disclosure comprises a ncRNA sequence having at least about 60%, about 65%, about 70%, about 75%, about 80%, about 85%, about 90%, about 91%, about 92%, about 93%, about 94%, about 95%, about 96%, about 97%, about 98%, about 99% identity to a sequence selected from SEQ ID NOs: 9-657 or portion thereof. In some embodiments, a splice editor of the disclosure comprises a ncRNA sequence selected from SEQ ID NOs: 9-657 or a portion thereof.

In some embodiments, the ncRNA sequence or portion thereof comprises a contiguous nucleotide sequence of at least about 5, about 6, about 7, about 8, about 9, about 10, about 11, about 12, about 13, about 14, about 15, about 16, about 17, about 18, about 19 or about 20 nucleotides in length, wherein the contiguous nucleotide sequence comprises a Sm sequence motif (e.g., an Sm sequence motif set forth in Table 1).

In some embodiments, the ncRNA sequence or portion thereof comprises a contiguous nucleotide sequence of about 5 to about 20, about 5 to about 30, about 5 to about 40, about 5 to about 50, about 10 to about 50, about 20 to about 50, about 30 to about 50, or about 40 to about 50 nucleotides in length, wherein the contiguous nucleotide sequence comprises a Sm sequence motif (e.g., an Sm sequence motif set forth in Table 1).

In some embodiments, the ncRNA sequence or portion thereof comprises a contiguous nucleotide sequence of about 30 to about 100, about 40 to about 100, about 50 to about 100, about 50 to about 150, about 50 to about 200, about 50 to about 250, about 100 to about 150, about 100 to about 200, about 100 to about 250, or about 100 to about 300 nucleotides in length, wherein the contiguous nucleotide sequence comprises a Sm sequence motif (e.g., an Sm sequence motif set forth in Table 1).

In some embodiments, the ncRNA sequence or portion thereof comprises a contiguous nucleotide sequence of about 30 to about 100, about 40 to about 100, about 50 to about 100, about 50 to about 150, about 50 to about 200, about 50 to about 250, about 100 to about 150, about 100 to about 200, about 100 to about 250, or about 100 to about 300 nucleotides in length, wherein the contiguous nucleotide sequence comprises a (i) H consensus sequence (e.g., a H consensus sequence set forth in Table 1); (ii) ACA consensus sequence (e.g., an ACA consensus sequence set forth in Table 1); or (iii) combination of (i)-(ii).

In some embodiments, the ncRNA sequence or portion thereof comprises a contiguous nucleotide sequence of about 30 to about 100, about 40 to about 100, about 50 to about 100, about 50 to about 150, about 50 to about 200, about 50 to about 250, about 100 to about 150, about 100 to about 200, about 100 to about 250, or about 100 to about 300 nucleotides in length, wherein the contiguous nucleotide sequence comprises a (i) C-box motif described herein (e.g., a C-box motif set forth in Table 1), (ii) C'-box motif described herein (e.g., a C'-box motif set forth in Table 1), (iii) D-box motif described herein (e.g., a D-box motif set forth in Table 1), (iv) a D'-box motif described herein (e.g., a D'-box motif set forth in Table 1), or (v) a combination of (i)-(iv).

In some embodiments, the ncRNA sequence or portion thereof comprises a nucleotide sequence having at least about 60%, about 65%, about 70%, about 75%, about 80%, about 85%, about 90%, about 91%, about 92%, about 93%, about 94%, about 95%, about 96%, about 97%, about 98%, about 99% identity to a sequence selected from SEQ ID NOs: 9-657, wherein the nucleotide sequence comprises a region of at least about 5, about 6, about 7, about 8, about 9, about 10, about 11, about 12, about 13, about 14, about 15, about 16, about 17, about 18, about 19 or about 20 nucleotides in length, wherein the region comprises one or more Sm sequence motifs (e.g., one or more Sm sequence motifs set forth in Table 1).

In some embodiments, the ncRNA sequence or portion thereof comprises a nucleotide sequence having at least about 60%, about 65%, about 70%, about 75%, about 80%, about 85%, about 90%, about 91%, about 92%, about 93%, about 94%, about 95%, about 96%, about 97%, about 98%, about 99% identity to a sequence selected from SEQ ID NOs: 9-657, wherein the nucleotide sequence comprises a region of at least about 5 to about 20, about 5 to about 30, about 5 to about 40, about 5 to about 50, about 10 to about 50, about 20 to about 50, about 30 to about 50, or about 40 to about 50 nucleotides in length, wherein the region comprises one or more Sm sequence motifs (e.g., one or more Sm sequence motifs set forth in Table 1).

In some embodiments, the ncRNA sequence or portion thereof comprises a nucleotide sequence having at least about 60%, about 65%, about 70%, about 75%, about 80%, about 85%, about 90%, about 91%, about 92%, about 93%, about 94%, about 95%, about 96%, about 97%, about 98%, about 99% identity to a sequence selected from SEQ ID NOs: 9-657, wherein the nucleotide sequence comprises a region of at least about 30 to about 100, about 40 to about 100, about 50 to about 100, about 50 to about 150, about 50 to about 200, about 50 to about 250, about 100 to about 150, about 100 to about 200, about 100 to about 250, or about 100 to about 300 nucleotides in length, wherein the region comprises one or more Sm sequence motifs (e.g., one or more Sm sequence motifs set forth in Table 1).

In some embodiments, the ncRNA sequence or portion thereof comprises a nucleotide sequence having at least about 60%, about 65%, about 70%, about 75%, about 80%, about 85%, about 90%, about 91%, about 92%, about 93%, about 94%, about 95%, about 96%, about 97%, about 98%, about 99% identity to a sequence selected from SEQ ID NOs: 9-657, wherein the nucleotide sequence comprises a region of at least about 30 to about 100, about 40 to about 100, about 50 to about 100, about 50 to about 150, about 50 to about 200, about 50 to about 250, about 100 to about 150, about 100 to about 200, about 100 to about 250, or about 100 to about 300 nucleotides in length, wherein the region comprises (i) an H consensus sequence (e.g., an H consensus sequence set forth in Table 1); (ii) an ACA consensus sequence (e.g., an ACA consensus sequence set forth in Table 1); or (iii) a combination of (i)-(ii).

In some embodiments, the ncRNA sequence or portion thereof comprises a nucleotide sequence having at least about 60%, about 65%, about 70%, about 75%, about 80%, about 85%, about 90%, about 91%, about 92%, about 93%, about 94%, about 95%, about 96%, about 97%, about 98%, about 99% identity to a sequence selected from SEQ ID NOs: 9-657, wherein the nucleotide sequence comprises a region of at least about 30 to about 100, about 40 to about 100, about 50 to about 100, about 50 to about 150, about 50 to about 200, about 50 to about 250, about 100 to about 150, about 100 to about 200, about 100 to about 250, or about 100 to about 300 nucleotides in length, (i) a C-box motif described herein (e.g., a C-box motif set forth in Table 1), (ii) a C'-box motif described herein (e.g., a C'-box motif set forth in Table 1), (iii) a D-box motif described herein (e.g., a D-box motif set forth in Table 1), (iv) a D'-box motif described herein (e.g., a D'-box motif set forth in Table 1), or (v) a combination of (i)-(iv).

In some embodiments, the ncRNA is an snRNA. In some embodiments, a splice editor nucleic acid molecule of the disclosure comprises a full-length snRNA or portion thereof comprising a nucleotide sequence comprising one or more sequence motifs described herein (e.g., one or more sequence motifs set forth in Table 1). In some embodiments, an snRNA sequence described herein or identified according to a method described herein is incorporated into a splice editor nucleic acid of the disclosure. In some embodiments, a full-length snRNA sequence described herein or identified according to a method described herein is incorporated into a splice editor nucleic acid of the disclosure. In some embodiments, a portion of a snRNA sequence described herein or identified according to a method described herein (e.g., a region of contiguous nucleotides in the snRNA) is incorporated into a splice editor nucleic acid of the disclosure. In some embodiments, the full-length snRNA or portion of the snRNA assembles into a small nuclear RNP (snRNP). In some embodiments, the full-length snRNA or the portion of the snRNA comprises one or more secondary RNA structures that assembles to form an snRNP. In some embodiments, the full-length snRNA or the portion of the snRNA comprises one or more sequence motifs that assembles to form an snRNP. In some embodiments, the full-length snRNA or the portion of the snRNA comprises (i) one or more one or more secondary RNA structures, and (ii) one or more sequence motifs, wherein (i), (ii), or both assemble to form an snRNP.

Exemplary metazoan snRNA systems include U1 and U11 snRNAs, which are snRNAs that guide spliceosome RNPs to splice sites (Black, et al (1985) Cell 42: 737-750; Kolossova, et al (1997) RNA 3: 227). Other snRNAs include U2, U4, U4atac, U5, U6, U6atac, and U12, which also form RNPs in the major and minor spliceosome (Turunen, et al (2013) RNA 4:61-76; Nguyen, et al (2015), Nature 523:47-52; Charenton, et al (2019) Science 364:362-367). U7 RNAs are responsible for histone pre-mRNA cleavage and polyadenylation (Strub, et al (1984) EMBO journal 3:2801-2807; Soldati, et al (1988), Molecular and Cellular Biology 8:1518-1524; Cotton, et al (1988) The EMBO Journal 7:801-808).

In some embodiments, a splice editor nucleic acid molecule of the disclosure comprises a full-length snRNA or portion thereof comprising a nucleotide sequence comprising one or more sequence motifs described herein (e.g., one or more sequence motifs set forth in Table 1), and wherein the snRNA is selected from RNU1-1, RNU1-100P, RNU1-101P, RNU1-103P, RNU1-104P, RNU1-105P, RNU1-107P, RNU1-108P, RNU1-109P, RNU1-112P, RNU1-114P, RNU1-115P, RNU1-116P, RNU1-117P, RNU1-119P, RNU1-11P, RNU1-123P, RNU1-124P, RNU1-125P, RNU1-128P, RNU1-129P, RNU1-130P, RNU1-131P, RNU1-132P, RNU1-133P, RNU1-134P, RNU1-136P, RNU1-138P, RNU1-139P, RNU1-140P, RNU1-141P, RNU1-142P, RNU1-143P, RNU1-146P, RNU1-148P, RNU1-149P, RNU1-14P, RNU1-150P, RNU1-151P, RNU1-153P, RNU1-154P, RNU1-155P, RNU1-15P, RNU1-16P, RNU1-17P, RNU1-18P, RNU1-19P, RNU1-2, RNU1-20P, RNU1-21P, RNU1-22P, RNU1-23P, RNU1-24P, RNU1-27P, RNU1-28P, RNU1-29P, RNU1-3, RNU1-30P, RNU1-31P, RNU1-32P, RNU1-33P, RNU1-34P, RNU1-35P, RNU1-36P, RNU1-38P, RNU1-39P, RNU1-4, RNU1-40P, RNU1-41P, RNU1-42P, RNU1-43P, RNU1-44P, RNU1-45P, RNU1-46P, RNU1-47P, RNU1-48P, RNU1-49P, RNU1-51P, RNU1-52P, RNU1-54P, RNU1-55P, RNU1-56P, RNU1-57P, RNU1-58P, RNU1-5P, RNU1-61P, RNU1-62P, RNU1-63P, RNU1-64P, RNU1-65P, RNU1-67P, RNU1-68P, RNU1-6P, RNU1-70P, RNU1-72P, RNU1-73P, RNU1-74P, RNU1-75P, RNU1-76P, RNU1-77P, RNU1-78P, RNU1-79P, RNU1-7P, RNU1-80P, RNU1-82P, RNU1-83P, RNU1-84P, RNU1-86P, RNU1-88P, RNU1-89P, RNU1-8P, RNU1-91P, RNU1-93P, RNU1-94P, RNU1-95P, RNU1-96P, RNU1-97P, RNU1-98P, RNU11, RNU11-2P, RNU11-3P, RNU11-4P, RNU11-5P, RNU11-6P, RNU12, RNU12-2P, RNU2-12P, RNU2-13P, RNU2-16P, RNU2-18P, RNU2-19P, RNU2-24P, RNU2-27P, RNU2-30P, RNU2-31P, RNU2-34P, RNU2-35P, RNU2-37P, RNU2-38P, RNU2-41P, RNU2-42P, RNU2-46P, RNU2-50P, RNU2-53P, RNU2-55P, RNU2-60P, RNU2-66P, RNU2-69P, RNU2-70P, RNU2-72P, RNU2-7P, RNU2-9P, RNU4-1, RNU4-10P, RNU4-11P, RNU4-12P, RNU4-13P, RNU4-14P, RNU4-15P, RNU4-16P, RNU4-17P, RNU4-18P, RNU4-2, RNU4-20P, RNU4-21P, RNU4-22P, RNU4-23P, RNU4-24P, RNU4-26P, RNU4-27P, RNU4-28P, RNU4-29P, RNU4-30P, RNU4-31P, RNU4-32P, RNU4-33P, RNU4-34P, RNU4-35P, RNU4-36P, RNU4-37P, RNU4-38P, RNU4-39P, RNU4-40P, RNU4-41P, RNU4-42P, RNU4-43P, RNU4-44P, RNU4-45P, RNU4-46P, RNU4-47P, RNU4-49P, RNU4-4P, RNU4-50P, RNU4-51P, RNU4-52P, RNU4-53P, RNU4-54P, RNU4-55P, RNU4-56P, RNU4-57P, RNU4-58P, RNU4-59P, RNU4-5P, RNU4-60P, RNU4-61P, RNU4-62P, RNU4-63P, RNU4-64P, RNU4-65P, RNU4-66P, RNU4-67P, RNU4-68P, RNU4-69P, RNU4-6P, RNU4-70P, RNU4-71P, RNU4-72P, RNU4-73P, RNU4-74P, RNU4-75P, RNU4-76P, RNU4-77P, RNU4-78P, RNU4-79P, RNU4-7P, RNU4-80P, RNU4-81P, RNU4-82P, RNU4-83P, RNU4-84P, RNU4-85P, RNU4-87P, RNU4-88P, RNU4-89P, RNU4-8P, RNU4-90P, RNU4-91P, RNU4-92P, RNU4-9P, RNU4ATAC, RNU4ATAC10P, RNU4ATAC11P, RNU4ATAC12P, RNU4ATAC13P, RNU4ATAC14P, RNU4ATAC15P, RNU4ATAC16P, RNU4ATAC17P, RNU4ATAC18P, RNU4ATAC2P, RNU4ATAC3P, RNU4ATAC4P, RNU4ATAC5P, RNU4ATAC6P, RNU4ATAC7P, RNU4ATAC8P, RNU4ATAC9P, RNU5A-1, RNU5A-2P, RNU5A-3P, RNU5A-4P, RNU5A-5P, RNU5A-6P, RNU5A-7P, RNU5A-8P, RNU5B-1, RNU5B-2P, RNU5B-3P, RNU5B-4P, RNU5B-6P, RNU5D-1, RNU5D-2P, RNU5E-1, RNU5E-10P, RNU5E-3P, RNU5E-4P, RNU5E-5P, RNU5E-6P, RNU5E-7P, RNU5E-8P, RNU5E-9P, RNU5F-1, RNU5F-2P, RNU5F-3P, RNU5F-4P, RNU5F-6P, RNU5F-7P, RNU5F-8P, RNU6-1, RNU6-1000P, RNU6-1001P, RNU6-1003P, RNU6-1004P, RNU6-1005P, RNU6-1006P, RNU6-1007P, RNU6-1008P, RNU6-

1009P, RNU6-100P, RNU6-110P, RNU6-1011P, RNU6-1012P, RNU6-1013P, RNU6-1014P, RNU6-1015P, RNU6-1016P, RNU6-1017P, RNU6-1018P, RNU6-1019P, RNU6-101P, RNU6-1020P, RNU6-1021P, RNU6-1022P, RNU6-1023P, RNU6-1024P, RNU6-1025P, RNU6-1026P, RNU6-1027P, RNU6-1028P, RNU6-1029P, RNU6-102P, RNU6-1031P, RNU6-1032P, RNU6-1034P, RNU6-1035P, RNU6-1036P, RNU6-1037P, RNU6-1038P, RNU6-1039P, RNU6-103P, RNU6-1040P, RNU6-1041P, RNU6-1042P, RNU6-1043P, RNU6-1044P, RNU6-1045P, RNU6-1046P, RNU6-1047P, RNU6-1048P, RNU6-1049P, RNU6-104P, RNU6-1050P, RNU6-1051P, RNU6-1052P, RNU6-1053P, RNU6-1054P, RNU6-1055P, RNU6-1056P, RNU6-1057P, RNU6-1059P, RNU6-105P, RNU6-1060P, RNU6-1061P, RNU6-1062P, RNU6-1064P, RNU6-1065P, RNU6-1066P, RNU6-1067P, RNU6-1068P, RNU6-1069P, RNU6-106P, RNU6-1071P, RNU6-1072P, RNU6-1073P, RNU6-1074P, RNU6-1075P, RNU6-1076P, RNU6-1077P, RNU6-1078P, RNU6-1079P, RNU6-107P, RNU6-1080P, RNU6-1081P, RNU6-1082P, RNU6-1083P, RNU6-1084P, RNU6-1085P, RNU6-1086P, RNU6-1087P, RNU6-1088P, RNU6-1089P, RNU6-108P, RNU6-1090P, RNU6-1091P, RNU6-1092P, RNU6-1093P, RNU6-1094P, RNU6-1095P, RNU6-1096P, RNU6-1097P, RNU6-1098P, RNU6-1099P, RNU6-109P, RNU6-10P, RNU6-1100P, RNU6-1101P, RNU6-1102P, RNU6-1103P, RNU6-1104P, RNU6-1105P, RNU6-1106P, RNU6-1107P, RNU6-1108P, RNU6-1109P, RNU6-110P, RNU6-1110P, RNU6-1111P, RNU6-1112P, RNU6-1113P, RNU6-1114P, RNU6-1115P, RNU6-1116P, RNU6-1117P, RNU6-1118P, RNU6-1119P, RNU6-111P, RNU6-1120P, RNU6-1121P, RNU6-1122P, RNU6-1123P, RNU6-1124P, RNU6-1125P, RNU6-1126P, RNU6-1127P, RNU6-1128P, RNU6-1129P, RNU6-112P, RNU6-1130P, RNU6-1131P, RNU6-1132P, RNU6-1133P, RNU6-1134P, RNU6-1135P, RNU6-1136P, RNU6-1137P, RNU6-1138P, RNU6-113P, RNU6-1140P, RNU6-1141P, RNU6-1143P, RNU6-1144P, RNU6-1145P, RNU6-1146P, RNU6-1147P, RNU6-1148P, RNU6-1149P, RNU6-114P, RNU6-1150P, RNU6-1151P, RNU6-1152P, RNU6-1153P, RNU6-1154P, RNU6-1155P, RNU6-1156P, RNU6-1157P, RNU6-1158P, RNU6-1159P, RNU6-115P, RNU6-1160P, RNU6-1161P, RNU6-1162P, RNU6-1163P, RNU6-1164P, RNU6-1165P, RNU6-1167P, RNU6-1168P, RNU6-1169P, RNU6-116P, RNU6-1170P, RNU6-1171P, RNU6-1172P, RNU6-1174P, RNU6-1175P, RNU6-1176P, RNU6-1177P, RNU6-1178P, RNU6-1179P, RNU6-117P, RNU6-1180P, RNU6-1181P, RNU6-1183P, RNU6-1184P, RNU6-1186P, RNU6-1187P, RNU6-1188P, RNU6-1189P, RNU6-118P, RNU6-1190P, RNU6-1191P, RNU6-1192P, RNU6-1193P, RNU6-1194P, RNU6-1195P, RNU6-1196P, RNU6-1197P, RNU6-1198P, RNU6-1199P, RNU6-119P, RNU6-11P, RNU6-1200P, RNU6-1201P, RNU6-1203P, RNU6-1204P, RNU6-1205P, RNU6-1206P, RNU6-1207P, RNU6-1208P, RNU6-1209P, RNU6-120P, RNU6-1210P, RNU6-1211P, RNU6-1212P, RNU6-1213P, RNU6-1214P, RNU6-1215P, RNU6-1216P, RNU6-1217P, RNU6-1218P, RNU6-1219P, RNU6-121P, RNU6-1220P, RNU6-1222P, RNU6-1223P, RNU6-1224P, RNU6-1225P, RNU6-1226P, RNU6-1227P, RNU6-1228P, RNU6-1229P, RNU6-122P, RNU6-1230P, RNU6-1231P, RNU6-1232P, RNU6-1233P, RNU6-1234P, RNU6-1235P, RNU6-1236P, RNU6-1237P, RNU6-1238P, RNU6-1239P, RNU6-123P, RNU6-1240P, RNU6-1241P, RNU6-1242P, RNU6-1243P, RNU6-1244P, RNU6-1245P, RNU6-1246P, RNU6-1247P, RNU6-1248P, RNU6-1249P, RNU6-1250P, RNU6-1251P, RNU6-1252P, RNU6-1254P, RNU6-1255P, RNU6-1256P, RNU6-1257P, RNU6-1258P, RNU6-125P, RNU6-1260P, RNU6-1261P, RNU6-1262P, RNU6-1263P, RNU6-1264P, RNU6-1265P, RNU6-1266P, RNU6-1267P, RNU6-1268P, RNU6-1269P, RNU6-126P, RNU6-1270P, RNU6-1271P, RNU6-1272P, RNU6-1273P, RNU6-1274P, RNU6-1275P, RNU6-1276P, RNU6-1277P, RNU6-1278P, RNU6-1279P, RNU6-127P, RNU6-1280P, RNU6-1281P, RNU6-1282P, RNU6-1283P, RNU6-1284P, RNU6-1285P, RNU6-1286P, RNU6-1287P, RNU6-1288P, RNU6-1289P, RNU6-128P, RNU6-1290P, RNU6-1291P, RNU6-1292P, RNU6-1293P, RNU6-1294P, RNU6-1296P, RNU6-1297P, RNU6-1298P, RNU6-1299P, RNU6-129P, RNU6-12P, RNU6-1300P, RNU6-1301P, RNU6-1303P, RNU6-1304P, RNU6-1305P, RNU6-1306P, RNU6-1307P, RNU6-1308P, RNU6-1309P, RNU6-130P, RNU6-1310P, RNU6-1311P, RNU6-1312P, RNU6-1313P, RNU6-1314P, RNU6-1315P, RNU6-1316P, RNU6-1317P, RNU6-1318P, RNU6-1319P, RNU6-131P, RNU6-1320P, RNU6-1321P, RNU6-1322P, RNU6-1323P, RNU6-1324P, RNU6-1325P, RNU6-1326P, RNU6-1327P, RNU6-1328P, RNU6-1329P, RNU6-132P, RNU6-1330P, RNU6-1331P, RNU6-1332P, RNU6-1333P, RNU6-1334P, RNU6-1335P, RNU6-1336P, RNU6-1337P, RNU6-1338P, RNU6-1339P, RNU6-133P, RNU6-1340P, RNU6-135P, RNU6-136P, RNU6-137P, RNU6-138P, RNU6-139P, RNU6-13P, RNU6-140P, RNU6-141P, RNU6-142P, RNU6-143P, RNU6-144P, RNU6-145P, RNU6-146P, RNU6-147P, RNU6-148P, RNU6-14P, RNU6-150P, RNU6-151P, RNU6-152P, RNU6-153P, RNU6-154P, RNU6-155P, RNU6-156P, RNU6-157P, RNU6-158P, RNU6-159P, RNU6-15P, RNU6-160P, RNU6-161P, RNU6-162P, RNU6-163P, RNU6-164P, RNU6-165P, RNU6-166P, RNU6-167P, RNU6-168P, RNU6-169P, RNU6-16P, RNU6-170P, RNU6-171P, RNU6-172P, RNU6-173P, RNU6-174P, RNU6-175P, RNU6-176P, RNU6-177P, RNU6-178P, RNU6-179P, RNU6-17P, RNU6-180P, RNU6-181P, RNU6-182P, RNU6-183P, RNU6-184P, RNU6-185P, RNU6-187P, RNU6-188P, RNU6-189P, RNU6-18P, RNU6-190P, RNU6-191P, RNU6-192P, RNU6-193P, RNU6-194P, RNU6-195P, RNU6-196P, RNU6-197P, RNU6-198P, RNU6-199P, RNU6-19P, RNU6-2, RNU6-200P, RNU6-201P, RNU6-202P, RNU6-203P, RNU6-204P, RNU6-205P, RNU6-206P, RNU6-207P, RNU6-208P, RNU6-209P, RNU6-20P, RNU6-210P, RNU6-211P, RNU6-212P, RNU6-213P, RNU6-214P, RNU6-215P, RNU6-216P, RNU6-217P, RNU6-218P, RNU6-219P, RNU6-21P, RNU6-220P, RNU6-221P, RNU6-222P, RNU6-223P, RNU6-224P, RNU6-225P, RNU6-226P, RNU6-227P, RNU6-228P, RNU6-229P, RNU6-22P, RNU6-230P, RNU6-231P, RNU6-232P, RNU6-233P, RNU6-234P, RNU6-235P, RNU6-236P, RNU6-237P, RNU6-238P, RNU6-239P, RNU6-23P, RNU6-240P, RNU6-241P, RNU6-242P, RNU6-243P, RNU6-244P, RNU6-245P, RNU6-246P, RNU6-247P, RNU6-248P, RNU6-249P, RNU6-24P, RNU6-250P, RNU6-251P, RNU6-252P, RNU6-253P, RNU6-254P, RNU6-255P, RNU6-256P, RNU6-257P, RNU6-258P, RNU6-259P, RNU6-25P, RNU6-260P, RNU6-261P, RNU6-262P, RNU6-263P, RNU6-264P, RNU6-266P, RNU6-267P, RNU6-268P, RNU6-269P, RNU6-26P, RNU6-270P, RNU6-271P, RNU6-272P, RNU6-273P, RNU6-274P, RNU6-275P, RNU6-276P, RNU6-277P, RNU6-278P, RNU6-279P, RNU6-27P, RNU6-280P, RNU6-281P, RNU6-282P, RNU6-283P, RNU6-284P, RNU6-285P, RNU6-286P, RNU6-287P, RNU6-288P, RNU6-289P, RNU6-28P, RNU6-290P, RNU6-291P, RNU6-293P, RNU6-294P, RNU6-295P, RNU6-296P, RNU6-297P, RNU6-298P, RNU6-299P, RNU6-29P, RNU6-300P, RNU6-301P, RNU6-302P, RNU6-303P, RNU6-304P, RNU6-306P, RNU6-307P, RNU6-308P, RNU6-309P, RNU6-30P, RNU6-310P, RNU6-311P, RNU6-312P, RNU6-313P, RNU6-314P, RNU6-315P, RNU6-316P, RNU6-317P, RNU6-318P, RNU6-319P, RNU6-31P, RNU6-320P, RNU6-321P, RNU6-322P, RNU6-

323P, RNU6-324P, RNU6-325P, RNU6-326P, RNU6-327P, RNU6-328P, RNU6-329P, RNU6-32P, RNU6-330P, RNU6-331P, RNU6-332P, RNU6-333P, RNU6-334P, RNU6-335P, RNU6-336P, RNU6-337P, RNU6-338P, RNU6-339P, RNU6-33P, RNU6-340P, RNU6-341P, RNU6-342P, RNU6-343P, RNU6-344P, RNU6-345P, RNU6-346P, RNU6-347P, RNU6-348P, RNU6-349P, RNU6-34P, RNU6-351P, RNU6-352P, RNU6-353P, RNU6-354P, RNU6-355P, RNU6-356P, RNU6-358P, RNU6-359P, RNU6-35P, RNU6-360P, RNU6-361P, RNU6-362P, RNU6-363P, RNU6-364P, RNU6-365P, RNU6-366P, RNU6-367P, RNU6-368P, RNU6-369P, RNU6-36P, RNU6-370P, RNU6-371P, RNU6-373P, RNU6-374P, RNU6-375P, RNU6-376P, RNU6-377P, RNU6-378P, RNU6-379P, RNU6-37P, RNU6-380P, RNU6-381P, RNU6-382P, RNU6-383P, RNU6-384P, RNU6-386P, RNU6-387P, RNU6-388P, RNU6-389P, RNU6-38P, RNU6-390P, RNU6-391P, RNU6-392P, RNU6-393P, RNU6-394P, RNU6-395P, RNU6-396P, RNU6-397P, RNU6-398P, RNU6-399P, RNU6-39P, RNU6-3P, RNU6-400P, RNU6-401P, RNU6-402P, RNU6-403P, RNU6-405P, RNU6-406P, RNU6-407P, RNU6-408P, RNU6-409P, RNU6-40P, RNU6-410P, RNU6-411P, RNU6-412P, RNU6-413P, RNU6-414P, RNU6-415P, RNU6-416P, RNU6-417P, RNU6-418P, RNU6-419P, RNU6-41P, RNU6-420P, RNU6-421P, RNU6-422P, RNU6-424P, RNU6-425P, RNU6-426P, RNU6-428P, RNU6-429P, RNU6-42P, RNU6-430P, RNU6-431P, RNU6-432P, RNU6-433P, RNU6-434P, RNU6-435P, RNU6-436P, RNU6-437P, RNU6-438P, RNU6-439P, RNU6-43P, RNU6-440P, RNU6-441P, RNU6-442P, RNU6-444P, RNU6-445P, RNU6-446P, RNU6-447P, RNU6-448P, RNU6-449P, RNU6-44P, RNU6-450P, RNU6-451P, RNU6-452P, RNU6-453P, RNU6-454P, RNU6-455P, RNU6-456P, RNU6-457P, RNU6-458P, RNU6-45P, RNU6-460P, RNU6-461P, RNU6-462P, RNU6-463P, RNU6-464P, RNU6-465P, RNU6-466P, RNU6-467P, RNU6-468P, RNU6-469P, RNU6-46P, RNU6-470P, RNU6-471P, RNU6-472P, RNU6-473P, RNU6-474P, RNU6-475P, RNU6-476P, RNU6-477P, RNU6-478P, RNU6-479P, RNU6-47P, RNU6-480P, RNU6-481P, RNU6-482P, RNU6-483P, RNU6-484P, RNU6-485P, RNU6-486P, RNU6-487P, RNU6-488P, RNU6-489P, RNU6-48P, RNU6-490P, RNU6-491P, RNU6-492P, RNU6-493P, RNU6-494P, RNU6-495P, RNU6-496P, RNU6-497P, RNU6-498P, RNU6-499P, RNU6-49P, RNU6-4P, RNU6-500P, RNU6-501P, RNU6-502P, RNU6-503P, RNU6-504P, RNU6-505P, RNU6-506P, RNU6-507P, RNU6-508P, RNU6-509P, RNU6-50P, RNU6-510P, RNU6-511P, RNU6-512P, RNU6-513P, RNU6-514P, RNU6-516P, RNU6-517P, RNU6-518P, RNU6-519P, RNU6-520P, RNU6-521P, RNU6-522P, RNU6-523P, RNU6-524P, RNU6-525P, RNU6-526P, RNU6-527P, RNU6-528P, RNU6-529P, RNU6-530P, RNU6-531P, RNU6-532P, RNU6-533P, RNU6-534P, RNU6-535P, RNU6-536P, RNU6-537P, RNU6-538P, RNU6-539P, RNU6-53P, RNU6-540P, RNU6-541P, RNU6-542P, RNU6-543P, RNU6-544P, RNU6-545P, RNU6-546P, RNU6-547P, RNU6-548P, RNU6-549P, RNU6-54P, RNU6-550P, RNU6-551P, RNU6-552P, RNU6-553P, RNU6-554P, RNU6-555P, RNU6-556P, RNU6-557P, RNU6-558P, RNU6-559P, RNU6-55P, RNU6-560P, RNU6-561P, RNU6-562P, RNU6-563P, RNU6-564P, RNU6-565P, RNU6-566P, RNU6-567P, RNU6-56P, RNU6-570P, RNU6-571P, RNU6-572P, RNU6-573P, RNU6-574P, RNU6-575P, RNU6-576P, RNU6-577P, RNU6-578P, RNU6-579P, RNU6-57P, RNU6-580P, RNU6-581P, RNU6-582P, RNU6-583P, RNU6-584P, RNU6-586P, RNU6-587P, RNU6-588P, RNU6-589P, RNU6-58P, RNU6-590P, RNU6-591P, RNU6-592P, RNU6-593P, RNU6-595P, RNU6-596P, RNU6-597P, RNU6-598P, RNU6-599P, RNU6-59P, RNU6-5P, RNU6-600P, RNU6-601P, RNU6-

602P, RNU6-603P, RNU6-604P, RNU6-605P, RNU6-606P, RNU6-607P, RNU6-608P, RNU6-609P, RNU6-60P, RNU6-610P, RNU6-611P, RNU6-612P, RNU6-613P, RNU6-614P, RNU6-615P, RNU6-616P, RNU6-617P, RNU6-618P, RNU6-619P, RNU6-61P, RNU6-620P, RNU6-621P, RNU6-622P, RNU6-623P, RNU6-624P, RNU6-625P, RNU6-626P, RNU6-627P, RNU6-628P, RNU6-629P, RNU6-62P, RNU6-630P, RNU6-631P, RNU6-632P, RNU6-633P, RNU6-634P, RNU6-635P, RNU6-636P, RNU6-637P, RNU6-638P, RNU6-639P, RNU6-63P, RNU6-640P, RNU6-641P, RNU6-642P, RNU6-643P, RNU6-644P, RNU6-645P, RNU6-646P, RNU6-647P, RNU6-648P, RNU6-649P, RNU6-64P, RNU6-650P, RNU6-651P, RNU6-652P, RNU6-653P, RNU6-654P, RNU6-655P, RNU6-656P, RNU6-657P, RNU6-658P, RNU6-659P, RNU6-65P, RNU6-660P, RNU6-661P, RNU6-662P, RNU6-663P, RNU6-664P, RNU6-665P, RNU6-666P, RNU6-667P, RNU6-668P, RNU6-669P, RNU6-66P, RNU6-670P, RNU6-672P, RNU6-673P, RNU6-674P, RNU6-675P, RNU6-677P, RNU6-678P, RNU6-679P, RNU6-67P, RNU6-680P, RNU6-681P, RNU6-682P, RNU6-684P, RNU6-685P, RNU6-686P, RNU6-687P, RNU6-689P, RNU6-68P, RNU6-690P, RNU6-692P, RNU6-693P, RNU6-694P, RNU6-695P, RNU6-696P, RNU6-697P, RNU6-698P, RNU6-699P, RNU6-6P, RNU6-7, RNU6-700P, RNU6-701P, RNU6-702P, RNU6-703P, RNU6-704P, RNU6-705P, RNU6-706P, RNU6-707P, RNU6-708P, RNU6-709P, RNU6-70P, RNU6-710P, RNU6-711P, RNU6-712P, RNU6-713P, RNU6-714P, RNU6-715P, RNU6-716P, RNU6-717P, RNU6-718P, RNU6-719P, RNU6-71P, RNU6-720P, RNU6-721P, RNU6-722P, RNU6-723P, RNU6-724P, RNU6-725P, RNU6-726P, RNU6-727P, RNU6-728P, RNU6-729P, RNU6-72P, RNU6-730P, RNU6-731P, RNU6-732P, RNU6-733P, RNU6-735P, RNU6-737P, RNU6-738P, RNU6-739P, RNU6-73P, RNU6-740P, RNU6-741P, RNU6-742P, RNU6-743P, RNU6-744P, RNU6-745P, RNU6-746P, RNU6-747P, RNU6-748P, RNU6-749P, RNU6-74P, RNU6-750P, RNU6-751P, RNU6-752P, RNU6-753P, RNU6-754P, RNU6-755P, RNU6-756P, RNU6-757P, RNU6-758P, RNU6-759P, RNU6-75P, RNU6-760P, RNU6-761P, RNU6-762P, RNU6-763P, RNU6-764P, RNU6-765P, RNU6-766P, RNU6-767P, RNU6-768P, RNU6-769P, RNU6-76P, RNU6-770P, RNU6-771P, RNU6-772P, RNU6-774P, RNU6-775P, RNU6-776P, RNU6-777P, RNU6-778P, RNU6-77P, RNU6-780P, RNU6-781P, RNU6-782P, RNU6-783P, RNU6-784P, RNU6-785P, RNU6-786P, RNU6-787P, RNU6-788P, RNU6-789P, RNU6-78P, RNU6-790P, RNU6-791P, RNU6-792P, RNU6-793P, RNU6-794P, RNU6-795P, RNU6-796P, RNU6-797P, RNU6-798P, RNU6-799P, RNU6-79P, RNU6-8, RNU6-800P, RNU6-801P, RNU6-803P, RNU6-804P, RNU6-805P, RNU6-806P, RNU6-807P, RNU6-808P, RNU6-809P, RNU6-80P, RNU6-810P, RNU6-811P, RNU6-812P, RNU6-813P, RNU6-815P, RNU6-816P, RNU6-817P, RNU6-818P, RNU6-819P, RNU6-81P, RNU6-820P, RNU6-821P, RNU6-822P, RNU6-823P, RNU6-824P, RNU6-826P, RNU6-827P, RNU6-828P, RNU6-829P, RNU6-82P, RNU6-830P, RNU6-831P, RNU6-832P, RNU6-833P, RNU6-834P, RNU6-835P, RNU6-836P, RNU6-837P, RNU6-838P, RNU6-839P, RNU6-83P, RNU6-840P, RNU6-841P, RNU6-842P, RNU6-843P, RNU6-844P, RNU6-845P, RNU6-847P, RNU6-848P, RNU6-849P, RNU6-84P, RNU6-850P, RNU6-851P, RNU6-853P, RNU6-854P, RNU6-855P, RNU6-856P, RNU6-857P, RNU6-858P, RNU6-859P, RNU6-85P, RNU6-860P, RNU6-861P, RNU6-862P, RNU6-863P, RNU6-864P, RNU6-865P, RNU6-866P, RNU6-867P, RNU6-869P, RNU6-86P, RNU6-871P, RNU6-873P, RNU6-874P, RNU6-875P, RNU6-876P, RNU6-877P, RNU6-878P, RNU6-879P, RNU6-87P, RNU6-880P, RNU6-881P, RNU6-882P, RNU6-883P, RNU6-884P, RNU6-885P,

RNU6-886P, RNU6-887P, RNU6-888P, RNU6-889P, RNU6-88P, RNU6-890P, RNU6-891P, RNU6-892P, RNU6-893P, RNU6-894P, RNU6-895P, RNU6-896P, RNU6-897P, RNU6-898P, RNU6-899P, RNU6-89P, RNU6-9, RNU6-900P, RNU6-901P, RNU6-902P, RNU6-903P, RNU6-904P, RNU6-905P, RNU6-906P, RNU6-907P, RNU6-908P, RNU6-909P, RNU6-90P, RNU6-910P, RNU6-911P, RNU6-912P, RNU6-913P, RNU6-914P, RNU6-915P, RNU6-916P, RNU6-917P, RNU6-918P, RNU6-919P, RNU6-91P, RNU6-920P, RNU6-921P, RNU6-922P, RNU6-923P, RNU6-924P, RNU6-925P, RNU6-926P, RNU6-927P, RNU6-928P, RNU6-929P, RNU6-92P, RNU6-930P, RNU6-931P, RNU6-932P, RNU6-933P, RNU6-934P, RNU6-935P, RNU6-936P, RNU6-937P, RNU6-938P, RNU6-939P, RNU6-940P, RNU6-941P, RNU6-942P, RNU6-943P, RNU6-944P, RNU6-945P, RNU6-946P, RNU6-947P, RNU6-948P, RNU6-949P, RNU6-94P, RNU6-950P, RNU6-951P, RNU6-952P, RNU6-953P, RNU6-954P, RNU6-955P, RNU6-956P, RNU6-957P, RNU6-958P, RNU6-959P, RNU6-95P, RNU6-960P, RNU6-961P, RNU6-964P, RNU6-965P, RNU6-966P, RNU6-967P, RNU6-968P, RNU6-969P, RNU6-970P, RNU6-971P, RNU6-972P, RNU6-973P, RNU6-974P, RNU6-975P, RNU6-976P, RNU6-977P, RNU6-978P, RNU6-979P, RNU6-97P, RNU6-980P, RNU6-982P, RNU6-983P, RNU6-984P, RNU6-985P, RNU6-986P, RNU6-987P, RNU6-988P, RNU6-989P, RNU6-98P, RNU6-990P, RNU6-991P, RNU6-992P, RNU6-993P, RNU6-994P, RNU6-995P, RNU6-996P, RNU6-997P, RNU6-998P, RNU6-999P, RNU6-99P, RNU6ATAC, RNU6ATAC10P, RNU6ATAC11P, RNU6ATAC12P, RNU6ATAC13P, RNU6ATAC14P, RNU6ATAC15P, RNU6ATAC16P, RNU6ATAC17P, RNU6ATAC18P, RNU6ATAC19P, RNU6ATAC20P, RNU6ATAC21P, RNU6ATAC22P, RNU6ATAC23P, RNU6ATAC24P, RNU6ATAC25P, RNU6ATAC26P, RNU6ATAC27P, RNU6ATAC28P, RNU6ATAC29P, RNU6ATAC2P, RNU6ATAC30P, RNU6ATAC31P, RNU6ATAC32P, RNU6ATAC33P, RNU6ATAC34P, RNU6ATAC36P, RNU6ATAC37P, RNU6ATAC38P, RNU6ATAC39P, RNU6ATAC3P, RNU6ATAC40P, RNU6ATAC41P, RNU6ATAC42P, RNU6ATAC4P, RNU6ATAC5P, RNU6ATAC6P, RNU6ATAC7P, RNU6ATAC8P, RNU6ATAC9P, RNU6V, RNU7-1, RNU7-102P, RNU7-103P, RNU7-104P, RNU7-105P, RNU7-106P, RNU7-107P, RNU7-10P, RNU7-110P, RNU7-111P, RNU7-113P, RNU7-115P, RNU7-116P, RNU7-119P, RNU7-11P, RNU7-120P, RNU7-121P, RNU7-123P, RNU7-124P, RNU7-125P, RNU7-126P, RNU7-127P, RNU7-128P, RNU7-129P, RNU7-12P, RNU7-130P, RNU7-133P, RNU7-134P, RNU7-136P, RNU7-137P, RNU7-138P, RNU7-13P, RNU7-140P, RNU7-141P, RNU7-143P, RNU7-144P, RNU7-147P, RNU7-148P, RNU7-149P, RNU7-14P, RNU7-151P, RNU7-152P, RNU7-153P, RNU7-154P, RNU7-155P, RNU7-156P, RNU7-157P, RNU7-159P, RNU7-160P, RNU7-161P, RNU7-164P, RNU7-165P, RNU7-167P, RNU7-169P, RNU7-170P, RNU7-171P, RNU7-172P, RNU7-173P, RNU7-174P, RNU7-175P, RNU7-176P, RNU7-179P, RNU7-180P, RNU7-181P, RNU7-182P, RNU7-183P, RNU7-185P, RNU7-186P, RNU7-187P, RNU7-188P, RNU7-18P, RNU7-190P, RNU7-192P, RNU7-193P, RNU7-194P, RNU7-195P, RNU7-196P, RNU7-197P, RNU7-19P, RNU7-200P, RNU7-20P, RNU7-21P, RNU7-22P, RNU7-23P, RNU7-24P, RNU7-25P, RNU7-26P, RNU7-27P, RNU7-28P, RNU7-29P, RNU7-2P, RNU7-30P, RNU7-34P, RNU7-35P, RNU7-37P, RNU7-38P, RNU7-3P, RNU7-40P, RNU7-41P, RNU7-43P, RNU7-45P, RNU7-46P, RNU7-47P, RNU7-48P, RNU7-49P, RNU7-4P, RNU7-50P, RNU7-51P, RNU7-52P, RNU7-53P, RNU7-54P,

RNU7-55P, RNU7-56P, RNU7-57P, RNU7-59P, RNU7-60P, RNU7-61P, RNU7-62P, RNU7-63P, RNU7-65P, RNU7-66P, RNU7-67P, RNU7-69P, RNU7-6P, RNU7-70P, RNU7-71P, RNU7-73P, RNU7-74P, RNU7-75P, RNU7-77P, RNU7-79P, RNU7-7P, RNU7-80P, RNU7-81P, RNU7-82P, RNU7-84P, RNU7-85P, RNU7-87P, RNU7-88P, RNU7-8P, RNU7-90P, RNU7-92P, RNU7-93P, RNU7-94P, RNU7-95P, RNU7-96P, RNU7-97P, RNU7-99P, RNU7-9P, RNVU1-1, RNVU1-14, RNVU1-15, RNVU1-17, RNVU1-18, RNVU1-19, RNVU1-2, RNVU1-21, RNVU1-22, RNVU1-23, RNVU1-24, RNVU1-25, RNVU1-26, RNVU1-27, RNVU1-28, RNVU1-29, RNVU1-2A, RNVU1-3, RNVU1-30, RNVU1-31, RNVU1-32, RNVU1-33, RNVU1-34, RNVU1-4, RNVU1-6, RNVU1-7, RNVU1-8, U1, U2, U4, U6, U7.

In some embodiments, a splice editor nucleic acid molecule of the disclosure comprises a full-length snRNA or portion thereof comprising a nucleotide sequence comprising one or more sequence motifs described herein (e.g., one or more sequence motifs set forth in Table 1), and wherein the snRNA is selected from a U1 snRNA, a U2 snRNA, a U4 snRNA, a U4atac snRNA, a U5 snRNA, a U6 snRNA, a U6atac snRNA, a U11 snRNA, a U12 snRNA, and a U7 snRNA.

In some embodiments, the snRNA is a U1 snRNA. In some embodiments, the U1 snRNA assembles into a U1 RNP. In some embodiments, the snRNA is a U2 snRNA. In some embodiments, the U2 snRNA assembles into a U2 RNP. In some embodiments, the snRNA is a U4 snRNA. In some embodiments, the U1 snRNA assembles into a U4 RNP. In some embodiments, the snRNA is a U4atac snRNA. In some embodiments, the U1 snRNA assembles into a U4atac RNP. In some embodiments, the snRNA is a U5 snRNA. In some embodiments, the U1 snRNA assembles into a U5 RNP. In some embodiments, the snRNA is a U6 snRNA. In some embodiments, the U1 snRNA assembles into a U6 RNP. In some embodiments, the snRNA is a U6atac snRNA. In some embodiments, the U1 snRNA assembles into a U6atac RNP. In some embodiments, the snRNA is a U7 snRNA. In some embodiments, the U1 snRNA assembles into a U7 RNP. In some embodiments, the snRNA is a U11 snRNA. In some embodiments, the U1 snRNA assembles into a U11 RNP. In some embodiments, the snRNA is a U12 snRNA. In some embodiments, the U1 snRNA assembles into a U12 RNP.

In some embodiments, the ncRNA comprises a Sm sequence motif. In some embodiments, the Sm sequence motif assembles with an Sm protein to form an RNP. In some embodiments, the Sm protein is B/B', D3, D2, D1, E, F, and G Sm proteins.

In some embodiments, a splice editor nucleic acid molecule of the disclosure comprises a full-length snoRNA or portion thereof comprising a nucleotide sequence comprising one or more sequence motifs described herein (e.g., one or more sequence motifs set forth in Table 1). In some embodiments, a snoRNA sequence described herein or identified according to a method described herein is incorporated into a splice editor nucleic acid of the disclosure. In some embodiments, a full-length snoRNA sequence described herein or identified according to a method described herein is incorporated into a splice editor nucleic acid of the disclosure. In some embodiments, a portion of a snoRNA sequence described herein or identified according to a method described herein (e.g., a region of contiguous nucleotides in the snRNA) is incorporated into a splice editor nucleic acid of the disclosure.

In some embodiments, the full-length snoRNA or portion thereof assembles into a small nucleolar RNP (snoRNP).

snoRNAs are responsible for RNA methylation and RNA pseudouridylation (Bachellerie 2002, Kiss 2004). There are two classes of snoRNAs, namely (i) H/ACA box snoRNAs which are responsible for pseudouridylation and (ii) C/D box snoRNAs which are responsible for 2'-O-ribose methylation (Jorjani 2016, Kufel 2019). snoRNAs can also form RNPs termed snoRNPs (Khanna 2006) and hybridize to their RNA targets via Watson-Crick base pairing (Jin 2007).

In some embodiments, the full-length snoRNA or portion thereof comprises an H/ACA box. In some embodiments, the H/ACA box comprises a nucleotide sequence comprising from 5' to 3' an H consensus sequence (e.g., an H consensus sequence comprising the sequence set forth in Table 1) and an ACA consensus sequence (e.g., an ACA consensus sequence comprising the sequence set forth in Table 1). In some embodiments, the H/ACA box snoRNA assembles to form an H/ACA snoRNP. In some embodiments, the full-length snoRNA or portion thereof comprises a C/D box. In some embodiment, the C/D box comprises a nucleotide sequence comprising from 5' to 3' a C consensus sequence (e.g., a C consensus sequence comprising the sequence set forth in Table 1), a D' consensus sequence (e.g., a D' consensus sequence comprising the sequence set forth in Table 1), a C' consensus sequence (e.g., a C' consensus sequence comprising the sequence set forth in Table 1), and a D consensus sequence (e.g., a D consensus sequence comprising the sequence set forth in Table 1). In some embodiments, the C/D box snoRNP assembles to form a C/D snoRNP.

In some embodiments, a splice editor nucleic acid molecule of the disclosure comprises a full-length snoRNA or portion thereof comprising a nucleotide sequence comprising one or more sequence motifs described herein (e.g., one or more sequence motifs set forth in Table 1), and wherein the snoRNA is selected from SCARNA18, SCARNA18B, SNORA1, SNORA10, SNORA108, SNORA10B, SNORA11, SNORA11B, SNORA11C, SNORA11D, SNORA11E, SNORA11F, SNORA11G, SNORA12, SNORA13, SNORA14A, SNORA14B, SNORA15, SNORA15B-1, SNORA15B-2, SNORA16A, SNORA16B, SNORA17A, SNORA17B, SNORA18, SNORA19, SNORA1B, SNORA20, SNORA20B, SNORA21, SNORA21B, SNORA22, SNORA22B, SNORA22C, SNORA24, SNORA24B, SNORA25, SNORA25B, SNORA26, SNORA27, SNORA28, SNORA29, SNORA2A, SNORA2B, SNORA2C, SNORA30, SNORA30B, SNORA31, SNORA31B, SNORA32, SNORA33, SNORA35, SNORA35B, SNORA36A, SNORA36B, SNORA36C, SNORA37, SNORA38, SNORA38B, SNORA3A, SNORA3B, SNORA3C, SNORA4, SNORA40, SNORA40B, SNORA40C, SNORA41, SNORA41B, SNORA44, SNORA46, SNORA47, SNORA48, SNORA48B, SNORA49, SNORA50A, SNORA50B, SNORA50C, SNORA50D, SNORA51, SNORA52, SNORA54, SNORA55, SNORA56, SNORA57, SNORA58, SNORA58B, SNORA59A, SNORA5A, SNORA5B, SNORA5C, SNORA6, SNORA60, SNORA61, SNORA62, SNORA63, SNORA63B, SNORA63C, SNORA63D, SNORA63E, SNORA64, SNORA65, SNORA66, SNORA67, SNORA68, SNORA68B, SNORA69, SNORA70, SNORA70B, SNORA70C, SNORA70D, SNORA70E, SNORA70F, SNORA70G, SNORA70H, SNORA70I, SNORA70J, SNORA71, SNORA71A, SNORA71C, SNORA71D, SNORA71E, SNORA72, SNORA73, SNORA74, SNORA74D, SNORA75, SNORA75B, SNORA77, SNORA77B, SNORA78, SNORA79, SNORA79B, SNORA7A, SNORA7B, SNORA8, SNORA80A, SNORA80B, SNORA80C, SNORA80D, SNORA80E, SNORA81, SNORA84, SNORA9, SNORA9B, SNORD10, SNORD100, SNORD101, SNORD102, SNORD104, SNORD105, SNORD105B, SNORD107, SNORD108, SNORD109A, SNORD109B, SNORD11, SNORD110, SNORD111, SNORD111B, SNORD112, SNORD113-1, SNORD113-2, SNORD113-3, SNORD113-4, SNORD113-5, SNORD113-6, SNORD113-7, SNORD113-8, SNORD113-9, SNORD114-1, SNORD114-10, SNORD114-11, SNORD114-12, SNORD114-13, SNORD114-14, SNORD114-15, SNORD114-16, SNORD114-17, SNORD114-18, SNORD114-19, SNORD114-2, SNORD114-20, SNORD114-21, SNORD114-22, SNORD114-23, SNORD114-24, SNORD114-25, SNORD114-26, SNORD114-27, SNORD114-28, SNORD114-29, SNORD114-3, SNORD114-30, SNORD114-31, SNORD114-4, SNORD114-5, SNORD114-6, SNORD114-7, SNORD114-9, SNORD115, SNORD115-1, SNORD115-10, SNORD115-11, SNORD115-12, SNORD115-13, SNORD115-14, SNORD115-15, SNORD115-16, SNORD115-17, SNORD115-18, SNORD115-19, SNORD115-2, SNORD115-20, SNORD115-21, SNORD115-22, SNORD115-23, SNORD115-24, SNORD115-25, SNORD115-26, SNORD115-27, SNORD115-28, SNORD115-29, SNORD115-3, SNORD115-30, SNORD115-31, SNORD115-32, SNORD115-33, SNORD115-34, SNORD115-35, SNORD115-36, SNORD115-37, SNORD115-38, SNORD115-39, SNORD115-4, SNORD115-40, SNORD115-41, SNORD115-42, SNORD115-43, SNORD115-44, SNORD115-45, SNORD115-46, SNORD115-47, SNORD115-48, SNORD115-5, SNORD115-6, SNORD115-7, SNORD115-8, SNORD115-9, SNORD116, SNORD116-1, SNORD116-10, SNORD116-11, SNORD116-12, SNORD116-13, SNORD116-14, SNORD116-15, SNORD116-16, SNORD116-17, SNORD116-18, SNORD116-19, SNORD116-2, SNORD116-20, SNORD116-21, SNORD116-22, SNORD116-23, SNORD116-24, SNORD116-25, SNORD116-26, SNORD116-27, SNORD116-28, SNORD116-29, SNORD116-3, SNORD116-30, SNORD116-4, SNORD116-5, SNORD116-6, SNORD116-7, SNORD116-8, SNORD116-9, SNORD117, SNORD118, SNORD11B, SNORD12, SNORD121A, SNORD121B, SNORD123, SNORD124, SNORD125, SNORD126, SNORD127, SNORD12B, SNORD12C, SNORD13, SNORD13D, SNORD13E, SNORD13P1, SNORD13P3, SNORD14, SNORD14A, SNORD14B, SNORD14C, SNORD14D, SNORD14E, SNORD15A, SNORD15B, SNORD16, SNORD18, SNORD18A, SNORD18B, SNORD18C, SNORD19, SNORD19B, SNORD19C, SNORD1A, SNORD1B, SNORD1C, SNORD2, SNORD20, SNORD21, SNORD22, SNORD23, SNORD24, SNORD25, SNORD26, SNORD27, SNORD28, SNORD28B, SNORD29, SNORD30, SNORD31B, SNORD32A, SNORD32B, SNORD33, SNORD34, SNORD35A, SNORD35B, SNORD36, SNORD36A, SNORD36B, SNORD36C, SNORD37, SNORD38A, SNORD38B, SNORD38C, SNORD38D, SNORD39, SNORD41, SNORD42, SNORD42A, SNORD42B, SNORD43, SNORD45A, SNORD45B, SNORD45C, SNORD46, SNORD48, SNORD49A, SNORD49B, SNORD4A, SNORD4B, SNORD5, SNORD50B, SNORD51, SNORD52, SNORD53, SNORD53B, SNORD54, SNORD55, SNORD56, SNORD56B, SNORD57, SNORD58, SNORD58A, SNORD58B, SNORD58C, SNORD59A, SNORD6, SNORD60, SNORD61, SNORD62, SNORD62A, SNORD62B, SNORD63, SNORD63B, SNORD64, SNORD65, SNORD65B, SNORD65C, SNORD66, SNORD67, SNORD68, SNORD69, SNORD7, SNORD70, SNORD70B, SNORD71, SNORD72, SNORD73A, SNORD73B, SNORD74B, SNORD77B, SNORD79, SNORD8, SNORD81, SNORD82, SNORD83, SNORD83A, SNORD83B, SNORD84, SNORD86, SNORD87, SNORD88A, SNORD88B, SNORD88C, SNORD89, SNORD9, SNORD90, SNORD92, SNORD93, SNORD94, SNORD95, SNORD96A, SNORD96B, SNORD97, SNORD98, SNORD99, U8, snoZ196.

In some embodiments, the ncRNA is a scaRNA. In some embodiments, a splice editor nucleic acid molecule of the disclosure comprises a full-length scaRNA or portion thereof comprising a nucleotide sequence comprising one or more sequence motifs described herein (e.g., one or more sequence motifs set forth in Table 1). In some embodiments, a scaRNA sequence described herein or identified according to a method described herein is incorporated into a splice editor nucleic acid of the disclosure. In some embodiments, a full-length scaRNA sequence described herein or identified according to a method described herein is incorporated into a splice editor nucleic acid of the disclosure. In some embodiments, a portion of a scaRNA sequence described herein or identified according to a method described herein (e.g., a region of contiguous nucleotides in the scaRNA) is incorporated into a splice editor nucleic acid of the disclosure. In some embodiments, the full-length scaRNA or portion thereof assembles into a small cajal body RNP (scaRNP). In some embodiments, the full-length scaRNA or the portion thereof comprises one or more secondary RNA structures that assembles to form a scaRNP. In some embodiments, the full-length scaRNA or the portion thereof comprises one or more sequence motifs that assembles to form a scaRNP. In some embodiments, the full-length scaRNA or the portion thereof comprises (i) one or more one or more secondary RNA structures, and (ii) one or more sequence motifs, wherein (i), (ii), or both assemble to form a scaRNP. In some embodiments, the full-length scaRNA or the portion thereof comprises an H/ACA box, wherein the H/ACA box comprises a nucleotide sequence comprising from 5' to 3' an H consensus sequence (e.g., an H consensus sequence comprising the sequence set forth in Table 1) and an ACA consensus sequence (e.g., an ACA consensus sequence comprising the sequence set forth in Table 1).

In some embodiments, a splice editor nucleic acid molecule of the disclosure comprises a full-length scaRNA or portion thereof comprising a nucleotide sequence comprising one or more sequence motifs described herein (e.g., one or more sequence motifs set forth in Table 1), wherein the scaRNA is selected from SCARNA1, SCARNA11, SCARNA14, SCARNA15, SCARNA17, SCARNA20, SCARNA21, SCARNA21B, SCARNA22, SCARNA23, SCARNA3, SCARNA4, SCARNA8.

In some embodiments, the ncRNA is a lncRNA. In some embodiments, a splice editor nucleic acid molecule of the disclosure comprises a full-length lncRNA or portion thereof comprising a nucleotide sequence comprising one or more sequence motifs described herein (e.g., one or more sequence motifs set forth in Table 1). In some embodiments, a lncRNA sequence described herein or identified according to a method described herein is incorporated into a splice editor nucleic acid of the disclosure. In some embodiments, a full-length lncRNA sequence described herein or identified according to a method described herein is incorporated into a splice editor nucleic acid of the disclosure. In some embodiments, a portion of a lncRNA sequence described herein or identified according to a method described herein (e.g., a region of contiguous nucleotides in the lncRNA) is incorporated into a splice editor nucleic acid of the disclosure. In some embodiments, the full-length lncRNA or portion thereof assembles into an RNP. In some embodiments, the full-length lncRNA or the portion thereof comprises one or more secondary RNA structures that assembles to form an RNP. In some embodiments, the full-length lncRNA or the portion thereof comprises one or more sequence motifs that assembles to form an RNP. In some embodiments, the full-length lncRNA or the portion thereof comprises (i) one or more one or more secondary RNA structures, and (ii) one or more sequence motifs, wherein (i), (ii), or both assemble to form an RNP.

In some embodiments, a splice editor nucleic acid molecule of the disclosure comprises a full-length lncRNA or portion thereof comprising a nucleotide sequence comprising one or more sequence motifs described herein (e.g., one or more sequence motifs set forth in Table 1), wherein the lncRNA is selected from AADACL2-AS1, ARHGEF26-AS1, ARMC2-AS1, BCAR3-AS1, C4B, CABIN1, CAPN15, CARS1-AS1, CASC19, CELF2-AS2, CPB2-AS1, EPHA5-AS1, ETV7-AS1, F11-AS1, FLG-AS1, GATA6-AS1, GLYCTK-AS1, HCG17, HCG27, HCG9, HHATL-AS1, HOTAIRM1, KIFC1, LINC00511, LINC00824, LINC01060, LINC01358, LINC01378, LINC01409, LINC01606, LINC01676, LINC01943, LINC02276, LINC02301, LINC02690, LINC02695, LINC02790, LINC02805, LRIG3-DT, LY6E-DT, MALAT1, MAP3K14, MAPK4, MEIOB, OR12D3, PCDH9-AS2, PHF1, PSMB1, SLC8A1-AS1, SNHG25, SPRY4-AS1, TEX41, TTTY17A, TTTY17B, UST-AS2, ZEB2-AS1, hsa-mir-1253, hsa-mir-423.

In some embodiments, the ncRNA is a miscRNA. In some embodiments, a splice editor nucleic acid molecule of the disclosure comprises a full-length miscRNA or portion thereof comprising a nucleotide sequence comprising one or more sequence motifs described herein (e.g., one or more sequence motifs set forth in Table 1). In some embodiments, a miscRNA sequence described herein or identified according to a method described herein is incorporated into a splice editor nucleic acid of the disclosure. In some embodiments, a full-length miscRNA sequence described herein or identified according to a method described herein is incorporated into a splice editor nucleic acid of the disclosure. In some embodiments, a portion of a miscRNA sequence described herein or identified according to a method described herein (e.g., a region of contiguous nucleotides in the miscRNA) is incorporated into a splice editor nucleic acid of the disclosure. In some embodiments, the full-length miscRNA or portion thereof assembles into an RNP. In some embodiments, the full-length miscRNA or the portion thereof comprises one or more secondary RNA structures that assembles to form an RNP. In some embodiments, the full-length miscRNA or the portion thereof comprises one or more sequence motifs that assembles to form an RNP. In some embodiments, the full-length miscRNA or the portion thereof comprises (i) one or more one or more secondary RNA structures, and (ii) one or more sequence motifs, wherein (i), (ii), or both assemble to form an RNP.

In some embodiments, a splice editor nucleic acid molecule of the disclosure comprises a full-length miscRNA or portion thereof comprising a nucleotide sequence comprising one or more sequence motifs described herein (e.g., one or more sequence motifs set forth in Table 1), wherein the miscRNA is selected from RN7SKP12, RN7SKP223, RN7SKP233, RN7SKP260, RN7SKP295, RN7SKP298, RN7SKP35, RN7SKP83, RN7SKP98, RNY1, RNY1P1, RNY1P10, RNY1P11, RNY1P12, RNY1P13, RNY1P14, RNY1P15, RNY1P16, RNY1P2, RNY1P3, RNY1P4, RNY1P5, RNY1P6, RNY1P7, RNY1P8, RNY1P9, RNY3, RNY3P1, RNY3P10, RNY3P11, RNY3P12, RNY3P13, RNY3P14, RNY3P15, RNY3P16, RNY3P2, RNY3P3, RNY3P4, RNY3P5, RNY3P7, RNY3P8, RNY3P9, RNY4, RNY4P10, RNY4P13, RNY4P14, RNY4P16, RNY4P17, RNY4P18, RNY4P19, RNY4P20, RNY4P23, RNY4P24, RNY4P25, RNY4P27, RNY4P28, RNY4P29, RNY4P3, RNY4P30, RNY4P34, RNY4P36, RNY4P37, RNY4P6, RNY4P7, RNY4P9, VTRNA1-1, VTRNA1-2, VTRNA1-3, VTRNA2-2P, VTRNA3-1P, and Vault, Y_RNA.

In some embodiments, the ncRNA is a Mt tRNA. In some embodiments, a splice editor nucleic acid molecule of the disclosure comprises a full-length Mt tRNA or portion thereof comprising a nucleotide sequence comprising one or more sequence motifs described herein (e.g., one or more sequence motifs set forth in Table 1). In some embodiments, a Mt tRNA sequence described herein or identified according to a method described herein is incorporated into a splice editor nucleic acid of the disclosure. In some embodiments, a full-length Mt tRNA sequence described herein or identified according to a method described herein is incorporated into a splice editor nucleic acid of the disclosure. In some embodiments, a portion of a Mt tRNA sequence described herein or identified according to a method described herein (e.g., a region of contiguous nucleotides in the Mt tRNA) is incorporated into a splice editor nucleic acid of the disclosure. In some embodiments, the full-length Mt tRNA or portion thereof assembles into an RNP. In some embodiments, the full-length Mt tRNA or the portion thereof comprises one or more secondary RNA structures that assembles to form an RNP. In some embodiments, the full-length Mt tRNA or the portion thereof comprises one or more sequence motifs that assembles to form an RNP. In some embodiments, the full-length Mt tRNA or the portion thereof comprises (i) one or more one or more secondary RNA structures, and (ii) one or more sequence motifs, wherein (i), (ii), or both assemble to form an RNP.

In some embodiments, a splice editor nucleic acid molecule of the disclosure comprises a full-length Mt RNA or portion thereof comprising a nucleotide sequence comprising one or more sequence motifs described herein (e.g., one or more sequence motifs set forth in Table 1), wherein the Mt tRNAs is selected from MT-TA, MT-TC, MT-TD, MT-TE, MT-TF, MT-TG, MT-TH, MT-TI, MT-TK, MT-TL1, MT-TL2, MT-TM, MT-TN, MT-TP, MT-TQ, MT-TR, MT-TS1, MT-TS2, MT-TT, MT-TV, MT-TW, and MT-TY.

In some embodiments, the ncRNA is an rRNA. In some embodiments, a splice editor nucleic acid molecule of the disclosure comprises a full-length rRNA or portion thereof comprising a nucleotide sequence comprising one or more sequence motifs described herein (e.g., one or more sequence motifs set forth in Table 1). In some embodiments, a rRNA sequence described herein or identified according to a method described herein is incorporated into a splice editor nucleic acid of the disclosure. In some embodiments, a full-length rRNA sequence described herein or identified according to a method described herein is incorporated into a splice editor nucleic acid of the disclosure. In some embodiments, a portion of a rRNA sequence described herein or identified according to a method described herein (e.g., a region of contiguous nucleotides in the rRNA) is incorporated into a splice editor nucleic acid of the disclosure. In some embodiments, the full-length rRNA or portion thereof assembles into an RNP. In some embodiments, the full-length rRNA or the portion thereof comprises one or more secondary RNA structures that assembles to form an RNP. In some embodiments, the full-length rRNA or the portion thereof comprises one or more sequence motifs that assembles to form an RNP. In some embodiments, the full-length rRNA or the portion thereof comprises (i) one or more one or more secondary RNA structures, and (ii) one or more sequence motifs, wherein (i), (ii), or both assemble to form an RNP.

In some embodiments, a splice editor nucleic acid molecule of the disclosure comprises a full-length rRNA or portion thereof comprising a nucleotide sequence comprising one or more sequence motifs described herein (e.g., one or more sequence motifs set forth in Table 1), wherein the rRNAs is selected from RNA5S1, RNA5S2, RNA5S3, RNA5S4, RNA5S5, RNA5S6, RNA5S7, RNA5S8, RNA5S9, RNA5S10, RNA5S11, RNA5S12, RNA5S13, RNA5S14, RNA5S15, RNA5S16, RNA5S17, RNR1, RNR2, RNR3, RNR4, RNR5, RNA18SN1, RNA18SN2, RNA18SN3, RNA18SN4, RNA18SN5, RNA28SN1, RNA28SN2, RNA28SN3, RNA28SN4, RNA28SN5, RNA45SN1, RNA45SN2, RNA45SN3, RNA45SN4, RNA45SN5, RNA5-8SN1, RNA5-8SN2, RNA5-8SN3, RNA5-8SN4, and RNA5-8SN5.

In some embodiments, the ncRNA is a vault RNA. In some embodiments, a splice editor nucleic acid molecule of the disclosure comprises a full-length vault RNA or portion thereof comprising a nucleotide sequence comprising one or more sequence motifs described herein (e.g., one or more sequence motifs set forth in Table 1). In some embodiments, a vault RNA sequence described herein or identified according to a method described herein is incorporated into a splice editor nucleic acid of the disclosure. In some embodiments, a full-length vault RNA sequence described herein or identified according to a method described herein is incorporated into a splice editor nucleic acid of the disclosure. In some embodiments, a portion of a vault RNA sequence described herein or identified according to a method described herein (e.g., a region of contiguous nucleotides in the vault RNA) is incorporated into a splice editor nucleic acid of the disclosure. In some embodiments, the full-length vault RNA or portion thereof assembles into an RNP. In some embodiments, the full-length vault RNA or the portion thereof comprises one or more secondary RNA structures that assembles to form an RNP. In some embodiments, the full-length vault RNA or the portion thereof comprises one or more sequence motifs that assembles to form an RNP. In some embodiments, the full-length vault RNA or the portion thereof comprises (i) one or more one or more secondary RNA structures, and (ii) one or more sequence motifs, wherein (i), (ii), or both assemble to form an RNP.

In some embodiments, a splice editor nucleic acid molecule of the disclosure comprises a vault RNA or portion thereof, wherein the vault RNA is VTRNA2-1.

Methods to Engineer a Splice Editor Nucleic Acid of the Disclosure

The present disclosure provides methods to engineer a splice editor nucleic acid described herein. In some embodiments, the method comprises (A) identifying one or more candidate ncRNAs; (B) obtaining a ncRNA sequence from the one or more candidate ncRNAs; and (C) producing a splice editor nucleic acid comprising a nucleotide sequence comprising (i) an intronic sequence comprising (a) the ncRNA sequence, and (b) one or more binding domains described herein; (ii) a splice acceptor and/or splice donor; and (iii) one or more exonic sequences, thereby providing a splice editor nucleic acid for targeting trans-splicing of the target RNA (e.g., target pre-mRNA). In some embodiments, the method comprises introducing the splice editor nucleic acid to a cell or population of cells and determining the efficiency of trans-splicing of the target RNA (e.g., target pre-mRNA) according to a method described herein. In some embodiments, the efficiency of trans-splicing of the splice editor nucleic acid is compared to that of a control nucleic acid. In some embodiments, the control nucleic acid comprises (i), (ii), and (iii) and lacks the ncRNA sequence.

Methods of Identifying Candidate ncRNA Sequences

In some embodiments, identifying one or more candidate ncRNA sequences comprises (i) obtaining one or more ncRNA sequences from a database and/or by experimental analysis of RNA expressed by a cell or organism as described herein; (ii) predicting the secondary structure formed by the one or more ncRNA sequences according to a method described herein; (iii) comparing the predicted secondary structure of (ii) to a reference secondary structure (e.g., a secondary structure present in a ncRNA known in the art); and (iv) selecting one or more candidate ncRNA sequences with a predicted secondary structure having substantial similarity to the reference secondary structure. Computational methods for predicting the secondary structures formed by a ncRNA sequence are known in the art (see, e.g., Lorenz, et al. ViennaRNA Package 2.0 Algorithms for Molecular Biology, 6:1 26, 2011). Methods for performing RNA sequence analysis by comparing predicted secondary structures to a reference secondary structure are also known in the art (see, e.g., Eddy, et al (1994) Nucleic Acids Res 22:2079).

In some embodiments, identifying one or more candidate ncRNA sequences comprises (i) obtaining one or more ncRNA sequences from a database and/or by experimental analysis of RNA expressed by a cell or organism as described herein; (ii) predicting the secondary structure formed by the one or more ncRNA sequences according to a method described herein; (iii) comparing the predicted secondary structure of (ii) to a reference secondary structure (e.g., a secondary structure present in a ncRNA known in the art); and (iv) selecting one or more candidate ncRNA sequences with a predicted secondary structure having substantial similarity to the reference secondary structure and comprising a sequence motif described herein (e.g., a sequence motif comprises one or more sequences set forth in Table 1).

In some embodiments, the one or more candidate ncRNA sequences are selected from any one or any combination of sequences set forth in SEQ ID NOs: 9-657

Method of Obtaining a ncRNA Sequence

In some embodiments, obtaining a ncRNA sequence for inclusion in a splice editor nucleic acid of the disclosure comprises (i) identifying one or more candidate ncRNA sequences as described herein; and (ii) selecting a ncRNA sequence from the one or more candidate ncRNA sequences.

In some embodiments, obtaining the ncRNA sequence comprises selecting a ncRNA sequence from the one or more candidate ncRNA sequences (e.g., one or more candidate ncRNA sequences selected from any one or any combination of sequences set forth in SEQ ID NOs: 9-657), wherein the ncRNA sequence is at least about 7, about 8, about 9, about 10, about 11, about 12, about 13, about 14, or about 15 nucleotides in length and comprises a Sm motif described herein (e.g., a Sm motif set forth in Table 1). In some embodiments, the ncRNA sequence is about 7 nucleotides in length and comprises a Sm motif described herein (e.g., a Sm motif set forth in Table 1). In some embodiments, the ncRNA sequence is about 8 nucleotides in length and comprises a Sm motif described herein (e.g., a Sm motif set forth in Table 1). In some embodiments, the ncRNA sequence is about 9 nucleotides in length and comprises a Sm motif described herein (e.g., a Sm motif set forth in Table 1). In some embodiments, the ncRNA sequence is about 10 nucleotides in length and comprises a Sm motif described herein (e.g., a Sm motif set forth in Table 1). In some embodiments, the ncRNA sequence is about 11 nucleotides in length and comprises a Sm motif described herein (e.g., a Sm motif set forth in Table 1). In some embodiments, the ncRNA sequence is about 12 nucleotides in length and comprises a Sm motif described herein (e.g., a Sm motif set forth in Table 1).

In some embodiments, obtaining the ncRNA sequence comprises selecting a ncRNA sequence from the one or more candidate ncRNA sequences (e.g., one or more candidate ncRNA sequences selected from any one or any combination of sequences set forth in SEQ ID NOs: 9-657), wherein the ncRNA sequence is at least about 40, about 45, about 50, about 55, about 60, about 65, about 70, about 75, about 80, about 85, about 90, about 95, or about 100 nucleotides in length and comprises a Sm motif described herein (e.g., a Sm motif set forth in Table 1).

In some embodiments, obtaining the ncRNA sequence comprises selecting a ncRNA sequence having at least about 60%, about 65%, about 70%, about 75%, about 80%, about 85%, about 90%, about 91%, about 92%, about 93%, about 94%, about 95%, about 96%, about 97%, about 98%, about 99% to one or more candidate ncRNA sequences or a portion thereof (e.g., one or more candidate ncRNA sequences selected from any one or any combination of sequences set forth in SEQ ID NOs: 9-657), wherein the ncRNA sequence is at least about 40, about 45, about 50, about 55, about 60, about 65, about 70, about 75, about 80, about 85, about 90, about 95, or about 100 nucleotides in length and comprises a Sm motif described herein (e.g., a Sm motif set forth in Table 1).

In some embodiments, obtaining the ncRNA sequence comprises selecting a ncRNA sequence from the one or more candidate ncRNA sequences (e.g., one or more candidate ncRNA sequences selected from any one or any combination of sequences set forth in SEQ ID NOs: 9-657), wherein the ncRNA sequence is at least about 40, about 45, about 50, about 55, about 60, about 65, about 70, about 75, about 80, about 85, about 90, about 95, or about 100 nucleotides in length and comprises a H-box motif described herein (e.g., a H-box motif set forth in Table 1).

In some embodiments, obtaining the ncRNA sequence comprises selecting a ncRNA sequence having at least about 60%, about 65%, about 70%, about 75%, about 80%, about 85%, about 90%, about 91%, about 92%, about 93%, about 94%, about 95%, about 96%, about 97%, about 98%, about 99% to one or more candidate ncRNA sequences or a portion thereof (e.g., one or more candidate ncRNA sequences selected from any one or any combination of sequences set forth in SEQ ID NOs: 9-657 or a portion thereof), wherein the ncRNA sequence is at least about 40, about 45, about 50, about 55, about 60, about 65, about 70, about 75, about 80, about 85, about 90, about 95, or about 100 nucleotides in length and comprises a H-box motif described herein (e.g., a H-box motif set forth in Table 1).

In some embodiments, obtaining the ncRNA sequence comprises selecting a ncRNA sequence from the one or more candidate ncRNA sequences (e.g., one or more candidate ncRNA sequences selected from any one or any combination of sequences set forth in SEQ ID NOs: 9-657), wherein the ncRNA sequence is at least about 40, about 45, about 50, about 55, about 60, about 65, about 70, about 75, about 80, about 85, about 90, about 95, or about 100 nucleotides in length and comprises an ACA-box motif described herein (e.g., an ACA-box motif set forth in Table 1).

In some embodiments, obtaining the ncRNA sequence comprises selecting a ncRNA sequence having at least about 60%, about 65%, about 70%, about 75%, about 80%, about 85%, about 90%, about 91%, about 92%, about 93%, about 94%, about 95%, about 96%, about 97%, about 98%, about 99% to one or more candidate ncRNA sequences or a portion thereof (e.g., one or more candidate ncRNA sequences selected from any one or any combination of sequences set forth in SEQ ID NOs: 9-657 or a portion thereof), wherein the ncRNA sequence is at least about 40, about 45, about 50, about 55, about 60, about 65, about 70, about 75, about 80, about 85, about 90, about 95, or about 100 nucleotides in length and comprises a ACA-box motif described herein (e.g., a ACA-box motif set forth in Table 1).

In some embodiments, obtaining the ncRNA sequence comprises selecting a ncRNA sequence from the one or more candidate ncRNA sequences (e.g., one or more candidate ncRNA sequences selected from any one or any combination of sequences set forth in SEQ ID NOs: 9-657), wherein the ncRNA sequence is at least about 40, about 45, about 50, about 55, about 60, about 65, about 70, about 75, about 80, about 85, about 90, about 95, or about 100 nucleotides in length and comprises an H-box and an ACA-box motif described herein (e.g., a H-box and a ACA-box motif set forth in Table 1).

In some embodiments, obtaining the ncRNA sequence comprises selecting a ncRNA sequence having at least about 60%, about 65%, about 70%, about 75%, about 80%, about 85%, about 90%, about 91%, about 92%, about 93%, about 94%, about 95%, about 96%, about 97%, about 98%, about 99% to one or more candidate ncRNA sequences or a portion thereof (e.g., one or more candidate ncRNA sequences selected from any one or any combination of sequences set forth in SEQ ID NOs: 9-657 or a portion thereof), wherein the ncRNA sequence is at least about 40, about 45, about 50, about 55, about 60, about 65, about 70, about 75, about 80, about 85, about 90, about 95, or about 100 nucleotides in length and comprises an H-box and an ACA-box motif described herein (e.g., a H-box and a ACA-box motif set forth in Table 1).

In some embodiments, obtaining the ncRNA sequence comprises selecting a ncRNA sequence from the one or more candidate ncRNA sequences (e.g., one or more candidate ncRNA sequences selected from any one or any combination of sequences set forth in SEQ ID NOs: 9-657), wherein the ncRNA sequence is at least about 40, about 45, about 50, about 55, about 60, about 65, about 70, about 75, about 80, about 85, about 90, about 95, or about 100 nucleotides in length and comprises a (i) C-box motif described herein (e.g., a C-box motif set forth in Table 1), (ii) C'-box motif described herein (e.g., a C'-box motif set forth in Table 1), (iii) D-box motif described herein (e.g., a D-box motif set forth in Table 1), (iv) a D'-box motif described herein (e.g., a D'-box motif set forth in Table 1), or (v) a combination of (i)-(iv).

In some embodiments, obtaining the ncRNA sequence comprises selecting a ncRNA sequence having at least about 60%, about 65%, about 70%, about 75%, about 80%, about 85%, about 90%, about 91%, about 92%, about 93%, about 94%, about 95%, about 96%, about 97%, about 98%, about 99% to one or more candidate ncRNA sequences or a portion thereof (e.g., one or more candidate ncRNA sequences selected from any one or any combination of sequences set forth in SEQ ID NOs: 9-657 or a portion thereof), wherein the sequence is at least about 40, about 45, about 50, about 55, about 60, about 65, about 70, about 75, about 80, about 85, about 90, about 95, or about 100 nucleotides in length and comprises a (i) C-box motif described herein (e.g., a C-box motif set forth in Table 1), (ii) C'-box motif described herein (e.g., a C'-box motif set forth in Table 1), (iii) D-box motif described herein (e.g., a D-box motif set forth in Table 1), (iv) a D'-box motif described herein (e.g., a D'-box motif set forth in Table 1), or (v) a combination of (i)-(iv).

Methods of Producing the Splice Editor Nucleic Acids

The splice editor nucleic acids provided by the disclosure are produced by suitable nucleic acid synthesis method or means known in the art. In some embodiments, the splice editor nucleic acid is produced as an RNA. In some embodiments, the splice editor nucleic acid is produced as a DNA. The present disclosure further provides delivery systems comprising the splice editor nucleic acid, e.g., a vector comprising the splice editor nucleic acid, a lipid particle comprising the splice editor nucleic acid.

Methods of producing the splice editor nucleic acids include, but are not limited to, in vitro transcription (IVT), synthetic and/or chemical synthesis methods, or a combination thereof. In some embodiments, enzymatic (e.g., IVT), solid-phase, liquid-phase, combined synthetic methods, small region synthesis, and ligation methods are utilized.

In some embodiments, the disclosure provides splice editor nucleic acids produced using IVT enzymatic synthesis methods. Methods of making polynucleotides by IVT are known in the art and are described in International Application PCT/US2013/30062.

In some embodiments, the disclosure provides splice editor nucleic acids chemically synthesized by any means described in the art. In some embodiments, the splice editor nucleic acids are produced by oligonucleotide synthesis. Oligonucleotide synthesis is the chemical synthesis of relatively short fragments or strands of single-stranded nucleic acids with a defined chemical structure (sequence). Methods of oligonucleotide synthesis are known in the art (see e.g., Reese (2005) Organic & Biomolecular Chemistry 3(21): 3851). While chemical synthetic procedures are continually expanding, purifications of such nucleic acids by procedures such as high performance liquid chromatography (HPLC, which avoids the use of gels such as PAGE) tends to become more challenging as polynucleotide lengths increase significantly beyond a hundred or so nucleotides. One approach used for generating nucleic acids of greater length is to produce two or more molecules that are ligated together.

Methods of Determining Splice Editor Nucleic Acid Tran Splicing Efficiency

In some embodiments, the disclosure provides methods to determine the efficiency of trans-splicing of a target RNA (e.g., pre-mRNA) using a splice editor nucleic acid molecule described herein.

In some embodiments, the method comprises use of a fluorescence-based splicing reporter assay. In some embodiments, the assay comprises contacting a reporter cell or population of cells with the splice editor nucleic acid molecule according to a method described herein (e.g., via transfection with a viral vector encoding the splice editor nucleic acid molecule), wherein the splice editor nucleic acid molecule comprises at least one exon encoding a reporter molecule, wherein a trans-splicing event is indicated by the presence of a fluorescent signal from the reporter molecule that is detected using a method known in the art. For example, in some embodiments, the reporter molecule is a fluorescent protein detected using fluorescence-activated cell sorting (FACS). For example, in some embodiments, the splice editor nucleic acid molecule comprises a nucleotide sequence encoding a first portion of a fluorescent protein and the target RNA comprises a nucleotide sequence encoding a second portion of a fluorescent protein, wherein the trans-splicing generates an RNA comprising a nucleotide sequence encoding the full-length fluorescent protein, and wherein the trans-splicing event is detected using a method of fluorescent measurement (e.g., FACS).

In some embodiments, the splice editor nucleic acid is introduced to a cell using a method described herein (e.g., via a viral or non-viral vector) for a duration, whereupon RNA from the cell is extracted and trans-splicing products are detected. For example, an mRNA spliced from a target RNA (e.g., a target pre-mRNA) is analyzed by a suitable method known in the art (e.g., end-point or quantitative RT-PCR or RNA sequencing). In some embodiments, a cell or population of cells is contacted with the splice editor nucleic acid molecule, wherein next-generating sequencing (NGS) techniques are used to determine the extent of trans-splicing. For example, in some embodiments, mRNA extracted from cells treated or contacted with a splice editor nucleic acid provided by the disclosure is enzymatically converted into cDNA, which is further by analyzed by NGS analysis to determine the extent of mRNA molecule comprising exonic sequence incorporated from the splice editor nucleic acid.

In some embodiments, trans-splicing is determined by protein sequence analysis of a polypeptide translated from an mRNA spliced from the pre-mRNA. In some embodiments, an RNA-guided molecule corrects a mutation by the incorporation of a corrected exon, wherein translation of the mRNA resulting from trans-splicing of the pre-mRNA and the splice editor nucleic acid generates a polypeptide comprising an amino acid sequence encoded by the corrected exon. The protein sequence analysis is performed using techniques including, but not limited to, Sanger sequencing, mass spectrometry, functional assays that measure an enzymatic activity of the polypeptide, or immunoblotting using an antibody reactive to the corrected amino acid sequence.

In some embodiments, trans-splicing is determined by measuring the activity of a protein translated from an mRNA spliced from the pre-mRNA. For example, in some embodiments, the protein is an enzyme and the method of measuring trans-splicing comprises measuring enzymatic activity using a functional ELISA.

In some embodiments, a method for measuring the efficiency of trans-splicing using a splice editor nucleic acid of the disclosure is described in U.S. application Ser. No. 16/994,230, incorporated herein by reference.

In some embodiments, a method for measuring the efficiency of trans-splicing using a splice editor nucleic acid of the disclosure is any one described in Chen, et al (2009) *Gene Ther* 16:211; Rindt, et al (2012) *Cell Mol Life Sci* 69:4191; Monjaret, et al (2014) *Mol Ther* 22:1176; Berger, et al (2015) *Mol Ther* 23:918.

In some embodiments, a method described herein is used to measure the efficiency of trans-splicing of a pre-mRNA using a splice editor nucleic acid molecule described herein.

In some embodiments, a splice editor nucleic acid molecule described herein comprising a nucleotide sequence comprising (i) at least one intronic sequence comprising one or more binding domains each having complementarity to a target sequence in the pre-mRNA and a ncRNA; (ii) one or more splice sites (e.g., a splice acceptor and/or splice donor); and (iii) at least one exonic sequence results in an efficiency of trans-splicing that is greater than the splice editor nucleic acid molecule without the ncRNA, as measured using a method described herein. In some embodiments, the splice editor nucleic acid molecule described herein results in an efficiency of trans-splicing that is increased by at least about 1.5-fold, about 2-fold, about 3-fold, about 4-fold, about 5-fold, about 10-fold, or about 20-fold compared to the efficiency of trans-splicing of a splice editor nucleic acid molecule without the ncRNA.

Exemplary Splice Editor Nucleic Acids

In some embodiments, the disclosure provides a nucleic acid of Subgroup I for targeting trans-splicing of a target RNA (e.g., pre-mRNA) in a cell, the nucleic acid comprising a nucleotide sequence comprising from 5' to 3': (a) at least one intronic sequence comprising (i) one or more binding domain sequences each with complementarity to a target sequence in the target RNA (e.g., pre-mRNA); (ii) a ncRNA sequence that forms a secondary structure and/or comprises a sequence motif to direct the one or more binding domain sequences to the target RNA (e.g., pre-mRNA); and (iii) one or more splicing signals; (b) a splice acceptor; and (c) at least one exonic sequence.

In some embodiments, the nucleic acid of Subgroup I comprises a nucleotide sequence comprising from 5' to 3': (a) at least one intronic sequence comprising (i) one or more binding domain sequences each with complementarity to a target sequence in the target RNA (e.g., pre-mRNA); (ii) a ncRNA sequence that forms a secondary structure and/or comprises a sequence motif to direct the one or more binding domain sequences to the target RNA (e.g., pre-mRNA); and (iii) one or more splicing signals, wherein the ncRNA is an snRNA; (b) a splice acceptor; and (c) at least one exonic sequence. In some embodiments, the snRNA is selected from a U1 snRNA, a U2 snRNA, a U4 snRNA, a U4atac snRNA, a U5 snRNA, a U6 snRNA, a U6atac snRNA, a U11 snRNA, a U12 snRNA, and a U7 snRNA.

In some embodiments, the nucleic acid of Subgroup I comprises a nucleotide sequence comprising from 5' to 3': (a) at least one intronic sequence comprising (i) one or more binding domain sequences each with complementarity to a target sequence in the target RNA (e.g., pre-mRNA); (ii) a ncRNA comprising a sequence motif to direct the one or more binding domain sequences to the target RNA (e.g., pre-mRNA), wherein the sequence motif selected from a Sm sequence motif and a Lsm sequence motif, and (iii) one or more splicing signals; (b) a splice acceptor; and (c) at least one exonic sequence.

In some embodiments, the nucleic acid of Subgroup I comprises a nucleotide sequence comprising from 5' to 3': (a) at least one intronic sequence comprising (i) one or more binding domain sequences each with complementarity to a target sequence in the target RNA (e.g., pre-mRNA); (ii) a ncRNA sequence that forms a secondary structure and comprises a sequence motif to direct the one or more binding domain sequences to the target RNA (e.g., pre-mRNA), wherein the sequence motif selected from a Sm sequence motif and a Lsm sequence motif, and (iii) one or more splicing signals; (b) a splice acceptor; and (c) at least one exonic sequence.

In some embodiments, the nucleic acid of Subgroup I comprises a nucleotide sequence comprising from 5' to 3': (a) at least one intronic sequence comprising (i) one or more binding domain sequences each with complementarity to a target sequence in the target RNA (e.g., pre-mRNA); (ii) a ncRNA sequence that forms a secondary structure and/or comprises a sequence motif that assembles to form an RNP that directs the binding domain to the target RNA (e.g., pre-mRNA); and (iii) one or more splicing signals; (b) a splice acceptor; and (c) at least one exonic sequence.

In some embodiments, the nucleic acid of Subgroup I comprises a nucleotide sequence comprising from 5' to 3': (a) at least one intronic sequence comprising (i) one or more binding domain sequences each with complementarity to a target sequence in the target RNA (e.g., pre-mRNA); (ii) a ncRNA sequence that forms a secondary structure and/or comprises a sequence motif that assembles to form an RNP that directs the one or more binding domains to the target RNA (e.g., pre-mRNA), wherein the ncRNA is an snRNA; and (iii) one or more splicing signals; (b) a splice acceptor; and (c) at least one exonic sequence. In some embodiments, the snRNA is selected from a U1 snRNA, a U2 snRNA, a U4 snRNA, a U4atac snRNA, a U5 snRNA, a U6 snRNA, a U6atac snRNA, a U11 snRNA, a U12 snRNA, and a U7 snRNA.

In some embodiments, the nucleic acid of Subgroup I comprises a nucleotide sequence comprising from 5' to 3': (a) at least one intronic sequence comprising (i) one or more binding domain sequences each with complementarity to a target sequence in the target RNA (e.g., pre-mRNA); (ii) a ncRNA sequence comprising a sequence motif that assembles to form an RNP that directs the binding domain to the target RNA (e.g., pre-mRNA), wherein the sequence motif selected from a Sm sequence motif and a Lsm sequence motif, and (iii) one or more splicing signals; (b) a splice acceptor; and (c) at least one exonic sequence.

In some embodiments, the nucleic acid of Subgroup I comprises a nucleotide sequence comprising from 5' to 3': (a) at least one intronic sequence comprising (i) one or more binding domain sequences each with complementarity to a target sequence in the target RNA (e.g., pre-mRNA); (ii) a ncRNA sequence that forms a secondary structure and comprises a sequence motif that assembles to form an RNP that directs the binding domain to the target RNA (e.g., pre-mRNA), wherein the sequence motif selected from a Sm sequence motif and a Lsm sequence motif; and (iii) one or more splicing signals; (b) a splice acceptor; and (c) at least one exonic sequence.

In some embodiments, the nucleic acid of Subgroup I comprises a nucleotide sequence comprising from 5' to 3': (a) at least one intronic sequence comprising (i) one or more binding domain sequences of about 4 to about 300 nucleotides each with complementarity to a target sequence in the target RNA (e.g., pre-mRNA); (ii) a ncRNA sequence of about 7 to about 300 nucleotides in length that forms a secondary structure and/or comprises a sequence motif to direct the one or more binding domain sequences to the target RNA (e.g., pre-mRNA); and (iii) one or more splicing signals; (b) a splice acceptor; and (c) at least one exonic sequence.

In some embodiments, the nucleic acid of Subgroup I comprises a nucleotide sequence comprising from 5' to 3': (a) at least one intronic sequence comprising (i) one or more binding domain sequences of about 4 to about 300 nucleotides each with complementarity to a target sequence in the target RNA (e.g., pre-mRNA); (ii) a ncRNA sequence of about 7 to about 300 nucleotides in length that forms a secondary structure and/or comprises a sequence motif to direct the one or more binding domain sequences to the target RNA (e.g., pre-mRNA), wherein the ncRNA is an snRNA; and (iii) one or more splicing signals; (b) a splice acceptor; and (c) at least one exonic sequence. In some embodiments, the snRNA is selected from a U1 snRNA, a U2 snRNA, a U4 snRNA, a U4atac snRNA, a U5 snRNA, a U6 snRNA, a U6atac snRNA, a U11 snRNA, a U12 snRNA, and a U7 snRNA.

In some embodiments, the nucleic acid of Subgroup I comprises a nucleotide sequence comprising from 5' to 3': (a) at least one intronic sequence comprising (i) one or more binding domain sequences of about 4 to about 300 nucleotides each with complementarity to a target sequence in the target RNA (e.g., pre-mRNA); (ii) a ncRNA sequence of about 7 to about 300 nucleotides in length comprising a sequence motif to direct the one or more binding domain sequences to the target RNA (e.g., pre-mRNA), wherein the sequence motif selected from a Sm sequence motif and a Lsm sequence motif, and (iii) one or more splicing signals; (b) a splice acceptor; and (c) at least one exonic sequence.

In some embodiments, the nucleic acid of Subgroup I comprises a nucleotide sequence comprising from 5' to 3': (a) at least one intronic sequence comprising (i) one or more binding domain sequences of about 4 to about 300 nucleotides each with complementarity to a target sequence in the target RNA (e.g., pre-mRNA); (ii) a ncRNA sequence of about 7 to about 300 nucleotides in length that forms a secondary structure and comprises a sequence motif to direct the one or more binding domain sequences to the target RNA (e.g., pre-mRNA), wherein the sequence motif selected from a Sm sequence motif and a Lsm sequence motif, and (iii) one or more splicing signals; (b) a splice acceptor; and (c) at least one exonic sequence.

In some embodiments, the nucleic acid of Subgroup I comprises a nucleotide sequence comprising from 5' to 3': (a) at least one intronic sequence comprising (i) one or more binding domain sequences of about 4 to about 300 nucleotides each with complementarity to a target sequence in the target RNA (e.g., pre-mRNA); (ii) a ncRNA sequence of about 7 to about 300 nucleotides in length which forms a secondary structure and/or comprises a sequence motif that assembles to form an RNP that directs the binding domain to the target RNA (e.g., pre-mRNA); and (iii) one or more splicing signals; (b) a splice acceptor; and (c) at least one exonic sequence.

In some embodiments, the nucleic acid of Subgroup I comprises a nucleotide sequence comprising from 5' to 3': (a) at least one intronic sequence comprising (i) one or more binding domain sequences of about 4 to about 300 nucleotides each with complementarity to a target sequence in the target RNA (e.g., pre-mRNA); (ii) a ncRNA sequence of about 7 to about 300 nucleotides in length which forms a secondary structure and/or comprises a sequence motif that assembles to form an RNP that directs the binding domain to the target RNA (e.g., pre-mRNA), wherein the ncRNA is an snRNA; and (iii) one or more splicing signals; (b) a splice acceptor; and (c) at least one exonic sequence. In some embodiments, the snRNA is selected from a U1 snRNA, a U2 snRNA, a U4 snRNA, a U4atac snRNA, a U5 snRNA, a U6 snRNA, a U6atac snRNA, a U11 snRNA, a U12 snRNA, and a U7 snRNA.

In some embodiments, the nucleic acid of Subgroup I comprises a nucleotide sequence comprising from 5' to 3': (a) at least one intronic sequence comprising (i) one or more binding domain sequences of about 4 to about 300 nucleotides each with complementarity to a target sequence in the target RNA (e.g., pre-mRNA); (ii) a ncRNA sequence of about 7 to about 300 nucleotides in comprising a sequence motif that assembles to form an RNP that directs the binding domain to the target RNA (e.g., pre-mRNA), wherein the sequence motif selected from a Sm sequence motif and a Lsm sequence motif, and (iii) one or more splicing signals; (b) a splice acceptor; and (c) at least one exonic sequence.

In some embodiments, the nucleic acid of Subgroup I comprises a nucleotide sequence comprising from 5' to 3': (a) at least one intronic sequence comprising (i) one or more binding domain sequences of about 4 to about 300 nucleotides each with complementarity to a target sequence in the target RNA (e.g., pre-mRNA); (ii) a ncRNA sequence of about 7 to about 300 nucleotides in length which forms a secondary structure and comprises a sequence motif that assembles to form an RNP that directs the binding domain to the target RNA (e.g., pre-mRNA), wherein the sequence motif selected from a Sm sequence motif and a Lsm sequence motif, and (iii) one or more splicing signals; (b) a splice acceptor; and (c) at least one exonic sequence.

In some embodiments, the nucleic acid of Subgroup I comprises one binding domain. In some embodiments, the nucleic acid of Subgroup I comprises two binding domains. In some embodiments, the nucleic acid of Subgroup I comprises three binding domains. In some embodiments, the nucleic acid of Subgroup I comprises four binding domains. In some embodiments, the nucleic acid of Subgroup I comprises five binding domains.

In some embodiments, the target RNA is a pre-mRNA. In some embodiments, the pre-mRNA comprises from 5' to 3': a 5' exon, a splice donor, an intron, a splice acceptor, and a 3' exon, wherein the 3' exon comprises a mutation. In some embodiments, each of the one or more binding domains of the nucleic acid of Subgroup I is complementary to a target sequence in the target RNA (e.g., pre-mRNA), wherein the target sequence is positioned in the 5' exon in the pre-mRNA. In some embodiments, the target sequence is proximal to the splice donor of the pre-mRNA. In some embodiments, the target sequence is within the intron of the pre-mRNA. In some embodiments, the target sequence is proximal to the splice acceptor of the pre-mRNA. In some embodiments, the target sequence is positioned in the 3' exon of the pre-mRNA. In some embodiments, trans-splicing occurs between the splice donor of the pre-mRNA and the splice acceptor of the nucleic acid of Subgroup I. In some embodiments, the trans-splicing results in ligation of the 3'end of the 5' exon of the pre-mRNA and the 5'end of the at least one exonic sequence of the nucleic acid of Subgroup I.

In some embodiments, the one or more splicing signals of the nucleic acid of Subgroup I comprises a branch point. In some embodiments, the one or more splicing signals of the nucleic acid of Subgroup I comprises a polypyrimidine tract. In some embodiments, the one or more splicing signals of the nucleic acid of Subgroup I comprises a branch point and polypyrimidine tract. In some embodiments, the one or more splicing signals further comprises a ISE. In some embodiments, the one or more splicing signals further comprises a ISS.

In some embodiments, the at least one exonic sequence of the nucleic acid of Subgroup I comprises an ESE. In some embodiments, the at least one exonic sequence of the nucleic acid of Subgroup I comprises an ESS.

In some embodiments, the disclosure provides a nucleic acid for targeting trans-splicing of a target RNA (e.g., pre-mRNA) in a cell, the nucleic acid comprising a nucleotide sequence comprising from 5' to 3': (a) at least one exonic sequence; (b) a splice donor; (c) at least one intronic sequence comprising (i) a ncRNA sequence, and (ii) one or more binding domain sequences each with complementarity to a target sequence in the target RNA (e.g., pre-mRNA), wherein the ncRNA forms a secondary structure and/or comprises a sequence motif to direct the one or more binding domain to the target RNA.

In some embodiments, the disclosure provides a nucleic acid of Subgroup II for targeting trans-splicing of a target RNA (e.g., pre-mRNA) in a cell, the nucleic acid comprising a nucleotide sequence comprising from 5' to 3': (a) at least one exonic sequence; (b) a splice donor; (c) at least one intronic sequence comprising (i) a ncRNA sequence, and (ii) one or more binding domain sequences each with complementarity to a target sequence in the target RNA (e.g., pre-mRNA), wherein the ncRNA forms a secondary structure and/or comprises a sequence motif to direct the one or more binding domain to the target RNA, and wherein the ncRNA is an snRNA. In some embodiments, the snRNA is selected from a U1 snRNA, a U2 snRNA, a U4 snRNA, a U4atac snRNA, a U5 snRNA, a U6 snRNA, a U6atac snRNA, a U11 snRNA, a U12 snRNA, and a U7 snRNA.

In some embodiments, the nucleic acid of Subgroup II comprises a nucleotide sequence comprising from 5' to 3': (a) at least one exonic sequence; (b) a splice donor; (c) at least one intronic sequence comprising (i) a ncRNA sequence, and (ii) one or more binding domain sequences each with complementarity to a target sequence in the target RNA (e.g., pre-mRNA), wherein the ncRNA sequence comprises a sequence motif to direct the one or more binding domain to the target RNA, and wherein the sequence motif selected from a Sm sequence motif and a Lsm sequence motif.

In some embodiments, the nucleic acid of Subgroup II comprises a nucleotide sequence comprising from 5' to 3': (a) at least one exonic sequence; (b) a splice donor; (c) at least one intronic sequence comprising (i) a ncRNA sequence, and (ii) one or more binding domain sequences each with complementarity to a target sequence in the target RNA (e.g., pre-mRNA), wherein the ncRNA sequence forms a secondary structure and comprises a sequence motif to direct the one or more binding domain to the target RNA, and wherein the sequence motif selected from a Sm sequence motif and a Lsm sequence motif.

In some embodiments, the nucleic acid of Subgroup II comprises a nucleotide sequence comprising from 5' to 3': (a) at least one exonic sequence; (b) a splice donor; (c) at least one intronic sequence comprising (i) a ncRNA sequence, and (ii) one or more binding domain sequences each with complementarity to a target sequence in the target RNA (e.g., pre-mRNA), wherein the ncRNA forms a secondary structure and/or comprises a sequence motif that assembles to form an RNP to direct the one or more binding domain to the target RNA.

In some embodiments, the nucleic acid of Subgroup II comprises a nucleotide sequence comprising from 5' to 3': (a) at least one exonic sequence; (b) a splice donor; (c) at least one intronic sequence comprising (i) a ncRNA sequence, and (ii) one or more binding domain sequences each with complementarity to a target sequence in the target RNA (e.g., pre-mRNA), wherein the ncRNA forms a secondary structure and/or comprises a sequence motif that assembles to form an RNP to direct the one or more binding domain to the target RNA, and wherein the ncRNA is an snRNA. In some embodiments, the snRNA is selected from a U1 snRNA, a U2 snRNA, a U4 snRNA, a U4atac snRNA, a U5 snRNA, a U6 snRNA, a U6atac snRNA, a U11 snRNA, a U12 snRNA, and a U7 snRNA.

In some embodiments, the nucleic acid of Subgroup II comprises a nucleotide sequence comprising from 5' to 3': (a) at least one exonic sequence; (b) a splice donor; (c) at least one intronic sequence comprising (i) a ncRNA sequence, and (ii) one or more binding domain sequences each with complementarity to a target sequence in the target RNA (e.g., pre-mRNA), wherein the ncRNA sequence comprises a sequence motif that assembles to form an RNP to direct the one or more binding domain to the target RNA, and wherein the sequence motif selected from a Sm sequence motif and a Lsm sequence motif.

In some embodiments, the nucleic acid of Subgroup II comprises a nucleotide sequence comprising from 5' to 3': (a) at least one exonic sequence; (b) a splice donor; (c) at least one intronic sequence comprising (i) a ncRNA sequence, and (ii) one or more binding domain sequences each with complementarity to a target sequence in the target RNA (e.g., pre-mRNA), wherein the ncRNA sequence forms a secondary structure and comprises a sequence motif that assembles to form an RNP to direct the one or more binding domain to the target RNA, and wherein the sequence motif selected from a Sm sequence motif and a Lsm sequence motif.

In some embodiments, the nucleic acid of Subgroup II comprises a nucleotide sequence comprising from 5' to 3': (a) at least one exonic sequence; (b) a splice donor; (c) at least one intronic sequence comprising (i) a ncRNA sequence of about 7 to about 300 nucleotides in length, and (ii) one or more binding domain sequences of about 4 to about 300 nucleotides each with complementarity to a target sequence in the target RNA (e.g., pre-mRNA), wherein the ncRNA forms a secondary structure and/or comprises a sequence motif to direct the one or more binding domain to the target RNA.

In some embodiments, the nucleic acid of Subgroup II comprises a nucleotide sequence comprising from 5' to 3': (a) at least one exonic sequence; (b) a splice donor; (c) at least one intronic sequence comprising (i) a ncRNA sequence of about 7 to about 300 nucleotides in length, and (ii) one or more binding domain sequences of about 4 to about 300 nucleotides each with complementarity to a target sequence in the target RNA (e.g., pre-mRNA), wherein the ncRNA forms a secondary structure and/or comprises a sequence motif to direct the one or more binding domain to the target RNA, and wherein the ncRNA is an snRNA. In some embodiments, the snRNA is selected from a U1 snRNA, a U2 snRNA, a U4 snRNA, a U4atac snRNA, a U5 snRNA, a U6 snRNA, a U6atac snRNA, a U11 snRNA, a U12 snRNA, and a U7 snRNA.

In some embodiments, the nucleic acid of Subgroup II comprises a nucleotide sequence comprising from 5' to 3': (a) at least one exonic sequence; (b) a splice donor; (c) at least one intronic sequence comprising (i) a ncRNA sequence of about 7 to about 300 nucleotides in length, and (ii) one or more binding domain sequences of about 4 to about 300 nucleotides each with complementarity to a target sequence in the target RNA (e.g., pre-mRNA), wherein the ncRNA sequence comprises a sequence motif to direct the one or more binding domain to the target RNA, and wherein the sequence motif selected from a Sm sequence motif and a Lsm sequence motif.

In some embodiments, the nucleic acid of Subgroup II comprises a nucleotide sequence comprising from 5' to 3': (a) at least one exonic sequence; (b) a splice donor; (c) at least one intronic sequence comprising (i) a ncRNA sequence of about 7 to about 300 nucleotides in length, and (ii) one or more binding domain sequences of about 4 to about 300 nucleotides each with complementarity to a target sequence in the target RNA (e.g., pre-mRNA), wherein the ncRNA sequence forms a secondary structure and comprises a sequence motif to direct the one or more binding domain to the target RNA, and wherein the sequence motif selected from a Sm sequence motif and a Lsm sequence motif.

In some embodiments, the nucleic acid of Subgroup II comprises a nucleotide sequence comprising from 5' to 3': (a) at least one exonic sequence; (b) a splice donor; (c) at least one intronic sequence comprising (i) a ncRNA sequence of about 7 to about 300 nucleotides in length, and (ii) one or more binding domain sequences of about 4 to about 300 nucleotides each with complementarity to a target sequence in the target RNA (e.g., pre-mRNA), wherein the ncRNA forms a secondary structure and/or comprises a sequence motif that assembles to form an RNP to direct the one or more binding domain to the target RNA.

In some embodiments, the nucleic acid of Subgroup II comprises a nucleotide sequence comprising from 5' to 3': (a) at least one exonic sequence; (b) a splice donor; (c) at least one intronic sequence comprising (i) a ncRNA sequence of about 7 to about 300 nucleotides in length, and (ii) one or more binding domain sequences of about 4 to about 300 nucleotides each with complementarity to a target sequence in the target RNA (e.g., pre-mRNA), wherein the ncRNA forms a secondary structure and/or comprises a sequence motif that assembles to form an RNP to direct the one or more binding domain to the target RNA, and wherein the ncRNA is an snRNA. In some embodiments, the snRNA is selected from a U1 snRNA, a U2 snRNA, a U4 snRNA, a U4atac snRNA, a U5 snRNA, a U6 snRNA, a U6atac snRNA, a U11 snRNA, a U12 snRNA, and a U7 snRNA.

In some embodiments, the nucleic acid of Subgroup II comprises a nucleotide sequence comprising from 5' to 3': (a) at least one exonic sequence; (b) a splice donor; (c) at least one intronic sequence comprising (i) a ncRNA sequence of about 7 to about 300 nucleotides in length, and (ii) one or more binding domain sequences of about 4 to about 300 nucleotides each with complementarity to a target sequence in the target RNA (e.g., pre-mRNA), wherein the ncRNA sequence comprises a sequence motif that assembles to form an RNP to direct the one or more binding domain to the target RNA, and wherein the sequence motif selected from a Sm sequence motif and a Lsm sequence motif.

In some embodiments, the nucleic acid of Subgroup II comprises a nucleotide sequence comprising from 5' to 3': (a) at least one exonic sequence; (b) a splice donor; (c) at least one intronic sequence comprising (i) a ncRNA sequence of about 7 to about 300 nucleotides in length, and (ii) one or more binding domain sequences of about 4 to about 300 nucleotides each with complementarity to a target sequence in the target RNA (e.g., pre-mRNA), wherein the ncRNA sequence forms a secondary structure and comprises a sequence motif that assembles to form an RNP to direct the one or more binding domain to the target RNA, and wherein the sequence motif selected from a Sm sequence motif and a Lsm sequence motif.

In some embodiments, the nucleic acid of Subgroup II comprises one binding domain. In some embodiments, the nucleic acid of Subgroup II comprises two binding domains. In some embodiments, the nucleic acid of Subgroup II comprises three binding domains. In some embodiments, the nucleic acid of Subgroup II comprises four binding domains. In some embodiments, the nucleic acid of Subgroup II comprises five binding domains.

In some embodiments, the target RNA is a pre-mRNA. In some embodiments, the pre-mRNA comprises from 5' to 3': a 5' exon, a splice donor, an intron, a splice acceptor, and a 3' exon, wherein the 5' exon comprises a mutation. In some embodiments, each of the one or more binding domains of the nucleic acid of Subgroup II is complementary to a target sequence in the target RNA (e.g., pre-mRNA), wherein the target sequence is positioned in the 5' exon in the pre-mRNA. In some embodiments, the target sequence is proximal to the splice donor of the pre-mRNA. In some embodiments, the target sequence is within the intron of the pre-mRNA. In some embodiments, the target sequence is proximal to the splice acceptor of the pre-mRNA. In some embodiments, the target sequence is positioned in the 3' exon of the pre-mRNA. In some embodiments, trans-splicing occurs between the splice donor of the nucleic acid of Subgroup II and the splice acceptor of the pre-mRNA. In some embodiments, the trans-splicing results in ligation of the 3'end of the 5' exon of the at least one exonic sequence of the nucleic acid of Subgroup II and the 5'end of the 3'exon of the pre-mRNA.

In some embodiments, the at least one exonic sequence of the nucleic acid of Subgroup II comprises an ESE. In some embodiments, the at least one exonic sequence of the nucleic acid of Subgroup II comprises an ESS.

In some embodiments, the disclosure provides a nucleic acid of Subgroup III for targeting trans-splicing of a target RNA (e.g., pre-mRNA) in a cell, the nucleic acid comprising a nucleotide sequence comprising from 5' to 3' (a) at least one intronic sequence comprising (i) a snoRNA sequence comprising an H/ACA box or a C/D box and one or more binding domain sequences each with complementarity to a pre-mRNA target sequence; and (ii) one or more splicing signals; (b) a splice acceptor; and (c) at least one exonic sequence.

In some embodiments, the disclosure provides a nucleic acid of Subgroup III for targeting trans-splicing of a target RNA (e.g., pre-mRNA) in a cell, the nucleic acid comprising a nucleotide sequence comprising from 5' to 3' (a) at least one intronic sequence comprising (i) a snoRNA sequence comprising an H/ACA box or a C/D box to direct the one or more binding domain sequences to the target RNA (e.g., pre-mRNA) and one or more binding domain sequences each with complementarity to a pre-mRNA target sequence; and (ii) one or more splicing signals; (b) a splice acceptor; and (c) at least one exonic sequence.

In some embodiments, the nucleic acid of Subgroup III comprises a nucleotide sequence comprising from 5' to 3' (a) at least one intronic sequence comprising (i) a snoRNA sequence comprising an H/ACA box or a C/D box that assembles to form an RNP to direct the one or more binding domain sequences to the target RNA (e.g., pre-mRNA) and one or more binding domain sequences each with complementarity to a pre-mRNA target sequence; and (ii) one or more splicing signals; (b) a splice acceptor; and (c) at least one exonic sequence.

In some embodiments, the nucleic acid of Subgroup III comprises a nucleotide sequence comprising from 5' to 3' (a) at least one intronic sequence comprising (i) a snoRNA sequence comprising an H/ACA box or a C/D box that directs the one or more binding domain sequences to the target RNA (e.g., pre-mRNA) and one or more binding domain sequences of about 4 to about 30 nucleotides in length, each with complementarity to a pre-mRNA target sequence; and (ii) one or more splicing signals; (b) a splice acceptor; and (c) at least one exonic sequence.

In some embodiments, the nucleic acid of Subgroup III comprises a nucleotide sequence comprising from 5' to 3' (a) at least one intronic sequence comprising (i) a snoRNA sequence comprising an H/ACA box or a C/D box that assembles to form an RNP to direct the one or more binding domain sequences to the target RNA (e.g., pre-mRNA) and one or more binding domain sequences of about 4 to about 30 nucleotides in length, each with complementarity to a pre-mRNA target sequence; and (ii) one or more splicing signals; (b) a splice acceptor; and (c) at least one exonic sequence.

In some embodiments, the target RNA is a pre-mRNA. In some embodiments, the pre-mRNA comprises from 5' to 3': a 5' exon, a splice donor, an intron, a splice acceptor, and a 3' exon, wherein the 3' exon comprises a mutation. In some embodiments, each of the one or more binding domains of the nucleic acid of Subgroup III is complementary to a target sequence in the target RNA (e.g., pre-mRNA), wherein the target sequence is positioned in the 5' exon in the pre-mRNA. In some embodiments, the target sequence is proximal to the splice donor of the pre-mRNA. In some embodiments, the target sequence is within the intron of the pre-mRNA. In some embodiments, the target sequence is proximal to the splice acceptor of the pre-mRNA. In some embodiments, the target sequence is positioned in the 3' exon of the pre-mRNA. In some embodiments, trans-splicing occurs between the splice donor of the pre-mRNA and the splice acceptor of the nucleic acid of Subgroup III. In some embodiments, the trans-splicing results in ligation of the 3'end of the 5' exon of the pre-mRNA and the 5'end of the at least one exonic sequence of the nucleic acid of Subgroup III.

In some embodiments, the one or more splicing signals of the nucleic acid of Subgroup III comprises a branch point. In some embodiments, the one or more splicing signals of the nucleic acid of Subgroup III comprises a polypyrimidine tract. In some embodiments, the one or more splicing signals of the nucleic acid of Subgroup III comprises a branch point and polypyrimidine tract. In some embodiments, the one or more splicing signals further comprises a ISE. In some embodiments, the one or more splicing signals further comprises a ISS.

In some embodiments, the at least one exonic sequence of the nucleic acid of Subgroup III comprises an ESE. In some embodiments, the at least one exonic sequence of the nucleic acid of Subgroup III comprises an ESS.

In some embodiments, the disclosure provides a nucleic acid of Subgroup IV for targeting trans-splicing of a target RNA (e.g., pre-mRNA) in a cell, the nucleic acid comprising a nucleotide sequence comprising from 5' to 3' (a) at least one exonic sequence; (b) a splice donor; and (c) at least one intronic sequence comprising a snoRNA sequence comprising an H/ACA box or a C/D box and one or more binding domain sequences each with complementarity to a pre-mRNA target sequence.

In some embodiments, the nucleic acid of Subgroup IV comprises a nucleotide sequence comprising from 5' to 3' (a) at least one exonic sequence; (b) a splice donor; and (c) at least one intronic sequence comprising a snoRNA sequence comprising an H/ACA box or a C/D box to direct the one or more binding domain sequences to the target RNA (e.g., pre-mRNA) and one or more binding domain sequences each with complementarity to a pre-mRNA target sequence.

In some embodiments, the nucleic acid of Subgroup IV comprises a nucleotide sequence comprising from 5' to 3' (a) at least one exonic sequence; (b) a splice donor; and (c) at least one intronic sequence comprising a snoRNA sequence comprising an H/ACA box or a C/D box that assembles to form an RNP to direct the one or more binding domain sequences to the target RNA (e.g., pre-mRNA) and one or more binding domain sequences, each with complementarity to a pre-mRNA target sequence.

In some embodiments, the nucleic acid of Subgroup IV comprises a nucleotide sequence comprising from 5' to 3' (a) at least one exonic sequence; (b) a splice donor; and (c) at least one intronic sequence comprising a snoRNA sequence comprising an H/ACA box or a C/D box to direct the one or more binding domain sequences to the target RNA (e.g., pre-mRNA) and one or more binding domain sequences of about 4 to about 30 nucleotides in length, each with complementarity to a pre-mRNA target sequence.

In some embodiments, the nucleic acid of Subgroup IV comprises a nucleotide sequence comprising from 5' to 3' (a) at least one exonic sequence; (b) a splice donor; and (c) at least one intronic sequence comprising a snoRNA sequence comprising an H/ACA box or a C/D box that assembles to form an RNP to direct the one or more binding domain sequences to the target RNA (e.g., pre-mRNA) and one or more binding domain sequences of about 4 to about 30 nucleotides in length, each with complementarity to a pre-mRNA target sequence.

In some embodiments, the target RNA is a pre-mRNA. In some embodiments, the pre-mRNA comprises from 5' to 3': a 5' exon, a splice donor, an intron, a splice acceptor, and a 3' exon, wherein the 5' exon comprises a mutation. In some embodiments, each of the one or more binding domains of the nucleic acid of Subgroup IV is complementary to a target sequence in the target RNA (e.g., pre-mRNA), wherein the target sequence is positioned in the 5' exon in the pre-mRNA. In some embodiments, the target sequence is proximal to the splice donor of the pre-mRNA. In some embodiments, the target sequence is within the intron of the pre-mRNA. In some embodiments, the target sequence is proximal to the splice acceptor of the pre-mRNA. In some embodiments, the target sequence is positioned in the 3' exon of the pre-mRNA. In some embodiments, trans-splicing occurs between the splice donor of the nucleic acid of Subgroup IV and the splice acceptor of the pre-mRNA. In some embodiments, the trans-splicing results in ligation of the 3'end of the 5' exon of the at least one exonic sequence of the nucleic acid of Subgroup IV and the 5'end of the 3'exon of the pre-mRNA.

In some embodiments, the at least one exonic sequence of the nucleic acid of Subgroup IV comprises an ESE. In some embodiments, the at least one exonic sequence of the nucleic acid of Subgroup IV comprises an ESS.

In some embodiments, the nucleic acid of Subgroup III or Subgroup IV comprises an H/ACA box, wherein the H/ACA box comprises a nucleotide sequence having from 5' to 3' an H consensus sequence and an ACA consensus sequence. In some embodiments, the one or more binding domain sequences of the nucleic acid of Subgroup III or Subgroup IV is positioned upstream the H consensus sequence. In some embodiments, the one or more binding domain sequences of the nucleic acid of Subgroup III or Subgroup IV is positioned downstream the ACA consensus sequence. In some embodiments, the one or more binding domain sequences of the nucleic acid of Subgroup III or Subgroup IV is positioned between the H consensus sequence and the ACA consensus sequence.

In some embodiments, the nucleic acid of Subgroup III or Subgroup IV comprises an H/ACA box comprising a nucleotide sequence having from 5' to 3' an H consensus sequence and an ACA consensus sequence; and one binding domain. In some embodiments, the one binding domain sequence is positioned upstream the H consensus sequence. In some embodiments, the one binding domain is positioned downstream the ACA consensus sequence. In some embodiments, the one binding domain sequence is positioned between the H consensus sequence and the ACA consensus sequence.

In some embodiments, the nucleic acid of Subgroup III or Subgroup IV comprises an H/ACA box comprising a nucleotide sequence having from 5' to 3' an H consensus sequence and an ACA consensus sequence, a first binding domain, and second binding domain. In some embodiments, the first binding domain sequence and the second binding domain sequence are each positioned upstream the H consensus sequence. In some embodiments, the first binding domain sequence and the second binding domain sequence are each positioned downstream the ACA consensus sequence. In some embodiments, the first binding domain sequence and the second binding domain sequence are each positioned between the H consensus sequence and the ACA consensus sequence. In some embodiments, the first binding domain sequence is positioned upstream the H consensus sequence and the second binding domain sequence is positioned between the H consensus sequence and the ACA consensus sequence or downstream the ACA consensus sequence. In some embodiments, the first binding domain sequence is positioned upstream the H consensus sequence or between the H consensus sequence and the ACA consensus sequence and the second binding domain sequence is positioned between the H consensus sequence and the ACA consensus sequence or downstream the ACA consensus sequence.

In some embodiments, the nucleic acid of Subgroup III or Subgroup IV comprises an H/ACA box and one binding domain, wherein the H/ACA box comprises a nucleotide sequence having from 5' to 3' an H consensus sequence and an ACA consensus sequence, and wherein the one binding domain is positioned upstream the H consensus sequence; downstream the ACA consensus sequence; or between the H consensus sequence and the ACA consensus sequence.

In some embodiments, the nucleic acid of Subgroup III or Subgroup IV comprises an H/ACA box and two binding domains, wherein the H/ACA box comprises a nucleotide sequence having from 5' to 3' an H consensus sequence and an ACA consensus sequence, and wherein the two binding domains are each independently positioned upstream the H consensus sequence; downstream the ACA consensus sequence; and/or between the H consensus sequence and the ACA consensus sequence.

In some embodiments, the nucleic acid of Subgroup III or Subgroup IV comprises an H/ACA box and three binding domains, wherein the H/ACA box comprises a nucleotide sequence having from 5' to 3' an H consensus sequence and an ACA consensus sequence, and wherein the three binding domains are each independently positioned upstream the H consensus sequence; downstream the ACA consensus sequence; and/or between the H consensus sequence and the ACA consensus sequence.

In some embodiments, the nucleic acid of Subgroup III or Subgroup IV comprises an H/ACA box and four binding domains, wherein the H/ACA box comprises a nucleotide sequence having from 5' to 3' an H consensus sequence and an ACA consensus sequence, and wherein the four binding domains are each independently positioned upstream the H consensus sequence; downstream the ACA consensus sequence; and/or between the H consensus sequence and the ACA consensus sequence.

In some embodiments, the nucleic acid of Subgroup III or Subgroup IV comprises an H/ACA box and five binding domains, wherein the H/ACA box comprises a nucleotide sequence having from 5' to 3' an H consensus sequence and an ACA consensus sequence, and wherein the five binding domains are each independently positioned upstream the H consensus sequence; downstream the ACA consensus sequence; and/or between the H consensus sequence and the ACA consensus sequence.

In some embodiments, the nucleic acid of Subgroup III or Subgroup IV comprises a C/D box, wherein the C/D box comprises a nucleotide sequence having from 5' to 3' a C consensus sequence, a D' consensus sequence, a C' consensus sequence, and a D consensus sequence. In some embodiments, the one or more binding domain sequences of the nucleic acid of Subgroup III or Subgroup IV is positioned upstream the C consensus sequence. In some embodiments, the one or more binding domain sequences of the nucleic acid of Subgroup III or Subgroup IV is positioned between the C consensus sequence and the D' consensus sequence. In some embodiments, the one or more binding domain sequences of the nucleic acid of Subgroup III or Subgroup IV is positioned between the C' consensus sequence and the D consensus sequence. In some embodiments, the one or more binding domain sequences of the nucleic acid of Subgroup III or Subgroup IV is positioned downstream the D consensus sequence.

In some embodiments, the nucleic acid of Subgroup III or Subgroup IV comprises a C/D box and one binding domain, wherein the C/D box comprises a nucleotide sequence having from 5' to 3' a C consensus sequence, a D' consensus sequence, a C' consensus sequence, and a D consensus sequence; and wherein the one binding domain is positioned upstream the C consensus sequence; between the C consensus sequence and the D' consensus sequence; between the C' consensus sequence and the D consensus sequence; or downstream the D consensus sequence.

In some embodiments, the nucleic acid of Subgroup III or Subgroup IV comprises a C/D box and two binding domains, wherein the C/D box comprises a nucleotide sequence having from 5' to 3' a C consensus sequence, a D' consensus sequence, a C' consensus sequence, and a D consensus sequence; and wherein the two binding domains are each independently positioned upstream the C consensus sequence; between the C consensus sequence and the D' consensus sequence; between the C' consensus sequence and the D consensus sequence; and/or downstream the D consensus sequence.

In some embodiments, the nucleic acid of Subgroup III or Subgroup IV comprises a C/D box and three binding domains, wherein the C/D box comprises a nucleotide sequence having from 5' to 3' a C consensus sequence, a D' consensus sequence, a C' consensus sequence, and a D consensus sequence; and wherein the three binding domains are each independently positioned upstream the C consensus sequence; between the C consensus sequence and the D' consensus sequence; between the C' consensus sequence and the D consensus sequence; and/or downstream the D consensus sequence.

In some embodiments, the nucleic acid of Subgroup III or Subgroup IV comprises a C/D box and four binding domains, wherein the C/D box comprises a nucleotide sequence having from 5' to 3' a C consensus sequence, a D' consensus sequence, a C' consensus sequence, and a D consensus sequence; and wherein the four binding domains are each independently positioned upstream the C consensus sequence; between the C consensus sequence and the D' consensus sequence; between the C' consensus sequence and the D consensus sequence; and/or downstream the D consensus sequence.

In some embodiments, the nucleic acid of Subgroup III or Subgroup IV comprises a C/D box and five binding domains, wherein the C/D box comprises a nucleotide sequence having from 5' to 3' a C consensus sequence, a D' consensus sequence, a C' consensus sequence, and a D consensus sequence; and wherein the five binding domains are each independently positioned upstream the C consensus sequence; between the C consensus sequence and the D' consensus sequence; between the C' consensus sequence and the D consensus sequence; and/or downstream the D consensus sequence.

In some embodiments, a nucleic acid of the disclosure (e.g., a nucleic acid of any one of Subgroups I-IV) comprises at least one binding domain sequence with full complementarity to the target sequence. In some embodiments, the nucleic acid comprises at least one binding domain sequence with partial complementarity to the target sequence (e.g., comprising at least 95% complementarity to the target sequence). In some embodiments, the nucleic acid comprises at least one binding domain sequence with full complementarity to the target sequence and at least one binding domain sequence with partial complementarity to the target sequence (e.g., comprising at least 95% complementarity to the target sequence).

In some embodiments, the nucleic acid of the disclosure (e.g., a nucleic acid of any one of Subgroups I-IV) has a sequence of up to about 20,000 nucleotides in length. In some embodiments, the sequence is up to about 10,000 nucleotides in length. In some embodiments, the sequence is up to about 9,000 nucleotides in length. In some embodiments, the sequence is up to about 8,000 nucleotides in length. In some embodiments, the sequence is up to about 7,000 nucleotides in length. In some embodiments, the sequence is up to about 6,000 nucleotides in length. In some embodiments, the sequence is up to about 5,000 nucleotides in length. In some embodiments, the sequence is about 50 to about 500 nucleotides in length. In some embodiments, the sequence about 50 to about 1000 nucleotides in length. In some embodiments, the sequence about 100 to about 500 nucleotides in length. In some embodiments, the sequence about 100 to about 1000 nucleotides in length. In some embodiments, the sequence about 500 to about 1000 nucleotides in length. In some embodiments, the sequence about 500 to about 2000 nucleotides in length. In some embodiments, the sequence about 500 to about 3,000 nucleotides in length. In some embodiments, the sequence about 500 to about 4,000 nucleotides in length. In some embodiments, the sequence about 500 to about 5,000 nucleotides in length. In some embodiments, the sequence about 1,000 to about 5,000 nucleotides in length. In some embodiments, the sequence about 1,000 to about 10,000 nucleotides in length. In some embodiments, the sequence about 5,000 to about 15,000 nucleotides in length. In some embodiments, the sequence about 5,000 to about 20,000 nucleotides in length.

In some embodiments, a splice editor nucleic acid molecule of the disclosure comprises a sequence selected from Table 3 or a portion thereof. Table 3 provides exemplary nucleotide sequences of splice editor nucleic acids of the disclosure. As presented in the table, the regions of the sequence are demarcated by hyphens (-) and identification of the regions from 5' to 3' are provided as Region 1, Region 2, Region 3, and optionally Region 4. In some embodiments, a splice editor nucleic acid molecule of the disclosure comprises a sequence having the formula 5'-[A]-[B]-3', wherein [A] is a nucleotide sequence selected from Table 3 and [B] is a sequence comprising from 5' to 3' a splice acceptor and one or more exonic sequences. In some embodiments, [A] comprises a nucleotide sequence selected from Table 3, wherein the RNA-binding domain is exchanged with an RNA-binding domain described herein.

In some embodiments, a splice editor nucleic acid molecule of the disclosure comprises from 5' to 3' one or more RNA binding domains described herein, a ncRNA sequence, an intronic sequence, a splice acceptor, and one or more exonic sequences, wherein the ncRNA sequence has about 90%, 95%, 98%, 99%, or 100% to a ncRNA sequence identified in Table 3. In some embodiments, a splice editor nucleic acid molecule of the disclosure comprises from 5' to 3' one or more exonic sequences, a splice donor, an intronic sequence, a ncRNA sequence, and one or more RNA binding domains described herein, wherein the ncRNA sequence has about 90%, 95%, 98%, 99%, or 100% to a ncRNA sequence identified in Table 3. In some embodiments, the intronic sequence has about 90%, 95%, 98%, 99%, or 100% to an intronic sequence identified in Table 3.

Vectors

In some embodiments, the disclosure provides a vector comprising one or more splice editor nucleic acid described herein. As used herein, the term "vector" refers to a nucleic acid molecule capable of transporting another nucleic acid to which it has been linked. In some embodiments, the vector is a DNA vector. In some embodiments, the vector is circular. In some embodiments, the vector is linear. Non-limiting exemplary vectors include plasmids, phagemids, cosmids, artificial chromosomes, minichromosomes, transposons, viral vectors, and expression vectors.

In some embodiments, the vector is an expression vector, wherein the expression vector is capable of directing the expression of nucleic acids to which it is operably linked. As used herein, an "expression vector" or "recombinant expression vector" refers to a replicon, such as plasmid, phage, virus, or cosmid, to which another DNA segment, i.e. an "insert", is attached so as to bring about the replication of the attached segment in a cell.

In some embodiments, the vector or expression vector is a plasmid. As used herein, a "plasmid" refers to a circular double-stranded DNA loop into which additional nucleic acid segments are ligated.

In some embodiments, the vector or expression vector is a viral vector, wherein additional nucleic acid segments are ligated into the viral genome. Non-limiting exemplary viral vectors include viral vectors based on vaccinia virus; poliovirus; adenovirus; adeno-associated virus; SV40; herpes simplex virus; human immunodeficiency virus; picornaviruses. Non-limiting exemplary viral vectors also include viral vectors based on a retrovirus such as a Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus. In some embodiments, the vectors is for use in eukaryotic target cells and includes, but is not limited to, pXT1, pSG5, pSVK3, pBPV, pMSG, and pSVLSV40 (Pharmacia).

In some embodiments, the vector comprises one or more transcription and/or translation control elements. In some embodiments, the more transcription and/or translation control elements used depends on the target cell population and the vector system. In some embodiments, any number of suitable transcription and translation control elements, including constitutive and inducible promoters, transcription enhancer elements, transcription terminators, etc. are used in the expression vector, such as those further described below.

In some embodiments, a vector comprising a splice editor nucleic acid of the disclosure is operably linked to a control element, e.g., a transcriptional control element, such as a promoter. In some embodiments, the transcriptional control element is functional in a eukaryotic cell, e.g., a mammalian cell, e.g., a human cell. In some embodiments, the splice editor nucleic acid sequence is operably linked to one or more control elements that enable expression in eukaryotic cells, e.g., mammalian cells, e.g., human cells.

In some embodiments, the expression vector comprises a promoter that is an inducible promoter (e.g., a heat shock promoter, tetracycline-regulated promoter, steroid-regulated promoter, metal-regulated promoter, estrogen receptor-regulated promoter, etc.). Examples of inducible promoters include, but are not limited to, T7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter (e.g., Tet-ON, Tet-OFF, etc.), steroid-regulated promoter, metal-regulated promoter, estrogen receptor-regulated promoter, etc. In some embodiments, an inducible promoters is regulated by molecules including, but not limited to, doxycycline; RNA polymerase, e.g., T7 RNA polymerase; an estrogen receptor; an estrogen receptor fusion; etc.

In some embodiments, the promoter is a constitutive promoter (e.g., CMV promoter, UBC promoter).

In some embodiments, the promoter is a spatially restricted and/or temporally restricted promoter (e.g., a tissue specific promoter, a cell type specific promoter, etc.). Spatially restricted promoters can also be referred to as enhancers, transcriptional control elements, control sequences, etc. Any convenient spatially restricted promoter is suitable for use in the present disclosure, and the choice of a suitable promoter (e.g., a liver-specific promoter, a brain specific promoter, a promoter that drives expression in a subset of neurons, a promoter that drives expression in the germline, a promoter that drives expression in the lungs, a promoter that drives expression in muscles, a promoter that drives expression in islet cells of the pancreas, etc.) will depend on the organism. For example, various spatially restricted promoters are known for plants, flies, worms, mammals, mice, etc. Thus, a spatially restricted promoter can be used to regulate the expression of a splice editor nucleic acid in a wide variety of different tissues and cell types, depending on the organism. Some spatially restricted promoters are also temporally restricted such that the promoter is in the "ON" state or "OFF" state during specific stages of embryonic development or during specific stages of a biological process. For illustration purposes, examples of spatially restricted promoters include, but are not limited to, liver-specific promoters, neuron-specific promoters, adipocyte-specific promoters, cardiomyocyte-specific promoters, smooth muscle-specific promoters, photoreceptor-specific promoters, etc.

Suitable promoters for use in the present disclosure include those derived from viruses and are referred to herein as viral promoters, or they include those derived from an organism, including prokaryotic or eukaryotic organisms. In some embodiments, a suitable promoter for use in the present disclosure include any promoter that drives expression by an RNA polymerase (e.g., pol I, pol II, pol III).

Exemplary promoters include, but are not limited to, the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31(17)), a human H1 promoter (H1), and the like.

Exemplary eukaryotic promoters (i.e., promoters functional in a eukaryotic cell) include, but are not limited to, those from cytomegalovirus (CMV) immediate early, herpes simplex virus (HSV) thymidine kinase, early and late SV40, long terminal repeats (LTRs) from retrovirus, human elongation factor-1 promoter (EF1), a hybrid construct comprising the cytomegalovirus (CMV) enhancer fused to the chicken beta-actin promoter (CAG), murine stem cell virus promoter (MSCV), phosphoglycerate kinase-1 locus promoter (PGK), and mouse metallothionein-I.

In some embodiments, the disclosure provides a vector comprising a splice editor nucleic acid described herein and an RNA polymerase III promoter (e.g., U6 and H1). Descriptions of and parameters for enhancing the use of such promoters are known in art, and additional information and approaches are regularly being described; see, e.g., Ma, H. et al., Molecular Therapy—Nucleic Acids 3, e161 (2014).

In some embodiments, the expression vector comprises a ribosome binding site for translation initiation and a transcription terminator. In some embodiments, the expression vector comprises appropriate sequences for amplifying expression. In some embodiments, the expression vector comprises nucleotide sequences encoding non-native tags (e.g., histidine tag, hemagglutinin tag, green fluorescent protein, etc.), for example, that are operably-linked to the splice editor nucleic acid.

Methods of introducing a nucleic acid to a host cell or a population of host cells are known in the art, and any known method can be used to introduce a nucleic acid (e.g., an expression construct) into a cell. In some embodiments, a splice editor nucleic acid molecule or vector comprising the splice editor nucleic acid molecule are provided to a population of cells using well-developed transfection techniques; see, e.g. Angel and Yanik (2010) PLoS ONE 5(7): e 11756, and the commercially available TransMessenger® reagents from Qiagen, Stemfect™ RNA Transfection Kit from Stemgent, and TransIT®-mRNA Transfection Kit from Mims Bio LLC (See, also Beumer et al. (2008). PNAS 105(50):19821-19826).

In some embodiments, the splice editor nucleic acid molecule is introduced to the cell or a population of cells as an RNA. In some embodiments, the RNA has chemistries suitable for delivery, tolerability, and stability within cells, e.g., following in vivo or in vitro administration. In some embodiments, the RNA is modified, e.g., comprises a modified sugar moiety, a modified internucleoside linkage, a modified nucleoside, a modified nucleotide and/or combinations thereof. In some embodiments, the modified RNA exhibits one or more of the following properties: is not immune stimulatory; is nuclease resistant; has improved cell uptake; has increased half-life; has increased translation efficiency; and/or is not toxic to cells or mammals, e.g., following contact with cells in vivo or ex vivo or in vitro.

Delivery Agents

In some embodiments, delivery of a splice editor nucleic acid described herein is performed by one or more methods described herein. In some embodiments, the splice editor nucleic acid is delivered by viral vectors, lipid nonaparticles (LNPs), synthetic polymers, or a combination thereof. In some embodiments, the methods of delivery described herein are suitable for administering a splice editor nucleic acid of the disclosure to a target cell population or target tissue for the purpose of cellular, ex vivo, or in vivo targeting of a pre-mRNA in the target cell or target tissue for trans-splicing.

In some embodiments, the delivery comprises administering the splice editor nucleic acid as RNA or DNA. In some embodiments, the delivery comprises administering the splice editor nucleic acid as a DNA formulated as an LNP or a polymeric nanoparticle. In some embodiments, the delivery comprises administering the splice editor nucleic acid as an RNA formulated as an LNP or a polymeric nanoparticle.

In some embodiments, the delivery comprises administering a recombinant expression vector comprising the splice editor nucleic acid (e.g., plasmid, viral vector). In some embodiments, the recombinant expression vector is a non-viral vector (e.g., a plasmid). In some embodiments, the recombinant expression vector is a viral vector (e.g., an AAV). In some embodiments, the delivery comprises formulation of the one or more recombinant expression vectors using LNPs or polymeric nanoparticles. In some embodiments, a combination of a viral vector and a non-viral delivery vehicle are used.

In some embodiments, the splice editor nucleic acid molecules are delivered by non-viral delivery vehicles including, but not limited to, nanoparticles, liposomes, ribonucleoproteins, positively charged peptides, small molecule-RNA conjugates, aptamer-RNA chimeras, and RNA-fusion protein complexes. Non-limiting exemplary non-viral delivery vehicles include those described in Peer and Lieberman, Gene Therapy, 18: 1127-1133 (2011) (which focuses on non-viral delivery vehicles for siRNA that are also useful for delivery of other polynucleotides).

Viral Delivery

In some embodiments, the splice editor nucleic acid molecules are delivered by viral delivery vehicles, such as AAV. In some embodiments, the viral vector (e.g., AAV vector) comprises one or more splice editor nucleic acid described herein. In some embodiments, the cloning capacity of the viral vector is sufficient to deliver the splice editor nucleic acid.

In some embodiments, a recombinant adeno-associated virus (rAAV) vector is used for delivery. Techniques to produce rAAV particles, in which an AAV genome to be packaged that includes the polynucleotide to be delivered (e.g., nucleic acid encoding one or more gRNAs and/or a site-directed endonuclease), rep and cap genes, and helper virus functions are provided to a cell are standard in the art. Production of rAAV typically requires that the following components are present within a single cell (denoted herein as a packaging cell): a rAAV genome, AAV rep and cap genes separate from (i.e., not in) the rAAV genome, and helper virus functions. The AAV rep and cap genes can be from any AAV serotype for which recombinant virus can be derived, and can be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10, AAV-11, AAV-12, AAV-13 AAV rh.74 and tropism modified AAV vectors. Production of pseudotyped rAAV is disclosed in, for example, U.S. Pat. No. 7,056,602.

In some embodiments, a method of generating a packaging cell involves creating a cell line that stably expresses all of the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line can then be infected with a helper virus, such as adenovirus. The advantages of this method are that the cells are selectable and are suitable for large-scale production of rAAV. Other examples of suitable methods employ adenovirus or baculovirus, rather than plasmids, to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); McLaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. Nos. 5,786,211; 5,871,982; and 6,258,595.

In addition to adeno-associated viral vectors, other viral vectors can be used. Such viral vectors include, but are not limited to, adenovirus, lentivirus, alphavirus, enterovirus, pestivirus, baculovirus, herpesvirus, Epstein Barr virus, papovavirus, poxvirus, vaccinia virus, and herpes simplex virus.

Nanoparticle Compositions

In some embodiments, the splice editor nucleic acids of the disclosure or a recombinant expression vector comprising the splice editor nucleic acid is delivered to a host cell (e.g., ex vivo) or a subject by a nanoparticle (e.g., a lipid nanoparticle). In some embodiments, the nucleic acid or expression vector is formulated in nanoparticles or other delivery vehicles, (e.g., polymeric nanoparticles) to facilitate cellular uptake and/or to protect them from degradation when delivered to a subject.

In some embodiments, a nanoparticle composition comprises a lipid. Lipid nanoparticles include, but are not limited to, liposomes and micelles. Any number of lipids may be present, including cationic and/or ionizable lipids, anionic lipids, neutral lipids, amphipathic lipids, conjugated lipids (e.g., PEGylated lipids), and/or structural lipids. Such lipids can be used alone or in combination.

Nanoparticles are ultrafine particles typically ranging between 1 and 100 to 500 nanometers (nm) in size with a surrounding interfacial layer and often exhibiting a size-related or size-dependent property. Nanoparticle compositions are myriad and encompass lipid nanoparticles (LNPs), liposomes (e.g., lipid vesicles), and lipoplexes. For example, a nanoparticle composition can be a liposome having a lipid bilayer with a diameter of 500 nm or less. In some embodiments, nanoparticle compositions are vesicles including one or more lipid bilayers. In certain embodiments, a nanoparticle composition includes two or more concentric bilayers separated by aqueous compartments. Lipid bilayers can be functionalized and/or crosslinked to one another. Lipid bilayers can include one or more ligands, proteins, or channels.

In some embodiments, the nanoparticle composition comprises a splice editor nucleic acid and/or a recombinant expression vector comprising the splice editor nucleic acid.

In some embodiments, the disclosure provides LNP compositions comprising: (a) a splice editor nucleic acid molecules described herein or an expression vector comprising the splice editor nucleic molecule; and (b) one or more lipid moieties selected from the group consisting of amino lipids, helper lipids, structural lipids, phospholipids, ionizable lipids, PEG lipids, lipoid, and cholesterol or cholesterol derivatives. In some embodiments, the disclosure provides LNP compositions comprising: (a) a splice editor nucleic acid molecules described herein or an expression vector comprising the splice editor nucleic molecule; and (b) one or more lipid moieties selected from the group consisting of ionizable lipids, amino lipids, anionic lipids, neutral lipids, amphipathic lipids, helper lipids, structural lipids, PEG lipids, and lipoids, and optionally (c) targeting moieties.

In some embodiments, the LNP composition comprise one or more lipid moieties promote or enhances cellular uptake by the apolipoprotein E (apoE)-low density lipoprotein receptor (LDLR) pathway. For example, certain ionizable lipids are known in the art for increasing cellular uptake of LNPs by the apoE-LDLR pathway (see, e.g., Semple, et al (2010) NAT BIOTECH 28:172). In some embodiments, the LNP composition comprises one or more lipid moieties that promote or enhances cellular uptake by an apoE-LDLR independent pathway.

In some embodiments, the LNPs of the present disclosure are formed by any method known in the art including, but not limited to, a continuous mixing method, a direct dilution process, and an in-line dilution process. Additional techniques and methods suitable for the preparation of the LNPs described herein include coacervation, microemulsions, supercritical fluid technologies, phase-inversion temperature (PIT) techniques.

Pharmaceutical Compositions

In some embodiments, the disclosure provides pharmaceutical compositions comprising a splice editor nucleic acid, recombinant expression vector, or delivery system described herein combined with an appropriate pharmaceutically acceptable carrier or diluent.

In some embodiments, the pharmaceutical composition comprises (1) one or more splice editor nucleic acids described herein, and (2) a pharmaceutically acceptable carrier or diluent. In some embodiments, the pharmaceutical composition comprises (1) an expression vector comprising a splice editor nucleic acid described herein, and (2) a pharmaceutically acceptable carrier or diluent. In some embodiments, the pharmaceutical composition comprises one or more splice editor nucleic acids or recombinant expression vector (e.g., AAV) comprising the one or more splice editor nucleic acids formulated as a lipid composition (e.g., LNP), and (2) a pharmaceutically acceptable carrier or diluent. In some embodiments, the pharmaceutical composition comprises a therapeutically effective amount of the one or more splice editor nucleic acids or recombinant expression vectors.

Exemplary pharmaceutically acceptable excipients such as carriers, solvents, stabilizers, adjuvants, diluents, etc., depending upon the particular mode of administration and dosage form. Contemplated pharmaceutical compositions can be generally formulated to achieve a physiologically compatible pH, depending on the formulation and route of administration. In some embodiments, the compositions comprise a therapeutically effective amount of the one or more splice editor nucleic acids or recombinant expression vectors, together with one or more pharmaceutically acceptable excipients.

Suitable excipients can include, for example, carrier molecules that include large, slowly metabolized macromolecules. Other exemplary excipients can include antioxidants, chelating agents, carbohydrates, stearic acid, liquids such as oils, water, saline, glycerol and ethanol, wetting or emulsifying agents, pH buffering substances, and the like.

Pharmaceutical compositions can be formulated into preparations in solutions, suppositories, injections. In some embodiments, the pharmaceutical composition is formulated to result in systemic administration of the one or more splice editor nucleic acids or recombinant expression vectors, for example, following enteral or parenteral administration. In some embodiments, the pharmaceutical composition is formulated to result in localized administration of the one or more splice editor nucleic acids or recombinant expression vectors, for example, following regional administration or implantation. In some embodiments, the pharmaceutical composition is formulated for immediate activity or for sustained release of the one or more splice editor nucleic acids or recombinant expression vectors.

Typically, an effective amount of a splice editor nucleic acid, recombinant expression vectors, or delivery system described herein, can be provided, for example, for use in a method of treating a subject having a disease or disorder. Methods of calculating the effective amount or effective dose are within the skill of one of ordinary skill in the art. The final amount to be administered is dependent upon the route of administration and upon the nature of the disorder that is to be treated. A competent clinician will be able to determine an effective amount of the splice editor nucleic acid, recombinant expression vectors, or delivery system described herein to administer to the patient to halt or reverse the progression of the disorder.

In some embodiments, based on animal data, and other information available for the trans-splicing system, a clinician can determine the maximum safe dose for an individual, depending on the route of administration. For instance, an intravenously administered dose can be more than an intrathecally administered dose, given the greater body of fluid into which the therapeutic composition is being administered. Similarly, compositions which are rapidly cleared from the body can be administered at higher doses, or in repeated doses, in order to maintain a therapeutic concentration. Utilizing ordinary skill, the competent clinician will be able to optimize the dosage of a particular therapeutic in the course of routine clinical trials.

For inclusion in a medicament, a splice editor nucleic acid, recombinant expression vectors, or delivery system described herein can be obtained from a suitable commercial source. In some embodiments, therapies based on a splice editor nucleic acid, recombinant expression vectors, or delivery system described herein to be used for therapeutic administration, must be sterile. Therapeutic compositions can be generally placed into a container having a sterile access port, for example, an intravenous solution bag or vial having a stopper pierceable by a hypodermic injection needle. In some embodiments, the therapeutic components are stored in unit or multi-dose containers, for example, sealed ampules or vials, as an aqueous solution or as a lyophilized formulation for reconstitution.

Methods and Use

In some embodiments, the disclosure provides cellular, ex vivo, and in vivo methods comprising use of the splice editor nucleic acid, recombinant expression vectors, or delivery system described herein to target trans-splicing of a target RNA (e.g., pre-mRNA) in a cell. In some embodiments, the methods comprise use of the splice editor nucleic acid, recombinant expression vectors, or delivery system described herein described herein to correct a mutation in a target RNA (e.g., pre-mRNA). In some embodiments, the disclosure provides methods of treating a patient with a disease or disorder, comprising administering a splice editor nucleic acid, recombinant expression vector, delivery system, or pharmaceutical composition described herein to target trans-splicing of a target RNA (e.g., pre-mRNA) in a target cell population and/or target tissue, thereby treating the disease or disorder.

Cellular RNA Editing

In some embodiments, the method comprises introducing a splice editor nucleic acid, recombinant expression vector, delivery system, or pharmaceutical composition described herein to a cell or cell population. In some embodiments, the method comprises contacting the cell with a splice editor nucleic acid, expression vector, delivery system, or pharmaceutical composition described herein. In some embodiments, the cell is a eukaryotic cell. In some embodiments, the eukaryotic cell is a mammalian cell. In some embodiments, the eukaryotic cell is a rodent cell. In some embodiments, the eukaryotic cell is a human cell. In some embodiments, the cell is a patient-derived cell.

The splice editor nucleic acid, recombinant expression vector, delivery system, or pharmaceutical composition described herein may be introduced into the cell via any methods known in the art, such as, e.g., viral or bacteriophage infection, transfection, conjugation, protoplast fusion, lipofection, electroporation, calcium phosphate precipitation, polyethyleneimine (PEI)-mediated transfection, DEAE-dextran-mediated transfection, liposome-mediated transfection, particle gun technology, calcium phosphate precipitation, shear-driven cell permeation, fusion to a cell-penetrating peptide followed by cell contact, microinjection, and nanoparticle-mediated delivery. In some embodiments, the vector system may be introduced into the cell via viral infection.

In some embodiments, the disclosure provides a method for targeting trans-splicing of a target RNA (e.g., pre-mRNA) in a cell, the method comprising contacting the cell with a splice editor nucleic acid, recombinant expression vector, delivery system, or pharmaceutical composition described herein, wherein when the cell is contacted with the splice editor nucleic acid, recombinant expression vector, delivery system, or pharmaceutical composition, the one or more binding domains of the splice editor nucleic acid binds to the target RNA (e.g., pre-mRNA) and trans-splicing results in ligation of one or more exons of the target RNA (e.g., pre-mRNA) to one or more exons of the splice editor nucleic acid.

In some embodiments, the disclosure provides a method for targeting trans-splicing of a pre-mRNA in a cell or a population of cells comprising a disease-causing mutation, the method comprising contacting the cell or population of cells with a splice editor nucleic acid, recombinant expression vector, delivery system, or pharmaceutical composition described herein, wherein when the cell is contacted with the splice editor nucleic acid, recombinant expression vector, delivery system, or pharmaceutical composition, the one or more binding domains of the splice editor nucleic acid binds to the pre-mRNA and trans-splicing results in ligation of one or more exons of the pre-mRNA to one or more exons of the splice editor nucleic acid, thereby resulting in a mRNA lacking the disease-causing mutation.

In some embodiments, the disclosure provides a method for targeting trans-splicing of a pre-mRNA in a cell or a population of cells derived from a patient having a disease or disorder, the method comprising contacting the cell or population of cells with a splice editor nucleic acid, recombinant expression vector, delivery system, or pharmaceutical composition described herein, wherein when the cell or population of cells is contacted with the splice editor nucleic acid, recombinant expression vector, delivery system, or pharmaceutical composition, the one or more binding domains of the splice editor nucleic acid binds to the target RNA (e.g., pre-mRNA) and trans-splicing results in ligation of one or more exons of the target RNA (e.g., pre-mRNA) to one or more exons of the splice editor nucleic acid, wherein the cell or population of cells is reintroduced to the patient, thereby treating or ameliorating the disease or disorder.

In Vivo RNA Editing

The present disclosure provides methods for treating a patient having a disease or disorder using the splice editor nucleic acid, recombinant expression vector, delivery system, or pharmaceutical composition described herein. In some embodiments, the disease or disorder is associated with one or more mutations in a target RNA, wherein the method targets trans-splicing of the target RNA to remove the one or more mutations.

In some embodiments, the disclosure provides a method of treating a patient having a disease or disorder, comprising administering to the patient a splice editor nucleic acid, recombinant expression vector, delivery system, or pharmaceutical composition described herein.

In some embodiments, the disclosure provides a method of treating a patient having a disease or disorder by targeting trans-splicing of a target RNA (e.g. pre-mRNA) in a target tissue or cell population, the method comprising administering to the patient a splice editor nucleic acid, recombinant expression vector, delivery system, or pharmaceutical composition described herein, wherein when the splice editor nucleic acid, recombinant expression vector, delivery system, or pharmaceutical composition is administered, the splice editor nucleic acid binds to a target RNA (e.g., pre-mRNA) and trans-splicing results in ligation of one or more exons of the target RNA (e.g., pre-mRNA) to one or more exons of the splice editor nucleic acid, thereby treating or ameliorating the disease or disorder.

In some embodiments, the disclosure provides a method of treating a patient having a disease or disorder associated with one or more mutations in a pre-mRNA in a target tissue or cell population, the method comprising administering to the patient a splice editor nucleic acid, recombinant expression vector, delivery system, or pharmaceutical composition described herein, wherein when the splice editor nucleic acid, recombinant expression vector, delivery system, or pharmaceutical composition is administered, the splice editor nucleic acid binds to a pre-mRNA and trans-splicing results in ligation of one or more exons of the pre-mRNA to one or more exons of the splice editor nucleic acid, wherein the trans-splicing results in an mRNA lacking the disease-causing mutation, thereby treating or ameliorating the disease or disorder.

In some embodiments, the route of administration is any sufficient for delivery of the splice editor nucleic acid, recombinant expression vector, delivery system, or pharmaceutical composition described herein to the target tissue or cell population as ascertained by one of skill in the art.

In some embodiments, administration of the splice editor nucleic acid, recombinant expression vector, delivery system, or pharmaceutical composition described herein results in correction of a mutation in a pre-mRNA in a target tissue or cell population in the patient.

The term "treatment" refers to the application of one or more methods described herein for the amelioration of a disease. In some embodiments, the specific procedure is the administration of a splice editor nucleic acid, recombinant expression vector, delivery system, or pharmaceutical composition described herein. "Treatment" of an individual (e.g. a mammal, such as a human) or a cell is any type of intervention used in an attempt to alter the natural course of the individual or cell. Treatment includes, but is not limited to, administration of a splice editor nucleic acid, recombinant expression vector, delivery system, or pharmaceutical composition described herein, and may be performed either prophylactically or subsequent to the initiation of a pathologic event or contact with an etiologic agent. Treatment includes any desirable effect on the symptoms or pathology of a disease or condition, and may include, for example, minimal changes or improvements in one or more measurable markers of the disease or condition, and may include, for example, minimal changes or improvements in one or more measurable markers of the disease or condition being treated.

The terms "patient," "subject," "individual," and the like are used interchangeably herein, and refer to any animal amenable to the methods described herein. In some embodiments, the patient, subject, or individual is a human.

Kits

The present disclosure provides kits for carrying out the methods described herein. In some embodiments, the kit comprises a splice editor nucleic acid, recombinant expression vector, delivery system, or pharmaceutical composition described herein.

In some embodiments, the kit comprises a splice editor nucleic acid, recombinant expression vector, delivery system or pharmaceutical composition described herein and a reagent for reconstitution and/or dilution of the splice editor nucleic acid, recombinant expression vector, delivery system or pharmaceutical composition.

In some embodiments, the kit comprise one or more additional reagents, where such additional reagents are selected from a buffer, a buffer for introducing the splice editor nucleic acid, recombinant expression vector, delivery system into a cell, a wash buffer, a control reagent, a control vector, a control polynucleotide, a reagent for in vitro production of the recombinant expression vector or delivery system, adaptors for sequencing and the like. A buffer can be a stabilization buffer, a reconstituting buffer, a diluting buffer, or the like. A kit can also comprise one or more components that can be used to facilitate or enhance the on-target binding or the trans-splicing of the splice editor nucleic acid.

In addition to the above-mentioned components, a kit can further comprise instructions for using the components of the kit to practice the methods. The instructions for practicing the methods can be recorded on a suitable recording medium. For example, the instructions can be printed on a substrate, such as paper or plastic, etc. The instructions can be present in the kits as a package insert, in the labeling of the container of the kit or components thereof (i.e., associated with the packaging or subpackaging), etc. The instructions can be present as an electronic storage data file present on a suitable computer readable storage medium, e.g. CD-ROM, diskette, flash drive, etc.

In some instances, the actual instructions are not present in the kit, but means for obtaining the instructions from a remote source (e.g. via the Internet), can be provided. An example of this case is a kit that comprises a web address where the instructions can be viewed and/or from which the instructions can be downloaded. As with the instructions, this means for obtaining the instructions can be recorded on a suitable substrate.

In some embodiments, the kit comprises a container comprising the splice editor nucleic acid, the recombinant expression vector, the delivery system, or the pharmaceutical composition described herein, and instructions for use targeting trans-splicing of a target RNA (e.g., pre-mRNA) in a cell or a population of cells.

In some embodiments, the kit comprises a container comprising the splice editor nucleic acid, the recombinant expression vector, the delivery system, or the pharmaceutical composition described herein, and instructions for administering the splice editor nucleic acid, the recombinant expression vector, the delivery system, or the pharmaceutical composition to a patient in need thereof to target trans-splicing of a target RNA (e.g., pre-mRNA) in a cell or a population of cells of the patient.

Definitions

As used herein, the term "pre-mRNA" refers to a precursor mRNA and is an RNA which contains both exons and intron(s). Pre-mRNA is a type of primary transcript that becomes a messenger RNA after processing. It is synthesized from a DNA template in the cell nucleus by transcription. In some embodiments, RNA is from a mammalian cell. In other embodiments, the RNA is from the mitochondria of a mammalian cell.

As used herein, the term "RNA-binding" is used to describe a molecule, protein, nucleic acid, or complex that specifically binds to RNA.

As used herein, a "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

EXAMPLES

Example 1: Selection of ncRNAs

Figure 1E:
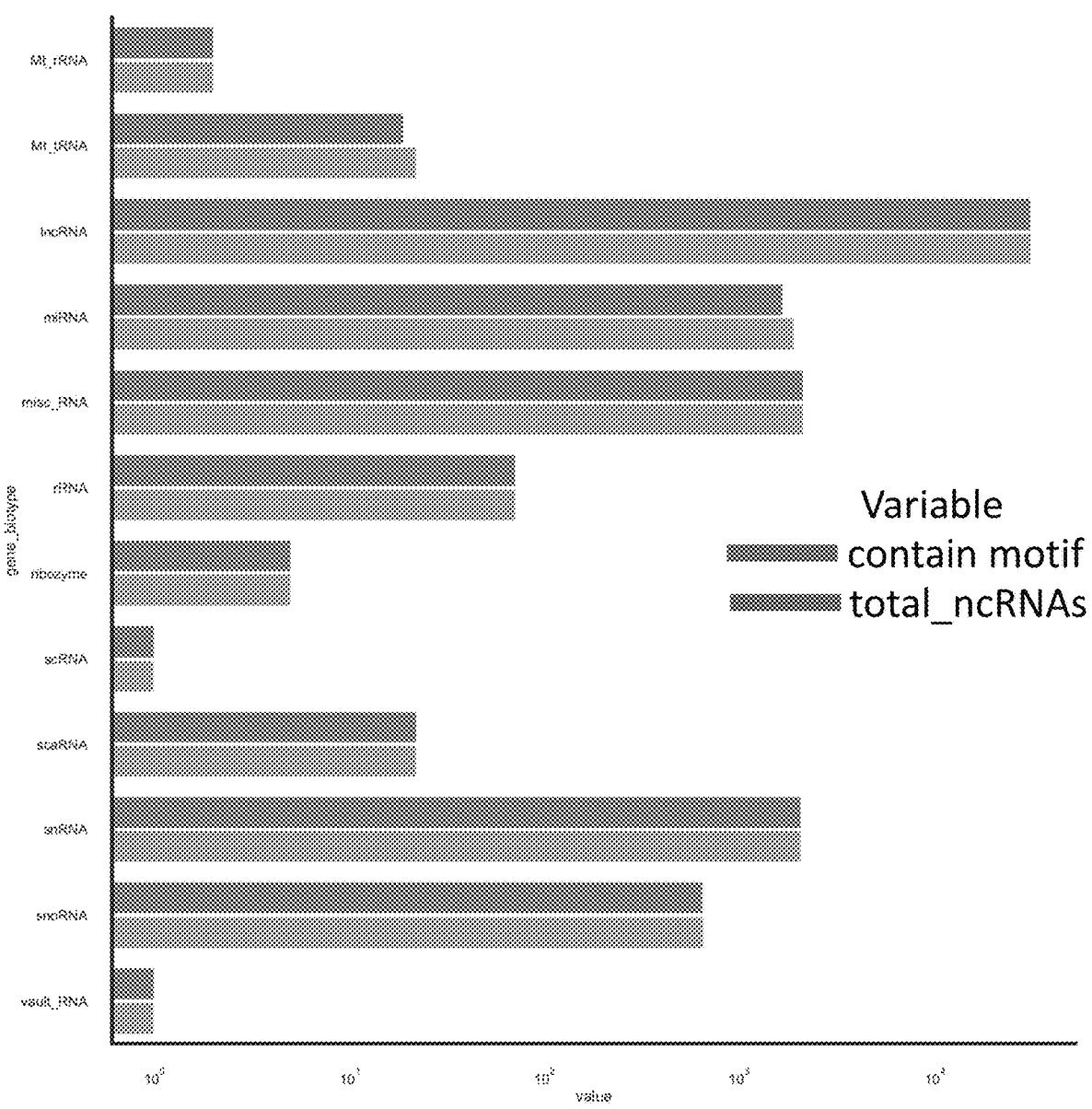
FIG. 1E provides a graph showing the proportion of ncRNAs identified as containing a sequence motif (Sm sequence motif, H/ACA box, and/or C/D box).

This Example describes the methods used to identify ncRNAs for inclusion in splice editors capable of targeting a pre-mRNA and producing a trans-splicing event. As shown in FIG. 1E, it was determined that nearly all ncRNA sequences mined from public databases contain a sequence motif identified in Table 1. RNAlib-2.5.1 software was used to predict the secondary structure of the ncRNA sequences identified in the public domain, including metazoan U1 snRNA sequences, U11 snRNA sequences, U7 snRNA sequences, Sm sequences, and H/ACA snoRNA sequences.

The predicted secondary structures were compared to known secondary structures using an RNA covariance model (see, e.g., Eddy, et al (1994) *Nucleic Acids Research*

Figure 1F:
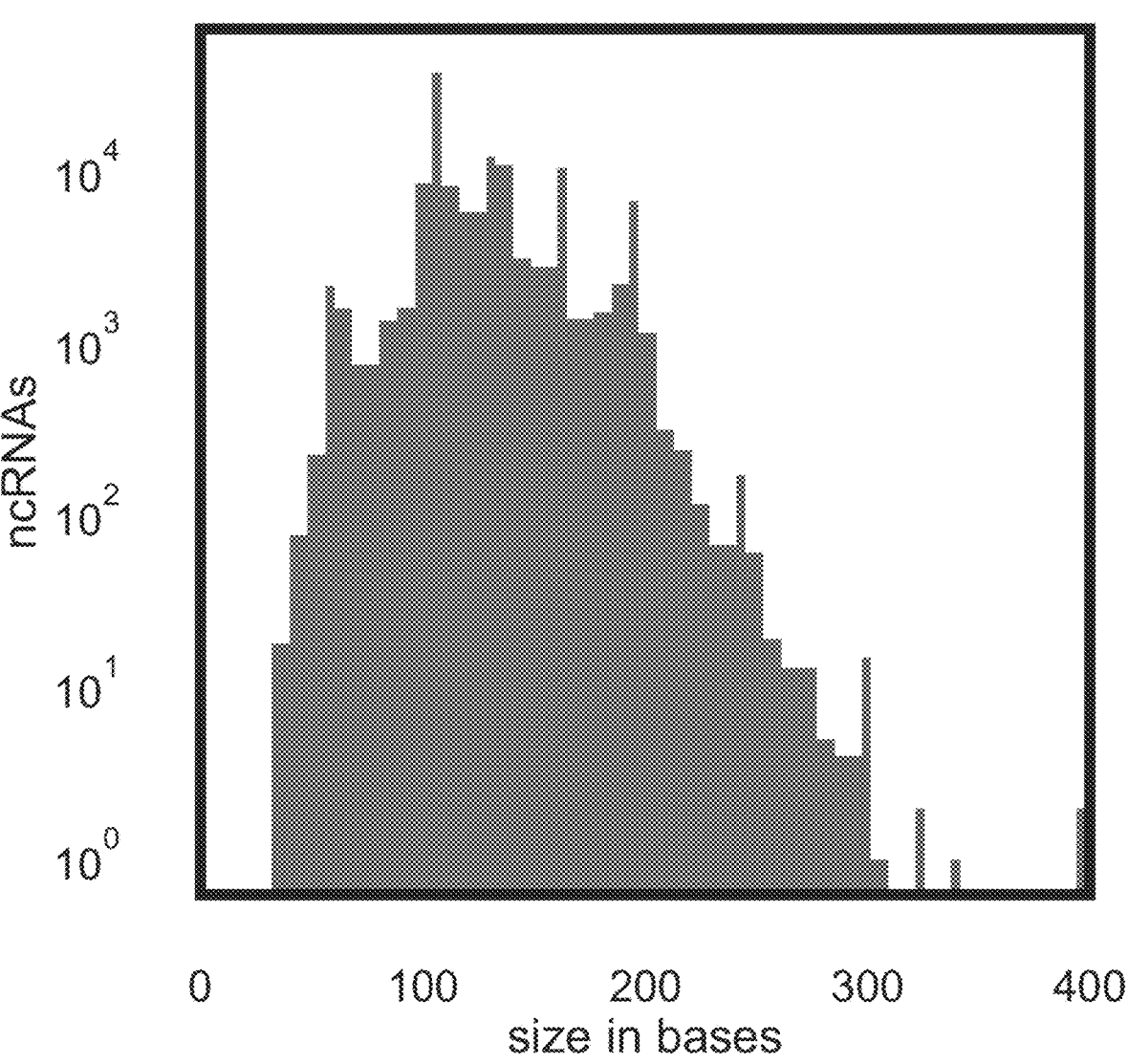
FIG. 1F provides a graph showing the length in number of nucleotides for exemplary ncRNAs of the disclosure.

22:2079-2088). ncRNA sequences having a predicted secondary structure with similarity to known secondary structures were selected for further evaluation. This approach provided more than 120,000 candidate ncRNA sequences. As shown in FIG. 1F, the candidate ncRNA sequences ranged from approximately 7 nucleotides to more than 300 nucleotides in length. Exemplary candidate ncRNA sequences that were identified by this computational analysis are set forth in SEQ ID NOs: 9-657.

Example 2: Design and Testing of Splice Editors for Trans-Splicing

Splice editor nucleic acid molecules were designed for targeted trans-splicing. The nucleic acid molecules comprise a nucleotide sequence with (a) an intronic sequence having (i) at least one binding domain sequence complementary to a target sequence in a pre-mRNA, and (ii) a ncRNA sequence; (b) a splice site; and (c) at least one exonic sequence. The ncRNA sequences were selected from the candidate ncRNAs identified as described in Example 1. The splice editor nucleic acid molecules were engineered to incorporate the entire candidate ncRNA sequence or a portion thereof comprising a secondary structure and/or sequence motif identified in Table 1.

Figure 2A:
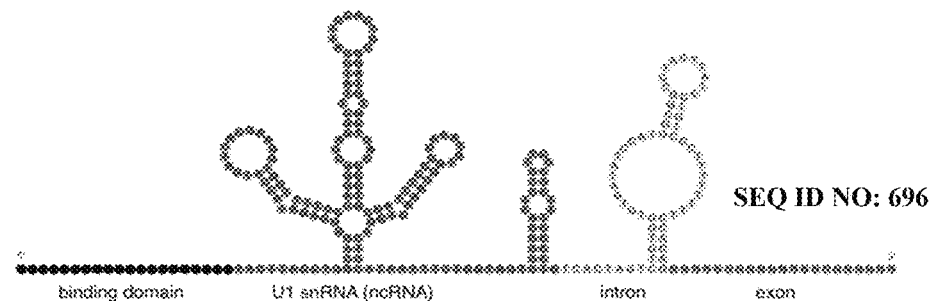
FIG. 2A, FIG. 2B, and FIG. 2C provide a schematic, without wishing to be bound by theory, depicting the extended and folded secondary structure of an exemplary splice editor nucleic acid molecule of the disclosure having 5' to 3' an RNA binding domain, U1 snRNA, intron, SA, and exon (SEQ ID NO: 696, SEQ ID NO: 697, and SEQ ID NO: 698) (FIG. 2A) and the interaction of the exemplary splice editor with a target pre-mRNA that initiates a trans-splicing event between the SD of the pre-mRNA and the SA of the exemplary splice editor (FIG. 2A, FIG. 2B).
Figure 2A:
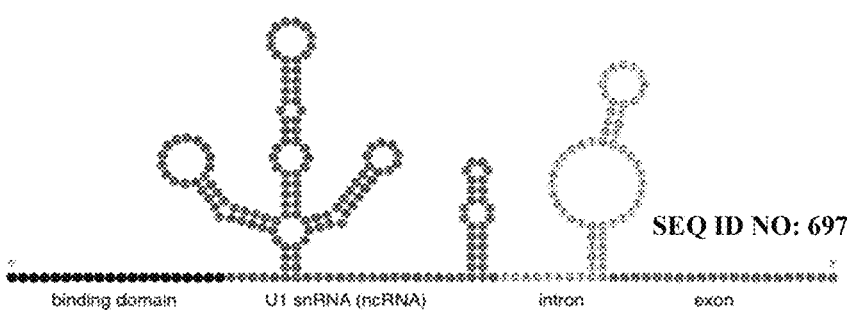
Figure 2A:
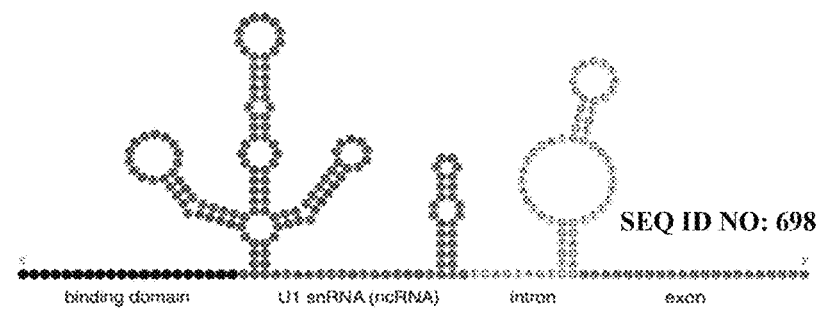
Figure 2A:
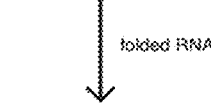
Figure 2A:
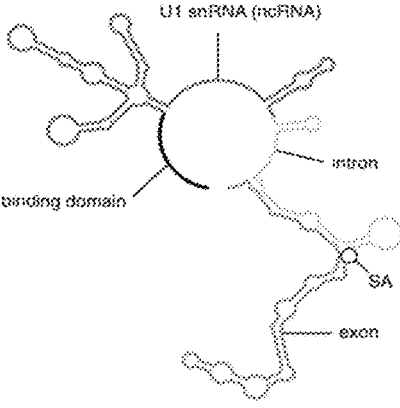
Figure 2B:
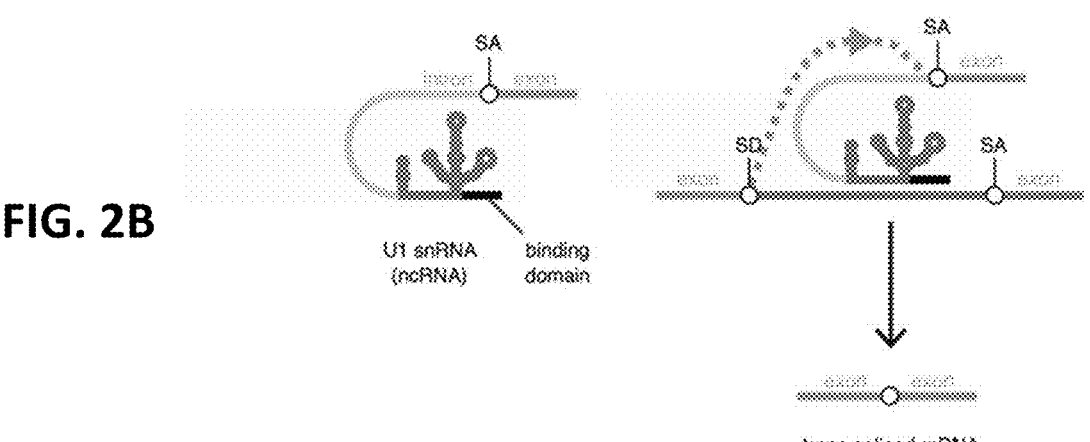
Figure 2C:
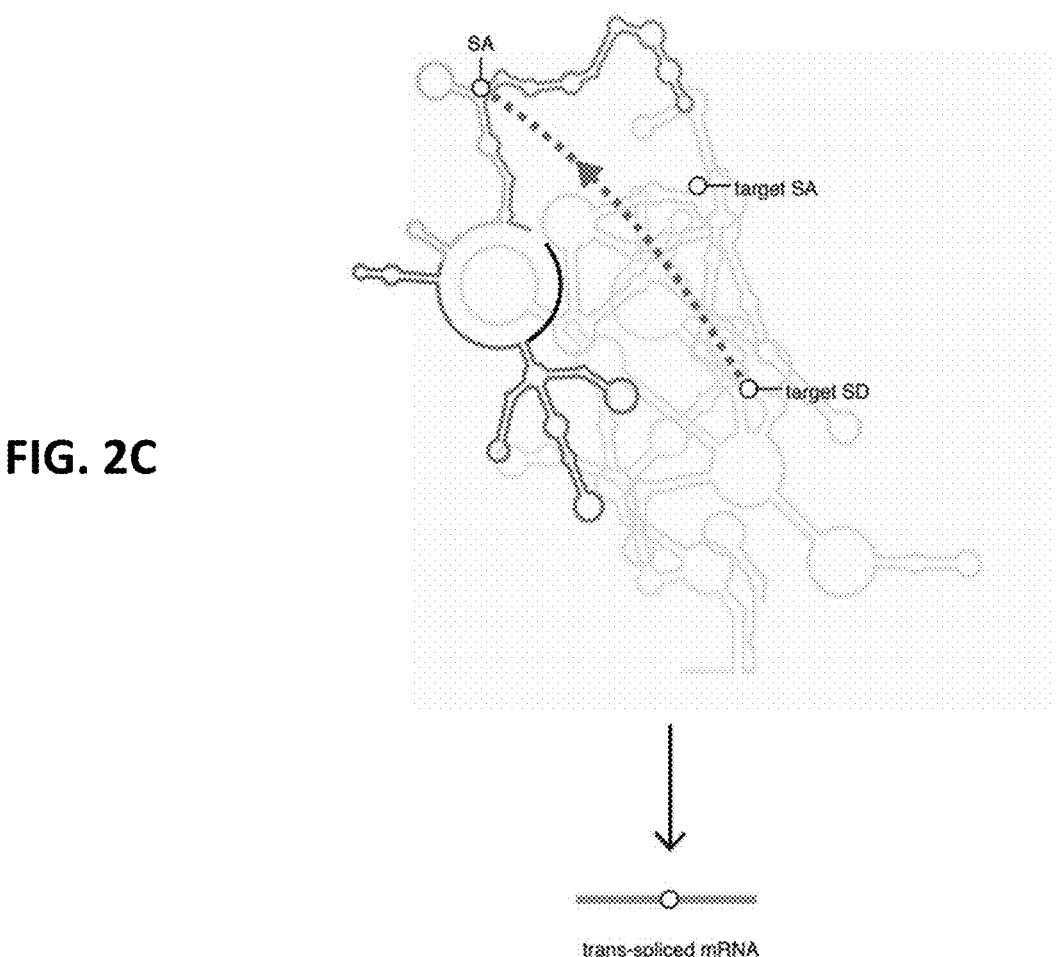
Figure 3A:
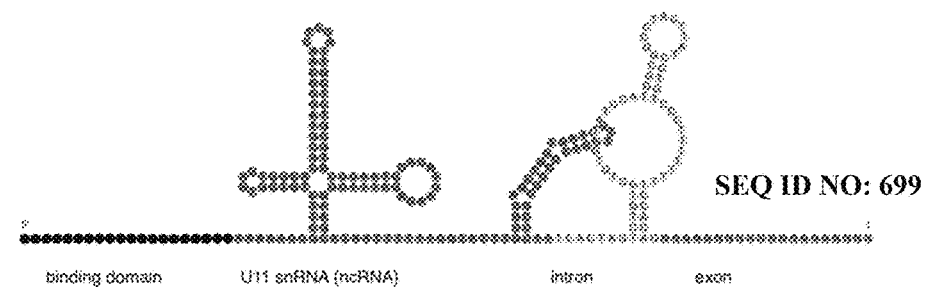
FIG. 3A, FIG. 3B, and FIG. 3C provide a schematic, without wishing to be bound by theory, depicting the extended and folded secondary structure of an exemplary splice editor nucleic acid molecule of the disclosure having 5' to 3' an RNA binding domain, U11 snRNA, intron, SA, and exon (SEQ ID NO: 699, SEQ ID NO: 700, and SEQ ID NO: 701) (FIG. 3A) and the interaction of the exemplary splice editor with a target pre-mRNA that initiates a trans-splicing event between the SD of the pre-mRNA and the SA of the exemplary splice editor (FIG. 3A, FIG. 3B).
Figure 3A:
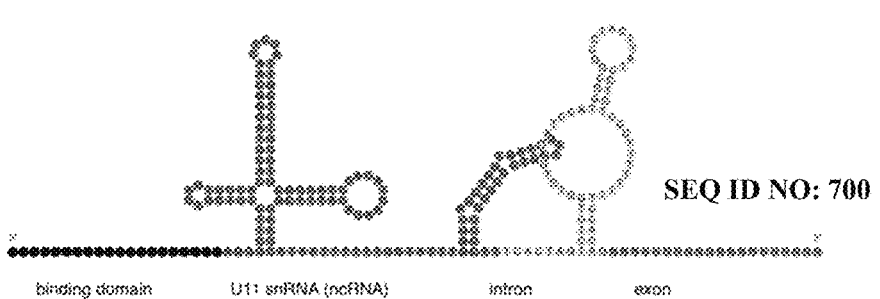
Figure 3A:
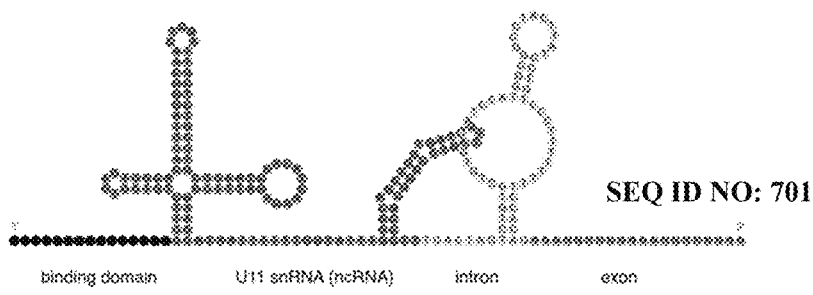
Figure 3A:
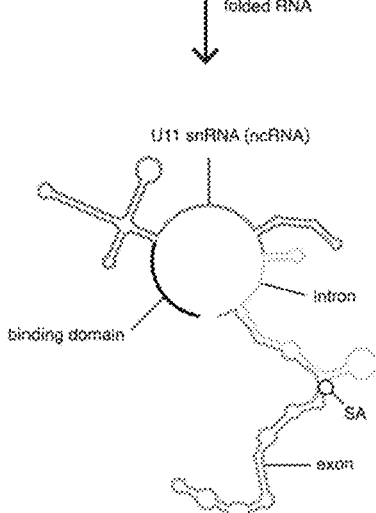
Figure 3B:
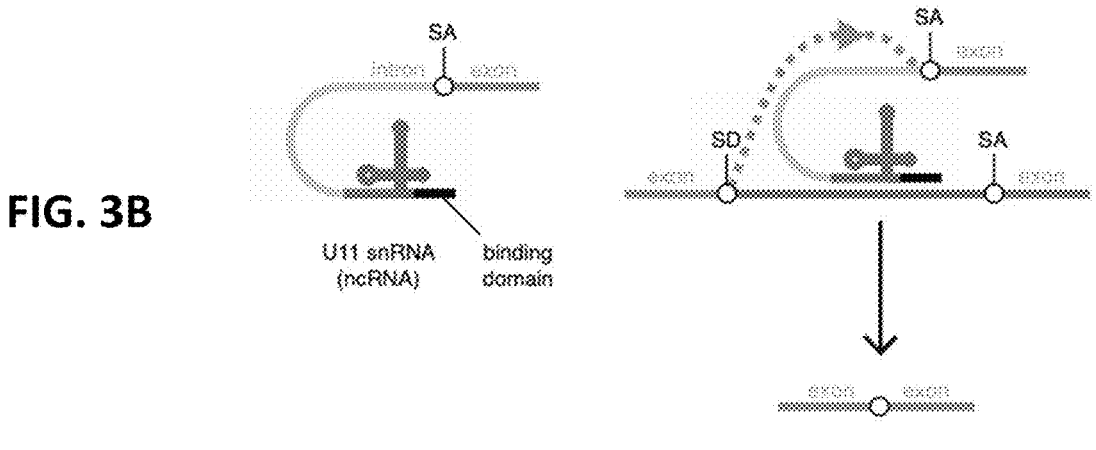
Figure 3C:
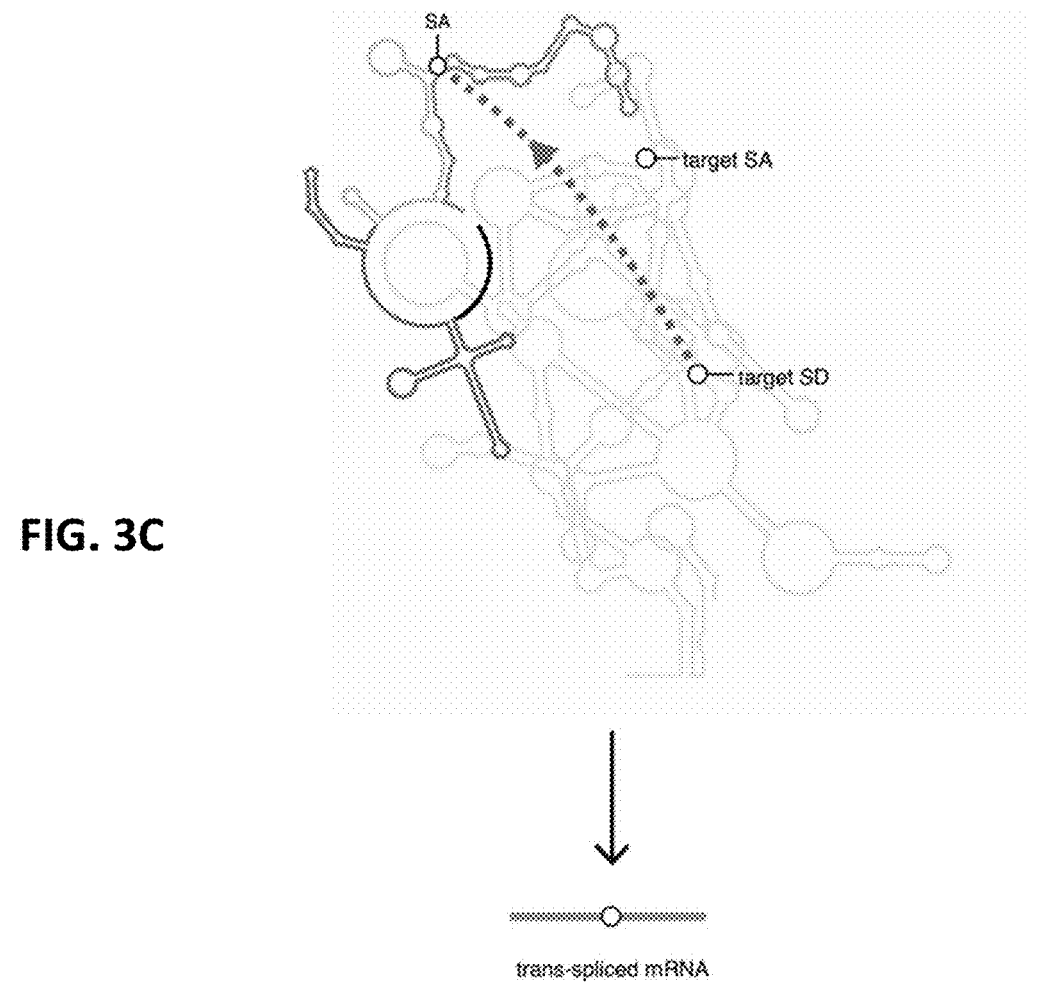

A first set of nucleic acid molecules were designed to have a ncRNA sequence derived from a snRNA and to undergo trans-splicing at a splice donor in a pre-mRNA (for correction of a mutation at the 5'end of an exon). The nucleic acid molecules had a nucleotide sequence arranged 5' to 3' (a) an intron having (i) a binding domain sequence, (ii) a snRNA sequence (a U1 snRNA; U11 snRNA; a Sm sequence motif and U7 snRNA; or a Sm sequence motif), (iii) a branch point, and (iv) a polypyrimidine tract; (b) a splice acceptor; and (c) an exon. Schematics of exemplary U1-based splice editor nucleic acid molecules are shown in FIG. 2A, FIG. 2B, and FIG. 2C and sequences are provided in the table of Table 3 (in rows of Table 3 in which the column titled "Region 2" is assigned a label of "U1_X_Y" in which X and Y are integers). Schematics of exemplary U11-based splice editor nucleic acid molecules are shown in FIG. 3A, FIG. 3B, and FIG. 3C and sequences are provided in the table of Table 3 (in rows of Table 3 in which the column titled "Region 2" is assigned a label of "U11_X_Y" in which X and Y are integers).

Figure 4A:
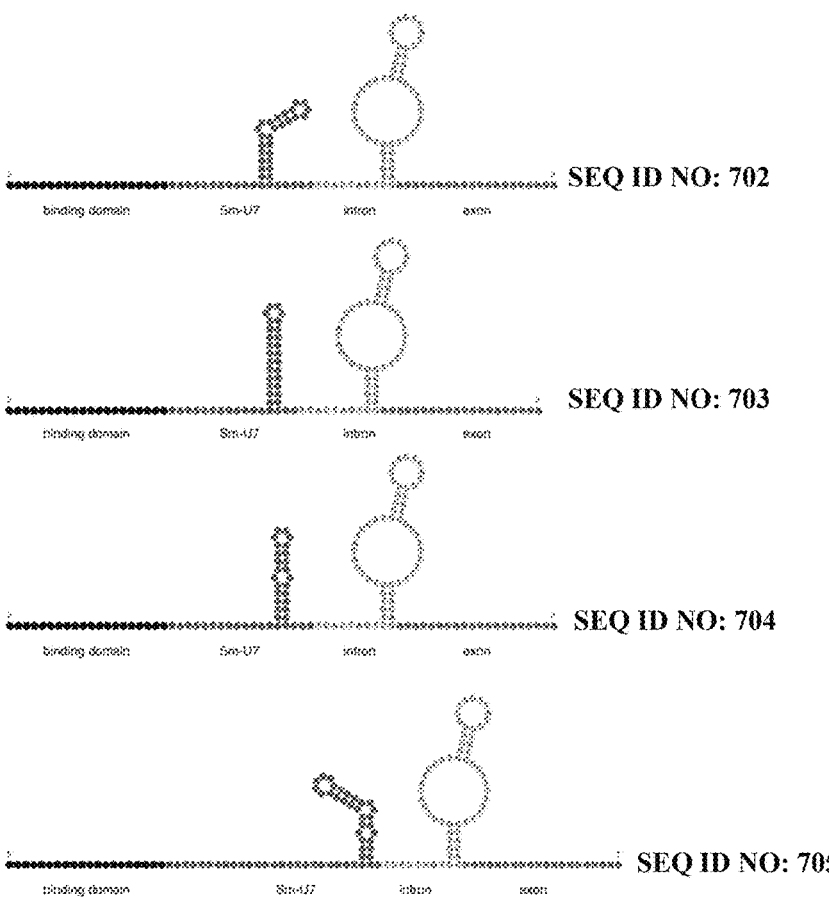
FIG. 4A, FIG. 4B, and FIG. 4C provide a schematic, without wishing to be bound by theory, depicting the extended and folded secondary structure of an exemplary splice editor nucleic acid molecule of the disclosure having 5' to 3' an RNA binding domain, an ncRNA having an Sm sequence motif and a U7 snRNA, intron, SA, and exon (SEQ ID NO: 702, SEQ ID NO: 703, SEQ ID NO: 704 and SEQ ID NO: 705) (FIG. 4A) and the interaction of the exemplary splice editor with a target pre-mRNA that initiates a trans-splicing event between the SD of the pre-mRNA and the SA of the exemplary splice editor (FIG. 4A, FIG. 4B, and FIG. 4C).
Figure 4A:
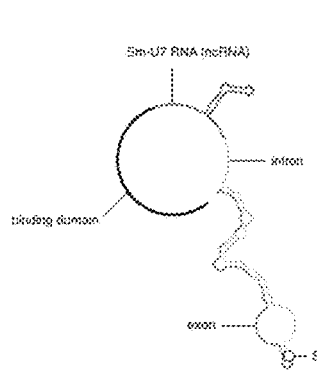
Figure 4B:
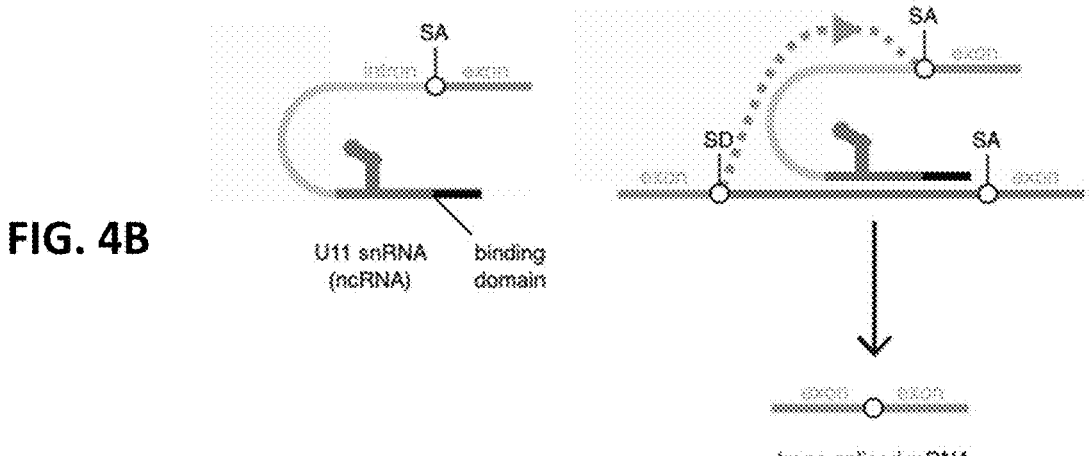
Figure 4C:
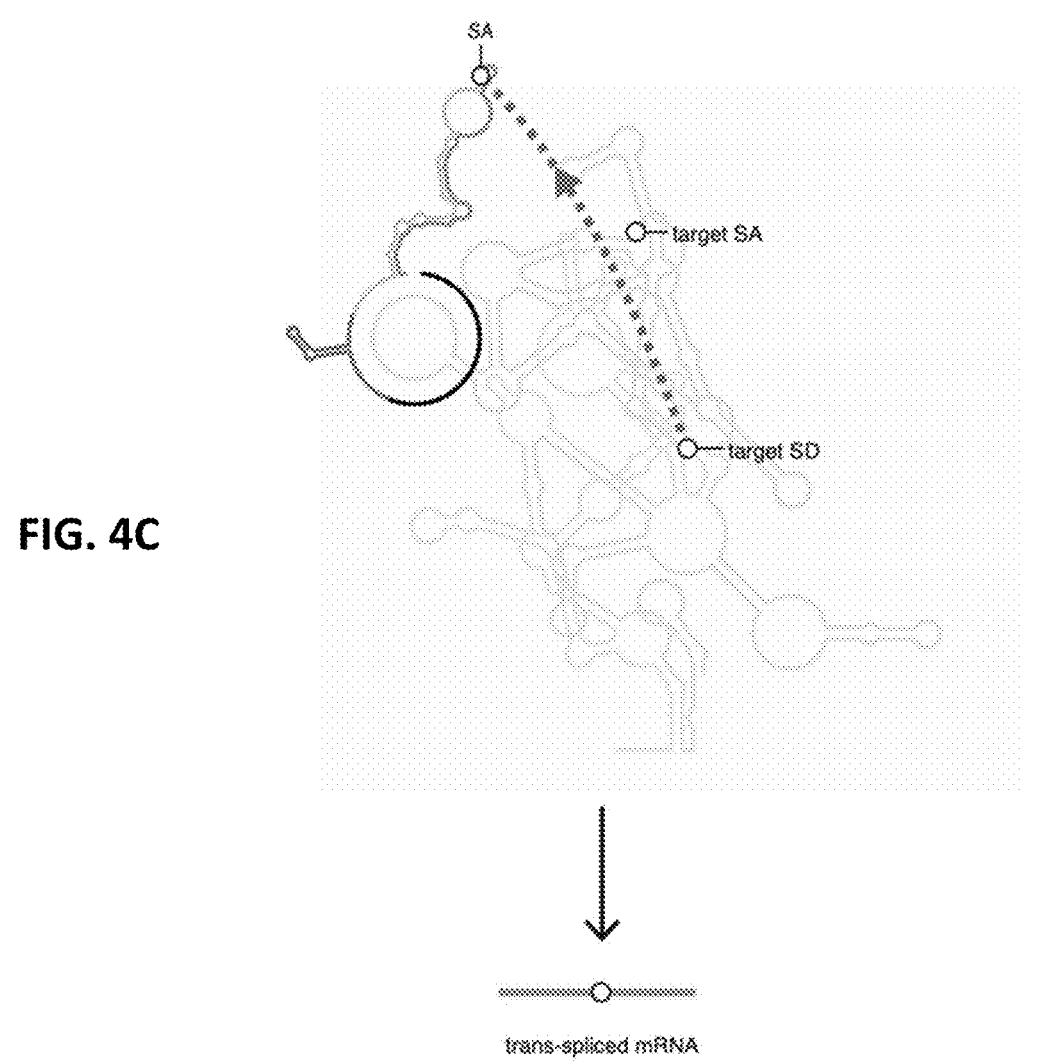
Figure 5B:
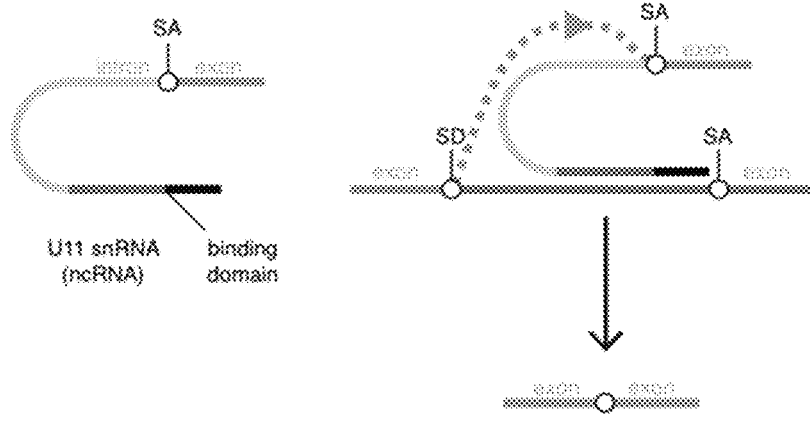
Figure 5C:
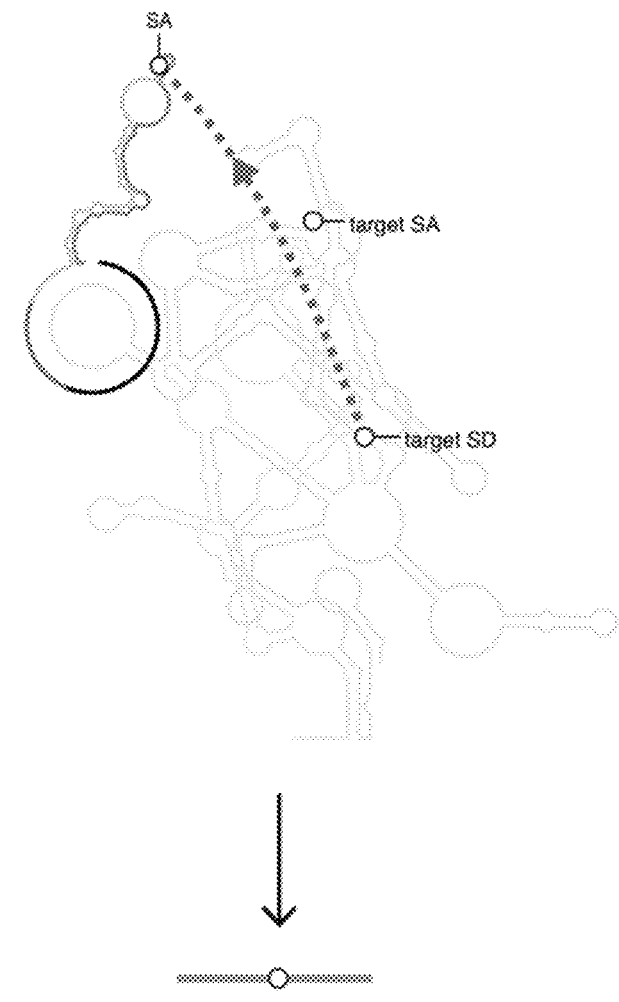

Schematics of exemplary U7-based splice editor nucleic acid molecules are shown in FIG. 4A, FIG. 4B, and FIG. 4C and sequences are provided in Table 3 (in rows of Table 3 in which the column titled "Region 2" is assigned a label beginning with "Sm_Z" in which Z is an integer and the column titled "Region 3" is assigned a label beginning with "U7_X" in which X is an integer). Schematics of exemplary Sm-based splice editor nucleic acid molecules are shown in FIG. 5A, FIG. 5B, and FIG. 5C and sequences are provided in Table 3 (in rows of Table 3 in which the column titled "Region 2" is assigned a label beginning with "Sm_Z" in which Z is an integer and the column titled "Region 3" is assigned a label "adeno_intron").

A second set of nucleic acid molecule were designed to have a ncRNA sequence derived from a H/ACA snoRNA and to undergo trans-splicing at a splice donor in a pre-mRNA (for correction of a mutation at the 5'end of an exon). The nucleic acid molecules had a nucleotide sequence arranged 5' to 3' (a) an intron having (i) a first and second binding domain inserted into an H/ACA box snoRNA sequence, (ii) a branch point, and (iii) a polypyrimidine tract; (b) a splice acceptor; and (c) an exon. Schematics of exemplary snoRNA-based splice editor nucleic acid molecules are shown in FIG. 6A, FIG. 6B, and FIG. 6C and sequences are provide in Table 3 (in rows of Table 3 in which the column titled "Region 1" is assigned a label beginning with "sno" "SNO" or "SCARNA").

The nucleic acid molecules are evaluated for trans-splicing by using reporter cells, where correct RNA edits generate a mRNA that produces a fluorescent protein. Splice editors are be introduced to the reporter cells via viral or non-viral methods. Viral methods include but are not limited to lentivirus, AAV, and adenovirus. Non-viral methods include but are not limited to transfection or electroporation. The cells are first transfected with a splice donor reporter construct encoding a pre-mRNA under control of a CMV promoter, the pre-mRNA comprising a blue fluorescent protein (BFP), a self-cleaving p2A linker, a truncated GFP (5'GFP), and a splice donor. The BFP is used to confirm stable expression of the reporter construct. The reporter construct has a matrix metallopeptidase 9 (MMP9) intron 1 and exon 2 downstream the splice donor to ensure splicing an event can occur, followed by a bovine growth hormone polyadenylation signal (bGHpA) to allow for stable expression of the construct. The splice editor nucleic acids have an exon that is the second half of the truncated GFP (3'GFP) and trans-splicing results in expression of full-length GFP. Reporter cells with correct edits generate signal via a fluorescent reporter and are sorted via FACS. Sorted cells are sequenced to identify active splice editors.

Example 3: Design and Testing of snoRNAs for Exon Skipping

In the experiments of this example, snoRNA guide constructs were developed that have hybridizing regions replaced to allow the snoRNA to serve as a guide for the RNP complex. The snoRNA guide constructs were tested for exon skipping in this example.

Figure 7A:
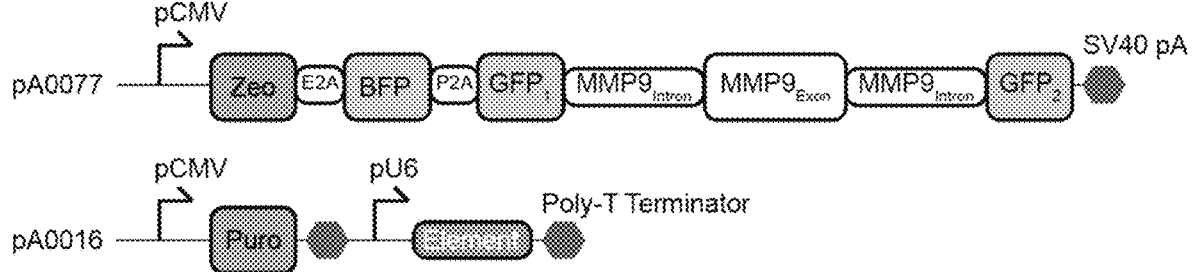
FIG. 7A is an image showing, without wishing to be bound by theory, the design of snoRNA guide constructs for exon skipping.

In these experiments, the snoRNA guide constructs were designed on a plasmid, along with a sequence that is complementary to a target sequence, to produce a snoRNP that occludes a splice site, and thereby allows for exon skipping. To test for exon skipping, splice acceptor targeting snoRNA guide molecules were designed on a plasmid (i.e., pA0077, FIG. 7A, Table 2), which also included intron and exon sites of the MMP9 gene and two GFP sites (FIG. 7A). An element was then introduced on a separate plasmid target (i.e., pA0016), which was present after the U6 promoter and before the poly-T terminator (FIG. 7A). The design of these constructs and plasmids allows the snoRNA to bind to the MMP9 gene splice site, thereby occluding the splice site and leading to GFP production, as shown in the volcano plot of FIG. 7B and the graph in FIG. 8.

Figure 7B:
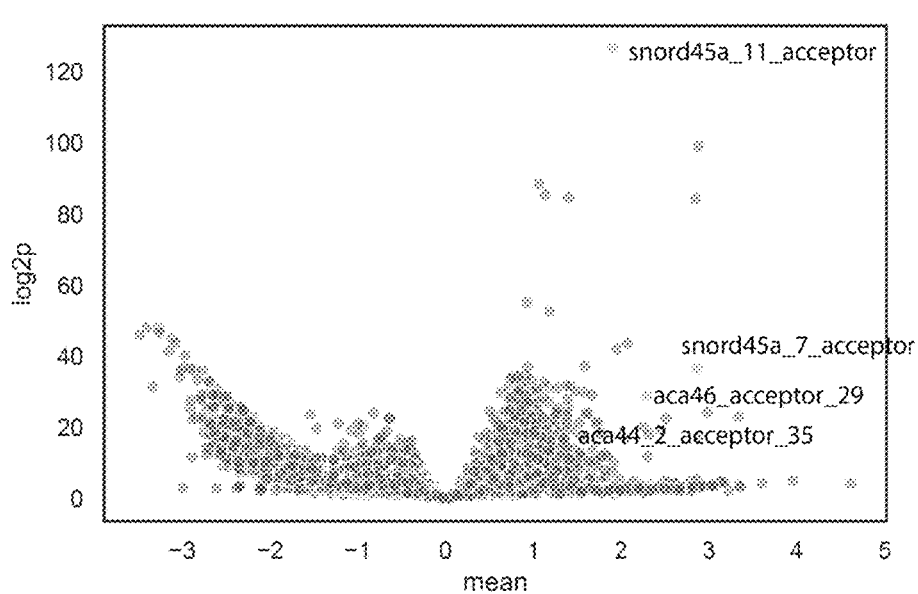
FIG. 7B is a graph showing exon skipping results for four splice acceptor targeting snoRNAs (i.e., labeled "snord45a_11_acceptor", "snord45a_7_acceptor", "aca46_acceptor_29", and "aca44_2_acceptor_35", and sequences shown in Table 4).
Figure 8:
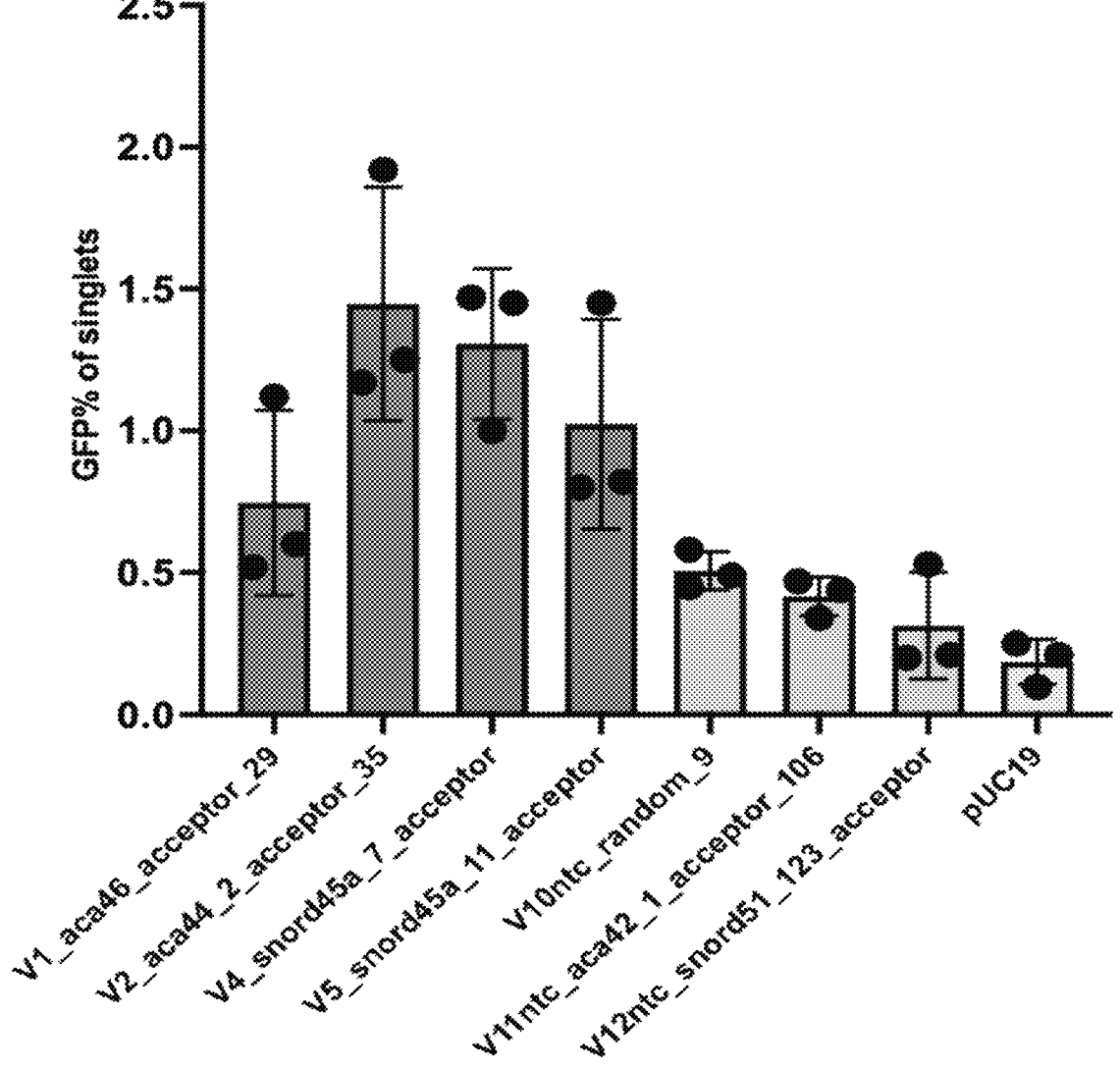
FIG. 8 is a graph showing GFP production as a result of exon skipping from four different splice acceptor targeting snoRNAs (i.e., labeled "V5_snord45a_11_acceptor", "V4_snord45a_7_acceptor", "V1_aca46_acceptor_29", and "V2_aca44_2_acceptor_35", and sequences shown in Table 4).
Figure 9:
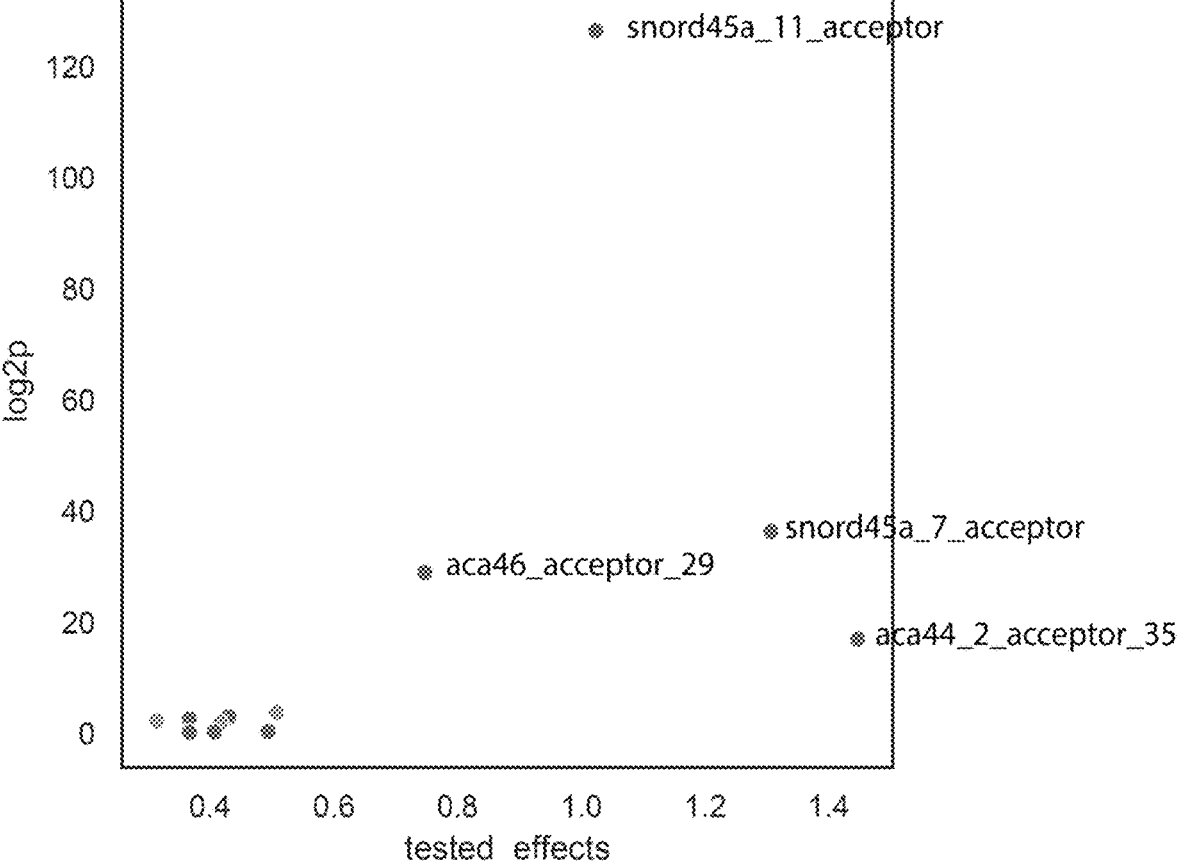
FIG. 9 is a graph showing exon skipping results for four splice acceptor targeting snoRNAs (i.e., labeled "snord45a_11_acceptor", "snord45a_7_acceptor", "aca46_acceptor_29", and "aca44_2_acceptor_35") compared to the four randomized guides of FIG. 8.

The four splice acceptor targeting snoRNA candidates of FIG. 7B (i.e., labeled "snord45a_11_acceptor", "snord45a_7_acceptor", "aca46_acceptor 29", and "aca44_2_acceptor_35", which were obtained from a high-throughput screen for exon skipping, and sequences shown in Table 4) were synthesized as IDT eBlocks and cloned into the pA0016 vector. The vector was transfected into a HEK293FT cell line that stably expresses a PiggyBAC-integrated MMP9 exon-skipping reporter (pA0077). This cell line was established by FACS sorting on reporter BFP expression for a highly-expressing single-cell clone. 100 ng element vector was transfected using Lipofectamine 2000 into HEK293FT cells seeded into a 96-well plate, such that cells were 90% confluent at the time of transfection. 48 hours post-transfection, cells were analyzed for GFP % by flow cytometry compared to Non-targeting Controls (ntc) or cells treated with pUC19. FIG. 8 is a graph showing GFP production as a result of exon skipping from four different splice acceptors targeting snoRNAs (i.e., snord is C/D snoRNA, and snora or aca is H/ACA, labeled "V5_snord45a_11_acceptor", "V4_snord45a_7_acceptor", "V1_aca46_acceptor_29", and "V2_aca44_2_acceptor_35", and sequences shown in Table 4) compared to four randomized guides (i.e., "V10ntc_random_9", "V11ntc_aca42_1_acceptor_106", "V12ntc_snord51_123_acceptor," pUC19 (plasmid alone)). The results in FIG. 7A, FIG. 7B, FIG. 8, and FIG. 9 demonstrate the snoRNAs disclosed herein guide exon skipping.

TABLE 4

| | Splice Acceptor sequences targeting snoRNAs | |
|---|---|---|
| SEQ ID NO: | Reference | Sequence |
| 674 | snord45a_11_acceptor | GGTCAATGATGTGTTGGCATGTATCAGGTATTCCT GTGGCTGATGTGTAATAACACTGGATGAAGGGAC ACACACTGAGACCT |
| 675 | snord45a_11_acceptor | TATGATAGGGACTTAGGGTG-ggtcaatgatgtgttggcatgtat caggtattcctgtggctgatgtgtaataacactggatgaagggac acacactgagacct |
| 676 | snord45a_11_acceptor | GGTCAATGATGTGTTGGCATGTATCAGGTATTCCT GTGGCTGATGTGTAATAACACTGGATGAAGGGAC ACACACTGAGACCT-tatgatagggacttagggtg |
| 677 | snord45a_7_acceptor | GGTCAATGATGTGTTGGCATGTATGGTACAGGTA TTCCTCTGATGTGTAATAACACTCTGTGGATGAAG GGACACTGAGACCT |
| 678 | snord45a_7_acceptor | TATGATAGGGACTTAGGGTG- ggtcaatgatgtgttggcatgtatggt acaggtattcctctgatgtgtaataacactctgtggatgaaggga cactgagacct |

TABLE 4-continued

| | Splice Acceptor sequences targeting snoRNAs | |
|---|---|---|

| SEQ ID NO: | Reference | Sequence |
|---|---|---|
| 679 | snord45a_7_acceptor | GGTCAATGATGTGTTGGCATGTATGGTACAGGTA TTCCTCTGATGTGTAATAACACTCTGTGGATGAAG GGACACTGAGACCT-tatgatagggacttagggtg |
| 680 | aca46_acceptor_29 | AGCACTATAAAGGGACCTGTGGATGGGAATATTC CCCATTCTTGGTACACACATAGTGCAAAAGAATT CCTGGCTCTCTGTTGCACAGCTGACTTGTGCCATT CTGCTGTTGCTGTATAGAGTTAAGGAACATGG |
| 681 | aca46_acceptor_29 | TATGATAGGGACTTAGGGTG- agcactataaagggacctgtggatgggaatattccccattcttgg tacacacatagtgcaaaagaattcctggctctctgttgcacagct gacttgtgccattctgctgttgctgtatagagttaaggaacatgg |
| 682 | aca46_acceptor_29 | AGCACTATAAAGGGACCTGTGGATGGGAATATTC CCCATTCTTGGTACACACATAGTGCAAAAGAATT CCTGGCTCTCTGTTGCACAGCTGACTTGTGCCATT CTGCTGTTGCTGTATAGAGTTAAGGAACATGG- tatgatagggacttagggtg |
| 683 | aca44_2_acceptor_35 | CAGCATGTTTCCAAGGGCTGTGGCTGGTCATAGC CATGGGATCTCCAACTGCATGCAAGAGCAACCTG GAAAGACACACACAGCGCAGGTCAGTACAATACC TGCAAGCTGCATGCCAGCTTTCCTATAATG |
| 684 | aca44_2_acceptor_35 | TATGATAGGGACTTAGGGTG- cagcatgtttccaagggctgtggctggtc atagccatgggatctccaactgcatgcaagagcaacctggaaaga cacacacagcgcaggtcagtacaatacctgcaagctgcatgccag ctttcctataatg |
| 685 | aca44_2_acceptor_35 | CAGCATGTTTCCAAGGGCTGTGGCTGGTCATAGC CATGGGATCTCCAACTGCATGCAAGAGCAACCTG GAAAGACACACACAGCGCAGGTCAGTACAATACC TGCAAGCTGCATGCCAGCTTTCCTATAATG- tatgatagggacttagggtg |

Format for the above sequences:
{Binding Motif}-{Sm consensus/Sm rand}-{U7/U7 rand}_{filler}

Example 4: Design and Testing of U7 snRNA for Trans-Splicing

Figure 10:
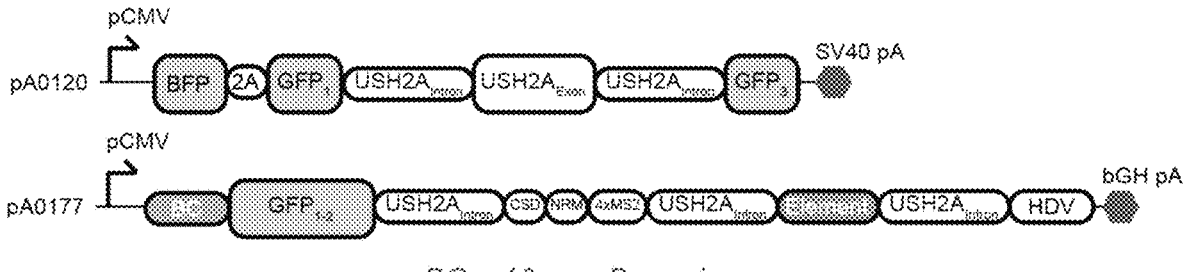
FIG. 10 is an image showing, without wishing to be bound by theory, the design of U7 guide constructs for trans-splicing.

In the experiments of this Example, U7 snRNA guide constructs were developed and tested for trans-splicing. The U7 snRNA guide constructs were designed on a plasmid, along with a sequence that is complementary to a target sequence, to produce a U7 snRNA construct that occludes a splice site, and thereby allows for trans-splicing. To test for trans-splicing, U7 snRNA guides were designed on a plasmid (i.e., pA0120, FIG. 10, Table 2), which also included intron and exon sites of the USH2A gene and two GFP sites (FIG. 10).

Figure 11:
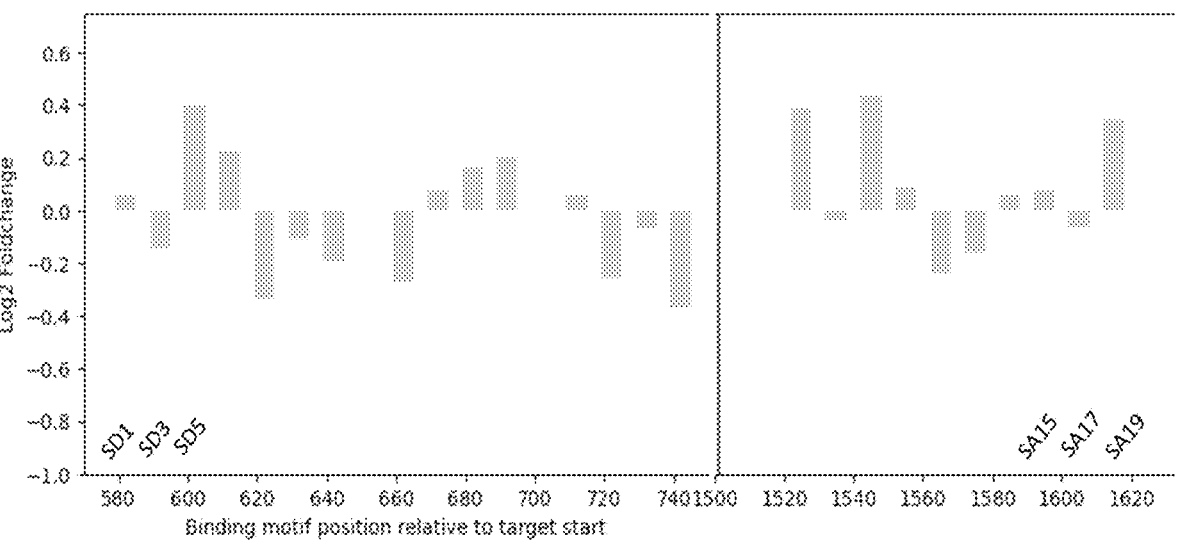
FIG. 11 is a graph showing the binding of the U7 guide constructs to different target elements and the effects of trans-splicing.
Figure 12:
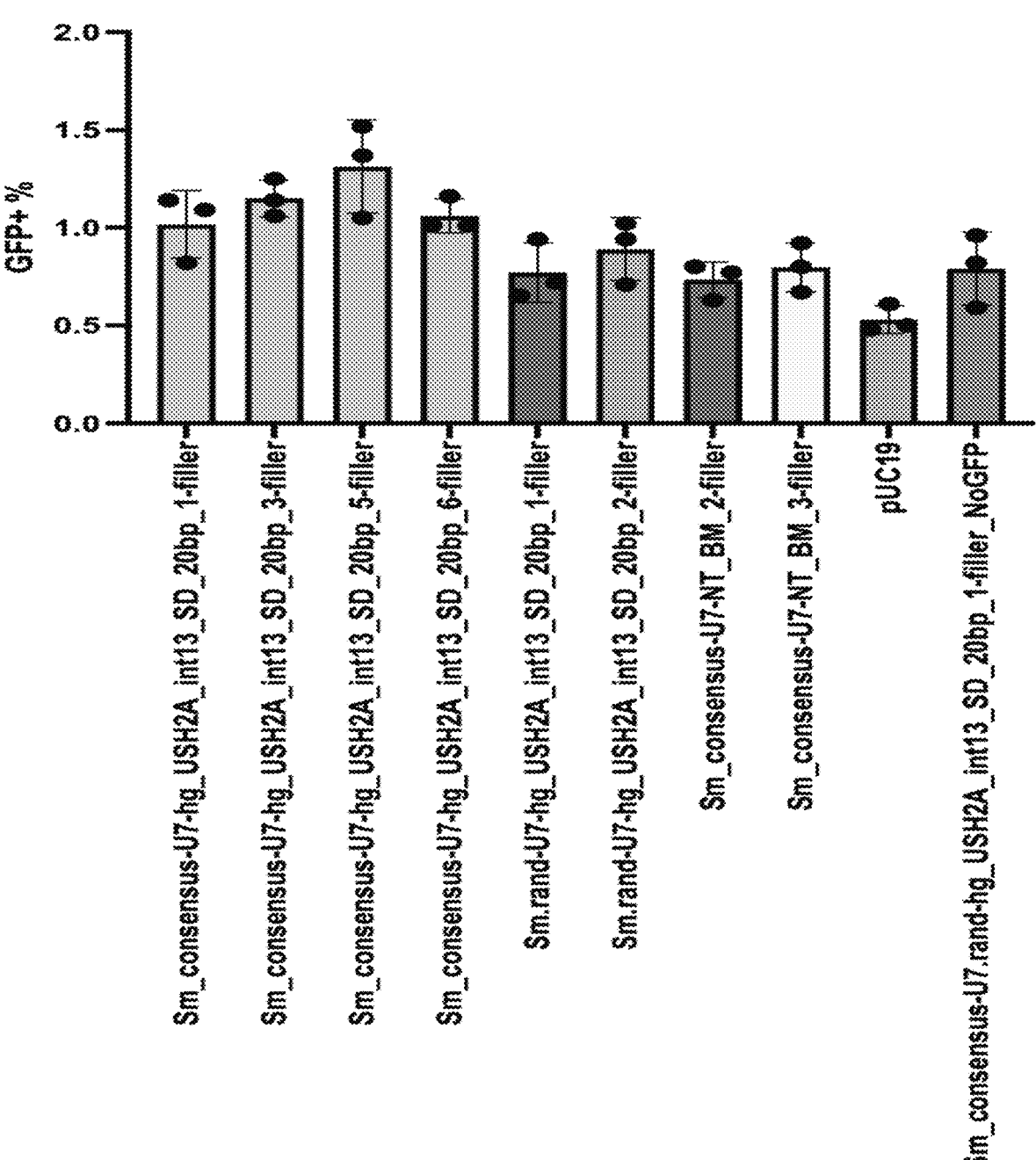
FIG. 12 is a graph showing independent validation of the results from FIG. 11. The first four bars from the left side show U7 constructs with specific targeting elements for trans-splicing, and the remaining bars on the graph show U7 constructs with non-targeting elements for trans-splicing.
Figure 13:
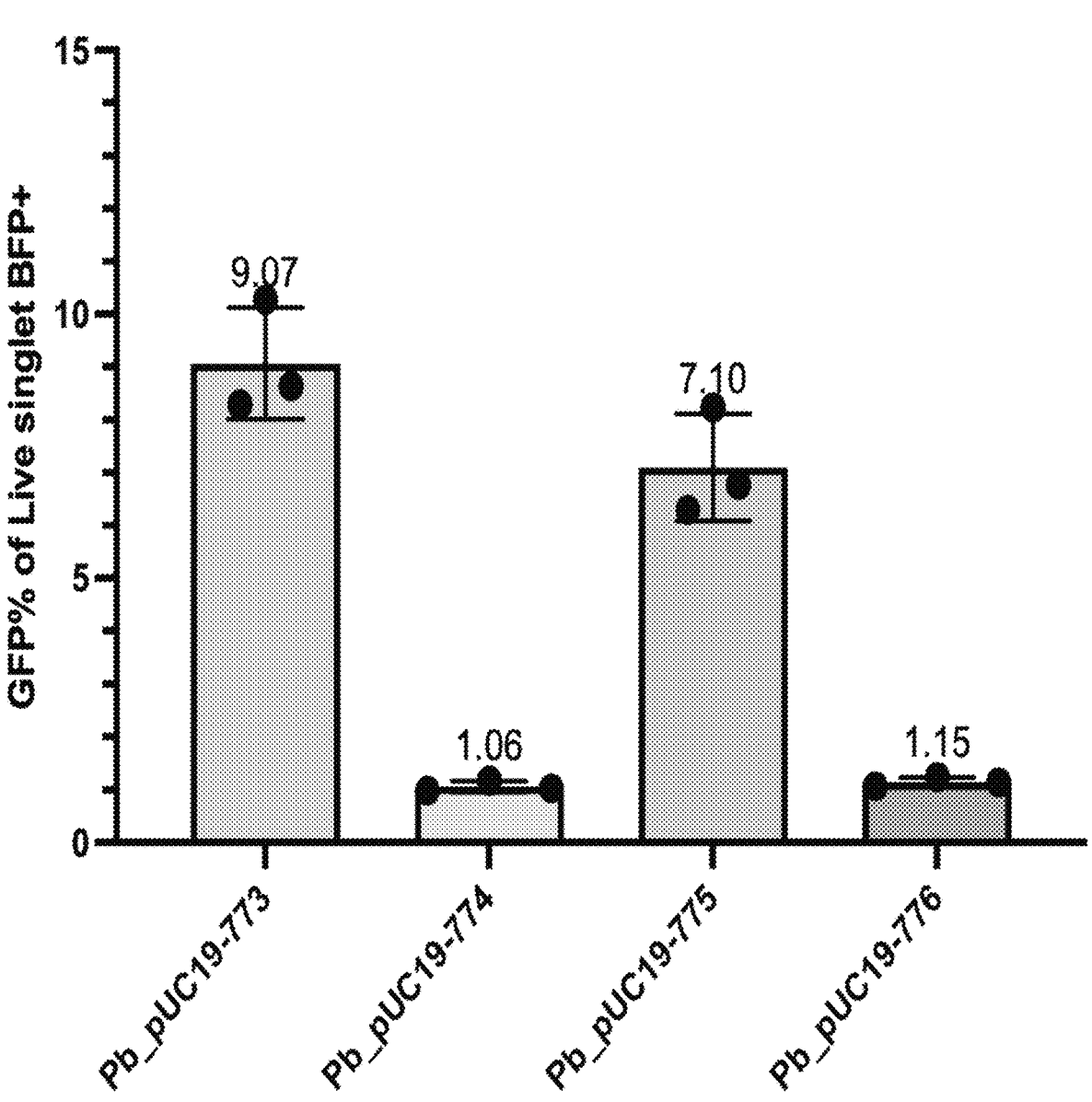
FIG. 13 is a graph showing U7 targeting piggybac-integrated USH2A (773; hybridizing region and hairpin intact) compared to non-targeting guides (774 and 776), and mutated U7 hairpins (775; intact hybridizing region, but hairpin region mutated).

An element was then introduced on a separate plasmid target (i.e., pA0177), which was present after the pCMV promoter and before the bGHpA (FIG. 10), and included additional GFP sites. In these experiments, trans-splicing is observed by the expression of GFP, since the GFP site of the plasmid target (i.e., pA0177) will replace and restore the GFP site of the pA0120 plasmid, thereby demonstrating trans-splicing by GFP expression. FIG. 11 is a graph showing the binding of the U7 snRNA guide constructs to different target elements and the effects of trans-splicing. FIG. 12 is a graph showing independent validation of the results from FIG. 11. The first four bars from the left side show U7 snRNA constructs with specific targeting elements for trans-splicing, and the remaining bars on the graph show U7 snRNA constructs with non-targeting elements for trans-splicing. These experiments show, inter alia, that targeting near the splice donor enhances trans-splicing. FIG. 13 is a graph showing U7 snRNA targeting piggybac-integrated USH2A (773; hybridizing region and hairpin intact) compared to non-targeting guides (774 and 776), and mutated U7 snRNA hairpins (775; intact hybdrizing region, but hairpin region mutated). These experiments further show, inter alia, that targeting a complementary region with a U7 snRNA construct that has both the hairpin and hybridizing region leads to significantly higher trans-splicing compared to a non-targeting control.

TABLE 2

| Category | description | element_seq |
|---|---|---|
| SD targeting | Sm_consensus-U7- hg_USH2A_int13_SD_20b p_1-filler | (SEQ ID NO: 658) ACACAGGCACTGGCCACTGA- AATTTTTGGAG- (SEQ ID NO: 659) taggctttctggcttttcaccggaaagcccct_AAATGATTAAATTAA |

TABLE 2-continued

| Category | description | element_seq |
|---|---|---|
| SD targeting | Sm_consensus-U7-hg_USH2A_int13_SD_20bp_3-filler | (SEQ ID NO: 660) GATTAGGCACACACAGGCAC-AATTTTTGGAG-<br>(SEQ ID NO: 661)<br>taggctttctggcttttcaccggaaagcccct_AAATGATTAAATTAA |
| SD targeting | Sm_consensus-U7-hg_USH2A_int13_SD_20bp_5-filler | (SEQ ID NO: 662) CTTCCTTGACGATTAGGCAC-AATTTTTGGAG-<br>(SEQ ID NO: 663)<br>taggctttctggcttttcaccggaaagcccct_AAATGATTAAATTAA |
| SD targeting | Sm_consensus-U7-hg_USH2A_int13_SD_20bp_6-filler | (SEQ ID NO: 664) ACCTTCTTCCTTGACGATTA-AATTTTTGGAG-<br>(SEQ ID NO: 665)<br>taggctttctggcttttcaccggaaagcccct_AAATGATTAAATTAA |
| Random U7 control | Sm.rand-U7-hg_USH2A_int13_SD_20bp_1-filler | (SEQ ID NO: 666) ACACAGGCACTGGCCACTGA-TGCGTGTCATT-<br>(SEQ ID NO: 667)<br>taggctttctggcttttcaccggaaagcccct_AAATGATTAAATTAA |
| Random U7 control | Sm.rand-U7-hg_USH2A_int13_SD_20bp_2-filler | (SEQ ID NO: 668) GGCACACACAGGCACTGGCC-TGCGTGTCATT-<br>(SEQ ID NO: 669)<br>taggctttctggcttttcaccggaaagcccct_AAATGATTAAATTAA |
| Random Sm control | Sm_consensus-U7-NT_BM_2-filler | (SEQ ID NO: 670) ACGAGCTCAGCCTATGCGAG-AATTTTTGGAG-<br>(SEQ ID NO: 671)<br>taggctttctggcttttcaccggaaagcccct_AAATGATTAAATTAA |
| Random Sm control | Sm_consensus-U7-NT_BM_3-filler | (SEQ ID NO: 672) CCACCTACCCTATCGTGCGG-AATTTTTGGAG-<br>(SEQ ID NO: 673)<br>taggctttctggcttttcaccggaaagcccct_AAATGATTAAATTAA |

Format for the above sequences:
(Binding Motif)-{Sm consensus/Sm rand}-{U7/U7rand}_{filler}

TABLE_3

SEQUENCE_LISTING

| SEQ ID NO | Name/ ID | Sequence |
|---|---|---|
| 1 | H box | ANANNA N = A, C, G, OR U |
| 2 | ACA box | ACA |
| 3 | Sm consensus motf | AAUUUUUGG |
| 4 | Sm U7 motif | AAUUUGUCU |
| 5 | C box | RUGAUGA R = A OR G |
| 6 | D box | CUGA |
| 7 | C' box | RUGAUGA |
| 8 | D' box | CUGA |
| 9 | U1_1_0 | AUACUUACGUAACAGGAGAAAAUACGGCCAUGAAGUUGGUGUUUCUCGGGG<br>GCGAUUUCUCCAUUGUACUCAGUAUGUGCUGACUGACUCCUGUUACUUCCA<br>CAUGUGGGGGAAACUGGACUGUAAUUUGUGGUGGUGGGGGAAUUGCGUUCGCG<br>C |
| 10 | U1_1_1 | UACUUACGUAACAGGAGAAAAUACGGCCAUGAAGUUGGUGUUUCUCGGGGG<br>CGAUUUCUCCAUUGUACUCAGUAUGUGCUGACUGACUCCUGUUACUUCCAC<br>AUGUGGGGGAAACUGGACUGUAAUUUGUGGUGGUGGGGGAAUUGCGUUCGCGC<br>U |

TABLE_3-continued

| | | SEQUENCE_LISTING |
|---|---|---|

| SEQ ID NO | Name/ ID | Sequence |
|---|---|---|
| 11 | U1_1_2 | ACUUACGUAACAGGAGAAAAUACGGCCAUGAAGUUGGUGUUUCUCGGGGGC GAUUUCUCCAUUGUACUCAGUAUGUGCUGACUGACUCCUGUUACUUCCACA UGUGGGGAAACUGGACUGUAAUUUGUGGUGGUGGGGAAUUGCGUUCGCGCU U |
| 12 | U1_1_3 | CUUACGUAACAGGAGAAAAUACGGCCAUGAAGUUGGUGUUUCUCGGGGGCG AUUUCUCCAUUGUACUCAGUAUGUGCUGACUGACUCCUGUUACUUCCACAU GUGGGGAAACUGGACUGUAAUUUGUGGUGGUGGGGAAUUGCGUUCGCGCUU U |
| 13 | U1_1_4 | UUACGUAACAGGAGAAAAUACGGCCAUGAAGUUGGUGUUUCUCGGGGGCGA UUUCUCCAUUGUACUCAGUAUGUGCUGACUGACUCCUGUUACUUCCACAUG UGGGGAAACUGGACUGUAAUUUGUGGUGGUGGGGAAUUGCGUUCGCGCUUU C |
| 14 | U1_1_5 | UACGUAACAGGAGAAAAUACGGCCAUGAAGUUGGUGUUUCUCGGGGGCGAU UUCUCCAUUGUACUCAGUAUGUGCUGACUGACUCCUGUUACUUCCACAUGU GGGGAAACUGGACUGUAAUUUGUGGUGGUGGGGAAUUGCGUUCGCGCUUUC U |
| 15 | U1_1_6 | ACGUAACAGGAGAAAAUACGGCCAUGAAGUUGGUGUUUCUCGGGGGCGAUU UCUCCAUUGUACUCAGUAUGUGCUGACUGACUCCUGUUACUUCCACAUGUG GGGAAACUGGACUGUAAUUUGUGGUGGUGGGGAAUUGCGUUCGCGCUUUCU U |
| 16 | U1_1_7 | CGUAACAGGAGAAAAUACGGCCAUGAAGUUGGUGUUUCUCGGGGGCGAUUU CUCCAUUGUACUCAGUAUGUGCUGACUGACUCCUGUUACUUCCACAUGUGG GGAAACUGGACUGUAAUUUGUGGUGGUGGGGAAUUGCGUUCGCGCUUUCUU C |
| 17 | U1_1_8 | GUAACAGGAGAAAAUACGGCCAUGAAGUUGGUGUUUCUCGGGGGCGAUUUC UCCAUUGUACUCAGUAUGUGCUGACUGACUCCUGUUACUUCCACAUGUGGG GAAACUGGACUGUAAUUUGUGGUGGUGGGGAAUUGCGUUCGCGCUUUCUUC U |
| 18 | U1_1_9 | UAACAGGAGAAAAUACGGCCAUGAAGUUGGUGUUUCUCGGGGGCGAUUUCU CCAUUGUACUCAGUAUGUGCUGACUGACUCCUGUUACUUCCACAUGUGGGG AAACUGGACUGUAAUUUGUGGUGGUGGGGAAUUGCGUUCGCGCUUUCUUCU |
| 19 | U1_2_0 | AUAUUUACUUGGCAGGGGAGAUAACGUGACCACGAAGGUGGUUUUCCCAGG GCUGAGGCUUAUUCAUUGUACUCCGGAUGUGCUGACCCCUGCGAUUUCCCC AAAUGUGGGAAACUCGACUGCAUAAUUUGUGGUAGUGGGGGGCUGUGUCCG U |
| 20 | U1_2_1 | UAUUUACUUGGCAGGGGAGAUAACGUGACCACGAAGGUGGUUUUCCCAGGG CUGAGGCUUAUUCAUUGUACUCCGGAUGUGCUGACCCCUGCGAUUUCCCCA AAUGUGGGAAACUCGACUGCAUAAUUUGUGGUAGUGGGGGGCUGUGUCCGU G |
| 21 | U1_2_2 | AUUUACUUGGCAGGGGAGAUAACGUGACCACGAAGGUGGUUUUCCCAGGGC UGAGGCUUAUUCAUUGUACUCCGGAUGUGCUGACCCCUGCGAUUUCCCCAA AUGUGGGAAACUCGACUGCAUAAUUUGUGGUAGUGGGGGGCUGUGUCCGUG C |
| 22 | U1_2_3 | UUUACUUGGCAGGGGAGAUAACGUGACCACGAAGGUGGUUUUCCCAGGGCU GAGGCUUAUUCAUUGUACUCCGGAUGUGCUGACCCCUGCGAUUUCCCCAAA UGUGGGAAACUCGACUGCAUAAUUUGUGGUAGUGGGGGGCUGUGUCCGUGC U |
| 23 | U1_2_4 | UUACUUGGCAGGGGAGAUAACGUGACCACGAAGGUGGUUUUCCCAGGGCUG AGGCUUAUUCAUUGUACUCCGGAUGUGCUGACCCCUGCGAUUUCCCCAAAU GUGGGAAACUCGACUGCAUAAUUUGUGGUAGUGGGGGGCUGUGUCCGUGCU U |
| 24 | U1_2_5 | UACUUGGCAGGGGAGAUAACGUGACCACGAAGGUGGUUUUCCCAGGGCUGA GGCUUAUUCAUUGUACUCCGGAUGUGCUGACCCCUGCGAUUUCCCCAAAUG UGGGAAACUCGACUGCAUAAUUUGUGGUAGUGGGGGGCUGUGUCCGUGCUU U |

US 12,668,800 B2

73 74

TABLE_3-continued

SEQUENCE_LISTING

| SEQ ID NO | Name/ ID | Sequence |
|---|---|---|
| 25 | U1_2_6 | ACUUGGCAGGGGAGAUAACGUGACCACGAAGGUGGUUUUCCCAGGGCUGAG<br>GCUUAUUCAUUGUACUCCGGAUGUGCUGACCCCUGCGAUUUCCCCAAAUGU<br>GGGAAACUCGACUGCAUAAUUUGUGGUAGUGGGGGGCUGUGUCCGUGCUUU<br>U |
| 26 | U1_2_7 | CUUGGCAGGGGAGAUAACGUGACCACGAAGGUGGUUUUCCCAGGGCUGAGG<br>CUUAUUCAUUGUACUCCGGAUGUGCUGACCCCUGCGAUUUCCCCAAAUGUG<br>GGAAACUCGACUGCAUAAUUUGUGGUAGUGGGGGGCUGUGUCCGUGCUUUU<br>C |
| 27 | U1_2_8 | UUGGCAGGGGAGAUAACGUGACCACGAAGGUGGUUUUCCCAGGGCUGAGGC<br>UUAUUCAUUGUACUCCGGAUGUGCUGACCCCUGCGAUUUCCCCAAAUGUGG<br>GAAACUCGACUGCAUAAUUUGUGGUAGUGGGGGGCUGUGUCCGUGCUUUUC<br>C |
| 28 | U1_2_9 | UGGCAGGGGAGAUAACGUGACCACGAAGGUGGUUUUCCCAGGGCUGAGGCU<br>UAUUCAUUGUACUCCGGAUGUGCUGACCCCUGCGAUUUCCCCAAAUGUGGG<br>AAACUCGACUGCAUAAUUUGUGGUAGUGGGGGGCUGUGUCCGUGCUUUUCC<br>C |
| 29 | U1_3_0 | AUACUUACCUGGCAGGGCAGAUACCAUGAUCUUAAAGGCAGUUUUCCCAGG<br>GCAAGGCUUAUCCAUUCCACUCUGGAUCCAUUAUAGGGGCAUGCUGAUCCC<br>UGGAAUUGCCCCAAAUGUGGGAAGCUCUACUGCAAAAUUUUUGGUAGUGAG<br>C |
| 30 | U1_3_1 | UACUUACCUGGCAGGGCAGAUACCAUGAUCUUAAAGGCAGUUUUCCCAGGG<br>CAAGGCUUAUCCAUUCCACUCUGGAUCCAUUAUAGGGGCAUGCUGAUCCCU<br>GGAAUUGCCCCAAAUGUGGGAAGCUCUACUGCAAAAUUUUUGGUAGUGAGC<br>G |
| 31 | U1_3_2 | ACUUACCUGGCAGGGCAGAUACCAUGAUCUUAAAGGCAGUUUUCCCAGGGC<br>AAGGCUUAUCCAUUCCACUCUGGAUCCAUUAUAGGGGCAUGCUGAUCCCUG<br>GAAUUGCCCCAAAUGUGGGAAGCUCUACUGCAAAAUUUUUGGUAGUGAGCG<br>A |
| 32 | U1_3_3 | CUUACCUGGCAGGGCAGAUACCAUGAUCUUAAAGGCAGUUUUCCCAGGGCA<br>AGGCUUAUCCAUUCCACUCUGGAUCCAUUAUAGGGGCAUGCUGAUCCCUGG<br>AAUUGCCCCAAAUGUGGGAAGCUCUACUGCAAAAUUUUUGGUAGUGAGCGA<br>U |
| 33 | U1_3_4 | UUACCUGGCAGGGCAGAUACCAUGAUCUUAAAGGCAGUUUUCCCAGGGCAA<br>GGCUUAUCCAUUCCACUCUGGAUCCAUUAUAGGGGCAUGCUGAUCCCUGGA<br>AUUGCCCCAAAUGUGGGAAGCUCUACUGCAAAAUUUUUGGUAGUGAGCGAU<br>G |
| 34 | U1_3_5 | UACCUGGCAGGGCAGAUACCAUGAUCUUAAAGGCAGUUUUCCCAGGGCAAG<br>GCUUAUCCAUUCCACUCUGGAUCCAUUAUAGGGGCAUGCUGAUCCCUGGAA<br>UUGCCCCAAAUGUGGGAAGCUCUACUGCAAAAUUUUUGGUAGUGAGCGAUG<br>G |
| 35 | U1_3_6 | ACCUGGCAGGGCAGAUACCAUGAUCUUAAAGGCAGUUUUCCCAGGGCAAGG<br>CUUAUCCAUUCCACUCUGGAUCCAUUAUAGGGGCAUGCUGAUCCCUGGAAU<br>UGCCCCAAAUGUGGGAAGCUCUACUGCAAAAUUUUUGGUAGUGAGCGAUGG<br>C |
| 36 | U1_3_7 | CCUGGCAGGGCAGAUACCAUGAUCUUAAAGGCAGUUUUCCCAGGGCAAGGC<br>UUAUCCAUUCCACUCUGGAUCCAUUAUAGGGGCAUGCUGAUCCCUGGAAUU<br>GCCCCAAAUGUGGGAAGCUCUACUGCAAAAUUUUUGGUAGUGAGCGAUGGC<br>A |
| 37 | U1_3_8 | CUGGCAGGGCAGAUACCAUGAUCUUAAAGGCAGUUUUCCCAGGGCAAGGCU<br>UAUCCAUUCCACUCUGGAUCCAUUAUAGGGGCAUGCUGAUCCCUGGAAUUG<br>CCCCAAAUGUGGGAAGCUCUACUGCAAAAUUUUUGGUAGUGAGCGAUGGCA<br>U |
| 38 | U1_3_9 | UGGCAGGGCAGAUACCAUGAUCUUAAAGGCAGUUUUCCCAGGGCAAGGCUU<br>AUCCAUUCCACUCUGGAUCCAUUAUAGGGGCAUGCUGAUCCCUGGAAUUGC<br>CCCAAAUGUGGGAAGCUCUACUGCAAAAUUUUUGGUAGUGAGCGAUGGCAU<br>U |
| 39 | U1_4_0 | AUACUUACCUGGCAGGGGAGAUACCAUGAUCACGAAGGUGGUUUUCCCAGG<br>GCGAGGCUUAUCCAUUGCACUCCGGAUGUGCUGACCCCUGCGAUUUCCCCA<br>AAUGUGGGAAACUCGACUGCAUAAUUUGUGGUAGUGGGGGACUGCGUUCGC<br>G |

TABLE_3-continued

SEQUENCE_LISTING

| SEQ ID NO | Name/ ID | Sequence |
|---|---|---|
| 40 | U1_4_1 | UACUUACCUGGCAGGGGAGAUACCAUGAUCACGAAGGUGGUUUUCCCAGGG CGAGGCUUAUCCAUUGCACUCCGGAUGUGCUGACCCCUGCGAUUUCCCCAA AUGUGGGAAACUCGACUGCAUAAUUUGUGGUAGUGGGGGACUGCGUUCGCG C |
| 41 | U1_4_2 | ACUUACCUGGCAGGGGAGAUACCAUGAUCACGAAGGUGGUUUUCCCAGGGC GAGGCUUAUCCAUUGCACUCCGGAUGUGCUGACCCCUGCGAUUUCCCCAAA UGUGGGAAACUCGACUGCAUAAUUUGUGGUAGUGGGGGACUGCGUUCGCGC U |
| 42 | U1_4_3 | CUUACCUGGCAGGGGAGAUACCAUGAUCACGAAGGUGGUUUUCCCAGGGCG AGGCUUAUCCAUUGCACUCCGGAUGUGCUGACCCCUGCGAUUUCCCCAAAU GUGGGAAACUCGACUGCAUAAUUUGUGGUAGUGGGGGACUGCGUUCGCGCU U |
| 43 | U1_4_4 | UUACCUGGCAGGGGAGAUACCAUGAUCACGAAGGUGGUUUUCCCAGGGCGA GGCUUAUCCAUUGCACUCCGGAUGUGCUGACCCCUGCGAUUUCCCCAAAUG UGGGAAACUCGACUGCAUAAUUUGUGGUAGUGGGGGACUGCGUUCGCGCUU U |
| 44 | U1_4_5 | UACCUGGCAGGGGAGAUACCAUGAUCACGAAGGUGGUUUUCCCAGGGCGAG GCUUAUCCAUUGCACUCCGGAUGUGCUGACCCCUGCGAUUUCCCCAAAUGU GGGAAACUCGACUGCAUAAUUUGUGGUAGUGGGGGACUGCGUUCGCGCUUU C |
| 45 | U1_4_6 | ACCUGGCAGGGGAGAUACCAUGAUCACGAAGGUGGUUUUCCCAGGGCGAGG CUUAUCCAUUGCACUCCGGAUGUGCUGACCCCUGCGAUUUCCCCAAAUGUG GGAAACUCGACUGCAUAAUUUGUGGUAGUGGGGGACUGCGUUCGCGCUUUC C |
| 46 | U1_4_7 | CCUGGCAGGGGAGAUACCAUGAUCACGAAGGUGGUUUUCCCAGGGCGAGGC UUAUCCAUUGCACUCCGGAUGUGCUGACCCCUGCGAUUUCCCCAAAUGUGG GAAACUCGACUGCAUAAUUUGUGGUAGUGGGGGACUGCGUUCGCGCUUUCC C |
| 47 | U1_4_8 | CUGGCAGGGGAGAUACCAUGAUCACGAAGGUGGUUUUCCCAGGGCGAGGCU UAUCCAUUGCACUCCGGAUGUGCUGACCCCUGCGAUUUCCCCAAAUGUGGG AAACUCGACUGCAUAAUUUGUGGUAGUGGGGGACUGCGUUCGCGCUUUCCC C |
| 48 | U1_4_9 | UGGCAGGGGAGAUACCAUGAUCACGAAGGUGGUUUUCCCAGGGCGAGGCUU AUCCAUUGCACUCCGGAUGUGCUGACCCCUGCGAUUUCCCCAAAUGUGGGA AACUCGACUGCAUAAUUUGUGGUAGUGGGGGACUGCGUUCGCGCUUUCCCC U |
| 49 | U1_5_0 | AUACUUCCCUGACAGGGGAGAUACCUAGGAAUCCAACUUCCCAGGGCAAGA CUGAUCUAUUGCACUAUGGAUGUGCCGACCCCUGAGAUUUACAAAAUUGUG GGAAACUCAACUGCAUAAUUUAUGGAAAUGAAGGACUGUGUUUGCGCUUUC A |
| 50 | U1_5_1 | UACUUCCCUGACAGGGGAGAUACCUAGGAAUCCAACUUCCCAGGGCAAGAC UGAUCUAUUGCACUAUGGAUGUGCCGACCCCUGAGAUUUACAAAAUUGUGG GAAACUCAACUGCAUAAUUUAUGGAAAUGAAGGACUGUGUUUGCGCUUUCA |
| 51 | U1_5_2 | ACUUCCCUGACAGGGGAGAUACCUAGGAAUCCAACUUCCCAGGGCAAGACU GAUCUAUUGCACUAUGGAUGUGCCGACCCCUGAGAUUUACAAAAUUGUGGG AAACUCAACUGCAUAAUUUAUGGAAAUGAAGGACUGUGUUUGCGCUUUCA |
| 52 | U1_5_3 | CUUCCCUGACAGGGGAGAUACCUAGGAAUCCAACUUCCCAGGGCAAGACUG AUCUAUUGCACUAUGGAUGUGCCGACCCCUGAGAUUUACAAAAUUGUGGGA AACUCAACUGCAUAAUUUAUGGAAAUGAAGGACUGUGUUUGCGCUUUCA |
| 53 | U1_5_4 | UUCCCUGACAGGGGAGAUACCUAGGAAUCCAACUUCCCAGGGCAAGACUGA UCUAUUGCACUAUGGAUGUGCCGACCCCUGAGAUUUACAAAAUUGUGGGAA ACUCAACUGCAUAAUUUAUGGAAAUGAAGGACUGUGUUUGCGCUUUCA |
| 54 | U1_5_5 | UCCCUGACAGGGGAGAUACCUAGGAAUCCAACUUCCCAGGGCAAGACUGAU CUAUUGCACUAUGGAUGUGCCGACCCCUGAGAUUUACAAAAUUGUGGGAAA CUCAACUGCAUAAUUUAUGGAAAUGAAGGACUGUGUUUGCGCUUUCA |
| 55 | U1_5_6 | CCCUGACAGGGGAGAUACCUAGGAAUCCAACUUCCCAGGGCAAGACUGAUC UAUUGCACUAUGGAUGUGCCGACCCCUGAGAUUUACAAAAUUGUGGGAAAC UCAACUGCAUAAUUUAUGGAAAUGAAGGACUGUGUUUGCGCUUUCA |

TABLE_3-continued

| | | SEQUENCE_LISTING |
|---|---|---|

| SEQ ID NO | Name/ ID | Sequence |
|---|---|---|
| 56 | U1_5_7 | CCUGACAGGGGAGAUACCUAGGAAUCCAACUUCCCAGGGCAAGACUGAUCU<br>AUUGCACUAUGGAUGUGCCGACCCCUGAGAUUUACAAAAUUGUGGGAAACU<br>CAACUGCAUAAUUUAUGGAAAUGAAGGACUGUGUUUGCGCUUUCA |
| 57 | U1_5_8 | CUGACAGGGGAGAUACCUAGGAAUCCAACUUCCCAGGGCAAGACUGAUCUA<br>UUGCACUAUGGAUGUGCCGACCCCUGAGAUUUACAAAAUUGUGGGAAACUC<br>AACUGCAUAAUUUAUGGAAAUGAAGGACUGUGUUUGCGCUUUCA |
| 58 | U1_5_9 | UGACAGGGGAGAUACCUAGGAAUCCAACUUCCCAGGGCAAGACUGAUCUAU<br>UGCACUAUGGAUGUGCCGACCCCUGAGAUUUACAAAAUUGUGGGAAACUCA<br>ACUGCAUAAUUUAUGGAAAUGAAGGACUGUGUUUGCGCUUUCA |
| 59 | U1_6_0 | AAACUUCUCUGCCAGGGGAGAUACCAUGAUCACAAAGGUGGCUUUCUCAGG<br>GAAAGGCUGAUUUAUUGCACUCCAGAUGUGCUGACCCCUGAGAUUUCUCCA<br>AAUGUGGGAAACUCAGCUGCAUAAUUUGUGGAAGCGAAGGACUGUGUUUGU<br>G |
| 60 | U1_6_1 | AACUUCUCUGCCAGGGGAGAUACCAUGAUCACAAAGGUGGCUUUCUCAGGG<br>AAAGGCUGAUUUAUUGCACUCCAGAUGUGCUGACCCCUGAGAUUUCUCCAA<br>AUGUGGGAAACUCAGCUGCAUAAUUUGUGGAAGCGAAGGACUGUGUUUGUG<br>C |
| 61 | U1_6_2 | ACUUCUCUGCCAGGGGAGAUACCAUGAUCACAAAGGUGGCUUUCUCAGGGA<br>AAGGCUGAUUUAUUGCACUCCAGAUGUGCUGACCCCUGAGAUUUCUCCAAA<br>UGUGGGAAACUCAGCUGCAUAAUUUGUGGAAGCGAAGGACUGUGUUUGUGC<br>U |
| 62 | U1_6_3 | CUUCUCUGCCAGGGGAGAUACCAUGAUCACAAAGGUGGCUUUCUCAGGGAA<br>AGGCUGAUUUAUUGCACUCCAGAUGUGCUGACCCCUGAGAUUUCUCCAAAU<br>GUGGGAAACUCAGCUGCAUAAUUUGUGGAAGCGAAGGACUGUGUUUGUGCU<br>U |
| 63 | U1_6_4 | UUCUCUGCCAGGGGAGAUACCAUGAUCACAAAGGUGGCUUUCUCAGGGAAA<br>GGCUGAUUUAUUGCACUCCAGAUGUGCUGACCCCUGAGAUUUCUCCAAAUG<br>UGGGAAACUCAGCUGCAUAAUUUGUGGAAGCGAAGGACUGUGUUUGUGCUU<br>U |
| 64 | U1_6_5 | UCUCUGCCAGGGGAGAUACCAUGAUCACAAAGGUGGCUUUCUCAGGGAAAG<br>GCUGAUUUAUUGCACUCCAGAUGUGCUGACCCCUGAGAUUUCUCCAAAUGU<br>GGGAAACUCAGCUGCAUAAUUUGUGGAAGCGAAGGACUGUGUUUGUGCUUU<br>C |
| 65 | U1_6_6 | CUCUGCCAGGGGAGAUACCAUGAUCACAAAGGUGGCUUUCUCAGGGAAAGG<br>CUGAUUUAUUGCACUCCAGAUGUGCUGACCCCUGAGAUUUCUCCAAAUGUG<br>GGAAACUCAGCUGCAUAAUUUGUGGAAGCGAAGGACUGUGUUUGUGCUUUC<br>A |
| 66 | U1_6_7 | UCUGCCAGGGGAGAUACCAUGAUCACAAAGGUGGCUUUCUCAGGGAAAGGC<br>UGAUUUAUUGCACUCCAGAUGUGCUGACCCCUGAGAUUUCUCCAAAUGUGG<br>GAAACUCAGCUGCAUAAUUUGUGGAAGCGAAGGACUGUGUUUGUGCUUUCA<br>U |
| 67 | U1_6_8 | CUGCCAGGGGAGAUACCAUGAUCACAAAGGUGGCUUUCUCAGGGAAAGGCU<br>GAUUUAUUGCACUCCAGAUGUGCUGACCCCUGAGAUUUCUCCAAAUGUGGG<br>AAACUCAGCUGCAUAAUUUGUGGAAGCGAAGGACUGUGUUUGUGCUUUCAU<br>G |
| 68 | U1_6_9 | UGCCAGGGGAGAUACCAUGAUCACAAAGGUGGCUUUCUCAGGGAAAGGCUG<br>AUUUAUUGCACUCCAGAUGUGCUGACCCCUGAGAUUUCUCCAAAUGUGGGA<br>AACUCAGCUGCAUAAUUUGUGGAAGCGAAGGACUGUGUUUGUGCUUUCAUG<br>U |
| 69 | U1_7_0 | AUACUUCUCUGCCAGGGGAGAUACUGUGAUCAUGAAGGUGGCUUUCCCAGG<br>GCAAGGCUGAUCUAUUGCAUUCUGGAUGUGCUGACUCCUACGAUUUCCCCA<br>AGUGUGGGAAACUCAACUGCAUAAUUUGUGGAAGUAAUGACUGUGUUUGCA<br>C |
| 70 | U1_7_1 | UACUUCUCUGCCAGGGGAGAUACUGUGAUCAUGAAGGUGGCUUUCCCAGGG<br>CAAGGCUGAUCUAUUGCAUUCUGGAUGUGCUGACUCCUACGAUUUCCCCAA<br>GUGUGGGAAACUCAACUGCAUAAUUUGUGGAAGUAAUGACUGUGUUUGCAC<br>U |

TABLE_3-continued

SEQUENCE_LISTING

| SEQ ID NO | Name/ ID | Sequence |
|---|---|---|
| 71 | U1_7_2 | ACUUCUCUGCCAGGGGAGAUACUGUGAUCAUGAAGGUGGCUUUCCCAGGGC AAGGCUGAUCUAUUGCAUUCUGGAUGUGCUGACUCCUACGAUUUCCCCAAG UGUGGGAAACUCAACUGCAUAAUUUGUGGAAGUAAUGACUGUGUUUGCACU U |
| 72 | U1_7_3 | CUUCUCUGCCAGGGGAGAUACUGUGAUCAUGAAGGUGGCUUUCCCAGGGCA AGGCUGAUCUAUUGCAUUCUGGAUGUGCUGACUCCUACGAUUUCCCCAAGU GUGGGAAACUCAACUGCAUAAUUUGUGGAAGUAAUGACUGUGUUUGCACUU U |
| 73 | U1_7_4 | UUCUCUGCCAGGGGAGAUACUGUGAUCAUGAAGGUGGCUUUCCCAGGGCAA GGCUGAUCUAUUGCAUUCUGGAUGUGCUGACUCCUACGAUUUCCCCAAGUG UGGGAAACUCAACUGCAUAAUUUGUGGAAGUAAUGACUGUGUUUGCACUUU C |
| 74 | U1_7_5 | UCUCUGCCAGGGGAGAUACUGUGAUCAUGAAGGUGGCUUUCCCAGGGCAAG GCUGAUCUAUUGCAUUCUGGAUGUGCUGACUCCUACGAUUUCCCCAAGUGU GGGAAACUCAACUGCAUAAUUUGUGGAAGUAAUGACUGUGUUUGCACUUUC A |
| 75 | U1_7_6 | CUCUGCCAGGGGAGAUACUGUGAUCAUGAAGGUGGCUUUCCCAGGGCAAGG CUGAUCUAUUGCAUUCUGGAUGUGCUGACUCCUACGAUUUCCCCAAGUGUG GGAAACUCAACUGCAUAAUUUGUGGAAGUAAUGACUGUGUUUGCACUUUCA C |
| 76 | U1_7_7 | UCUGCCAGGGGAGAUACUGUGAUCAUGAAGGUGGCUUUCCCAGGGCAAGGC UGAUCUAUUGCAUUCUGGAUGUGCUGACUCCUACGAUUUCCCCAAGUGUGG GAAACUCAACUGCAUAAUUUGUGGAAGUAAUGACUGUGUUUGCACUUUCAC G |
| 77 | U1_7_8 | CUGCCAGGGGAGAUACUGUGAUCAUGAAGGUGGCUUUCCCAGGGCAAGGCU GAUCUAUUGCAUUCUGGAUGUGCUGACUCCUACGAUUUCCCCAAGUGUGGG AAACUCAACUGCAUAAUUUGUGGAAGUAAUGACUGUGUUUGCACUUUCACG U |
| 78 | U1_7_9 | UGCCAGGGGAGAUACUGUGAUCAUGAAGGUGGCUUUCCCAGGGCAAGGCUG AUCUAUUGCAUUCUGGAUGUGCUGACUCCUACGAUUUCCCCAAGUGUGGGA AACUCAACUGCAUAAUUUGUGGAAGUAAUGACUGUGUUUGCACUUUCACGU |
| 79 | U1_8_0 | AUACUUCCCUGCCAGGGGAGAUACCGUGAUCAUGAAGGUGGCUUUCCCAGG GAAAGGCCGAUAUGUUGCACUCUAGAUGUGCUGACCCGUGAGAUUUCCCCA AAUGUGGGACACUCAAAUGCAUAAUUGGUGGAAGUGAAGGACUGUGUUUGU G |
| 80 | U1_8_1 | UACUUCCCUGCCAGGGGAGAUACCGUGAUCAUGAAGGUGGCUUUCCCAGGG AAAGGCCGAUAUGUUGCACUCUAGAUGUGCUGACCCGUGAGAUUUCCCCAA AUGUGGGACACUCAAAUGCAUAAUUGGUGGAAGUGAAGGACUGUGUUUGUG C |
| 81 | U1_8_2 | ACUUCCCUGCCAGGGGAGAUACCGUGAUCAUGAAGGUGGCUUUCCCAGGGA AAGGCCGAUAUGUUGCACUCUAGAUGUGCUGACCCGUGAGAUUUCCCCAAA UGUGGGACACUCAAAUGCAUAAUUGGUGGAAGUGAAGGACUGUGUUUGUGC U |
| 82 | U1_8_3 | CUUCCCUGCCAGGGGAGAUACCGUGAUCAUGAAGGUGGCUUUCCCAGGGAA AGGCCGAUAUGUUGCACUCUAGAUGUGCUGACCCGUGAGAUUUCCCCAAAU GUGGGACACUCAAAUGCAUAAUUGGUGGAAGUGAAGGACUGUGUUUGUGCU U |
| 83 | U1_8_4 | UUCCCUGCCAGGGGAGAUACCGUGAUCAUGAAGGUGGCUUUCCCAGGGAAA GGCCGAUAUGUUGCACUCUAGAUGUGCUGACCCGUGAGAUUUCCCCAAAUG UGGGACACUCAAAUGCAUAAUUGGUGGAAGUGAAGGACUGUGUUUGUGCUU U |
| 84 | U1_8_5 | UCCCUGCCAGGGGAGAUACCGUGAUCAUGAAGGUGGCUUUCCCAGGGAAAG GCCGAUAUGUUGCACUCUAGAUGUGCUGACCCGUGAGAUUUCCCCAAAUGU GGGACACUCAAAUGCAUAAUUGGUGGAAGUGAAGGACUGUGUUUGUGCUUU C |
| 85 | U1_8_6 | CCCUGCCAGGGGAGAUACCGUGAUCAUGAAGGUGGCUUUCCCAGGGAAAGG CCGAUAUGUUGCACUCUAGAUGUGCUGACCCGUGAGAUUUCCCCAAAUGUG GGACACUCAAAUGCAUAAUUGGUGGAAGUGAAGGACUGUGUUUGUGCUUUC A |

TABLE_3-continued

SEQUENCE_LISTING

| SEQ ID NO | Name/ ID | Sequence |
|---|---|---|
| 86 | U1_8_7 | CCUGCCAGGGGAGAUACCGUGAUCAUGAAGGUGGCUUUCCCAGGGAAAGGC CGAUAUGUUGCACUCUAGAUGUGCUGACCCGUGAGAUUUCCCCAAAUGUGG GACACUCAAAUGCAUAAUUGGUGGAAGUGAAGGACUGUGUUUGUGCUUUCA |
| 87 | U1_8_8 | CUGCCAGGGGAGAUACCGUGAUCAUGAAGGUGGCUUUCCCAGGGAAAGGCC GAUAUGUUGCACUCUAGAUGUGCUGACCCGUGAGAUUUCCCCAAAUGUGGG ACACUCAAAUGCAUAAUUGGUGGAAGUGAAGGACUGUGUUUGUGCUUUCA |
| 88 | U1_8_9 | UGCCAGGGGAGAUACCGUGAUCAUGAAGGUGGCUUUCCCAGGGAAAGGCCG AUAUGUUGCACUCUAGAUGUGCUGACCCGUGAGAUUUCCCCAAAUGUGGGA CACUCAAAUGCAUAAUUGGUGGAAGUGAAGGACUGUGUUUGUGCUUUCA |
| 89 | U1_9_0 | UUAACUACCUGACAGAGGAGAUACUGUGAUCAUGAAAGUGGUUUUUCCUAGG GCAAGACUUAUCCGUUGCACUCCAGAUGUGCUGACUCAUGCAAUUUCCCCA AAUGUGGGAAACUCGACUACAUAAUUUCUGGUGGUAGGGGACUGCGUUCAU G |
| 90 | U1_9_1 | UAACUACCUGACAGAGGAGAUACUGUGAUCAUGAAAGUGGUUUUUCCUAGGG CAAGACUUAUCCGUUGCACUCCAGAUGUGCUGACUCAUGCAAUUUCCCCAA AUGUGGGAAACUCGACUACAUAAUUUCUGGUGGUAGGGGACUGCGUUCAUG U |
| 91 | U1_9_2 | AACUACCUGACAGAGGAGAUACUGUGAUCAUGAAAGUGGUUUUUCCUAGGGC AAGACUUAUCCGUUGCACUCCAGAUGUGCUGACUCAUGCAAUUUCCCCAAA UGUGGGAAACUCGACUACAUAAUUUCUGGUGGUAGGGGACUGCGUUCAUGU U |
| 92 | U1_9_3 | ACUACCUGACAGAGGAGAUACUGUGAUCAUGAAAGUGGUUUUUCCUAGGGCA AGACUUAUCCGUUGCACUCCAGAUGUGCUGACUCAUGCAAUUUCCCCAAAU GUGGGAAACUCGACUACAUAAUUUCUGGUGGUAGGGGACUGCGUUCAUGUU C |
| 93 | U1_9_4 | CUACCUGACAGAGGAGAUACUGUGAUCAUGAAAGUGGUUUUUCCUAGGGCAA GACUUAUCCGUUGCACUCCAGAUGUGCUGACUCAUGCAAUUUCCCCAAAUG UGGGAAACUCGACUACAUAAUUUCUGGUGGUAGGGGACUGCGUUCAUGUUC U |
| 94 | U1_9_5 | UACCUGACAGAGGAGAUACUGUGAUCAUGAAAGUGGUUUUUCCUAGGGCAAG ACUUAUCCGUUGCACUCCAGAUGUGCUGACUCAUGCAAUUUCCCCAAAUGU GGGAAACUCGACUACAUAAUUUCUGGUGGUAGGGGACUGCGUUCAUGUUCU C |
| 95 | U1_9_6 | ACCUGACAGAGGAGAUACUGUGAUCAUGAAAGUGGUUUUUCCUAGGGCAAGA CUUAUCCGUUGCACUCCAGAUGUGCUGACUCAUGCAAUUUCCCCAAAUGUG GGAAACUCGACUACAUAAUUUCUGGUGGUAGGGGACUGCGUUCAUGUUCUC C |
| 96 | U1_9_7 | CCUGACAGAGGAGAUACUGUGAUCAUGAAAGUGGUUUUUCCUAGGGCAAGAC UUAUCCGUUGCACUCCAGAUGUGCUGACUCAUGCAAUUUCCCCAAAUGUGG GAAACUCGACUACAUAAUUUCUGGUGGUAGGGGACUGCGUUCAUGUUCUCC C |
| 97 | U1_9_8 | CUGACAGAGGAGAUACUGUGAUCAUGAAAGUGGUUUUUCCUAGGGCAAGACU UAUCCGUUGCACUCCAGAUGUGCUGACUCAUGCAAUUUCCCCAAAUGUGGG AAACUCGACUACAUAAUUUCUGGUGGUAGGGGACUGCGUUCAUGUUCUCCC C |
| 98 | U1_9_9 | UGACAGAGGAGAUACUGUGAUCAUGAAAGUGGUUUUUCCUAGGGCAAGACUU AUCCGUUGCACUCCAGAUGUGCUGACUCAUGCAAUUUCCCCAAAUGUGGGA AACUCGACUACAUAAUUUCUGGUGGUAGGGGACUGCGUUCAUGUUCUCCCC U |
| 99 | U1_10_0 | AGACUUAUCUGGCAGGGGAGACACCAUGAACAUGAGGAUAGUUUUCCCAAG GCAAGUUUCAACCCUUGCACUCUAGAUGAUGAGAUUACUUAAUGGGUACAA UGCAUGUGAUUUGGGUAAUGGAUACUGUAGAAACACUGACGUCAC |
| 100 | U1_10_1 | GACUUAUCUGGCAGGGGAGACACCAUGAACAUGAGGAUAGUUUUCCCAAGG CAAGUUUCAACCCUUGCACUCUAGAUGAUGAGAUUACUUAAUGGGUACAAU GCAUGUGAUUUGGGUAAUGGAUACUGUAGAAACACUGACGUCAC |
| 101 | U1_10_2 | ACUUAUCUGGCAGGGGAGACACCAUGAACAUGAGGAUAGUUUUCCCAAGGC AAGUUUCAACCCUUGCACUCUAGAUGAUGAGAUUACUUAAUGGGUACAAUG CAUGUGAUUUGGGUAAUGGAUACUGUAGAAACACUGACGUCAC |

TABLE_3-continued

SEQUENCE_LISTING

| SEQ ID NO | Name/ ID | Sequence |
|-----------|----------|----------|
| 102 | U1_10_3 | CUUAUCUGGCAGGGGAGACACCAUGAACAUGAGGAUAGUUUUCCCAAGGCA AGUUUCAACCCUUGCACUCUAGAUGAUGAGAUUACUUAAUGGGUACAAUGC AUGUGAUUUGGGUAAUGGAUACUGUAGAAACACUGACGUCAC |
| 103 | U1_10_4 | UUAUCUGGCAGGGGAGACACCAUGAACAUGAGGAUAGUUUUCCCAAGGCAA GUUUCAACCCUUGCACUCUAGAUGAUGAGAUUACUUAAUGGGUACAAUGCA UGUGAUUUGGGUAAUGGAUACUGUAGAAACACUGACGUCAC |
| 104 | U1_10_5 | UAUCUGGCAGGGGAGACACCAUGAACAUGAGGAUAGUUUUCCCAAGGCAAG UUUCAACCCUUGCACUCUAGAUGAUGAGAUUACUUAAUGGGUACAAUGCAU GUGAUUUGGGUAAUGGAUACUGUAGAAACACUGACGUCAC |
| 105 | U1_10_6 | AUCUGGCAGGGGAGACACCAUGAACAUGAGGAUAGUUUUCCCAAGGCAAGU UUCAACCCUUGCACUCUAGAUGAUGAGAUUACUUAAUGGGUACAAUGCAUG UGAUUUGGGUAAUGGAUACUGUAGAAACACUGACGUCAC |
| 106 | U1_10_7 | UCUGGCAGGGGAGACACCAUGAACAUGAGGAUAGUUUUCCCAAGGCAAGUU UCAACCCUUGCACUCUAGAUGAUGAGAUUACUUAAUGGGUACAAUGCAUGU GAUUUGGGUAAUGGAUACUGUAGAAACACUGACGUCAC |
| 107 | U1_10_8 | CUGGCAGGGGAGACACCAUGAACAUGAGGAUAGUUUUCCCAAGGCAAGUUU CAACCCUUGCACUCUAGAUGAUGAGAUUACUUAAUGGGUACAAUGCAUGUG AUUUGGGUAAUGGAUACUGUAGAAACACUGACGUCAC |
| 108 | U1_10_9 | UGGCAGGGGAGACACCAUGAACAUGAGGAUAGUUUUCCCAAGGCAAGUUUC AACCCUUGCACUCUAGAUGAUGAGAUUACUUAAUGGGUACAAUGCAUGUGA UUUGGGUAAUGGAUACUGUAGAAACACUGACGUCAC |
| 109 | U1_11_0 | AGACUCAUCUGGCAGCGGAGAUACCAUGAACAUCACGGUAGUUUUCCCAAA GCAAGUUUCCACCCUUGCACUCCGGAUGAUGAGACAUUACUUAAUGGAUAC AAUGCAUGUGAUUUGAGUGAUGGAUACUGUGGAAACACCGACUUCAC |
| 110 | U1_11_1 | GACUCAUCUGGCAGCGGAGAUACCAUGAACAUCACGGUAGUUUUCCCAAAG CAAGUUUCCACCCUUGCACUCCGGAUGAUGAGACAUUACUUAAUGGAUACA AUGCAUGUGAUUUGAGUGAUGGAUACUGUGGAAACACCGACUUCAC |
| 111 | U1_11_2 | ACUCAUCUGGCAGCGGAGAUACCAUGAACAUCACGGUAGUUUUCCCAAAGC AAGUUUCCACCCUUGCACUCCGGAUGAUGAGACAUUACUUAAUGGAUACAA UGCAUGUGAUUUGAGUGAUGGAUACUGUGGAAACACCGACUUCAC |
| 112 | U1_11_3 | CUCAUCUGGCAGCGGAGAUACCAUGAACAUCACGGUAGUUUUCCCAAAGCA AGUUUCCACCCUUGCACUCCGGAUGAUGAGACAUUACUUAAUGGAUACAAU GCAUGUGAUUUGAGUGAUGGAUACUGUGGAAACACCGACUUCAC |
| 113 | U1_11_4 | UCAUCUGGCAGCGGAGAUACCAUGAACAUCACGGUAGUUUUCCCAAAGCAA GUUUCCACCCUUGCACUCCGGAUGAUGAGACAUUACUUAAUGGAUACAAUG CAUGUGAUUUGAGUGAUGGAUACUGUGGAAACACCGACUUCAC |
| 114 | U1_11_5 | CAUCUGGCAGCGGAGAUACCAUGAACAUCACGGUAGUUUUCCCAAAGCAAG UUUCCACCCUUGCACUCCGGAUGAUGAGACAUUACUUAAUGGAUACAAUGC AUGUGAUUUGAGUGAUGGAUACUGUGGAAACACCGACUUCAC |
| 115 | U1_11_6 | AUCUGGCAGCGGAGAUACCAUGAACAUCACGGUAGUUUUCCCAAAGCAAGU UUCCACCCUUGCACUCCGGAUGAUGAGACAUUACUUAAUGGAUACAAUGCA UGUGAUUUGAGUGAUGGAUACUGUGGAAACACCGACUUCAC |
| 116 | U1_11_7 | UCUGGCAGCGGAGAUACCAUGAACAUCACGGUAGUUUUCCCAAAGCAAGUU UCCACCCUUGCACUCCGGAUGAUGAGACAUUACUUAAUGGAUACAAUGCAU GUGAUUUGAGUGAUGGAUACUGUGGAAACACCGACUUCAC |
| 117 | U1_11_8 | CUGGCAGCGGAGAUACCAUGAACAUCACGGUAGUUUUCCCAAAGCAAGUUU CCACCCUUGCACUCCGGAUGAUGAGACAUUACUUAAUGGAUACAAUGCAUG UGAUUUGAGUGAUGGAUACUGUGGAAACACCGACUUCAC |
| 118 | U1_11_9 | UGGCAGCGGAGAUACCAUGAACAUCACGGUAGUUUUCCCAAAGCAAGUUUC CACCCUUGCACUCCGGAUGAUGAGACAUUACUUAAUGGAUACAAUGCAUGU GAUUUGAGUGAUGGAUACUGUGGAAACACCGACUUCAC |
| 119 | U1_12_0 | AGACUUGGCAGGGGAGAUAGCAUGAUCACGAAGGUGGUUUUCCCAAGGCAA GAUUUAUUCACUGCACUCUGGAUGUGCUGACCCCUACGAUUUCCGCCCAUU GGGGAAGCUUGACUGCUUAGUUUGUUGUGGCAGGGGACUGUGUUCACACUU U |

TABLE_3-continued

SEQUENCE_LISTING

| SEQ ID NO | Name/ ID | Sequence |
|---|---|---|
| 120 | U1_12_1 | GACUUGGCAGGGGAGAUAGCAUGAUCACGAAGGUGGUUUUCCCAAGGCAAG AUUUAUUCACUGCACUCUGGAUGUGCUGACCCCUACGAUUUCCGCCCAAUG GGGAAGCUUGACUGCUUAGUUUGUUGUGGCAGGGGACUGUGUUCACACUUU U |
| 121 | U1_12_2 | ACUUGGCAGGGGAGAUAGCAUGAUCACGAAGGUGGUUUUCCCAAGGCAAGA UUUAUUCACUGCACUCUGGAUGUGCUGACCCCUACGAUUUCCGCCCAAUGG GGAAGCUUGACUGCUUAGUUUGUUGUGGCAGGGGACUGUGUUCACACUUUU C |
| 122 | U1_12_3 | CUUGGCAGGGGAGAUAGCAUGAUCACGAAGGUGGUUUUCCCAAGGCAAGAU UUAUUCACUGCACUCUGGAUGUGCUGACCCCUACGAUUUCCGCCCAAUGGG GAAGCUUGACUGCUUAGUUUGUUGUGGCAGGGGACUGUGUUCACACUUUUC C |
| 123 | U1_12_4 | UUGGCAGGGGAGAUAGCAUGAUCACGAAGGUGGUUUUCCCAAGGCAAGAUU UAUUCACUGCACUCUGGAUGUGCUGACCCCUACGAUUUCCGCCCAAUGGGG AAGCUUGACUGCUUAGUUUGUUGUGGCAGGGGACUGUGUUCACACUUUUCC C |
| 124 | U1_12_5 | UGGCAGGGGAGAUAGCAUGAUCACGAAGGUGGUUUUCCCAAGGCAAGAUUU AUUCACUGCACUCUGGAUGUGCUGACCCCUACGAUUUCCGCCCAAUGGGGA AGCUUGACUGCUUAGUUUGUUGUGGCAGGGGACUGUGUUCACACUUUUCCC G |
| 125 | U1_12_6 | GGCAGGGGAGAUAGCAUGAUCACGAAGGUGGUUUUCCCAAGGCAAGAUUUA UUCACUGCACUCUGGAUGUGCUGACCCCUACGAUUUCCGCCCAAUGGGGAA GCUUGACUGCUUAGUUUGUUGUGGCAGGGGACUGUGUUCACACUUUUCCCG G |
| 126 | U1_12_7 | GCAGGGGAGAUAGCAUGAUCACGAAGGUGGUUUUCCCAAGGCAAGAUUUAU UCACUGCACUCUGGAUGUGCUGACCCCUACGAUUUCCGCCCAAUGGGGAAG CUUGACUGCUUAGUUUGUUGUGGCAGGGGACUGUGUUCACACUUUUCCCGG |
| 127 | U1_12_8 | CAGGGGAGAUAGCAUGAUCACGAAGGUGGUUUUCCCAAGGCAAGAUUUAUU CACUGCACUCUGGAUGUGCUGACCCCUACGAUUUCCGCCCAAUGGGGGAAGC UUGACUGCUUAGUUUGUUGUGGCAGGGGACUGUGUUCACACUUUUCCCGG |
| 128 | U1_12_9 | AGGGGAGAUAGCAUGAUCACGAAGGUGGUUUUCCCAAGGCAAGAUUUAUUC ACUGCACUCUGGAUGUGCUGACCCCUACGAUUUCCGCCCAAUGGGGAAGCU UGACUGCUUAGUUUGUUGUGGCAGGGGACUGUGUUCACACUUUUCCCGG |
| 129 | U1_13_10 | AUACUUAACAUGGCAGAGGAGAUAUCAUAAUCACAAAGGUAGUUUUCCCAG GGCAAGCCUUAUCCACUGCAUUCCAGAUGUGCUCACCUCUGUGGUUUCCCC AAAUGUGGAAAACUGGACUGCAUAAUUUGUGGUAGCGGGGGACUGCAUUAA U |
| 130 | U1_13_1 | UACUUAACAUGGCAGAGGAGAUAUCAUAAUCACAAAGGUAGUUUUCCCAGG GCAAGCCUUAUCCACUGCAUUCCAGAUGUGCUCACCUCUGUGGUUUCCCCA AAUGUGGAAAACUGGACUGCAUAAUUUGUGGUAGCGGGGGACUGCAUUAAU A |
| 131 | U1_13_2 | ACUUAACAUGGCAGAGGAGAUAUCAUAAUCACAAAGGUAGUUUUCCCAGGG CAAGCCUUAUCCACUGCAUUCCAGAUGUGCUCACCUCUGUGGUUUCCCCAA AUGUGGAAAACUGGACUGCAUAAUUUGUGGUAGCGGGGGACUGCAUUAAUA C |
| 132 | U1_13_3 | CUUAACAUGGCAGAGGAGAUAUCAUAAUCACAAAGGUAGUUUUCCCAGGGC AAGCCUUAUCCACUGCAUUCCAGAUGUGCUCACCUCUGUGGUUUCCCCAAA UGUGGAAAACUGGACUGCAUAAUUUGUGGUAGCGGGGGACUGCAUUAAUAC C |
| 133 | U1_13_4 | UUAACAUGGCAGAGGAGAUAUCAUAAUCACAAAGGUAGUUUUCCCAGGGCA AGCCUUAUCCACUGCAUUCCAGAUGUGCUCACCUCUGUGGUUUCCCCAAAU GUGGAAAACUGGACUGCAUAAUUUGUGGUAGCGGGGGACUGCAUUAAUACC U |
| 134 | U1_13_5 | UAACAUGGCAGAGGAGAUAUCAUAAUCACAAAGGUAGUUUUCCCAGGGCAA GCCUUAUCCACUGCAUUCCAGAUGUGCUCACCUCUGUGGUUUCCCCAAAUG UGGAAAACUGGACUGCAUAAUUUGUGGUAGCGGGGGACUGCAUUAAUACCU U |

TABLE_3-continued

SEQUENCE_LISTING

| SEQ ID NO | Name/ ID | Sequence |
|---|---|---|
| 135 | U1_13_6 | AACAUGGCAGAGGAGAUAUCAUAAUCACAAAGGUAGUUUUCCCAGGGCAAG CCUUAUCCACUGCAUUCCAGAUGUGCUCACCUCUGUGGUUUCCCCAAAUGU GGAAAACUGGACUGCAUAAUUUGUGGUAGCGGGGGACUGCAUUAAUACCUU C |
| 136 | U1_13_7 | ACAUGGCAGAGGAGAUAUCAUAAUCACAAAGGUAGUUUUCCCAGGGCAAGC CUUAUCCACUGCAUUCCAGAUGUGCUCACCUCUGUGGUUUCCCCAAAUGUG GAAAACUGGACUGCAUAAUUUGUGGUAGCGGGGGACUGCAUUAAUACCUUC C |
| 137 | U1_13_8 | CAUGGCAGAGGAGAUAUCAUAAUCACAAAGGUAGUUUUCCCAGGGCAAGCC UUAUCCACUGCAUUCCAGAUGUGCUCACCUCUGUGGUUUCCCCAAAUGUGG AAAACUGGACUGCAUAAUUUGUGGUAGCGGGGGACUGCAUUAAUACCUUCC U |
| 138 | U1_13_9 | AUGGCAGAGGAGAUAUCAUAAUCACAAAGGUAGUUUUCCCAGGGCAAGCCU UAUCCACUGCAUUCCAGAUGUGCUCACCUCUGUGGUUUCCCCAAAUGUGGA AAACUGGACUGCAUAAUUUGUGGUAGCGGGGGACUGCAUUAAUACCUUCCU C |
| 139 | U11_1_0 | AAAAAGGGCUUCUGCUGUGAGUGGCACACAUAGGGCAUCGUUUGCUCUUGG UGCCAGAAUCAACAUCAAGAGAUUUCAGAAGCAUAAUUUUUUGGUACUUGG GCAGCUGGUGAUCAUUGGUCCUGUAGCCCUU |
| 140 | U11_1_1 | AAAAGGGCUUCUGCUGUGAGUGGCACACAUAGGGCAUCGUUUGCUCUUGGU GCCAGAAUCAACAUCAAGAGAUUUCAGAAGCAUAAUUUUUUGGUACUUGGG CAGCUGGUGAUCAUUGGUCCUGUAGCCCUU |
| 141 | U11_1_2 | AAAGGGCUUCUGCUGUGAGUGGCACACAUAGGGCAUCGUUUGCUCUUGGUG CCAGAAUCAACAUCAAGAGAUUUCAGAAGCAUAAUUUUUUGGUACUUGGGC AGCUGGUGAUCAUUGGUCCUGUAGCCCUU |
| 142 | U11_1_3 | AAGGGCUUCUGCUGUGAGUGGCACACAUAGGGCAUCGUUUGCUCUUGGUGC CAGAAUCAACAUCAAGAGAUUUCAGAAGCAUAAUUUUUUGGUACUUGGGCA GCUGGUGAUCAUUGGUCCUGUAGCCCUU |
| 143 | U11_1_4 | AGGGCUUCUGCUGUGAGUGGCACACAUAGGGCAUCGUUUGCUCUUGGUGCC AGAAUCAACAUCAAGAGAUUUCAGAAGCAUAAUUUUUUGGUACUUGGGCAG CUGGUGAUCAUUGGUCCUGUAGCCCUU |
| 144 | U11_1_5 | GGGCUUCUGCUGUGAGUGGCACACAUAGGGCAUCGUUUGCUCUUGGUGCCA GAAUCAACAUCAAGAGAUUUCAGAAGCAUAAUUUUUUGGUACUUGGGCAGC UGGUGAUCAUUGGUCCUGUAGCCCUU |
| 145 | U11_1_6 | GGCUUCUGCUGUGAGUGGCACACAUAGGGCAUCGUUUGCUCUUGGUGCCAG AAUCAACAUCAAGAGAUUUCAGAAGCAUAAUUUUUUGGUACUUGGGCAGCU GGUGAUCAUUGGUCCUGUAGCCCUU |
| 146 | U11_1_7 | GCUUCUGCUGUGAGUGGCACACAUAGGGCAUCGUUUGCUCUUGGUGCCAGA AUCAACAUCAAGAGAUUUCAGAAGCAUAAUUUUUUGGUACUUGGGCAGCUG GUGAUCAUUGGUCCUGUAGCCCUU |
| 147 | U11_1_8 | CUUCUGCUGUGAGUGGCACACAUAGGGCAUCGUUUGCUCUUGGUGCCAGAA UCAACAUCAAGAGAUUUCAGAAGCAUAAUUUUUUGGUACUUGGGCAGCUGG UGAUCAUUGGUCCUGUAGCCCUU |
| 148 | U11_1_9 | UUCUGCUGUGAGUGGCACACAUAGGGCAUCGUUUGCUCUUGGUGCCAGAAU CAACAUCAAGAGAUUUCAGAAGCAUAAUUUUUUGGUACUUGGGCAGCUGGU GAUCAUUGGUCCUGUAGCCCUU |
| 149 | U11_2_0 | AAAAAAAGCUGCUGUUGUGAGUGAUACAUGCAGGGCAACUUGAUUGCUCUU AGUGCAGAAUUGACAUCAAGGAAUUUUGGAAGUAUAAUUUUUUGGCAGGUG GAUAGCGGUUGUAUUAGUCCAUUCUC |
| 150 | U11_2_1 | AAAAAAGCUGCUGUUGUGAGUGAUACAUGCAGGGCAACUUGAUUGCUCUUA GUGCAGAAUUGACAUCAAGGAAUUUUGGAAGUAUAAUUUUUUGGCAGGUGG AUAGCGGUUGUAUUAGUCCAUUCUC |
| 151 | U11_2_2 | AAAAAGCUGCUGUUGUGAGUGAUACAUGCAGGGCAACUUGAUUGCUCUUAG UGCAGAAUUGACAUCAAGGAAUUUUGGAAGUAUAAUUUUUUGGCAGGUGGA UAGCGGUUGUAUUAGUCCAUUCUC |

TABLE_3-continued

SEQUENCE_LISTING

| SEQ ID NO | Name/ ID | Sequence |
|---|---|---|
| 152 | U11_2_3 | AAAAGCUGCUGUUGUGAGUGAUACAUGCAGGGCAACUUGAUUGCUCUUAGU GCAGAAUUGACAUCAAGGAAUUUUGGAAGUAUAAUUUUUUGGCAGGUGGAU AGCUGGUUGUAUUAGUCCAUUCUC |
| 153 | U11_2_4 | AAAGCUGCUGUUGUGAGUGAUACAUGCAGGGCAACUUGAUUGCUCUUAGUG CAGAAUUGACAUCAAGGAAUUUUGGAAGUAUAAUUUUUUGGCAGGUGGAUA GCUGGUUGUAUUAGUCCAUUCUC |
| 154 | U11_2_5 | AAGCUGCUGUUGUGAGUGAUACAUGCAGGGCAACUUGAUUGCUCUUAGUGC AGAAUUGACAUCAAGGAAUUUUGGAAGUAUAAUUUUUUGGCAGGUGGAUAG CUGGUUGUAUUAGUCCAUUCUC |
| 155 | U11_2_6 | AGCUGCUGUUGUGAGUGAUACAUGCAGGGCAACUUGAUUGCUCUUAGUGCA GAAUUGACAUCAAGGAAUUUUGGAAGUAUAAUUUUUUGGCAGGUGGAUAGC UGGUUGUAUUAGUCCAUUCUC |
| 156 | U11_2_7 | GCUGCUGUUGUGAGUGAUACAUGCAGGGCAACUUGAUUGCUCUUAGUGCAG AAUUGACAUCAAGGAAUUUUGGAAGUAUAAUUUUUUGGCAGGUGGAUAGCU GGUUGUAUUAGUCCAUUCUC |
| 157 | U11_2_8 | CUGCUGUUGUGAGUGAUACAUGCAGGGCAACUUGAUUGCUCUUAGUGCAGA AUUGACAUCAAGGAAUUUUGGAAGUAUAAUUUUUUGGCAGGUGGAUAGCUG GUUGUAUUAGUCCAUUCUC |
| 158 | U11_2_9 | UGCUGUUGUGAGUGAUACAUGCAGGGCAACUUGAUUGCUCUUAGUGCAGAA UUGACAUCAAGGAAUUUUGGAAGUAUAAUUUUUUGGCAGGUGGAUAGCUGG UUGUAUUAGUCCAUUCUC |
| 159 | U11_3_0 | AAAAAGGGCUUCUGUCAUGAGUGGCACACAUAGGACAACUCAAUUUCUCUU CAUGCAGAAUAAACAUCAAGAGAUUUUGGAAGCGUAAUUUUUGGUAGUUGG GCAGCUGGUGAUCACUGGUGCCAGCACCCUU |
| 160 | U11_3_1 | AAAAGGGCUUCUGUCAUGAGUGGCACACAUAGGACAACUCAAUUUCUCUUC AUGCAGAAUAAACAUCAAGAGAUUUUGGAAGCGUAAUUUUUGGUAGUUGGG CAGCUGGUGAUCACUGGUGCCAGCACCCUU |
| 161 | U11_3_2 | AAAGGGCUUCUGUCAUGAGUGGCACACAUAGGACAACUCAAUUUCUCUUCA UGCAGAAUAAACAUCAAGAGAUUUUGGAAGCGUAAUUUUUGGUAGUUGGGC AGCUGGUGAUCACUGGUGCCAGCACCCUU |
| 162 | U11_3_3 | AAGGGCUUCUGUCAUGAGUGGCACACAUAGGACAACUCAAUUUCUCUUCAU GCAGAAUAAACAUCAAGAGAUUUUGGAAGCGUAAUUUUUGGUAGUUGGGCA GCUGGUGAUCACUGGUGCCAGCACCCUU |
| 163 | U11_3_4 | AGGGCUUCUGUCAUGAGUGGCACACAUAGGACAACUCAAUUUCUCUUCAUG CAGAAUAAACAUCAAGAGAUUUUGGAAGCGUAAUUUUUGGUAGUUGGGCAG CUGGUGAUCACUGGUGCCAGCACCCUU |
| 164 | U11_3_5 | GGGCUUCUGUCAUGAGUGGCACACAUAGGACAACUCAAUUUCUCUUCAUGC AGAAUAAACAUCAAGAGAUUUUGGAAGCGUAAUUUUUGGUAGUUGGGCAGC UGGUGAUCACUGGUGCCAGCACCCUU |
| 165 | U11_3_6 | GGCUUCUGUCAUGAGUGGCACACAUAGGACAACUCAAUUUCUCUUCAUGCA GAAUAAACAUCAAGAGAUUUUGGAAGCGUAAUUUUUGGUAGUUGGGCAGCU GGUGAUCACUGGUGCCAGCACCCUU |
| 166 | U11_3_7 | GCUUCUGUCAUGAGUGGCACACAUAGGACAACUCAAUUUCUCUUCAUGCAG AAUAAACAUCAAGAGAUUUUGGAAGCGUAAUUUUUGGUAGUUGGGCAGCUG GUGAUCACUGGUGCCAGCACCCUU |
| 167 | U11_3_8 | CUUCUGUCAUGAGUGGCACACAUAGGACAACUCAAUUUCUCUUCAUGCAGA AUAAACAUCAAGAGAUUUUGGAAGCGUAAUUUUUGGUAGUUGGGCAGCUGG UGAUCACUGGUGCCAGCACCCUU |
| 168 | U11_3_9 | UUCUGUCAUGAGUGGCACACAUAGGACAACUCAAUUUCUCUUCAUGCAGAA UAAACAUCAAGAGAUUUUGGAAGCGUAAUUUUUGGUAGUUGGGCAGCUGGU GAUCACUGGUGCCAGCACCCUU |
| 169 | U11_4_0 | AAAAAGGGCUUCUGUCAUGAGUGGCCUAUGUAGGGCAACCAGAUUGCUCUU CAUGUGGAAUUGACAUCAAGAGCUUUCAGAAGUGUAUUUUUUGGAAGUUGG GCAGCUGGUAAUCAUUGGUCUUGGCAUCCUU |

TABLE_3-continued

SEQUENCE_LISTING

| SEQ ID NO | Name/ ID | Sequence |
|---|---|---|
| 170 | U11_4_1 | AAAAGGGCUUCUGUCAUGAGUGGCCUAUGUAGGGCAACCAGAUUGCUCUUC<br>AUGUGGAAUUGACAUCAAGAGCUUUCAGAAGUGUAUUUUUUGGAAGUUGGG<br>CAGCUGGUAAUCAUUGGUCUUGGCAUCCUU |
| 171 | U11_4_2 | AAAGGGCUUCUGUCAUGAGUGGCCUAUGUAGGGCAACCAGAUUGCUCUUCA<br>UGUGGAAUUGACAUCAAGAGCUUUCAGAAGUGUAUUUUUUGGAAGUUGGGC<br>AGCUGGUAAUCAUUGGUCUUGGCAUCCUU |
| 172 | U11_4_3 | AAGGGCUUCUGUCAUGAGUGGCCUAUGUAGGGCAACCAGAUUGCUCUUCAU<br>GUGGAAUUGACAUCAAGAGCUUUCAGAAGUGUAUUUUUUGGAAGUUGGGCA<br>GCUGGUAAUCAUUGGUCUUGGCAUCCUU |
| 173 | U11_4_4 | AGGGCUUCUGUCAUGAGUGGCCUAUGUAGGGCAACCAGAUUGCUCUUCAUG<br>UGGAAUUGACAUCAAGAGCUUUCAGAAGUGUAUUUUUUGGAAGUUGGGCAG<br>CUGGUAAUCAUUGGUCUUGGCAUCCUU |
| 174 | U11_4_5 | GGGCUUCUGUCAUGAGUGGCCUAUGUAGGGCAACCAGAUUGCUCUUCAUGU<br>GGAAUUGACAUCAAGAGCUUUCAGAAGUGUAUUUUUUGGAAGUUGGGCAGC<br>UGGUAAUCAUUGGUCUUGGCAUCCUU |
| 175 | U11_4_6 | GGCUUCUGUCAUGAGUGGCCUAUGUAGGGCAACCAGAUUGCUCUUCAUGUG<br>GAAUUGACAUCAAGAGCUUUCAGAAGUGUAUUUUUUGGAAGUUGGGCAGCU<br>GGUAAUCAUUGGUCUUGGCAUCCUU |
| 176 | U11_4_7 | GCUUCUGUCAUGAGUGGCCUAUGUAGGGCAACCAGAUUGCUCUUCAUGUGG<br>AAUUGACAUCAAGAGCUUUCAGAAGUGUAUUUUUUGGAAGUUGGGCAGCUG<br>GUAAUCAUUGGUCUUGGCAUCCUU |
| 177 | U11_4_8 | CUUCUGUCAUGAGUGGCCUAUGUAGGGCAACCAGAUUGCUCUUCAUGUGGA<br>AUUGACAUCAAGAGCUUUCAGAAGUGUAUUUUUUGGAAGUUGGGCAGCUGG<br>UAAUCAUUGGUCUUGGCAUCCUU |
| 178 | U11_4_9 | UUCUGUCAUGAGUGGCCUAUGUAGGGCAACCAGAUUGCUCUUCAUGUGGAA<br>UUGACAUCAAGAGCUUUCAGAAGUGUAUUUUUUGGAAGUUGGGCAGCUGGU<br>AAUCAUUGGUCUUGGCAUCCUU |
| 179 | U11_5_0 | AAAGGGGCUUCUGUCAUGAGUGGCACACAUUGGGCAACUCAACUGCUCUU<br>CAUGAGGAAUCAACAUCAGGAGGUUUUGGAAGAAUGAUUUUUUUGGUAGUU<br>GGGCAGCUUGUGAGAAAAAAAUGUUUUCAGGCAAAUCCUC |
| 180 | U11_5_1 | AAGGGGGCUUCUGUCAUGAGUGGCACACAUUGGGCAACUCAACUGCUCUUC<br>AUGAGGAAUCAACAUCAGGAGGUUUUGGAAGAAUGAUUUUUUUUGGUAGUUG<br>GGCAGCUUGUGAGAAAAAAAUGUUUUCAGGCAAAUCCUC |
| 181 | U11_5_2 | AGGGGGCUUCUGUCAUGAGUGGCACACAUUGGGCAACUCAACUGCUCUUCA<br>UGAGGAAUCAACAUCAGGAGGUUUUGGAAGAAUGAUUUUUUUUGGUAGUUGG<br>GCAGCUUGUGAGAAAAAAAUGUUUUCAGGCAAAUCCUC |
| 182 | U11_5_3 | GGGGGCUUCUGUCAUGAGUGGCACACAUUGGGCAACUCAACUGCUCUUCAU<br>GAGGAAUCAACAUCAGGAGGUUUUGGAAGAAUGAUUUUUUUUGGUAGUUGGG<br>CAGCUUGUGAGAAAAAAAUGUUUUCAGGCAAAUCCUC |
| 183 | U11_5_4 | GGGGCUUCUGUCAUGAGUGGCACACAUUGGGCAACUCAACUGCUCUUCAUG<br>AGGAAUCAACAUCAGGAGGUUUUGGAAGAAUGAUUUUUUUUGGUAGUUGGGC<br>AGCUUGUGAGAAAAAAAUGUUUUCAGGCAAAUCCUC |
| 184 | U11_5_5 | GGGCUUCUGUCAUGAGUGGCACACAUUGGGCAACUCAACUGCUCUUCAUGA<br>GGAAUCAACAUCAGGAGGUUUUGGAAGAAUGAUUUUUUUUGGUAGUUGGGCA<br>GCUUGUGAGAAAAAAAUGUUUUCAGGCAAAUCCUC |
| 185 | U11_5_6 | GGCUUCUGUCAUGAGUGGCACACAUUGGGCAACUCAACUGCUCUUCAUGAG<br>GAAUCAACAUCAGGAGGUUUUGGAAGAAUGAUUUUUUUUGGUAGUUGGGCAG<br>CUUGUGAGAAAAAAAUGUUUUCAGGCAAAUCCUC |
| 186 | U11_5_7 | GCUUCUGUCAUGAGUGGCACACAUUGGGCAACUCAACUGCUCUUCAUGAGG<br>AAUCAACAUCAGGAGGUUUUGGAAGAAUGAUUUUUUUUGGUAGUUGGGCAGC<br>UUGUGAGAAAAAAAUGUUUUCAGGCAAAUCCUC |
| 187 | U11_5_8 | CUUCUGUCAUGAGUGGCACACAUUGGGCAACUCAACUGCUCUUCAUGAGGA<br>AUCAACAUCAGGAGGUUUUGGAAGAAUGAUUUUUUUUGGUAGUUGGGCAGCU<br>UGUGAGAAAAAAAUGUUUUCAGGCAAAUCCUC |

TABLE_3-continued

SEQUENCE_LISTING

| SEQ ID NO | Name/ ID | Sequence |
|---|---|---|
| 188 | U11_5_9 | UUCUGUCAUGAGUGGCACACAUUGGGCAACUCAACUGCUCUUCAUGAGGAA UCAACAUCAGGAGGUUUUGGAAGAAUGAUUUUUUUGGUAGUUGGGCAGCUU GUGAGAAAAAAAUGUUUUCAGGCAAAUCCUC |
| 189 | U11_6_0 | AAAAAGGGCUUCUGUCGUGAGUGGCACACGUAGGGCAACUCGAUUGCUCUG CGUGCGGAAUCGACAUCAAGAGAUUUCGGAAGCAUAAUUUUUUGGUAUUUG GGCAGCUGGUGAUCGUUGGUCCCGGCGCCCUU |
| 190 | U11_6_1 | AAAAGGGCUUCUGUCGUGAGUGGCACACGUAGGGCAACUCGAUUGCUCUGC GUGCGGAAUCGACAUCAAGAGAUUUCGGAAGCAUAAUUUUUUUGGUAUUUGG GCAGCUGGUGAUCGUUGGUCCCGGCGCCCUU |
| 191 | U11_6_2 | AAAGGGCUUCUGUCGUGAGUGGCACACGUAGGGCAACUCGAUUGCUCUGCG UGCGGAAUCGACAUCAAGAGAUUUCGGAAGCAUAAUUUUUUUGGUAUUUGGG CAGCUGGUGAUCGUUGGUCCCGGCGCCCUU |
| 192 | U11_6_3 | AAGGGCUUCUGUCGUGAGUGGCACACGUAGGGCAACUCGAUUGCUCUGCGU GCGGAAUCGACAUCAAGAGAUUUCGGAAGCAUAAUUUUUUUGGUAUUUGGGC AGCUGGUGAUCGUUGGUCCCGGCGCCCUU |
| 193 | U11_6_4 | AGGGCUUCUGUCGUGAGUGGCACACGUAGGGCAACUCGAUUGCUCUGCGUG CGGAAUCGACAUCAAGAGAUUUCGGAAGCAUAAUUUUUUUGGUAUUUGGGCA GCUGGUGAUCGUUGGUCCCGGCGCCCUU |
| 194 | U11_6_5 | GGGCUUCUGUCGUGAGUGGCACACGUAGGGCAACUCGAUUGCUCUGCGUGC GGAAUCGACAUCAAGAGAUUUCGGAAGCAUAAUUUUUUUGGUAUUUGGGCAG CUGGUGAUCGUUGGUCCCGGCGCCCUU |
| 195 | U11_6_6 | GGCUUCUGUCGUGAGUGGCACACGUAGGGCAACUCGAUUGCUCUGCGUGCG GAAUCGACAUCAAGAGAUUUCGGAAGCAUAAUUUUUUUGGUAUUUGGGCAGC UGGUGAUCGUUGGUCCCGGCGCCCUU |
| 196 | U11_6_7 | GCUUCUGUCGUGAGUGGCACACGUAGGGCAACUCGAUUGCUCUGCGUGCGG AAUCGACAUCAAGAGAUUUCGGAAGCAUAAUUUUUUUGGUAUUUGGGCAGCU GGUGAUCGUUGGUCCCGGCGCCCUU |
| 197 | U11_6_8 | CUUCUGUCGUGAGUGGCACACGUAGGGCAACUCGAUUGCUCUGCGUGCGGA AUCGACAUCAAGAGAUUUCGGAAGCAUAAUUUUUUUGGUAUUUGGGCAGCUG GUGAUCGUUGGUCCCGGCGCCCUU |
| 198 | U11_6_9 | UUCUGUCGUGAGUGGCACACGUAGGGCAACUCGAUUGCUCUGCGUGCGGAA UCGACAUCAAGAGAUUUCGGAAGCAUAAUUUUUUUGGUAUUUGGGCAGCUGG UGAUCGUUGGUCCCGGCGCCCUU |
| 199 | U11_7_0 | AAAAAGGGCUUCUGUCGUGAGUGGCACACGUAGGGCAACUCGAUUGCUCUG CGUGCGGAAUCGACAUCAAGAGAUUUCGGAAGCAUAAUUUUUUUGGUAUUUG GGCAGCUGGUGAUCGUUGGUCCCGGCGCC |
| 200 | U11_7_1 | AAAAGGGCUUCUGUCGUGAGUGGCACACGUAGGGCAACUCGAUUGCUCUGC GUGCGGAAUCGACAUCAAGAGAUUUCGGAAGCAUAAUUUUUUUGGUAUUUGG GCAGCUGGUGAUCGUUGGUCCCGGCGCC |
| 201 | U11_7_2 | AAAGGGCUUCUGUCGUGAGUGGCACACGUAGGGCAACUCGAUUGCUCUGCG UGCGGAAUCGACAUCAAGAGAUUUCGGAAGCAUAAUUUUUUUGGUAUUUGGG CAGCUGGUGAUCGUUGGUCCCGGCGCC |
| 202 | U11_7_3 | AAGGGCUUCUGUCGUGAGUGGCACACGUAGGGCAACUCGAUUGCUCUGCGU GCGGAAUCGACAUCAAGAGAUUUCGGAAGCAUAAUUUUUUUGGUAUUUGGGC AGCUGGUGAUCGUUGGUCCCGGCGCC |
| 203 | U11_7_4 | AGGGCUUCUGUCGUGAGUGGCACACGUAGGGCAACUCGAUUGCUCUGCGUG CGGAAUCGACAUCAAGAGAUUUCGGAAGCAUAAUUUUUUUGGUAUUUGGGCA GCUGGUGAUCGUUGGUCCCGGCGCC |
| 204 | U11_7_5 | GGGCUUCUGUCGUGAGUGGCACACGUAGGGCAACUCGAUUGCUCUGCGUGC GGAAUCGACAUCAAGAGAUUUCGGAAGCAUAAUUUUUUUGGUAUUUGGGCAG CUGGUGAUCGUUGGUCCCGGCGCC |
| 205 | U11_7_6 | GGCUUCUGUCGUGAGUGGCACACGUAGGGCAACUCGAUUGCUCUGCGUGCG GAAUCGACAUCAAGAGAUUUCGGAAGCAUAAUUUUUUUGGUAUUUGGGCAGC UGGUGAUCGUUGGUCCCGGCGCC |

TABLE_3-continued

| | SEQUENCE_LISTING | |
|---|---|---|

| SEQ ID NO | Name/ ID | Sequence |
|---|---|---|
| 206 | U11_7_7 | GCUUCUGUCGUGAGUGGCACACGUAGGGCAACUCGAUUGCUCUGCGUGCGG AAUCGACAUCAAGAGAUUUCGGAAGCAUAAUUUUUUGGUAUUUGGGCAGCU GGUGAUCGUUGGUCCCGGCGCC |
| 207 | U11_7_8 | CUUCUGUCGUGAGUGGCACACGUAGGGCAACUCGAUUGCUCUGCGUGCGGA AUCGACAUCAAGAGAUUUCGGAAGCAUAAUUUUUUGGUAUUUGGGCAGCUG GUGAUCGUUGGUCCCGGCGCC |
| 208 | U11_7_9 | UUCUGUCGUGAGUGGCACACGUAGGGCAACUCGAUUGCUCUGCGUGCGGAA UCGACAUCAAGAGAUUUCGGAAGCAUAAUUUUUUGGUAUUUGGGCAGCUGG UGAUCGUUGGUCCCGGCGCC |
| 209 | Sm_ consensus | AAUUUUUGGAG |
| 210 | Sm_1 | AAUUUUUGGAG |
| 211 | Sm_2 | UAUUUUUGGAG |
| 212 | Sm_3 | GAUUUUUGGAG |
| 213 | Sm_4 | CAUUUUUGGAG |
| 214 | Sm_5 | AUUUUUUGGAG |
| 215 | Sm_6 | AGUUUUUGGAG |
| 216 | Sm_7 | ACUUUUUGGAG |
| 217 | Sm_8 | AAAUUUUGGAG |
| 218 | Sm_9 | AAGUUUUGGAG |
| 219 | Sm_10 | AACUUUUGGAG |
| 220 | Sm_11 | AAUAUUUGGAG |
| 221 | Sm_12 | AAUGUUUGGAG |
| 222 | Sm_13 | AAUCUUUGGAG |
| 223 | Sm_14 | AAUUAUUGGAG |
| 224 | Sm_15 | AAUUGUUGGAG |
| 225 | Sm_16 | AAUUCUUGGAG |
| 226 | Sm_17 | AAUUUAUGGAG |
| 227 | Sm_18 | AAUUUGUGGAG |
| 228 | Sm_19 | AAUUUCUGGAG |
| 229 | Sm_20 | AAUUUUAGGAG |
| 230 | Sm_21 | AAUUUUGGGAG |
| 231 | Sm_22 | AAUUUUCGGAG |
| 232 | Sm_23 | AAUUUUUAGAG |
| 233 | Sm_24 | AAUUUUUUGAG |
| 234 | Sm_25 | AAUUUUUCGAG |
| 235 | Sm_26 | AAUUUUUGAAG |
| 236 | Sm_27 | AAUUUUUGUAG |
| 237 | Sm_28 | AAUUUUUGCAG |
| 238 | Sm_29 | AAUUUUUGGUG |
| 239 | Sm_30 | AAUUUUUGGGG |

TABLE_3-continued

| SEQ ID NO | Name/ ID | Sequence |
|---|---|---|
| | | SEQUENCE_LISTING |
| 240 | Sm_31 | AAUUUUUGGCG |
| 241 | Sm_32 | AAUUUUUGGAA |
| 242 | Sm_33 | AAUUUUUGGAU |
| 243 | Sm_34 | AAUUUUUGGAC |
| 244 | Sm_35 | AAUGUUUUGAG |
| 245 | Sm_36 | AAUUUGUGUAG |
| 246 | Sm_37 | AGUUUUUGGAA |
| 247 | Sm_38 | AUUUUGUGGAG |
| 248 | Sm_39 | AAUGUUUGCAG |
| 249 | Sm_40 | AAUGUUUGGGAG |
| 250 | Sm_41 | AAUUGCUGGAG |
| 251 | Sm_42 | AAUUUUAGCAG |
| 252 | Sm_43 | AAGGUUUGGAG |
| 253 | Sm_44 | GAUUUGUGGAG |
| 254 | Sm_45 | ACUUUUUGGAA |
| 255 | Sm_46 | AAAUUAUGGAG |
| 256 | Sm_47 | AAUUUUUGCGAG |
| 257 | Sm_48 | AAUUUCUGGAA |
| 258 | Sm_49 | UAUUUUUGGUG |
| 259 | Sm_50 | GAUUUUAGGAG |
| 260 | Sm_51 | AAUCUGUGGAG |
| 261 | Sm_52 | AAAUUUUAGAG |
| 262 | Sm_53 | AAUUUUUCGAC |
| 263 | Sm_54 | AAUUUUUGGGU |
| 264 | Sm_55 | AAUCUUUGGAA |
| 265 | Sm_56 | AAUUAUUGGUG |
| 266 | Sm_57 | AAUUUUUAAGAG |
| 267 | Sm_58 | AAUGUUAGGAG |
| 268 | Sm_59 | AAUUUUUAGAAG |
| 269 | Sm_60 | AUUUUUUGGCG |
| 270 | Sm_61 | AACUUUUGGUG |
| 271 | Sm_62 | AAUGUUUGGAU |
| 272 | Sm_63 | AAUUUUAGGAU |
| 273 | Sm_64 | AAUUUUUGAUG |
| 274 | Sm_65 | AAUUCUUGGUG |
| 275 | Sm_66 | AAUCCUUGGAG |
| 276 | Sm_67 | AAUUUUUCAAG |

TABLE_3-continued

| SEQ ID NO | Name/ ID | Sequence |
|---|---|---|
| | | SEQUENCE_LISTING |
| 277 | Sm_68 | CAUUUUUGCAG |
| 278 | Sm_69 | CAUUUUUCGAG |
| 279 | Sm_70 | AAUUUUGGGCG |
| 280 | Sm_71 | AGUUUUUGCAG |
| 281 | Sm_72 | AAAAUUUGGAG |
| 282 | Sm_73 | AACUCUUGGAG |
| 283 | Sm_74 | AAUUUGUGGAC |
| 284 | Sm_75 | ACUUUUUGGUG |
| 285 | Sm_76 | AUUUUUUGAAG |
| 286 | Sm_77 | AUUUUUUGGAA |
| 287 | Sm_78 | AAGUUAUGGAG |
| 288 | Sm_79 | CAUUUCUGGAG |
| 289 | Sm_80 | AGUUCUUGGAG |
| 290 | Sm_81 | AAUUUUGGAAG |
| 291 | Sm_82 | AGUAUUUGGAG |
| 292 | Sm_83 | AAUUUUUGGGC |
| 293 | Sm_84 | AAUUCUUGUAG |
| 294 | Sm_85 | AAUUUUGGGAA |
| 295 | Sm_86 | UAUUUUUUGAG |
| 296 | Sm_87 | AACUUUUGUAG |
| 297 | Sm_88 | AAUUAUUGCAG |
| 298 | Sm_89 | AAUUUUUUGGUA |
| 299 | Sm_90 | AAUUUUCGAAG |
| 300 | Sm_91 | UAUCUUUGGAG |
| 301 | Sm_92 | AAUUUUUCGUG |
| 302 | Sm_93 | AAUCUUUGGCG |
| 303 | Sm_94 | GAUUUAUGGAG |
| 304 | Sm_95 | AAUUUUUCGAA |
| 305 | Sm_96 | CCUUUUUGGAG |
| 306 | Sm_97 | UAUUUUUGAAG |
| 307 | Sm_98 | AAUUUUUGUAA |
| 308 | Sm_99 | AAUUUUGAGAG |
| 309 | Sm_100 | AAGUAUUGGAG |
| 310 | Sm_101 | AAUUUUUAGGAC |
| 311 | Sm_102 | AAUUUUUUAAAG |
| 312 | Sm_103 | AAUUCUUGGAU |
| 313 | Sm_104 | AAUUUGUGGUG |

TABLE_3-continued

SEQUENCE_LISTING

| SEQ ID NO | Name/ID | Sequence |
|---|---|---|
| 314 | Sm_105 | AAUUUUCGGGG |
| 315 | Sm_106 | ACUUUUUUGAG |
| 316 | Sm_107 | AAGUUUCGGAG |
| 317 | Sm_108 | ACUUUUGGGAG |
| 318 | Sm_109 | GACUUUUGGAG |
| 319 | Sm_110 | CUUUUUUGGAG |
| 320 | Sm_111 | CAUUGUUGGAG |
| 321 | Sm_112 | AAUAUUUUGAG |
| 322 | Sm_113 | AAGUUUUGGCG |
| 323 | Sm_114 | AAUUUUAGGAA |
| 324 | Sm_115 | AACUUGUGGAG |
| 325 | Sm_116 | AUUUUUUGGGG |
| 326 | Sm_117 | AAUUUUUAGAU |
| 327 | Sm_118 | UAUUUUGGGAG |
| 328 | Sm_119 | AAUUUGUGGGG |
| 329 | Sm_120 | AAUUUUUAGGG |
| 330 | Sm_121 | AAUUUUCGUAG |
| 331 | Sm_122 | AAUUUUCUGAG |
| 332 | Sm_123 | GAUUCUUGGAG |
| 333 | Sm_124 | AAUCUUUGGAU |
| 334 | Sm_125 | AAAUUUUGGCG |
| 335 | Sm_126 | AAUCAUUGGAG |
| 336 | Sm_127 | AACUUUUGGCG |
| 337 | Sm_128 | AAUUUUUGGGA |
| 338 | Sm_129 | AAUGUUUGGUG |
| 339 | Sm_130 | AAUUUAUGCAG |
| 340 | Sm_131 | AAUCUCUGGAG |
| 341 | Sm_132 | AGUUUGUGGAG |
| 342 | Sm_133 | AAGUUUUGGAU |
| 343 | Sm_134 | UAUUUUUGGCG |
| 344 | Sm_135 | AAUUUCUGAAG |
| 345 | Sm_136 | UAUUUCUGGAG |
| 346 | Sm_137 | AAUUUUUGCUG |
| 347 | Sm_138 | AAAUCUUGGAG |
| 348 | Sm_139 | AAAUUUUUGAG |
| 349 | Sm_140 | UAUUUUUGUAG |
| 350 | Sm_141 | GAUUAUUGGAG |

TABLE_3-continued

| SEQ ID NO | Name/ ID | Sequence |
|---|---|---|
| 351 | Sm_142 | AAGUUCUGGAG |
| 352 | Sm_143 | AAUCUUUGAAG |
| 353 | Sm_144 | AAAUAUUGGAG |
| 354 | Sm_145 | AACUAUUGGAG |
| 355 | Sm_146 | AAUAUAUGGAG |
| 356 | Sm_147 | AUUCUUUGGAG |
| 357 | Sm_148 | GAUUUUUGAAG |
| 358 | Sm_149 | AAGUUUUGGUG |
| 359 | Sm_150 | AAUCUUUGCAG |
| 360 | Sm_151 | ACUUUUUGGCG |
| 361 | Sm_152 | GAUUUUGGGAG |
| 362 | Sm_153 | CAUUUUUGGAA |
| 363 | Sm_154 | AAUUUUUUGAC |
| 364 | Sm_155 | AAAUUUUGCAG |
| 365 | Sm_156 | ACUUUUUGAAG |
| 366 | Sm_157 | AGUCUUUGGAG |
| 367 | Sm_158 | AGUUUAUGGAG |
| 368 | Sm_159 | ACUUCUUGGAG |
| 369 | Sm_160 | AAUUUUUUCAG |
| 370 | Sm_161 | AAUUUUCGGAU |
| 371 | Sm_162 | AAUUUUUGUAU |
| 372 | Sm_163 | AAUGUCUGGAG |
| 373 | Sm_164 | AAUUGUUGGGG |
| 374 | Sm_165 | AAUUUAUGGAC |
| 375 | Sm_166 | AAUUUAUGAAG |
| 376 | Sm_167 | AAUUUAUGGGG |
| 377 | Sm_168 | AAUUUGUCGAG |
| 378 | Sm_169 | AAUUGUUGGAA |
| 379 | Sm_170 | UGUUUUUGGAG |
| 380 | Sm_171 | AAAUUUAGGAG |
| 381 | Sm_172 | AAUUUUUUGUG |
| 382 | Sm_173 | CAUUCUUGGAG |
| 383 | Sm_174 | AAUUCUCGGAG |
| 384 | Sm_175 | AAUUUUUAUAG |
| 385 | Sm_176 | ACUUUUUAGAG |
| 386 | Sm_177 | AAUUGUUAGAG |
| 387 | Sm_178 | CGUUUUUGGAG |

TABLE_3-continued

| | | SEQUENCE_LISTING |
|---|---|---|
| SEQ ID NO | Name/ ID | Sequence |
| 388 | Sm_179 | AAUUUUUGCGG |
| 389 | Sm_181 | AAGUUUUGAAG |
| 390 | Sm_181 | AAUUUUCGGAA |
| 391 | Sm_182 | AAUUUUUCCAG |
| 392 | Sm_183 | AUUUUUUGUAG |
| 393 | Sm_184 | AAUCUUUAGAG |
| 394 | Sm_185 | AAUUUUACGAG |
| 395 | Sm_186 | CAUUUUUGGCG |
| 396 | Sm_187 | AAUUUGCGGAG |
| 397 | Sm_188 | CAUCUUUGGAG |
| 398 | Sm_189 | AACUUUUGAAG |
| 399 | Sm_190 | AAUUUUUCUAG |
| 400 | U7_1 | CAGGUUUUCCAGUGUUCACUGAAAUUUGUCUCU |
| 401 | U7_2 | AAGGUUUUCUGGUCUUUAUCAGAAAGCCUCC |
| 402 | U7_3 | CAGGUUUUCUGGUUUUUCACUGCAAAACCCCA |
| 403 | U7_4 | CAGACUUUACGGUGCUUACCAGAAAGCUCCC |
| 404 | U7_5 | CACGUUUUCCGGUUGUCACUCCCAGGUAGGCUGGGGAAGAGGCAU |
| 405 | U7_6 | CAGUCUUUCCAGUUUUUGCCGGAAAGCCCCU |
| 406 | U7_7 | CAGGCUUUCUGGUUUUUGCCAGAAAGCCCCC |
| 407 | U7_8 | CAGGUUUUUCAGUUUUUCACCAGAAUGCCCAC |
| 408 | U7_9 | CAGGUUUUCUGGUCUUUACUGGAAAGCCCAA |
| 409 | U7_10 | CAGGCUUUCCGGUUUUUACCAGAAAGCCCCC |
| 410 | U7_11 | CAGGUUUUUCGGUUUUUACUGGAAAGCCCCA |
| 411 | U7_12 | CAGGCUUUCCAGUAAAUACAGGAAAGCCCUC |
| 412 | U7_13 | CAGGCUUUCCGGUUUUUGCUGGAAAGACUCC |
| 413 | U7_14 | AAGGUUUUCUGGUCUUUACUGAAAAGCCCCA |
| 414 | U7_15 | UGGGCUUUCUGUUUUUUACGAGAAAGUCCUC |
| 415 | U7_16 | CAGAUUUCUCAGUUUUCACUGGAAACCCUU |
| 416 | U7_17 | CAGGUUUUCCUGUCUUCACCGGAACUCCCCA |
| 417 | U7_18 | CAGGUUUUCUGGUUUGCACUAGAAAAACCAUA |
| 418 | U7_19 | CAGAUUUUCUGGUUUUUACCAGAAAAUUUAA |
| 419 | U7_20 | CAGGUCUUCUUGUUUUUACUGGAAAAUCCUC |
| 420 | U7_21 | CAGGUUUUCCGGUCUUCACCAGAAAACCCCU |
| 421 | U7_22 | CAGGUUUUCCGAUUUUUACUGGAAAGCCCUU |
| 422 | U7_23 | CAGGUUUUCUGGUUUUUCCAGAAAACCUCC |
| 423 | U7_24 | CAGGUUUUCCAGUUUUUCACUGGAACCUCU |
| 424 | U7_25 | CCGGCUUUCCAGUUUUUGCCGGAAAGCCCCC |

TABLE_3-continued

SEQUENCE_LISTING

| SEQ ID NO | Name/ ID | Sequence |
|---|---|---|
| 425 | U7_26 | CAGGUUUUCUGGUUUUUUACCAGAACUUAA |
| 426 | U7_27 | CACGUUUUCCGGUUGUCACUCCCAGGUGGGCUCGGGAAGAGGCAU |
| 427 | U7_28 | CAGGCUUUCCGGUCUUUACCGGAAAGCCUAU |
| 428 | U7_29 | CAGGCUUUCUGGUUUUUUGCCGGAAAGCCCUC |
| 429 | U7_30 | CAGGCUUUCAGGUCUUUGCCAGAAAGCCCCA |
| 430 | U7_31 | CAGGCUUUCUUGUUUUUCACUGGAAGCCUCC |
| 431 | U7_32 | CAGGUUUUUCAGUCUUCACCGGAAAGCUCCC |
| 432 | U7_33 | CAGAUUUUCUGGUUUUUCACCACGAAAGAAAUGUCAUU |
| 433 | U7_34 | CAGUUCUCCUGGAUUUUUACAGGAAAACCCC |
| 434 | U7_35 | CAGGCUUUCUGGCAUUUGCCAGAAAGCCCUG |
| 435 | U7_36 | CAGACUUUCCUGUUUUUUAACAGAAAGCCCCC |
| 436 | U7_37 | CAGGCUUUCCGGUUUUUUGCUGGAAAGCUCCC |
| 437 | U7_38 | CAGCUUUUCCAGUUUUUCACUGAGGUAAA |
| 438 | U7_39 | UAGGUUUUCUGGUUUUUUAUUGGGAAAUCACA |
| 439 | U7_40 | CAGGGUUUCUGGUGGUACCAGCAGACUCCACA |
| 440 | U7_41 | CAAGUUUCCCAGUUUUUCACUGGAACCUCCG |
| 441 | U7_42 | CAGAUUUUCCAGUUUUUUACUAGAAACCCCCC |
| 442 | U7_43 | CAGGGUUUCCAGUUUUUCACUGUAUACCAUCC |
| 443 | U7_44 | CAAGUUCUCUGGUCUUUCACUGGAAAACCCAU |
| 444 | U7_45 | UAGAUUUUCUGGUCUUUACCAGAAAGACUCC |
| 445 | U7_46 | GCAGGUUUUCUGGUUUUUUAUUGGAAAACCUUC |
| 446 | U7_47 | CAGGUUUUCCACUUUUUCACCAGAAACUGCCUCU |
| 447 | U7_48 | UAGGCUUUCCGGUUUUUUGCAGGAAAGCCCCC |
| 448 | U7_49 | CAGGUUUUCCAGUCUUUACCAGAAAGCCACU |
| 449 | U7_50 | CAGGUUUUUUGGUCUUCACAGGAAACUUCCCCU |
| 450 | U7_51 | CAGGUUUUCUGCUUUUUCACUGGAAGACUCCC |
| 451 | U7_52 | CAGACUUUCCAGUUUUUGCCAGAAAGCCCAC |
| 452 | U7_53 | CAGGCUUUCUGGUUUUUUGCCCAAAAGCCUCU |
| 453 | U7_54 | CAGGUUUUCCAAUCUUCACUGAAAAGCUUUA |
| 454 | U7_55 | CUGGUUCCUAGUCUUCACUGGAAGCACCCUC |
| 455 | U7_56 | GGCUUUCCGCUCUUCAUUGGAAAGCCCAU |
| 456 | U7_57 | CAGGUUUUUCAGUUUUUUAGCAGAAAACCUCC |
| 457 | U7_58 | CAGGUUCUCUGGUUUUUUACUGAAACCAAA |
| 458 | U7_59 | CAGGUUUUCCAGUCUUCACUGGAAAGCCCUU |
| 459 | U7_60 | CAGGCUUUCUGGUUUUUUGCCGGAAGGCCUCC |
| 460 | U7_61 | CAGGUUUUCUGUUUUUUUAACUAGAAAACUCCC |
| 461 | U7_62 | UAGGCUUUCUGGUUUUUUGCUGGAAAGCCCCC |

TABLE_3-continued

| SEQUENCE_LISTING | | |
|---|---|---|
| SEQ ID NO | Name/ ID | Sequence |
| 462 | U7_63 | CAGGUUUCCCGGUUUUUACCAGAAAAAUCUAA |
| 463 | U7_64 | CAGGUUUUCCAGUCUUUACCAGAAAUGCCCCC |
| 464 | U7_65 | GGUUUUCUGGUCAUCGCUGGAAACACCCUC |
| 465 | U7_66 | CAACCUUUCUGGUUUUUGCUAGAAAGUUCUC |
| 466 | U7_67 | CAGGCCUUUGGGUCUUUACUGGAAAACCCCU |
| 467 | U7_68 | UAUGUUUUCCGGUUUUUCACUCCCAGGUAGGCUCGG |
| 468 | U7_69 | CAAAUUUUCUGGCUUUUCCAGGAAAAUCCCC |
| 469 | U7_70 | UAGGUUUUCCAGUGACCAGAAAAUCCUC |
| 470 | U7_71 | CAGGUCUUCGGGUUUUUAACUGGAAACCUUC |
| 471 | U7_72 | GCAGGCUUUCCAGUUUUUUCUGGAAAGCCUCA |
| 472 | U7_73 | GGCUUUCUGGUUUUUACUGGAAAGCCCCC |
| 473 | U7_74 | CAGGUUUCCCAGUAUUCACCGGAAAGCUCCA |
| 474 | U7_75 | CAGGCUUUCUAGUUUUUCCCACACUAAGAAACAAAAAAACCUGU |
| 475 | U7_76 | GCAAGCUUUCUGGUUUUUGGCCAAAAAGCCACC |
| 476 | U7_77 | UUCUGGUUUUCACCAGAAACCACU |
| 477 | U7_78 | GCAAGUUUUCUAGCCUGUACCGAAAGCCUCA |
| 478 | U7_79 | AAGUUUUCUUGUUUUUACCAGAAAACUCCU |
| 479 | U7_80 | GGCUUUCCAAUUUUUGCCAGAAAGCCCCC |
| 480 | U7_81 | AGCUGGUUUUCUGGUUUUUCACCGGAAGACCCAU |
| 481 | U7_82 | CAGGCCUUCUGGUUUUUUGCUGGGAAGUCCCCA |
| 482 | U7_83 | CAGGUUUUCCAGUUUGUACCAGAAAACCCCU |
| 483 | U7_84 | CAGGUUUCACCCAAAAACCCAC |
| 484 | U7_85 | UAGGCUUUCUGGCUUUUUACCGGAAAGCCCCU |
| 485 | U7_86 | CAGGGUUUCUGGUUUUUCACCAGGAAACAAAA |
| 486 | U7_87 | CAGGUUUUCCUGUCUUUACUAGAAACCCCUC |
| 487 | U7_88 | CAGGUUUUAUAGGUUUUUACCAGAAAACUUCC |
| 488 | U7_89 | CAGGCUUCCCAAUUUUUGCUGGAAAGCCCCU |
| 489 | U7_90 | CAGGCUUUUUGGGUUAGGUCAGAAAGUCCCC |
| 490 | U7_91 | CAGGUUUUUGGUUUUUUAGCGAAACCCUC |
| 491 | U7_92 | CAGGCUUUCUGGUUUUUCACCAUAAAAUGCCCCA |
| 492 | U7_93 | CAGGUCUUCGGGGUUUUUACAAAAAGAAGAAGAAAUCCACCCCC |
| 493 | U7_94 | CAAGUUCUCUGGUCUCCCAACAAGAAACCCCC |
| 494 | U7_95 | CAGGAUUUCUGGUUUCUGGUGGAAAGCUCCCAU |
| 495 | U7_96 | AGGCUUUCCAGUUUUUGCUGGAAAGCCCCU |
| 496 | U7_97 | CAGGUUUUCCAGUCUUUGUCAAAUGCCUUC |
| 497 | U7_98 | CAGGCUUUCCAGUUUUUUGCCAGUGUGAACCCAAA |
| 498 | U7_99 | CAGGCUUUCUGGUUUUUUAUCAGAAAGCCUCC |

US 12,668,800 B2

TABLE_3-continued

SEQUENCE_LISTING

| SEQ ID NO | Name/ ID | Sequence |
|---|---|---|
| 499 | U7_100 | GAGGUUUUCUGGUUUUUCACCAGAACCAACCCUU |
| 500 | U7_101 | CAGAUUUUCCAGCUUUUACUGGAAGCCCCCU |
| 501 | U7_102 | CAGGUUUUCUGGUUUUUCACUGGAAAAUACCUCA |
| 502 | U7_103 | CAUGUUUUUUGGUGUUAAUAAAAACCCGCACAC |
| 503 | U7_104 | AAGGCUUUCCGGUUUUUUGCAGGAAAGCAACC |
| 504 | U7_105 | AGUCUUUCCGGGUUUUUGUCAGAAAGGCCCU |
| 505 | U7_106 | GCAGGUUUUCUGGUUUCUACUGGAAGCUUCU |
| 506 | U7_107 | CAGGCUUUCUGGUUUUUUACUGGAAAGCCCCU |
| 507 | U7_108 | CAGGCUUUCCAAUUUUUGCCAGAAAGCUCCC |
| 508 | U7_109 | CAGGUUUUCUGGUUCUCACCAGAAAACGCCA |
| 509 | U7_110 | CAGGUUUUCUGGUCUUCACUGGAAGACCACU |
| 510 | U7_111 | CAGGUGGUUUUCCGGUCUUUACCAGUAAGCCCCC |
| 511 | U7_112 | CAGGUUUUCCAGUUUCUACCAGAAACCCCUA |
| 512 | U7_113 | CAGGUUUUCUGGUCUUUACCAGAAAAGUCUCC |
| 513 | U7_114 | CCAGGCUUUCUGGUUUUUACCGGAAAGCCCCG |
| 514 | U7_115 | CAGGUUUUUCACUUUUUUACUAGAAAAACCAGU |
| 515 | U7_116 | UAGGCUUUCUGGGGAGGUCUUUACCAGAAAGCCUCC |
| 516 | U7_117 | UACAUUUUCCAGUUUUUCACCAGGAAUCUGCCU |
| 517 | U7_118 | UAGGUUUUCCAGUUUUUCACCAGAAAAUCCCG |
| 518 | U7_119 | CAGGUUUUCUGGUUUUUUACGAGACUCCCCCA |
| 519 | U7_120 | CAGGCUUUCUGUUUUUUGCUAAAAUCCUCC |
| 520 | U7_121 | CUGGGCGUACUGGCUCACGCCUAUAAUCCCAA |
| 521 | U7_122 | GGCUCUCCGGUUUUUGCCAGAAUGCCCAC |
| 522 | U7_123 | UGGGUUUUCUGGUGAAAACUAGACUGCCCCC |
| 523 | U7_124 | CAGGCUUUCUGGUUUUUUACAGGAAGGCCCCU |
| 524 | U7_125 | GGUUUUCUGGUUCUCACUGGAAAACCCCC |
| 525 | U7_126 | CAGGCUUUCCGGUAAAGACUGGAAAGCCCCU |
| 526 | U7_127 | CAGGUUUUCCAGUUUUUACCAGAAAACUCUC |
| 527 | U7_110_C1A | AAGGUUUUCUGGUCUUCACUGGAAGACCACU |
| 528 | U7_110_C1G | GAGGUUUUCUGGUCUUCACUGGAAGACCACU |
| 529 | U7_110_C1T | UAGGUUUUCUGGUCUUCACUGGAAGACCACU |
| 530 | U7_110_A2C | CCGGUUUUCUGGUCUUCACUGGAAGACCACU |
| 531 | U7_110_A2G | CGGGUUUUCUGGUCUUCACUGGAAGACCACU |
| 532 | U7_110_A2T | CUGGUUUUCUGGUCUUCACUGGAAGACCACU |

TABLE_3-continued

| | | |
|---|---|---|
| | | SEQUENCE_LISTING |

| SEQ ID NO | Name/ ID | Sequence |
|---|---|---|
| 533 | U7_110_ G3T_ C28A | CAUGUUUUCUGGUCUUCACUGGAAGACAACU |
| 534 | U7_110_ G3C_ C28G | CACGUUUUCUGGUCUUCACUGGAAGACGACU |
| 535 | U7_110_ G3A_ C28T | CAAGUUUUCUGGUCUUCACUGGAAGACUACU |
| 536 | U7_110_ G4C_ C27G | CAGCUUUUCUGGUCUUCACUGGAAGAGCACU |
| 537 | U7_110_ G4A_ C27T | CAGAUUUUCUGGUCUUCACUGGAAGAUCACU |
| 538 | U7_110_ G4T_ C27A | CAGUUUUUCUGGUCUUCACUGGAAGAACACU |
| 539 | U7_110_ T5G_ A26C | CAGGGUUUCUGGUCUUCACUGGAAGCCCACU |
| 540 | U7_110_ T5A_ A26T | CAGGAUUUCUGGUCUUCACUGGAAGUCCACU |
| 541 | U7_110_ T5C_ A26G | CAGGCUUUCUGGUCUUCACUGGAAGGCCACU |
| 542 | U7_110_ T6G_ G25C | CAGGUGUUCUGGUCUUCACUGGAACACCACU |
| 543 | U7_110_ T6A_ G25T | CAGGUAUUCUGGUCUUCACUGGAAUACCACU |
| 544 | U7_110_ T6C_ G25G | CAGGUCUUCUGGUCUUCACUGGAAGACCACU |
| 545 | U7_110_ T6T_ G25A | CAGGUUUUCUGGUCUUCACUGGAAAACCACU |
| 546 | U7_110_ T7C_ A24G | CAGGUUCUCUGGUCUUCACUGGAGGACCACU |
| 547 | U7_110_ T7G_ A24C | CAGGUUGUCUGGUCUUCACUGGACGACCACU |
| 548 | U7_110_ T7A_ A24T | CAGGUUAUCUGGUCUUCACUGGAUGACCACU |
| 549 | U7_110_ T8A_ A23T | CAGGUUUACUGGUCUUCACUGGUAGACCACU |
| 550 | U7_110_ T8G_ A23C | CAGGUUUGCUGGUCUUCACUGGCAGACCACU |

TABLE_3-continued

| | | SEQUENCE_LISTING |
| --- | --- | --- |
| SEQ ID NO | Name/ ID | Sequence |
| 551 | U7_110_ T8C_ A23G | CAGGUUUCCUGGUCUUCACUGGGAGACCACU |
| 552 | U7_11_ 0C9T_ G22A | CAGGUUUUUUGGUCUUCACUGAAAGACCACU |
| 553 | U7_110_ C9G_ G22C | CAGGUUUUGUGGUCUUCACUGCAAGACCACU |
| 554 | U7_110_ C9A_ G22T | CAGGUUUUAUGGUCUUCACUGUAAGACCACU |
| 555 | U7_110_ T10C_ G21G | CAGGUUUUCCGGUCUUCACUGGAAGACCACU |
| 556 | U7_110_ T10A_ G21T | CAGGUUUUCAGGUCUUCACUUGAAGACCACU |
| 557 | U7_110_ T10T_ G21A | CAGGUUUUCUGGUCUUCACUAGAAGACCACU |
| 558 | U7_110_ T10G_ G21C | CAGGUUUUCGGGUCUUCACUCGAAGACCACU |
| 559 | U7_110_ G11T_ T20A | CAGGUUUUCUUGUCUUCACAGGAAGACCACU |
| 560 | U7_110_ G11A_ T20T | CAGGUUUUCUAGUCUUCACUGGAAGACCACU |
| 561 | U7_110_ G11G_ T20C | CAGGUUUUCUGGUCUUCACCGGAAGACCACU |
| 562 | U7_110_ G11C_ T20G | CAGGUUUUCUCGUCUUCACGGGAAGACCACU |
| 563 | U7_110_ G12T_ C19A | CAGGUUUUCUGUUCUUCAAUGGAAGACCACU |
| 564 | U7_110_ G12A_ C19T | CAGGUUUUCUGAUCUUCAUUGGAAGACCACU |
| 565 | U7_110_ G12C_ C19G | CAGGUUUUCUGCUCUUCAGUGGAAGACCACU |
| 566 | U7_110_ T13C_G A18 | CAGGUUUUCUGGCCUUCGCUGGAAGACCACU |
| 567 | U7_110_ T13G_ A18C | CAGGUUUUCUGGGCUUCCCUGGAAGACCACU |
| 568 | U7_110_ T13A_ A18T | CAGGUUUUCUGGACUUCUCUGGAAGACCACU |
| 569 | U7_110_ C14T | CAGGUUUUCUGGUUUUCACUGGAAGACCACU |

TABLE_3-continued

| SEQ ID NO | Name/ ID | Sequence |
|---|---|---|
| 570 | U7_110_ C14A | CAGGUUUUCUGGUAUUCACUGGAAGACCACU |
| 571 | U7_110_ C14G | CAGGUUUUCUGGUGUUCACUGGAAGACCACU |
| 572 | U7_110_ T15A | CAGGUUUUCUGGUCAUCACUGGAAGACCACU |
| 573 | U7_110_ T15G | CAGGUUUUCUGGUCGUCACUGGAAGACCACU |
| 574 | U7_110_ T15C | CAGGUUUUCUGGUCCUCACUGGAAGACCACU |
| 575 | U7_110_ T16A | CAGGUUUUCUGGUCUACACUGGAAGACCACU |
| 576 | U7_110_ T16G | CAGGUUUUCUGGUCUGCACUGGAAGACCACU |
| 577 | U7_110_ T16C | CAGGUUUUCUGGUCUCCACUGGAAGACCACU |
| 578 | U7_110_ C17A | CAGGUUUUCUGGUCUUAACUGGAAGACCACU |
| 579 | U7_110_ C17G | CAGGUUUUCUGGUCUUGACUGGAAGACCACU |
| 580 | U7_110_ C17T | CAGGUUUUCUGGUCUUUACUGGAAGACCACU |
| 581 | U7_110_ A29G | CAGGUUUUCUGGUCUUCACUGGAAGACCGCU |
| 582 | U7_110_ A29C | CAGGUUUUCUGGUCUUCACUGGAAGACCCCU |
| 583 | U7_110_ A29T | CAGGUUUUCUGGUCUUCACUGGAAGACCUCU |
| 584 | U7_110_ C30G | CAGGUUUUCUGGUCUUCACUGGAAGACCAGU |
| 585 | U7_110_ C30T | CAGGUUUUCUGGUCUUCACUGGAAGACCAUU |
| 586 | U7_110_ C30A | CAGGUUUUCUGGUCUUCACUGGAAGACCAAU |
| 587 | U7_110_ T31A | CAGGUUUUCUGGUCUUCACUGGAAGACCACA |
| 588 | U7_110_ T31G | CAGGUUUUCUGGUCUUCACUGGAAGACCACG |
| 589 | U7_110_ T31C | CAGGUUUUCUGGUCUUCACUGGAAGACCACC |
| 590 | SNORA38 | UCCUCCUACAAAGGCGUGUCUGUGGUUCCCUGUCUUUGGACACGUAAGAAU UGGAGGAAAAUAAAUGUGGAUUUGGGAAACUUUGAGGCCAGCUUGCUUCUU GCAGGCUCAUGAUCAACCAAUCUCACAUAA |
| 591 | SNORA24 | CUCCAUGUAUCUUUGGGACCUGUCAGCCGUGGCAGUCUCCCUUCCUAGCCA UGGAAGAGCAUAUCCUUGUUUAUUGGCAAAGCUGUCACCAUUUAAUUGGUA UCAGAUUCUGACUUGCACAAGUAACAUUC |
| 592 | SNORA72 | CUGCGAAUAUUCUCGCUGUUCUGAUUUUGUAAUAGUCAGGACAGGCUAAAC AUUCGCUAUAUUAAGACCAUGCAUGUGUCCCCAAACCUAGUUCUUUCCCUA GGUCUGGUUUCAUAAAUGCUGGUGAUAAAC |
| 593 | SNORA15 | GCAUGGCCGAAUACUGUGUUUUUAUCAGUAGUUUACACAGCCAGACACCAU GCAAAAGCAGUCUUCCCUUUAGAAUGACUGAUGGUAUGCUAAGGUUUUUCA UAGCAUAUCAUUAUUAAAGGUGAAUACAAAU |

TABLE_3-continued

| SEQUENCE_LISTING |
| --- |

| SEQ ID NO | Name/ ID | Sequence |
| --- | --- | --- |
| 594 | SNORA8 | UGCACUGCAUGGUAUCUGCACUCAGCAGUUUACACCUGCUAGGGUGUUCAA AGGUCAGUGCUAUAGAAAUUCAGUAUCUGGCAUCGUUGGUUUUCUUGGCUU UGUGCUUGUUAAACCUGGUAUUUCUACUGAUACAGUA |
| 595 | SNORA52 | UGGUCCAUCCUAAUCCCUGCCGGUCCAUCUGUGGCCUGCCAGGUUUCGCUU GUGGACCAGAGCACCCUAGAAGCCUCACCCGAGGAGUGAGCAGGGCUCCAG UGGGCUCACGUCAUGGGCACUUCUAGACACUC |
| 596 | SNORA60 | CACCUGCAUUCAAAAAUGAUCACGGGCUGCCUGUGCUCUGGUCAUCAAUAA CGCAGGGAGAGGAAUUGCUGAAAGCCGUUUCCCGUGUUUGGAGGGUUCACA CCUGUCCCUUUCAAAUGCUGGCGCUUUCACACAC |
| 597 | SNORA14A | UGCAUUCUUAAACCCUCUUGGUGGCUUCCCUGUAAAUGCUUCCAAGAUAUG AGCGAAUGCUAUAGAAAUUGCAGGAAAGUCCAAAGGGCUGCGCGUCUCCUG UGGCUCAGUCUUAUUUCAUACCUGCAACAUCU |
| 598 | SNORA68 | AUUGCACCUAAACCCAAGAAUCACUGUUUCUUAUAGCGGUGGUUUAAACAG AGGUGCAAACAGCAAGCGGAUCUUGUCGCCUUUGGGGGGCUGUGGCCGUGC CCCUCAAAGUGAAUUUGGAGGUUCCACAACU |
| 599 | SNORA20 | CUUCCCAUUUAUUUGCUGCUUGUAGUCUCACAGUGAUACGAGCAGUUAUAC GCAUGGGAUAAAAUAACAUUGGGCCACUGUAAAUUGAGAUGAAGUAACCAU UUUCAUCUCUUCUGCAGGGACUAGACAUUG |
| 600 | SNORA14B | CUGCAUUCUUAAACCCUCUUGGUAGCUUCGUUCUAAGUGCUUCCAAGAUAU GAGUGAAUGCUAUAGAAAUUGCAGGGGAGUCCAAAGGGCUGCGCUUCUCCC GUGGCUCAGUCUUAUUUCAUACCUGCGACAUCU |
| 601 | SNORA63 | AGGCAGGAUCUAGUUACAUUGUAGCUGUGAAGUGCUGCAUUGUCUUUGCCC CCUGCUCAAAAUAAAACUGUUACCUUUCAAGCCCUGUCUGCCAUGGUGCUG UAGCAGCAGGGAUGUUUGGUCUCAUACAU |
| 602 | SCARNA4 | ACUGGAGGACUAAGGAGGCUGGGUCUGAUGAGGCAAGAUUUUGCUGAUACA UUGCUCCUAGAAAAAAGGGUUGGCAAGAGCAGCCCUGGAGACUCACACGGC UGACUGUUCUACCCAACACUC |
| 603 | SNORA63C | AAGCAGGAUUCAGACUACAAUAUAGCUGUUAAGUGCUGUAUUGUCAUUCCC CCUGCUCAAAUUAAAGUUGUUUCUUAACUAUACCCAUCUGCUAUUCUGUAG CAGCCAGGGAUGCUUGGUCACAUACAU |
| 604 | SNORA51 | GGCUUCCUAGUACUUACCAUGGUCUGUGUUCUUACGCUGACUGUAUAGAAA CAGGAGGCAGAGUAAACCGACCCCACAUAUACCUCAGCCCAGGCCCUGUGC UGCGUCUGUAUUGUGAAUCAGGAGACAUGG |
| 605 | SCARNA21 | UGGCUCGAUUUCCUGGGGGGUGGUCUCAGCCCCACUCCACCUCCCCUCAGCC GAGCCUAGAGUAGAGGGGCCAGGCAUCCUCCCCAGGGGAGGGGCGUUGAAG CAAGGAGCCUCUCCUGGGCUGUCCUAGCCUCACAUUU |
| 606 | SNORA18 | GUUGAGGUCUAUCCCGAUAGGUCUUUUCCUGUAGCCUGCACGUUGUUGGAA AUGCCUCAUAGAGUAACUCUGUGAUUUUACUUUACUUACAGGACUAUUGUU ACAUCUGUGGGAAGGAACCACAAGACAGUU |
| 607 | SNORA68B | UUCUCACCUAAACCCAAGAAUCACUGUUUCUUAUAGCGGUGGUUUAAACAG AGGUGCAAACAGCAAGUGAAUCUCGUCGCCUUUGCGGGGCUGUGGCCAUGC CCCUCAAAGGAAAUUUGGAGGCUCUACAGCC |
| 608 | SNORA25 | AGGUCAUUUCAAAGAGGUCUUGUGAGGCGUGUGAAACCAAGAGCUCUUAACA CUGCGACCAAAGAUGGAAGUUCUCUAUAGGAUGCCAUGGCAUUUGAUGGUG CUAUGUUUUCUUGAGGAGAUAUAAGA |
| 609 | SNORA38B | CCCUCCUACAAAGGCAUGUCUAUAGUUCCUUGUCUUUGGACAUGUAAGAAU UGGAGGCAAAGAAAUGUGGACUUGGAGAAAUCUGGGGCCAGCUUGCUCUCC GCAGGCUCAAGAUCAACCAUCCCACAUAG |
| 610 | SNORA77 | GCAGACUCACUAUGCACCUGACUGUACUUCCAGGCAGGUGCUUUUUCUGUC UGCCAGAGAAACAUUCCAGGGUGCUGUGGCUGCCUCACCUAUCCAGGGCGA UGCAGCUCCCUGGGGACACAGGU |
| 611 | SNORA77B | GCAGACUCACUCUGCAUCUGACUAUACUUCCAGGCGGGUGCUUUUUCUGUC UGCCAGAUAAACAUUCCAGGGUGCUGUGGCCGCCUCACGUAUCCAGAGUGA UGCAGCUCCCUGGGGACACAGGU |

TABLE_3-continued

SEQUENCE_LISTING

| SEQ ID NO | Name/ ID | Sequence |
|---|---|---|
| 612 | SNORA79B | UGAUGGCUGUUCCUCUCACUGCUUGAAGCCUUAGGCAGUGGGAUUUUGAUC<br>CAUCAUAUAUCAAAAAUGGCUUAUCUUCACUCAGGGCACCAUGAGGAUGGG<br>CUGGCUGUCCGUUAGUGCCUUCUGAUUUUUGCGGAGUCAAACAAUU |
| 613 | SNORA70EL5 | CUGGGGAAUUCAAACUUGUGUUAAGAAAAUGUGUCCCAGUGUGCAAUGGCU<br>GCAAACAGCAGCUUCCUUGGUAGUGUAUGCAGCCUGUUUGUUGUACGGGUU<br>GCUCUAAAGGGCCUUGGAGACAGUC |
| 614 | SNORA25L6 | AGGUCACUUCAAAGAGGGCUUGUGGGGCUGUGAAACCAAGAGGUCUUAACA<br>GUAUGACCAAAAACUGAAGUUCUCUAUAGGAUGCUGUAGCACUCAAUGGUG<br>CUAUGUUUUCCUCAGGAGAUAUGA |
| 615 | SNORA104 | CUGUCCGUUGCUGGCUUCACAAGUACUAGUAUAAUUUUUAAAAUGUUUUAU<br>UAUUUUGAAAAUAAUGUUGUAAUUCAUGCCAGGGACUGACAAAAGACUUGA<br>GACAGGAUGGUUAUUCUUGUCAGCUAAGGUCACAUUG |
| 616 | SNORA98 | UCCAAACAGACACUGAUGGCACCUUCUGCCAUUUAGGAAUUUGUUUUUAAA<br>CAGACAUUUGUCUAGAUAUUUCCUUUGUGGCCUCCUCCCCAUCAAAAGUCA<br>AUCAAACAUCG |
| 617 | ACA59 | GCCCUAUGUUAAAAUUUUAAUUCUGCACUUACUAACUAUCUUGGGAACCUU<br>GGGCAAGUAACCAACCUCUUGUGCUUUGGGUUUCCUCAUUGGUAAAAUGGGG<br>AUAACAGUACUUACCUCACAGAGUUGUUGAGAGGAACAAAU |
| 618 | SNORA63B | AUGCAGGUACUGUUACAAUACAACUGAUGUGUUUUGUUGUCGUUCCCCCUG<br>CUUAAAGCACUUGAUGCAUAACUCUGUCUACCUUCAUUCCGUAGUAAGACA<br>GAGACGCUUGGCUUCAGACAUUU |
| 619 | SNORA120 | UCACUGCCCUGCUCACCCUUCCUGAGUCCGGCCGGCAAGGGUAACUCUGGGA<br>GCAUCGUAGAGGGCAGAGAAGAAGAAACCCUGAGGUCCCAUUAUGUCAGCC<br>CCUUCUAUCACACGGGAGGAGACUGAGGACAGAAAGGGAACAGAG |
| 620 | SNORA116 | CUUUUCUCAGUGGUGCAAGAAGAUUAAGCCACAUUCUGGCUUUAGAGAGGC<br>AUUUCUGAGAGAGAUGAAGGACACUUCGUUCCCCAGCCCCAACCUAAGCAU<br>GUGACUGUACUCACCUUGUCAGAUGCUGUUGGAACCUGGCUGACA |
| 621 | SCARNA15 | CUGGAGGACUAAGGAGGCUGGGGUCUGAUGAGGCAAGAUUUUGCUGAUACAU<br>UGCUCCUAGAAAAAAGGGUUGGCAAGAGCAGCCCUGGAGACUCACACGGCU<br>GACUGUUCUACCCAACACUC |
| 622 | snoU109 | UAGUGUGGAACUGUCUACUCCUCAUUCCUGUGGAAGCAGGAAUACAUUCAU<br>AACAUGCUCCAUUAAAAAAGGAGUUCUAGGCCAGGCAGCGUGCCUCAUGCC<br>UGGAAUCCCAGCACUU |
| 623 | SNORA68L2 | AUACCUAAACCCAAGAAUCACUUUCUUAUAGUGAUGAUUUAAACAGAUGCA<br>AACAGCGAGCACAUCUUGUCACCUUUGCGGGACUGUGGCUGUGCCCCUCGC<br>AGUAAAUUUGGAGGUUCUACAUCC |
| 624 | SNORA63E | AGGCAGGAUCUAGUUACAUUGUAGCUGUGAAGUGCUGCAUUGUCUUUGCCC<br>CCUGCUCAAAAUAAACUGUUACCUUUCAAGCCCUGUCUGCCAUGGUGCUG<br>UAGCAGCAGGGAUGUUUGGUCUCAUACAUGU |
| 625 | SNORA75 | CACUAGAAGACAGAAUUCACAGAAGUAGCAUUUCACCUUUUGCCUUUACAG<br>AAGUAUAUUUGGCUGUUUUGUGAGACAUUC |
| 626 | SNORA95 | ACUUUUACAGGUAGAAUAGUAAAGCACAGUGUUGAUUGCCCAAGAUUUAUU<br>UUACUUUGAAAAAAUUAGAAAUUUAUUACUAUAGCAAAUGUCUAGAACUUU<br>GGAAACAAGU |
| 627 | SNORA31B | AUGCAUCUAUUUGACAGACCUGGAGCAGUUGCUAUCUGCUGCUAUGGUUUC<br>CACCACAGAUGCAAGAAGAACAUGUCCUUGCGCUUUCCGUCUGUCUAAUUG<br>UGGCAGCUGAGAUUGAAUAGAGGAAUACAGGA |
| 628 | SNORA50_1 | AAGCACUGCCUUUGAACCUGAUGUGUCUUGUUUUGUAGCUUCACGGGCCAAG<br>CAACAGUGCUAGAGCAUAACGACUUGUUAUAACUGGGGCUCUUCAGCUCUC<br>AACUGAACUGCUCUUUUAAAAACAAGGUACAUUU |
| 629 | SNORA50_2 | AAGCACUGCCUUUGAACCUGAUGUGUCUUGUUUUGUAGCUUCACGGGCCAAG<br>CAACAGUGCUAGAGCAUAACGACUUGUUAUAACUGGGGCUCUUCAGCUCUC<br>AACUGAACUGCUCUUUUAAAAACAAGGUACAUUU |
| 630 | ACA13 | AGCCUUUGUGUUGCCCAUUCACUUUGGAAACUAGUGAAUGUGGUGUCAAAA<br>AAGGCGUAAAUUAAACGCUUUGCAGCCUUUUCCUGCCCUUAAAAUUUGAUAC<br>CUUUGGUGUAGGAGCUGCAUAAGUAACAGUU |

TABLE_3-continued

SEQUENCE_LISTING

| SEQ ID NO | Name/ ID | Sequence |
|---|---|---|
| 631 | ACA36_2 | UUCCAAAGUGUUGAGUUCAGUCCAGGGCAGCUUCCCUGUUCUGUUAAUUAA ACUUUGGGACAUUAAAAUGGGCUAAGGGAGAUGAUUGGGUAGAAAGUAUUA UUCUAUUCAUUUGCCUCCCAGCCUACAAAA |
| 632 | ACA28_1 | AAGCAACACUCUGUGGCAGAUGAUCAAAACUGUCUGACACAAUUUGAGCUU GCUAUAGCAAGAAAGUCUAACCUAUUCCGGUGUUCUCUCUCCCAUGAGACA AGCCGUUAUAUAGACUUAAACAGU |
| 633 | ACA28_2 | AAGCAACACUCUGUGGCAGAUGAUCAAAACUGUCUGACACAAUUUGAGCUU GCUAUAGCAAGAAAGUCUAACCUAUUCCGGUGUUCUCUCUCCCAUGAGACA AGCCGUUAUAUAGACUUAAACAGU |
| 634 | ACA41 | UUCCACAGCUACUGGUCUGCAGCUGUUCUUAUGGUAGCAGUUGUGGCAUUC CUCUGUGGGAAAGAAACUGUUAACACAAACACCUCUUUCUUAGCAAAACAG AAAGUGGGUAUAUAUGUGUGACAGACACAA |
| 635 | ACA5_2 | UGCAGCCGUGUCAAAUUCAGUACCUGUCCUAUGCAUGGUAGGCACUGGCCC AGAAGGCUGCCACAGAAACACUGUGACUCAUGGGCCCUGUUCCUGUGUCCC AGGCUCAGGGAUAAAUUUGGUUACAGACAUCA |
| 636 | ACA8_1 | UGCACUGCAUGGUAUCUGCACUCAGCAGUUUACACCUGCUAGGGUGUUCAA AGGUCAGUGCUAUAGAAAUUCAGUAUCUGGCAUCGUUGGUUUUCUUGGCUU UGUGCUUGUUAAACCUGGUAUUUCUACUGAUACAGUA |
| 637 | ACA8_2 | UGCACUGCAUGGUAUCUGCACUCAGCAGUUUACACCUGCUAGGGUGUUCAA AGGUCAGUGCUAUAGAAAUUCAGUAUCUGGCAUCGUUGGUUUUCUUGGCUU UGUGCUUGUUAAACCUGGUAUUUCUACUGAUACAGUA |
| 638 | ACA5_1 | UGCAGCCGUGUCAAUUCAGUACCUGUCCUAUGCAUGGUAGGCACUGGCCCA GAAGGCUGCCACAGAAACACUGUGACUCAUGGGCCCUGUUCCUGUGUCCCA GGCUCAGGGAUAAAUUUGGUUACAGACAUCA |
| 639 | ACA36_1 | UUCCAAAGUGUUGAGUUCAGUCCAGGGCAGCUUCCCUGUUCUGUUAAUUAA ACUUUGGGACAUUAAAAUGGGCUAAGGGAGAUGAUUGGGUAGAAAGUAUUA UUCUAUUCAUUUGCCUCCCAGCCUACAAAA |
| 640 | ACA42_1 | UGGUAAUGGAUUUAUGGUGGGUCCUUCUCUGUGGGCCUCUCAUAGUGUACC CAUGCCAUAGCAAAUGGCAGCCUCGAACCAUUGCCCAGUCCCCUUACCUGU GGGCUGUGAGCACUGAAGGGGGUUGCACAGUG |
| 641 | ACA42_2 | UGGUAAUGGAUUUAUGGUGGGUCCUUCUCUGUGGGCCUCUCAUAGUGUACC CAUGCCAUAGCAAAUGGCAGCCUCGAACCAUUGCCCAGUCCCCUUACCUGU GGGCUGUGAGCACUGAAGGGGGUUGCACAGUG |
| 642 | ACA44_1 | CAGCAUGUUUCCAAGGGCUGUGGCUGGUCAUAGCCAUGGGAUCUCCAACUG CAUGCAAGAGCAACCUGGAAAGACUUUGACAGCGCAGGUCAGUACAAUACC UGCAAGCUGCCACUCAGCUUUCCUAUAAUG |
| 643 | ACA44_2 | CAGCAUGUUUCCAAGGGCUGUGGCUGGUCAUAGCCAUGGGAUCUCCAACUG CAUGCAAGAGCAACCUGGAAAGACUUUGACAGCGCAGGUCAGUACAAUACC UGCAAGCUGCCACUCAGCUUUCCUAUAAUG |
| 644 | ACA10_2 | GGUCUCUCAGCUCCGCUUAACCACACGGGUCCAGUGUGUGCUUGGCGUGUU UUCAGGGAGGCAGAGAAAGGCUCUCCUAAUGCACGACAGACCCGCCCAGAA UGGCCUCUCUGUUCCUAGGAGUGCGACAAUU |
| 645 | ACA46 | AGCACUAUAUUUAAACCUGUGGAUGGGAAUAUUCCCCAUUCUUGGUUACGC UGUAGUGCAAAAGAAUUCCUGGCUCUCUGUUGCACAGCUGACUUGUGCCAU UCUGCUGUUGCUGUAUAGAGUUAAGGAACAUGG |
| 646 | ACA10_1 | GGUCUCUCAGCUCCGCUUAACCACACGGGUCCAGUGUGUGCUUGGCGUGUU UUCAGGGAGGCAGAGAAAGGCUCUCCUAAUGCACGACAGACCCGCCCAGAA UGGCCUCUCUGUUCCUAGGAGUGCGACAAUU |
| 647 | ACA1 | UGCCUCAUUCUAGAGAAUGGGCACUGUUGAUCAUGGUGUCCAAAAAUAGUU AAUGUGGGCUAAAUUGAGACAGGUUAUGCUUCCAUCACAGUAUGCAUAUUGC AGUGGUGACAAUGAGACCUGUAACAUUU |
| 648 | ACA2A_1 | UAGGCCCUGAAUCAAGACCAAUGGUUUGCUGUAGCUGUUGGUUUCAAACAG GAGCUAAGAGUGAUGUCUUCCUUGUGGUCUGUUGGCUAUUCAGUAUUCCAG UGCGAAUUGCCAAUUCAGUUGGAAGAAACAUAG |

TABLE_3-continued

SEQUENCE_LISTING

| SEQ ID NO | Name/ ID | Sequence |
|---|---|---|
| 649 | ACA2A_2 | UAGGCCCUGAAUCAAGACCAAUGGUUUGCUGUAGCUGUUGGUUUCAAACAG GAGCUAAGAGUGAUGUCUUCCUUGUGGUCUGUUGGCUAUUCAGUAUUCCAG UGCGAAUUGCCAAUUCAGUUGGAAGAAACAUAG |
| 650 | ACA3_1 | AUCGAGGCUAGAGUCACGCUUGGGUAUCGGCUAUUGCCUGAGUGUGCUAGA GUCCUCGAAGAGUAACUGCUGACCUUAUUCACUGGCUGUGGGCCUUAUGGC ACAGUCAGUCACCAGGUUAGAGACAUGC |
| 651 | ACA3_2 | AUCGAGGCUAGAGUCACGCUUGGGUAUCGGCUAUUGCCUGAGUGUGCUAGA GUCCUCGAAGAGUAACUGCUGACCUUAUUCACUGGCUGUGGGCCUUAUGGC ACAGUCAGUCACCAGGUUAGAGACAUGC |
| 652 | ACA6 | UGCACACUAUUAAAGCUCAGGGUGGAGGCCAGUCUUGGCUCAUGAACUUCU GAGUGUCGGAAGUGUGCUAUAUCAAUGGCAGGAUUUUCGCUAACACCAGUA GAGCUUGCCUCUAUGACUGGAGUUUGGUAGUACUCGCUGCCACAUAG |
| 653 | ACA7_1 | GACCUCCUGGGAUCGCAUCUGGAGAGUGCCUAGUAUUCUGCCAGCUUCGGA AAGGGAGGGAAAGCAAGCCUGGCAGAGGCACCCAUUCCAUUCCCAGCUUGC UCCGUAGCUGGCGAUUGGAAGACACUCUGCGACAGUG |
| 654 | ACA7_2 | GACCUCCUGGGAUCGCAUCUGGAGAGUGCCUAGUAUUCUGCCAGCUUCGGA AAGGGAGGGAAAGCAAGCCUGGCAGAGGCACCCAUUCCAUUCCCAGCUUGC UCCGUAGCUGGCGAUUGGAAGACACUCUGCGACAGUG |
| 655 | ACA9_1 | UAGCAAGCCUCCAGCGUGCUUGGGUCUGCGGUGACCCUAUGCAUUCCUUCA GUGCUUGCUAGAACAGUUUUGAAACGGUUUGAGGCCUUGCCCUGCUCCAUC CAGAGCAAGGUUAUAGAAAUUUCAGACAAUG |
| 656 | ACA9_2 | UAGCAAGCCUCCAGCGUGCUUGGGUCUGCGGUGACCCUAUGCAUUCCUUCA GUGCUUGCUAGAACAGUUUUGAAACGGUUUGAGGCCUUGCCCUGCUCCAUC CAGAGCAAGGUUAUAGAAAUUUCAGACAAUG |
| 657 | ACA16 | UUGGCCCUUAUCGAAGCUGCAGCUGCUUCCGCAUAGCUGCUGUGGUCAAAA AGGAGCCCAGAGUGACAGUUUUCCUUGACGGUCGCCGUUCUGUUUGUUGUA ACUGAUCUGCAACAUUUUGGGAAAAUACAGUU |

The invention claimed is:

1. A method for trans-splicing one or more pre-mRNA target sequences in a eukaryotic cell comprising:

(a) contacting the eukaryotic cell comprising the one or more pre-mRNA target sequences with one or more trans-splicing RNA molecules wherein each trans-splicing RNA molecule comprises:

(i) at least one sequence comprising a non-coding RNA (ncRNA), wherein the ncRNA is a small nucleolar RNA (snoRNA) sequence of 50 to 300 nucleotides in length, wherein the snoRNA sequence comprises:

a C box having the polynucleotide sequence of RUGAUGA, wherein R is A or G, a D box having the polynucleotide sequence of CUGA, a C' box having the polynucleotide sequence of RUGAUGA, wherein R is A or G, and a D' box having the polynucleotide sequence of CUGA;

(ii) at least one splice acceptor site or splice donor site;

(iii) at least one exonic sequence, wherein the at least one splice acceptor site or splice donor site is located at a 3' boundary of the at least one exonic sequence, and wherein the at least one splice acceptor site or splice donor site and the at least one exonic sequence is located 5' of the snoRNA sequence; and (iv) one or more binding domains, each comprising a nucleic acid sequence of 4 to 300 nucleotides in length, and having at least 95% complementarity to the one or more pre-mRNA target sequences, wherein the snoRNA sequence comprises at least one binding domain positioned (i) upstream of the C box; (ii) between the C box and the D' box; (iii) between the C' box and the D box; (iv) downstream of the D box; or (v) a combination of (i)-(iv);

(b) binding at least a portion of the one or more binding domains of the one or more trans-splicing RNA molecules to the one or more pre-mRNA target sequences via complementary base pairing;

(c) recruiting a ribonucleoprotein (RNP) to direct splicing of the at least one exonic sequence into the one or more pre-mRNA target sequences; and (d) splicing the at least one exonic sequence into the one or more pre-mRNA target sequences.

2. The method of claim 1, wherein the one or more binding domains comprise 2 binding domains, or wherein the one or more binding domains comprise more than 2 binding domains.

3. The method of claim 1, wherein the one or more binding domains are each 5 to 20, 5 to 30, 5 to 40, 5 to 50, 10 to 50, 10 to 100, 20 to 100, 30 to 100, 40 to 100, 50 to 100, 50 to 150, 50 to 200, 50 to 250, 100 to 150, 100 to 200, 100 to 250, or 100 to 300 nucleotides in length, and each have 95% complementarity to the one or more pre-mRNA target sequences.

4. The method of claim 1, wherein the one or more binding domains comprise 4 to 30 nucleotides having at least 95% complementarity to the one or more pre-mRNA target sequences.

5. The method of claim 1, wherein the one or more pre-mRNA target sequences comprises an USH2A pre-mRNA sequence, or wherein the one or more pre-mRNA target sequences comprises intron 12 and/or exon 13 of an USH2A pre-mRNA.

6. The method of claim 1, wherein the snoRNA sequence comprises a nucleic acid sequence of SNORD45A, SNORD51, SNORD10, or SNORD70.

7. The method of claim 1, wherein the one or more trans-splicing RNA molecules further comprises one or more splicing signals.

8. The method of claim 7, wherein the one or more splicing signals are selected from an exonic splicing enhancer (ESE), an intronic splicing enhancer (ISE), an exonic splicing silencer (ESS), intronic splicing silencer (ISS), a polypyrimidine tract, a branch point, and a combination thereof.

9. The method of claim 1, wherein the one or more trans-splicing RNA molecules comprises one or more polypyrimidine tracts, one or more branch points, and at least one splice acceptor site or splice donor site and is suitable for 5' editing of the one or more pre-mRNA target sequences.

10. The method of claim 1, wherein the contacting step comprises contacting the cell with a plasmid, viral vector, or non-viral vector encoding the one or more trans-splicing RNA molecules; and/or wherein the contacting step comprises using a delivery vehicle comprising a lipid nanoparticle (LNP) or a polymeric nanoparticle.

11. The method of claim 1, wherein the contacting step comprises contacting the cell with multiple plasmids, viral vectors, or non-viral vectors encoding distinct trans-splicing RNA molecules; and/or wherein the contacting step comprises using a delivery vehicle comprising a lipid nanoparticle (LNP) or a polymeric nanoparticle.

* * * * *